United States Patent
Shim et al.

(10) Patent No.: US 10,472,682 B2
(45) Date of Patent: Nov. 12, 2019

(54) PREDICTION OF EFFECT OF A C-MET INHIBITOR USING MUTATION OF KRAS OR BRAF

(71) Applicant: Samsung Electronics Co., Ltd., Suwon-si, Gyeonggi-do (KR)

(72) Inventors: Seon Hui Shim, Daejeon (KR); Soo Yeon Jung, Seongnam-si (KR); Kyung Ah Kim, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 234 days.

(21) Appl. No.: 14/869,563

(22) Filed: Sep. 29, 2015

(65) Prior Publication Data

US 2016/0090635 A1   Mar. 31, 2016

(30) Foreign Application Priority Data

Sep. 29, 2014 (KR) .................. 10-2014-0130560

(51) Int. Cl.
| | |
|---|---|
| *C12Q 1/6886* | (2018.01) |
| *C07K 16/30* | (2006.01) |
| *C07K 16/28* | (2006.01) |
| *A61K 39/00* | (2006.01) |

(52) U.S. Cl.
CPC ........ *C12Q 1/6886* (2013.01); *C07K 16/2863* (2013.01); *C07K 16/30* (2013.01); *A61K 2039/505* (2013.01); *C07K 2317/24* (2013.01); *C07K 2317/52* (2013.01); *C07K 2317/53* (2013.01); *C07K 2317/565* (2013.01); *C07K 2317/567* (2013.01); *C07K 2317/622* (2013.01); *C07K 2317/73* (2013.01); *C12Q 2600/106* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | |
|---|---|---|
| 8,129,114 B2 | 3/2012 | Ford et al. |
| 2009/0075267 A1 | 3/2009 | Siena et al. |
| 2011/0104176 A1* | 5/2011 | Cheong .............. C07K 16/2863 424/152.1 |
| 2011/0217309 A1 | 9/2011 | Buck et al. |
| 2012/0288862 A1 | 11/2012 | Xu et al. |
| 2012/0295258 A1 | 11/2012 | Hoon |

FOREIGN PATENT DOCUMENTS

KR   2011-0047698 A   5/2011

OTHER PUBLICATIONS

Fiala et al. (Cancer Genetics, 206: 26-31, 2013).*
Xu et al. (Clin Cancer Res, 17(13): 4425-4438, 2011).*
Blank et al. (Clin Cancer Res, 17(19): 6338-6346, 2011).*
Heidorn et al. (Cell, 140: 209-221, 2010).*
Stabile et al. (Cancers, 2: 2153-2170, 2010).*
Kamata et al. (Cancer Res., 70: 8475-8486, 2010).*
Mariuzza (Annu. Rev. Biophys. Biophys. Chem., 16: 139-159, 1987).*
Dokmanovic et al., "Trastuzumab-Resistance and Breast Cancer", *Breast Cancer—Carcinogenesis, Cell Growth and Signalling Pathways*, pp. 171-204 (2011).
Hurwitz et al., "The Clinical Benefit of Bevacizumab in Metastatic Colorectal Cancer is Independent of K-ras Mutation Status: Analysis of a Phase III Study of Bevacizumab with Chemotherapy in Previously Untreated Metastatic Colorectal Cancer", *Oncologist*,14:22-28 (2009).
Ince et al., "Association of k-ras, b-raf, and p53 Status With the Treatment Effect of Bevacizumab", *Journal of National Cancer Institute*, 97(13): 981-989 (2005).

* cited by examiner

*Primary Examiner* — Nelson B Moseley, II
(74) *Attorney, Agent, or Firm* — Leydig, Voit & Mayer, Ltd.

(57) ABSTRACT

A method for predicting and/or monitoring the efficacy of a c-Met inhibitor using a biomarker; a method for selecting a subject suitable for the application of a c-Met inhibitor using a biomarker; and a method for preventing and/or treating cancer comprising administering a c-Met inhibitor to the selected subject.

17 Claims, 29 Drawing Sheets

Specification includes a Sequence Listing.

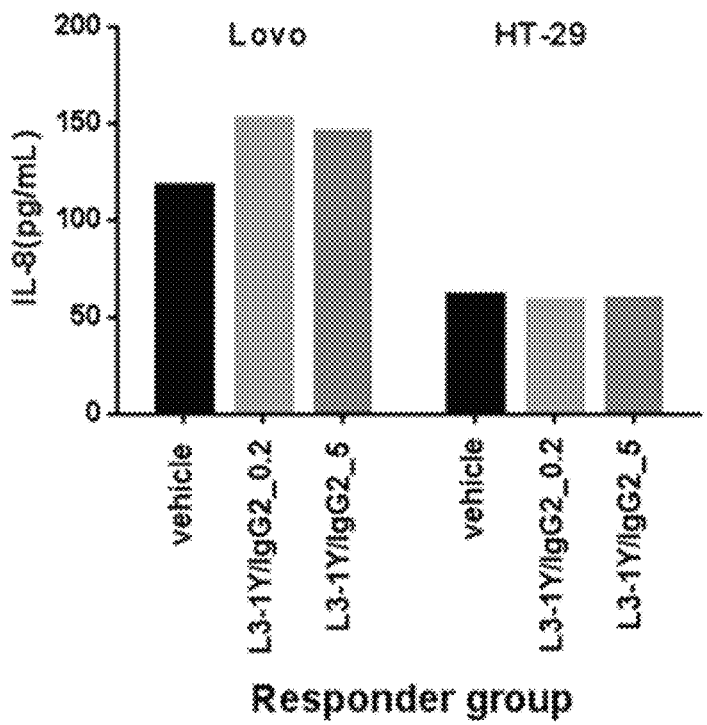
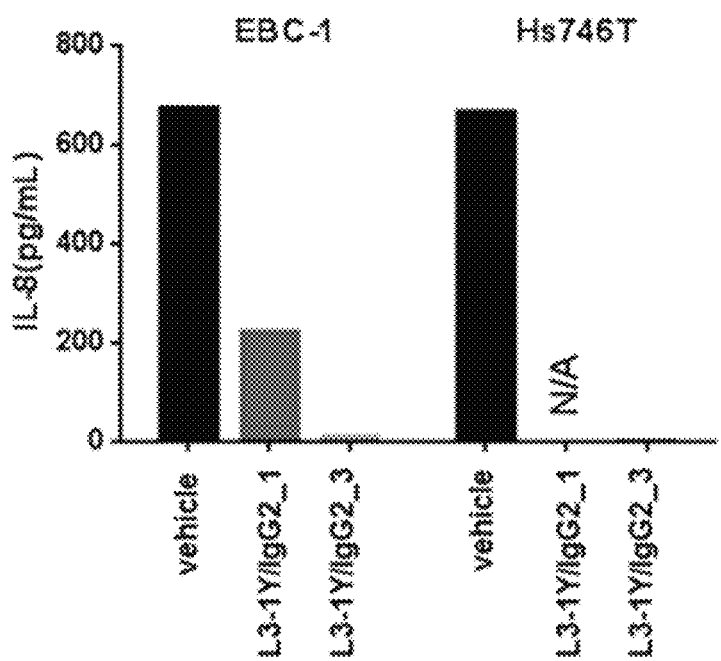

IL-8 CBA EBC-1

FIG. 19 B
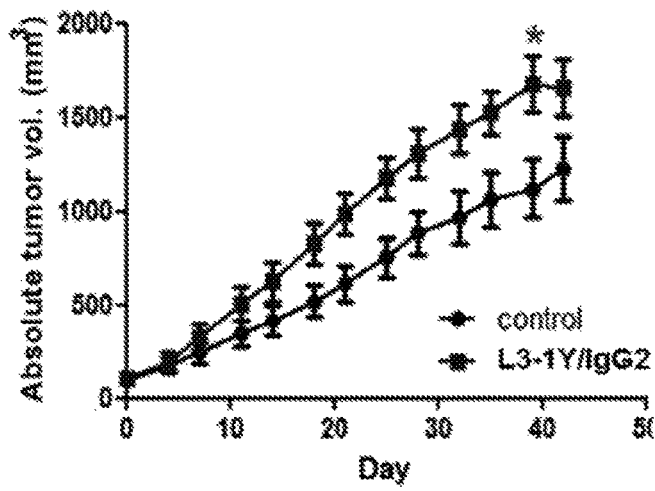
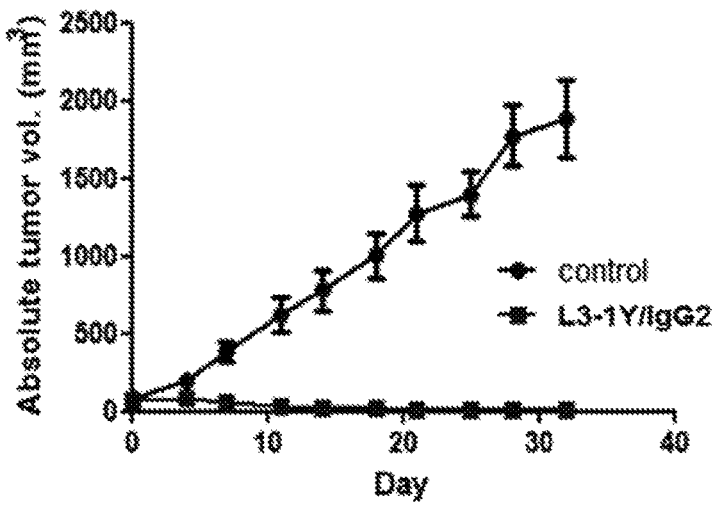

SEQUENCE LISTING

```
<160> NUMBER OF SEQ ID NOS: 115

<210> SEQ ID NO 1
<211> LENGTH: 5
<212> TYPE: PRT
<213> ORGANISM: Artificial Sequence
<220> FEATURE:
<223> OTHER INFORMATION: Synthetic heavy chain CDR1 of AbF46

<400> SEQUENCE: 1

Asp Tyr Tyr Met Ser
1               5

<210> SEQ ID NO 2
```

```
<211> LENGTH: 19
<212> TYPE: PRT
<213> ORGANISM: Artificial Sequence
<220> FEATURE:
<223> OTHER INFORMATION: Synthetic heavy chain CDR2 of AbF46

<400> SEQUENCE: 2

Phe Ile Arg Asn Lys Ala Asn Gly Tyr Thr Thr Glu Tyr Ser Ala Ser
1               5                   10                  15

Val Lys Gly

<210> SEQ ID NO 3
<211> LENGTH: 6
<212> TYPE: PRT
<213> ORGANISM: Artificial Sequence
<220> FEATURE:
<223> OTHER INFORMATION: Synthetic heavy chain CDR3 of AbF46

<400> SEQUENCE: 3

Asp Asn Trp Phe Ala Tyr
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic heavy chain CDR1 of c-Met antibody
<220> FEATURE:
<221> NAME/KEY: MOD_RES
<222> LOCATION: (1)
<223> OTHER INFORMATION: Xaa is Pro or Ser or absent
<220> FEATURE:
<221> NAME/KEY: MOD_RES
<222> LOCATION: (2)
<223> OTHER INFORMATION: Xaa is Glu or Asp

<400> SEQUENCE: 4

Xaa Xaa Tyr Tyr Met Ser
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic heavy chain CDR2 of c-Met antibody
<220> FEATURE:
<221> NAME/KEY: MOD_RES
<222> LOCATION: (3)
<223> OTHER INFORMATION: Xaa is Asn or Lys
<220> FEATURE:
<221> NAME/KEY: MOD_RES
<222> LOCATION: (4)
<223> OTHER INFORMATION: Xaa is Ala or Val
<220> FEATURE:
<221> NAME/KEY: MOD_RES
<222> LOCATION: (7)
<223> OTHER INFORMATION: Xaa is Asn or Thr

<400> SEQUENCE: 5

Arg Asn Xaa Xaa Asn Gly Xaa Thr
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic heavy chain CDR3 of c-Met antibody
```

```
<220> FEATURE:
<221> NAME/KEY: MOD_RES
<222> LOCATION: (5)
<223> OTHER INFORMATION: Xaa is Ser or Thr

<400> SEQUENCE: 6

Asp Asn Trp Leu Xaa Tyr
1               5

<210> SEQ ID NO 7
<211> LENGTH: 17
<212> TYPE: PRT
<213> ORGANISM: Artificial Sequence
<220> FEATURE:
<223> OTHER INFORMATION: Synthetic light chain CDR1 of c-Met antibody
<220> FEATURE:
<221> NAME/KEY: MOD_RES
<222> LOCATION: (4)
<223> OTHER INFORMATION: Xaa is His, Arg, Gln or Lys
<220> FEATURE:
<221> NAME/KEY: MOD_RES
<222> LOCATION: (9)
<223> OTHER INFORMATION: Xaa is Ser or Trp
<220> FEATURE:
<221> NAME/KEY: MOD_RES
<222> LOCATION: (12)
<223> OTHER INFORMATION: Xaa is His or Gln
<220> FEATURE:
<221> NAME/KEY: MOD_RES
<222> LOCATION: (13)
<223> OTHER INFORMATION: Xaa is Lys or Asn

<400> SEQUENCE: 7

Lys Ser Ser Xaa Ser Leu Leu Ala Xaa Gly Asn Xaa Xaa Asn Tyr Leu
1               5                   10                  15

Ala

<210> SEQ ID NO 8
<211> LENGTH: 7
<212> TYPE: PRT
<213> ORGANISM: Artificial Sequence
<220> FEATURE:
<223> OTHER INFORMATION: Synthetic light chain CDR2 of c-Met antibody
<220> FEATURE:
<221> NAME/KEY: MOD_RES
<222> LOCATION: (2)
<223> OTHER INFORMATION: Xaa is Ala or Gly
<220> FEATURE:
<221> NAME/KEY: MOD_RES
<222> LOCATION: (4)
<223> OTHER INFORMATION: Xaa is Thr or Lys
<220> FEATURE:
<221> NAME/KEY: MOD_RES
<222> LOCATION: (7)
<223> OTHER INFORMATION: Xaa is Ser or Pro

<400> SEQUENCE: 8

Trp Xaa Ser Xaa Arg Val Xaa
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic light chain CDR3 of c-Met antibody
<220> FEATURE:
<221> NAME/KEY: MOD_RES
<222> LOCATION: (1)
<223> OTHER INFORMATION: Xaa is Gly, Ala or Gln
<220> FEATURE:
<221> NAME/KEY: MOD_RES
```

```
<222> LOCATION: (6)
<223> OTHER INFORMATION: Xaa is Arg, His, Ser, Ala, Gly or Lys
<220> FEATURE:
<221> NAME/KEY: MOD_RES
<222> LOCATION: (8)
<223> OTHER INFORMATION: Xaa is Leu, Tyr, Phe or Met

<400> SEQUENCE: 9

Xaa Gln Ser Tyr Ser Xaa Pro Xaa Thr
1               5

<210> SEQ ID NO 10
<211> LENGTH: 17
<212> TYPE: PRT
<213> ORGANISM: Artificial Sequence
<220> FEATURE:
<223> OTHER INFORMATION: Synthetic light chain CDR1 of AbF46

<400> SEQUENCE: 10

Lys Ser Ser Gln Ser Leu Leu Ala Ser Gly Asn Gln Asn Asn Tyr Leu
1               5                   10                  15

Ala

<210> SEQ ID NO 11
<211> LENGTH: 7
<212> TYPE: PRT
<213> ORGANISM: Artificial Sequence
<220> FEATURE:
<223> OTHER INFORMATION: Synthetic light chain CDR2 of AbF46

<400> SEQUENCE: 11

Trp Ala Ser Thr Arg Val Ser
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic light chain CDR3 of AbF46

<400> SEQUENCE: 12

Gln Gln Ser Tyr Ser Ala Pro Leu Thr
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic CDR-L3 derived from L3-1 clone

<400> SEQUENCE: 13

Gln Gln Ser Tyr Ser Arg Pro Tyr Thr
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic CDR-L3 derived from L3-2 clone

<400> SEQUENCE: 14

Gly Gln Ser Tyr Ser Arg Pro Leu Thr
1               5
```

<210> SEQ ID NO 15
<211> LENGTH: 9
<212> TYPE: PRT
<213> ORGANISM: Artificial Sequence
<220> FEATURE:
<223> OTHER INFORMATION: Synthetic CDR-L3 derived from L3-3 clone

<400> SEQUENCE: 15

Ala Gln Ser Tyr Ser His Pro Phe Ser
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic CDR-L3 derived from L3-5 clone

<400> SEQUENCE: 16

Gln Gln Ser Tyr Ser Arg Pro Phe Thr
1               5

<210> SEQ ID NO 17
<211> LENGTH: 117
<212> TYPE: PRT
<213> ORGANISM: Artificial Sequence
<220> FEATURE:
<223> OTHER INFORMATION: Synthetic heavy chain variable region of anti
      c-Met humanized antibody(huAbF46-H4)

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 18
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys

```
                35                  40                  45
Ala Pro Lys Met Leu Ile Ile Trp Ala Ser Thr Arg Val Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Ser Tyr Ser Arg Pro Tyr Thr Phe Gly Gln Gly Thr Lys Val Glu Ile
                100                 105                 110

Lys Arg

<210> SEQ ID NO 19
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 19

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
                 20                  25                  30

Gly Asn Gln Asn Asn Tyr Leu Ala Trp His Gln Gln Lys Pro Gly Lys
                 35                  40                  45

Ala Pro Lys Met Leu Ile Ile Trp Ala Ser Thr Arg Val Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gly Gln
                 85                  90                  95

Ser Tyr Ser Arg Pro Leu Thr Phe Gly Gln Gly Thr Lys Val Glu Ile
                100                 105                 110

Lys Arg

<210> SEQ ID NO 20
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 20

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
                 20                  25                  30

Gly Asn Gln Asn Asn Tyr Leu Ala Trp His Gln Gln Lys Pro Gly Lys
                 35                  40                  45

Ala Pro Lys Met Leu Ile Ile Trp Ala Ser Thr Arg Val Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Ala Gln
                 85                  90                  95
```

```
Ser Tyr Ser His Pro Phe Ser Phe Gly Gln Gly Thr Lys Val Glu Ile
                100                 105                 110

Lys Arg

<210> SEQ ID NO 21
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Phe Thr Phe Gly Gln Gly Thr Lys Val Glu Ile
                100                 105                 110

Lys Arg

<210> SEQ ID NO 22
<211> LENGTH: 6
<212> TYPE: PRT
<213> ORGANISM: Artificial Sequence
<220> FEATURE:
<223> OTHER INFORMATION: Synthetic CDR-H1 derived from H11-4 clone

<400> SEQUENCE: 22

Pro Glu Tyr Tyr Met Ser
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic CDR-H1 derived from YC151 clone

<400> SEQUENCE: 23

Pro Asp Tyr Tyr Met Ser
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic CDR-H1 derived from YC193 clone

<400> SEQUENCE: 24

Ser Asp Tyr Tyr Met Ser
1               5
```

```
<210> SEQ ID NO 25
<211> LENGTH: 8
<212> TYPE: PRT
<213> ORGANISM: Artificial Sequence
<220> FEATURE:
<223> OTHER INFORMATION: Synthetic CDR-H2 derived from YC244 clone

<400> SEQUENCE: 25

Arg Asn Asn Ala Asn Gly Asn Thr
1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic CDR-H2 derived from YC321 clone

<400> SEQUENCE: 26

Arg Asn Lys Val Asn Gly Tyr Thr
1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic CDR-H3 derived from YC354 clone

<400> SEQUENCE: 27

Asp Asn Trp Leu Ser Tyr
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic CDR-H3 derived from YC374 clone

<400> SEQUENCE: 28

Asp Asn Trp Leu Thr Tyr
1               5

<210> SEQ ID NO 29
<211> LENGTH: 17
<212> TYPE: PRT
<213> ORGANISM: Artificial Sequence
<220> FEATURE:
<223> OTHER INFORMATION: Synthetic CDR-L1 derived from L1-1 clone

<400> SEQUENCE: 29

Lys Ser Ser His Ser Leu Leu Ala Ser Gly Asn Gln Asn Asn Tyr Leu
1               5                   10                  15

Ala

<210> SEQ ID NO 30
<211> LENGTH: 17
<212> TYPE: PRT
<213> ORGANISM: Artificial Sequence
<220> FEATURE:
<223> OTHER INFORMATION: Synthetic CDR-L1 derived from L1-3 clone

<400> SEQUENCE: 30

Lys Ser Ser Arg Ser Leu Leu Ser Ser Gly Asn His Lys Asn Tyr Leu
1               5                   10                  15
```

Ala

```
<210> SEQ ID NO 31
<211> LENGTH: 17
<212> TYPE: PRT
<213> ORGANISM: Artificial Sequence
<220> FEATURE:
<223> OTHER INFORMATION: Synthetic CDR-L1 derived from L1-4 clone

<400> SEQUENCE: 31
```

Lys Ser Ser Lys Ser Leu Leu Ala Ser Gly Asn Gln Asn Asn Tyr Leu
1               5                   10                  15

Ala

```
<210> SEQ ID NO 32
<211> LENGTH: 17
<212> TYPE: PRT
<213> ORGANISM: Artificial Sequence
<220> FEATURE:
<223> OTHER INFORMATION: Synthetic CDR-L1 derived from L1-12 clone

<400> SEQUENCE: 32
```

Lys Ser Ser Arg Ser Leu Leu Ala Ser Gly Asn Gln Asn Asn Tyr Leu
1               5                   10                  15

Ala

```
<210> SEQ ID NO 33
<211> LENGTH: 17
<212> TYPE: PRT
<213> ORGANISM: Artificial Sequence
<220> FEATURE:
<223> OTHER INFORMATION: Synthetic CDR-L1 derived from L1-22 clone

<400> SEQUENCE: 33
```

Lys Ser Ser His Ser Leu Leu Ala Ser Gly Asn Gln Asn Asn Tyr Leu
1               5                   10                  15

Ala

```
<210> SEQ ID NO 34
<211> LENGTH: 7
<212> TYPE: PRT
<213> ORGANISM: Artificial Sequence
<220> FEATURE:
<223> OTHER INFORMATION: Synthetic CDR-L2 derived from L2-9 clone

<400> SEQUENCE: 34
```

Trp Ala Ser Lys Arg Val Ser
1               5

```
<210> SEQ ID NO 35
<211> LENGTH: 7
<212> TYPE: PRT
<213> ORGANISM: Artificial Sequence
<220> FEATURE:
<223> OTHER INFORMATION: Synthetic CDR-L2 derived from L2-12 clone

<400> SEQUENCE: 35
```

Trp Gly Ser Thr Arg Val Ser
1               5

```
<210> SEQ ID NO 36
<211> LENGTH: 7
<212> TYPE: PRT
<213> ORGANISM: Artificial Sequence
<220> FEATURE:
```

-continued

<223> OTHER INFORMATION: Synthetic CDR-L2 derived from L2-16 clone

<400> SEQUENCE: 36

Trp Gly Ser Thr Arg Val Pro
1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic CDR-L3 derived from L3-32 clone

<400> SEQUENCE: 37

Gln Gln Ser Tyr Ser Lys Pro Phe Thr
1               5

<210> SEQ ID NO 38
<211> LENGTH: 1416
<212> TYPE: DNA
<213> ORGANISM: Artificial Sequence
<220> FEATURE:
<223> OTHER INFORMATION: Synthetic nucleotide sequence of heavy chain of
      chAbF46
<220> FEATURE:
<221> NAME/KEY: misc_feature
<222> LOCATION: (1)..(6)
<223> OTHER INFORMATION: EcoRI restriction site
<220> FEATURE:
<221> NAME/KEY: misc_feature
<222> LOCATION: (7)..(66)
<223> OTHER INFORMATION: signal sequence
<220> FEATURE:
<221> NAME/KEY: misc_feature
<222> LOCATION: (67)..(417)
<223> OTHER INFORMATION: VH - heavy chain variable region
<220> FEATURE:
<221> NAME/KEY: misc_feature
<222> LOCATION: (418)..(423)
<223> OTHER INFORMATION: NdeI restriction site
<220> FEATURE:
<221> NAME/KEY: misc_feature
<222> LOCATION: (418)..(1407)
<223> OTHER INFORMATION: CH - heavy chain constant region
<220> FEATURE:
<221> NAME/KEY: misc_feature
<222> LOCATION: (1408)..(1410)
<223> OTHER INFORMATION: TGA - stop codon
<220> FEATURE:
<221> NAME/KEY: misc_feature
<222> LOCATION: (1411)..(1416)
<223> OTHER INFORMATION: XhoI restriction site

<400> SEQUENCE: 38
gaattcgccg ccaccatgga atggagctgg gttttctcg taacactttt aaatggtatc      60
cagtgtgagg tgaagctggt ggagtctgga ggaggcttgg tacagcctgg ggttctctg    120 agactctcct gtgcaacttc tgggttcacc ttcactgatt actacatgag ctgggtccgc    180
cagcctccag aaaggcact tgagtggttg ggttttatta gaaacaaagc taatggttac    240
acaacagagt acagtgcatc tgtgaagggt cggttcacca tctccagaga taattcccaa    300
agcatcctct atcttcaaat ggacaccctg agagctgagg acagtgccac ttattactgt    360
gcaagagata actggtttgc ttactggggc caagggactc tggtcactgt ctctgcagct    420
agcaccaagg gcccatcggt cttccccctg gcaccctcct ccaagagcac ctctgggggc    480
acagcggccc tgggctgcct ggtcaaggac tacttccccg aaccggtgac ggtgtcgtgg    540
aactcaggcg ccctgaccag cggcgtgcac accttcccgg ctgtcctaca gtcctcagga    600

```
ctctactccc tcagcagcgt ggtgaccgtg ccctccagca gcttgggcac ccagacctac      660
atctgcaacg tgaatcacaa gcccagcaac accaaggtgg acaagaaagt tgagcccaaa      720
tcttgtgaca aaactcacac atgcccaccg tgcccagcac ctgaactcct gggggggaccg     780 tcagtcttcc tcttcccccc aaaacccaag gacaccctca tgatctcccg gacccctgag      840
gtcacatgcg tggtggtgga cgtgagccac gaagaccctg aggtcaagtt caactggtac      900
gtggacggcg tggaggtgca taatgccaag acaaagccgc gggaggagca gtacaacagc      960
acgtaccgtg tggtcagcgt cctcaccgtc ctgcaccagg actggctgaa tggcaaggag     1020
tacaagtgca aggtctccaa caaagccctc ccagccccca tcgagaaaac catctccaaa     1080
gccaaagggc agccccgaga accacaggtg tacaccctgc ccccatcccg ggaggagatg     1140
accaagaacc aggtcagcct gacctgcctg gtcaaaggct tctatcccag cgacatcgcc     1200
gtggagtggg agagcaatgg gcagccggag aacaactaca agaccacgcc tcccgtgctg     1260
gactccgacg gctccttctt cctctacagc aagctcaccg tggacaagag caggtggcag     1320
caggggaacg tcttctcatg ctccgtgatg catgaggctc tgcacaacca ctacacgcag     1380
aagagcctct ccctgtctcc gggtaaatga ctcgag                              1416
```

```
<210> SEQ ID NO 39
<211> LENGTH: 759
<212> TYPE: DNA
<213> ORGANISM: Artificial Sequence
<220> FEATURE:
<223> OTHER INFORMATION: Synthetic nucleotide sequence of light chain of
      chAbF46
<220> FEATURE:
<221> NAME/KEY: misc_difference
<222> LOCATION: (1)..(6)
<223> OTHER INFORMATION: EcoRI restriction site
<220> FEATURE:
<221> NAME/KEY: misc_difference
<222> LOCATION: (7)..(90)
<223> OTHER INFORMATION: signal sequence
<220> FEATURE:
<221> NAME/KEY: misc_difference
<222> LOCATION: (91)..(432)
<223> OTHER INFORMATION: VL - light chain variable region
<220> FEATURE:
<221> NAME/KEY: misc_difference
<222> LOCATION: (430)..(435)
<223> OTHER INFORMATION: BsiWI restriction site
<220> FEATURE:
<221> NAME/KEY: misc_difference
<222> LOCATION: (433)..(750)
<223> OTHER INFORMATION: CL - light chain constant region
<220> FEATURE:
<221> NAME/KEY: misc_difference
<222> LOCATION: (751)..(753)
<223> OTHER INFORMATION: stop codon
<220> FEATURE:
<221> NAME/KEY: misc_difference
<222> LOCATION: (754)..(759)
<223> OTHER INFORMATION: XhoI restriction site

<400> SEQUENCE: 39
gaattcacta gtgattaatt cgccgccacc atggattcac aggcccaggt cctcatgttg       60
ctgctgctat cggtatctgg tacctgtgga cattttgat gacccagtc tccatcctcc        120 ctgactgtgt cagcaggaga gaaggtcact atgagctgca agtccagtca gagtcttta      180 gctagtggca accaaaataa ctacttggcc tggcaccagc agaaaccagg acgatctcct     240
aaaatgctga tatttggggc atccactagg gtatctggag tccctgatcg cttcataggc     300
agtggatctg ggacggattt cactctgacc atcaacagtg tgcaggctga agatctggct     360
```

```
gtttattact gtcagcagtc ctacagcgct ccgctcacgt tcggtgctgg gaccaagctg      420
gagctgaaac gtacggtggc tgcaccatct gtcttcatct cccgccatc tgatgagcag       480 ttgaaatctg gaactgcctc tgttgtgtgc ctgctgaata acttctatcc cagagaggcc      540
aaagtacagt ggaaggtgga taacgccctc caatcgggta actcccagga gagtgtcaca      600
gagcaggaca gcaaggacag cacctacagc ctcagcagca ccctgacgct gagcaaagca      660
gactacgaga acacaaagt ctacgcctgc gaagtcaccc atcagggcct gagctcgccc       720
gtcacaaaga gcttcaacag gggagagtgt tgactcgag                             759
```

<210> SEQ ID NO 40
<211> LENGTH: 447
<212> TYPE: PRT
<213> ORGANISM: Artificial Sequence
<220> FEATURE:
<223> OTHER INFORMATION: Synthetic amino acid sequence of H1-heavy

<400> SEQUENCE: 40

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
```

```
                    290                 295                 300
Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                    325                 330                 335

Ser Lys Ala Lys Gly Gln Pro Arg Glu Pro Gln Val Tyr Thr Leu Pro
                340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                    405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
            435                 440                 445

<210> SEQ ID NO 41
<211> LENGTH: 447
<212> TYPE: PRT
<213> ORGANISM: Artificial Sequence
<220> FEATURE:
<223> OTHER INFORMATION: Synthetic amino acid sequence of H3-heavy

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
```

```
                210                 215                 220
Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
                275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
                435                 440                 445

<210> SEQ ID NO 42
<211> LENGTH: 447
<212> TYPE: PRT
<213> ORGANISM: Artificial Sequence
<220> FEATURE:
<223> OTHER INFORMATION: Synthetic amino acid sequence of H4-heavy

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
                20                  25                  30

Tyr Met Ser Trp Val Arg Gln Ala Pro Gly Lys Gly Leu Glu Trp Leu
            35                  40                  45

Gly Phe Ile Arg Asn Lys Ala Asn Gly Tyr Thr Thr Glu Tyr Ser Ala
        50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
```

```
                130               135                140
Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
        210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 43
<211> LENGTH: 220
<212> TYPE: PRT
<213> ORGANISM: Artificial Sequence
<220> FEATURE:
<223> OTHER INFORMATION: Synthetic amino acid sequence of H1-light

<400> SEQUENCE: 43

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp His Gln Gln Lys Pro Gly Gln
        35                  40                  45

Pro Pro Lys Met Leu Ile Ile Trp Ala Ser Thr Arg Val Ser Gly Val
```

```
            50                  55                  60
Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gly Gly Thr Lys Val Glu Ile
                100                 105                 110

Lys Arg Thr Val Ala Ala Pro Ser Val Phe Ile Phe Pro Pro Ser Asp
                115                 120                 125

Glu Gln Leu Lys Ser Gly Thr Ala Ser Val Val Cys Leu Leu Asn Asn
                130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
                195                 200                 205

Ser Pro Val Thr Lys Ser Phe Asn Arg Gly Glu Cys
                210                 215                 220

<210> SEQ ID NO 44
<211> LENGTH: 220
<212> TYPE: PRT
<213> ORGANISM: Artificial Sequence
<220> FEATURE:
<223> OTHER INFORMATION: Synthetic amino acid sequence of H2-light

<400> SEQUENCE: 44

Asp Ile Val Met Thr Gln Thr Pro Leu Ser Leu Pro Val Thr Pro Gly
1               5                   10                  15

Glu Pro Ala Ser Ile Ser Cys Lys Ser Ser Gln Ser Leu Leu Ala Ser
                20                  25                  30

Gly Asn Gln Asn Asn Tyr Leu Ala Trp His Leu Gln Lys Pro Gly Gln
                35                  40                  45

Ser Pro Gln Met Leu Ile Ile Trp Ala Ser Thr Arg Val Ser Gly Val
50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Gln Gln
                85                  90                  95

Ser Tyr Ser Ala Pro Leu Thr Phe Gly Gln Gly Thr Lys Leu Glu Leu
                100                 105                 110

Lys Arg Thr Val Ala Ala Pro Ser Val Phe Ile Phe Pro Pro Ser Asp
                115                 120                 125

Glu Gln Leu Lys Ser Gly Thr Ala Ser Val Val Cys Leu Leu Asn Asn
                130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
```

```
            195                 200                 205
Ser Pro Val Thr Lys Ser Phe Asn Arg Gly Glu Cys
    210                 215                 220

<210> SEQ ID NO 45
<211> LENGTH: 220
<212> TYPE: PRT
<213> ORGANISM: Artificial Sequence
<220> FEATURE:
<223> OTHER INFORMATION: Synthetic amino acid sequence of H3-light

<400> SEQUENCE: 45

Asp Ile Val Met Thr Gln Ser Pro Asp Ser Leu Ala Val Ser Leu Gly
1               5                   10                  15

Glu Arg Ala Thr Ile Asn Cys Lys Ser Gln Ser Leu Leu Ala Ser
            20                  25                  30

Gly Asn Gln Asn Asn Tyr Leu Ala Trp Tyr Gln Gln Lys Pro Gly Gln
        35                  40                  45

Pro Pro Lys Leu Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 46
<211> LENGTH: 219
<212> TYPE: PRT
<213> ORGANISM: Artificial Sequence
<220> FEATURE:
<223> OTHER INFORMATION: Synthetic amino acid sequence of H4-light

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60
```

| | | | | | | | | | | | | |
|---|---|---|---|---|---|---|---|---|---|---|---|---|
|Pro|Ser|Arg|Phe|Ser|Gly|Ser|Gly|Ser|Gly|Thr|Asp|Phe|Thr|Leu|Thr|
|65| | | |70| | | |75| | | |80|

Ile Ser Ser Leu Gln Pro Glu Asp Phe Ala Thr Tyr Tyr Cys Gln Gln
                85                  90                  95

Ser Tyr Ser Ala Pro Leu Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu
    210                 215

<210> SEQ ID NO 47
<211> LENGTH: 1350
<212> TYPE: DNA
<213> ORGANISM: Artificial Sequence
<220> FEATURE:
<223> OTHER INFORMATION: Synthetic nucleotide sequence of H1-heavy

<400> SEQUENCE: 47

```
gaggtgcagc tggtggagtc tgggggaggc ttggtccagc ctggagggtc cctgagactc      60
tcctgtgcag cctctggatt caccttcact gactactaca tgagctgggt ccgccaggct     120
ccagggaagg ggctggagtg gttgggcttt attagaaaca agctaacgg ttacaccaca      180
gaatacagtg cgtctgtgaa aggcagattc accatctcaa gagataattc aaagaactca     240
ctgtatctgc aaatgaacag cctgaaaacc gaggacacgg ccgtgtatta ctgtgctaga     300
gataactggt ttgcttactg gggtcaagga accctggtca ccgtctcctc ggctagcacc     360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
aacgtgaatc acaagcccag caacaccaag gtggacaaga agttgagcc caaatcttgt     660
gacaaaactc acacatgccc accgtgccca gcacctgaac tcctgggggg accgtcagtc     720
ttcctcttcc ccccaaaacc caaggacacc ctcatgatct cccggacccc tgaggtcaca     780
tgcgtggtgg tggacgtgag ccacgaagac cctgaggtca agttcaactg gtacgtggac     840
ggcgtggagg tgcataatgc caagacaaag ccgcgggagg agcagtacaa cagcacgtac     900
cgtgtggtca gcgtcctcac cgtcctgcac caggactggc tgaatggcaa ggagtacaag     960
tgcaaggtct ccaacaaagc cctcccagcc cccatcgaga aaaccatctc caaagccaaa    1020
ggcagccccg agaaccacag gtgtacaccc tgcccccat cccgggagga gatgaccaag    1080
aaccaggtca gcctgacctg cctggtcaaa ggcttctatc ccagcgacat cgccgtggag    1140
tgggagagca atgggcagcc ggagaacaac tacaagacca cgcctcccgt gctggactcc    1200
```

```
gacggctcct tcttcctcta cagcaagctc accgtggaca agagcaggtg gcagcagggg    1260
aacgtcttct catgctccgt gatgcatgag gctctgcaca accactacac gcagaagagc    1320
ctctccctgt ctccgggtaa atgactcgag                                     1350
```

<210> SEQ ID NO 48
<211> LENGTH: 1350
<212> TYPE: DNA
<213> ORGANISM: Artificial Sequence
<220> FEATURE:
<223> OTHER INFORMATION: Synthetic nucleotide sequence of H3-heavy

<400> SEQUENCE: 48

```
gaggtgcagc tggtggagtc tgggggaggc ttggtccagc ctggagggtc cctgagactc     60
tcctgtgcag cctctggatt caccttcact gactactaca tgagctgggt ccgccaggct    120
ccagggaagg ggctggagtg gttgggcttt attagaaaca agctaacgg ttacaccaca     180 gaatacagtg cgtctgtgaa aggcagattc accatctcaa gagataattc aaagaactca    240
ctgtatctgc aaatgaacag cctgcgtgct gaggacacgg ccgtgtatta ctgtgctaga    300
gataactggt tgcttactg gggtcaagga accctggtca ccgtctcctc ggctagcacc     360
aagggcccat cggtcttccc cctggcaccc tcctccaaga gcacctctgg gggcacagcg    420
gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacccagac ctacatctgc    600
aacgtgaatc acaagcccag caacaccaag gtggacaaga agttgagcc caaatcttgt     660 gacaaaactc acacatgccc accgtgccca gcacctgaac tcctgggggg accgtcagtc    720
ttcctcttcc cccaaaaccc aaggacaccc tcatgatct cccggacccc tgaggtcaca     780
tgcgtggtgg tggacgtgag ccacgaagac cctgaggtca agttcaactg gtacgtggac    840
ggcgtggagg tgcataatgc caagacaaag ccgcgggagg agcagtacaa cagcacgtac    900
cgtgtggtca gcgtcctcac cgtcctgcac caggactggc tgaatggcaa ggagtacaag    960
tgcaaggtct ccaacaaagc cctcccagcc cccatcgaga aaaccatctc caaagccaaa   1020
gggcagcccc gagaaccaca ggtgtacacc ctgcccccat cccgggagga tgaccaag     1080 aaccaggtca gcctgacctg cctggtcaaa ggcttctatc ccagcgacat cgccgtggag   1140
tgggagagca atgggcagcc ggagaacaac tacaagacca cgcctcccgt gctggactcc   1200
gacggctcct tcttcctcta cagcaagctc accgtggaca gagcaggtg gcagcagggg   1260 aacgtcttct catgctccgt gatgcatgag gctctgcaca accactacac gcagaagagc   1320
ctctccctgt ctccgggtaa atgactcgag                                    1350
```

<210> SEQ ID NO 49
<211> LENGTH: 1350
<212> TYPE: DNA
<213> ORGANISM: Artificial Sequence
<220> FEATURE:
<223> OTHER INFORMATION: Synthetic nucleotide sequence of H4-heavy

<400> SEQUENCE: 49

```
gaggttcagc tggtggagtc tggcggtggc ctggtgcagc caggggggctc actccgtttg     60 tcctgtgcag cttctggctt caccttcact gattactaca tgagctgggt gcgtcaggcc    120
ccgggtaagg gcctggaatg gttgggtttt attagaaaca agctaatgg ttacacaaca    180
```

```
gagtacagtg catctgtgaa gggtcgtttc actataagca gagataattc caaaaacaca      240
ctgtacctgc agatgaacag cctgcgtgct gaggacactg ccgtctatta ttgtgctaga      300
gataactggt ttgcttactg gggccaaggg actctggtca ccgtctcctc ggctagcacc      360
aagggcccat cggtcttccc cctggcaccc tcctccaaga gcacctctgg gggcacagcg      420
gccctgggct gcctggtcaa ggactacttc cccgaaccgg tgacggtgtc gtggaactca      480
ggcgccctga ccagcggcgt gcacaccttc ccggctgtcc tacagtcctc aggactctac      540
tccctcagca gcgtggtgac cgtgccctcc agcagcttgg gcacccagac ctacatctgc      600
aacgtgaatc acaagcccag caacaccaag gtggacaaga agttgagcc caaatcttgt       660
gacaaaactc acacatgccc accgtgccca gcacctgaac tcctgggggg accgtcagtc      720
ttcctcttcc ccccaaaacc caaggacacc ctcatgatct cccggacccc tgaggtcaca      780
tgcgtggtgg tggacgtgag ccacgaagac cctgaggtca agttcaactg gtacgtggac      840
ggcgtggagg tgcataatgc caagacaaag ccgcgggagg agcagtacaa cagcacgtac      900
cgtgtggtca gcgtcctcac cgtcctgcac caggactggc tgaatggcaa ggagtacaag      960
tgcaaggtct ccaacaaagc cctcccagcc cccatcgaga aaaccatctc caaagccaaa     1020
gggcagcccc gagaaccaca ggtgtacacc ctgcccccat cccgggagga gatgaccaag     1080
aaccaggtca gcctgacctg cctggtcaaa ggcttctatc ccagcgacat cgccgtggag     1140
tgggagagca atgggcagcc ggagaacaac tacaagacca cgcctcccgt gctggactcc     1200
gacggctcct tcttcctcta cagcaagctc accgtggaca gagcaggtg gcagcagggg      1260
aacgtcttct catgctccgt gatgcatgag gctctgcaca accactacac gcagaagagc     1320
ctctccctgt ctccgggtaa atgactcgag                                       1350
```

<210> SEQ ID NO 50
<211> LENGTH: 669
<212> TYPE: DNA
<213> ORGANISM: Artificial Sequence
<220> FEATURE:
<223> OTHER INFORMATION: Synthetic nucleotide sequence of H1-light

<400> SEQUENCE: 50

```
gacatcgtga tgacccagtc tccagactcc ctggctgtgt ctctgggcga gagggccacc       60
atcaactgca gtccagcca gagtctttta gctagcggca accaaaataa ctacttagct       120
tggcaccagc agaaaccagg acagcctcct aagatgctca tttatttggc atctacccgg      180
gtatccgggg tccctgaccg attcagtggc agcgggtctg ggacagattt cactctcacc      240
atcagcagcc tgcaggctga agatgtggca gtttattact gtcagcaatc ctatagtgct      300
cctctcacgt tcggaggcgg taccaaggtg gagatcaaac gtacggtggc tgcaccatct      360
gtcttcatct tcccgccatc tgatgagcag ttgaaatctg gaactgcctc tgttgtgtgc     420
ctgctgaata acttctatcc cagagaggcc aaagtacagt ggaaggtgga taacgccctc      480
caatcgggta actcccagga gagtgtcaca gagcaggaca gcaaggacag cacctacagc      540
ctcagcagca ccctgacgct gagcaaagca gactacgaga aacacaaagt ctacgcctgc      600
gaagtcaccc atcagggcct gagctcgccc gtcacaaaga gcttcaacag gggagagtgt     660
tgactcgag                                                              669
```

<210> SEQ ID NO 51
<211> LENGTH: 669
<212> TYPE: DNA
<213> ORGANISM: Artificial Sequence
<220> FEATURE:
<223> OTHER INFORMATION: Synthetic nucleotide sequence of H2-light

<400> SEQUENCE: 51

| | |
|---|---:|
| gatattgtga tgacccagac tccactctcc ctgcccgtca cccctggaga gccggcctcc | 60 |
| atctcctgca agtccagtca gagtcttta gctagtggac caaaataa ctacttggcc | 120 |
| tggcacctgc agaagccagg gcagtctcca cagatgctga tcatttgggc atccactagg | 180 |
| gtatctggag tcccagacag gttcagtggc agtgggtcag gcactgattt cacactgaaa | 240 |
| atcagcaggg tggaggctga ggatgttgga gtttattact gccagcagtc ctacagcgct | 300 |
| ccgctcacgt tcggacaggg taccaagctg gagctcaaac gtacggtggc tgcaccatct | 360 |
| gtcttcatct tcccgccatc tgatgagcag ttgaaatctg gaactgcctc tgttgtgtgc | 420 |
| ctgctgaata acttctatcc cagagaggcc aaagtacagt ggaaggtgga taacgccctc | 480 |
| caatcgggta actcccagga gagtgtcaca gagcaggaca gcaaggacag cacctacagc | 540 |
| ctcagcagca ccctgacgct gagcaaagca gactacgaga aacacaaagt ctacgcctgc | 600 |
| gaagtcaccc atcagggcct gagctcgccc gtcacaaaga gcttcaacag gggagagtgt | 660 |
| tgactcgag | 669 |

<210> SEQ ID NO 52
<211> LENGTH: 669
<212> TYPE: DNA
<213> ORGANISM: Artificial Sequence
<220> FEATURE:
<223> OTHER INFORMATION: Synthetic nucleotide sequence of H3-light

<400> SEQUENCE: 52

| | |
|---|---:|
| gacatcgtga tgacccagtc tccagactcc ctggctgtgt ctctgggcga gagggccacc | 60 |
| atcaactgca agtccagcca gagtctttta gctagcggca ccaaaataa ctacttagct | 120 |
| tggtaccagc agaaaccagg acagcctcct aagctgctca tttatttggc atctacccgg | 180 |
| gtatccgggg tccctgaccg attcagtggc agcgggtctg ggacagattt cactctcacc | 240 |
| atcagcagcc tgcaggctga agatgtggca gtttattact gtcagcaatc ctatagtgct | 300 |
| cctctcacgt tcggaggcgg taccaaggtg gagatcaaac gtacggtggc tgcaccatct | 360 |
| gtcttcatct tcccgccatc tgatgagcag ttgaaatctg gaactgcctc tgttgtgtgc | 420 |
| ctgctgaata acttctatcc cagagaggcc aaagtacagt ggaaggtgga taacgccctc | 480 |
| caatcgggta actcccagga gagtgtcaca gagcaggaca gcaaggacag cacctacagc | 540 |
| ctcagcagca ccctgacgct gagcaaagca gactacgaga aacacaaagt ctacgcctgc | 600 |
| gaagtcaccc atcagggcct gagctcgccc gtcacaaaga gcttcaacag gggagagtgt | 660 |
| tgactcgag | 669 |

<210> SEQ ID NO 53
<211> LENGTH: 669
<212> TYPE: DNA
<213> ORGANISM: Artificial Sequence
<220> FEATURE:
<223> OTHER INFORMATION: Synthetic nucleotide sequence of H4-light

<400> SEQUENCE: 53

| | |
|---|---:|
| gatatccaga tgacccagtc cccgagctcc ctgtccgcct ctgtgggcga tagggtcacc | 60 |
| atcacctgca agtccagtca gagtctttta gctagtggac caaaataa ctacttggcc | 120 |
| tggcaccaac agaaaccagg aaaagctccg aaaatgctga ttatttgggc atccactagg | 180 |

```
gtatctggag tcccttctcg cttctctgga tccgggtctg ggacggattt cactctgacc    240
atcagcagtc tgcagccgga agacttcgca acttattact gtcagcagtc ctacagcgct    300
ccgctcacgt tcggacaggg taccaaggtg gagatcaaac gtacggtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga acacaaagt ctacgcctgc     600 gaagtcaccc atcagggcct gagctcgccc gtcacaaaga gcttcaacag gggagagtgt    660
tgactcgag                                                             669
```

<210> SEQ ID NO 54
<211> LENGTH: 23
<212> TYPE: PRT
<213> ORGANISM: Artificial Sequence
<220> FEATURE:
<223> OTHER INFORMATION: Synthetic linker between VH and VL

<400> SEQUENCE: 54

Gly Leu Gly Gly Leu Gly Gly Gly Ser Gly Gly Gly Gly Ser Gly
1               5                   10                  15

Gly Ser Ser Gly Val Gly Ser
            20

<210> SEQ ID NO 55
<211> LENGTH: 1088
<212> TYPE: DNA
<213> ORGANISM: Artificial Sequence
<220> FEATURE:
<223> OTHER INFORMATION: Synthetic polynucleotide encoding scFv of
      huAbF46 antibody

<400> SEQUENCE: 55

```
gctagcgttt tagcagaagt tcaattggtt gaatctggtg gtggtttggt tcaaccaggt     60
ggttctttga gattgtcttg tgctgcttct ggttttactt tcaccgatta ttacatgtcc    120
tgggttagac aagctccagg taaaggtttg gaatggttgg gtttcattag aaacaaggct    180
aacggttaca ctaccgaata ttctgcttct gttaagggta gattcaccat ttctagagac    240
aactctaaga cacccttgta cttgcaaatg aactccttga gagctgaaga tactgctgtt    300
tattactgcg ctagagataa ttggtttgct tattggggtc aaggtacttt ggttactgtt    360
tcttctggcc tcggggggcct cggaggagga ggtagtggcg gaggaggctc cggtggatcc    420
agcggtgtgg gttccgatat tcaaatgacc caatctccat cttctttgtc tgcttcagtt    480
ggtgatagag ttaccattac ttgtaagtcc tcccaatctt tgttggcttc tggtaatcag    540
aacaattact ggcttggca tcaacaaaaa ccaggtaaag ctccaaagat gttgattatt    600
tgggcttcta ccagagtttc tggtgttcca tctagatttt ctggttctgg ttccggtact    660
gattttactt tgaccatttc atccttgcaa ccagaagatt cgctactta ctactgtcaa    720 caatcttact ctgctccatt gacttttggt caagtacaa aggtcgaaat caagagagaa    780
ttcggtaagc ctatccctaa ccctctcctc ggtctcgatt ctacgggtgg tgtggatct    840 ggtggtggtg gttctggtgg tggtggttct caggaactga caactatatg cgagcaaatc    900
ccctcaccaa cttagaatc gacgccgtac tctttgtcaa cgactactat ttggccaac    960 gggaaggcaa tgcaaggagt ttttgaatat tacaaatcag taacgtttgt cagtaattgc   1020
```

```
ggttctcacc cctcaacaac tagcaaaggc agccccataa acacacagta tgttttttga    1080
gtttaaac                                                             1088
```

<210> SEQ ID NO 56
<211> LENGTH: 5597
<212> TYPE: DNA
<213> ORGANISM: Artificial Sequence
<220> FEATURE:
<223> OTHER INFORMATION: Synthetic expression vector including
      polynucleotide encoding scFv of huAbF46 antibody
<220> FEATURE:
<221> NAME/KEY: misc_difference
<222> LOCATION: (573)..(578)
<223> OTHER INFORMATION: NheI restriction site
<220> FEATURE:
<221> NAME/KEY: misc_difference
<222> LOCATION: (588)..(938)
<223> OTHER INFORMATION: huAbF46 VH
<220> FEATURE:
<221> NAME/KEY: misc_difference
<222> LOCATION: (939)..(1007)
<223> OTHER INFORMATION: linker
<220> FEATURE:
<221> NAME/KEY: misc_difference
<222> LOCATION: (1008)..(1349)
<223> OTHER INFORMATION: huAbF46 VL
<220> FEATURE:
<221> NAME/KEY: misc_difference
<222> LOCATION: (1350)..(1355)
<223> OTHER INFORMATION: EcoRI restriction site
<220> FEATURE:
<221> NAME/KEY: misc_difference
<222> LOCATION: (1356)..(1397)
<223> OTHER INFORMATION: V5 epitope
<220> FEATURE:
<221> NAME/KEY: misc_difference
<222> LOCATION: (1398)..(1442)
<223> OTHER INFORMATION: (G4S)3 linker
<220> FEATURE:
<221> NAME/KEY: misc_difference
<222> LOCATION: (1443)..(1649)
<223> OTHER INFORMATION: Aga2
<220> FEATURE:
<221> NAME/KEY: misc_difference
<222> LOCATION: (1650)..(1652)
<223> OTHER INFORMATION: TGA(stop codon)
<220> FEATURE:
<221> NAME/KEY: misc_difference
<222> LOCATION: (1653)..(1660)
<223> OTHER INFORMATION: PmeI restriction site

<400> SEQUENCE: 56

```
acggattaga agccgccgag cgggtgacag ccctccgaag gaagactctc ctccgtgcgt     60
cctcgtcttc accggtcgcg ttcctgaaac gcagatgtgc ctcgcgccgc actgctccga    120
acaataaaga ttctacaata ctagctttta tggttatgaa gaggaaaaat tggcagtaac    180
ctggccccac aaaccttcaa atgaacgaat caaattaaca accataggat gataatgcga    240
ttagtttttt agccttattt ctggggtaat taatcagcga agcgatgatt tttgatctat    300
taacagatat ataaatgcaa aaactgcata accactttaa ctaatacttt caacattttc    360
ggtttgtatt acttcttatt caaatgtaat aaaagtatca acaaaaaatt gttaatatac    420
ctctatactt taacgtcaag gagaaaaaac cccggatcgg actactagca gctgtaatac    480
gactcactat agggaatatt aagctaattc tacttcatac attttcaatt aagatgcagt    540
tacttcgctg ttttttcaata ttttctgtta ttgctagcgt tttagcagaa gttcaattgg    600
ttgaatctgg tggtggtttg gttcaaccag gtggttcttt gagattgtct tgtgctgctt    660
ctggttttac tttcaccgat tattacatgt cctgggttag acaagctcca ggtaaaggtt    720
```

```
tggaatggtt gggtttcatt agaaacaagg ctaacggtta cactaccgaa tattctgctt    780
ctgttaaggg tagattcacc atttctagag acaactctaa gaacaccttg tacttgcaaa    840
tgaactcctt gagagctgaa gatactgctg tttattactg cgctagagat aattggtttg    900
cttattgggg tcaaggtact ttggttactg tttcttctgg cctcggggc ctcggaggag     960 gaggtagtgg cggaggaggc tccggtggat ccagcggtgt gggttccgat attcaaatga   1020
cccaatctcc atcttctttg tctgcttcag ttggtgatag agttaccatt acttgtaagt   1080
cctcccaatc tttgttggct tctggtaatc agaacaatta cttggcttgg catcaacaaa   1140
aaccaggtaa agctccaaag atgttgatta tttgggcttc taccagagtt tctggtgttc   1200
catctagatt ttctggttct ggttccgta ctgatttttac tttgaccatt tcatccttgc    1260
aaccagaaga tttcgctact tactactgtc aacaatctta ctctgctcca ttgacttttg   1320
gtcaaggtac aaaggtcgaa atcaagagag aattcggtaa gcctatccct aaccctctcc   1380
tcggtctcga ttctacgggt ggtggtggat ctggtggtgg tggttctggt ggtggtggtt   1440
ctcaggaact gacaactata tgcgagcaaa tcccctcacc aactttagaa tcgacgccgt   1500
actctttgtc aacgactact attttggcca acgggaaggc aatgcaagga gttttgaat    1560 attacaaatc agtaacgttt gtcagtaatt gcggttctca cccctcaaca actagcaaag   1620
gcagccccat aaacacacag tatgtttttt gagtttaaac ccgctgatct gataacaaca   1680
gtgtagatgt aacaaaatcg actttgttcc cactgtactt ttagctcgta caaaatacaa   1740 tatactttc atttctccgt aaacaacatg ttttcccatg taatatcctt ttctattttt     1800
cgttccgtta ccaactttac acatacttta tatagctatt cacttctata cactaaaaaa   1860
ctaagacaat tttaatttg ctgcctgcca tatttcaatt tgttataaat tcctataatt     1920
tatcctatta gtagctaaaa aaagatgaat gtgaatcgaa tcctaagaga attgggcaag   1980
tgcacaaaca atacttaaat aaatactact cagtaataac ctatttctta gcattttga    2040 cgaaatttgc tattttgtta gagtctttta caccatttgt ctccacacct ccgcttacat   2100
caacaccaat aacgccattt aatctaagcg catcaccaac attttctggc gtcagtccac   2160
cagctaacat aaaatgtaag ctctcggggc tctcttgcct tccaacccag tcagaaatcg   2220
agttccaatc caaaagttca cctgtcccac ctgcttctga atcaaacaag ggaataaacg   2280
aatgaggttt ctgtgaagct gcactgagta gtatgttgca gtcttttgga aatacgagtc   2340
ttttaataac tggcaaaccg aggaactctt ggtattcttg ccacgactca tctccgtgca   2400
gttggacgat atcaatgccg taatcattga ccagagccaa aacatcctcc ttaggttgat   2460
tacgaaacac gccaaccaag tatttcggag tgcctgaact attttatat gcttttacaa    2520 gacttgaaat tttccttgca ataaccgggt caattgttct ctttctattg ggcacacata   2580
taatacccag caagtcagca tcggaatcta gagcacattc tgcggcctct gtgctctgca   2640
agccgcaaac tttcaccaat ggaccagaac tacctgtgaa attaataaca gacatactcc   2700
aagctgcctt tgtgtgctta atcacgtata ctcacgtgct caatagtcac caatgccctc   2760
cctcttggcc ctctccttt cttttttcga ccgaatttct tgaagacgaa agggcctcgt    2820
gatacgccta ttttttatagg ttaatgtcat gataataatg gtttcttagg acggatcgct  2880
tgcctgtaac ttacacgcgc ctcgtatctt ttaatgatgg aataatttgg gaatttactc   2940 tgtgttatt tattttatg ttttgtattt ggatttagga agtaaataa agaaggtaga      3000 agagttacgg aatgaagaaa aaaaaataaa caaaggttta aaaaatttca acaaaaagcg   3060
tactttacat atatatttat tagacaagaa aagcagatta aatagatata cattcgatta   3120
```

```
acgataagta aaatgtaaaa tcacaggatt ttcgtgtgtg gtcttctaca cagacaagat    3180
gaaacaattc ggcattaata cctgagagca ggaagagcaa gataaaaggt agtatttgtt    3240
ggcgatcccc ctagagtctt ttacatcttc ggaaaacaaa aactattttt tctttaattt    3300 cttttttac tttctatttt taatttatat atttatatta aaaaatttaa attataatta    3360
tttttatagc acgtgatgaa aaggacccag gtggcacttt tcggggaaat gtgcgcggaa    3420
cccctatttg tttattttc taaatacatt caaatatgta tccgctcatg agacaataac    3480
cctgataaat gcttcaataa tattgaaaaa ggaagagtat gagtattcaa catttccgtg    3540
tcgcccttat tcccttttt gcggcatttt gccttcctgt ttttgctcac ccagaaacgc    3600
tggtgaaagt aaaagatgct gaagatcagt tgggtgcacg agtgggttac atcgaactgg    3660
atctcaacag cggtaagatc cttgagagtt ttcgccccga agaacgtttt ccaatgatga    3720
gcacttttaa agttctgcta tgtggcgcgg tattatcccg tgttgacgcc gggcaagagc    3780
aactcggtcg ccgcatacac tattctcaga atgacttggt tgagtactca ccagtcacag    3840
aaaagcatct tacggatggc atgacagtaa gagaattatg cagtgctgcc ataaccatga    3900
gtgataacac tgcggccaac ttacttctga caacgatcgg aggaccgaag gagctaaccg    3960
cttttttgca caacatgggg gatcatgtaa ctcgccttga tcgttgggaa ccggagctga    4020
atgaagccat accaaacgac gagcgtgaca ccacgatgcc tgtagcaatg gcaacaacgt    4080
tgcgcaaact attaactggc gaactactta ctctagcttc ccggcaacaa ttaatagact    4140
ggatggaggc ggataaagtt gcaggaccac ttctgcgctc ggcccttccg gctggctggt    4200
ttattgctga taaatctgga gccggtgagc gtgggtctcg cggtatcatt gcagcactgg    4260
ggccagatgg taagccctcc cgtatcgtag ttatctacac gacgggcagt caggcaacta    4320
tggatgaacg aaatagacag atcgctgaga taggtgcctc actgattaag cattggtaac    4380
tgtcagacca agtttactca tatatacttt agattgattt aaaacttcat ttttaattta    4440
aaaggatcta ggtgaagatc ctttttgata atctcatgac caaaatccct aacgtgagt    4500 tttcgttcca ctgagcgtca gaccccgtag aaaagatcaa aggatcttct tgagatcctt    4560
tttttctgcg cgtaatctgc tgcttgcaaa caaaaaaacc accgctacca gcggtggttt    4620
gtttgccgga tcaagagcta ccaactcttt ttccgaaggt aactggcttc agcagagcgc    4680
agataccaaa tactgtcctt ctagtgtagc cgtagttagg ccaccacttc aagaactctg    4740
tagcaccgcc tacatacctc gctctgctaa tcctgttacc agtggctgct gccagtggcg    4800
ataagtcgtg tcttaccggg ttggactcaa gacgatagtt accggataag gcgcagcggt    4860
cgggctgaac ggggggttcg tgcacacagc ccagcttgga gcgaacgacc tacaccgaac    4920
tgagatacct acagcgtgag cattgagaaa gcgccacgct tcccgaaggg agaaaggcgg    4980
acaggtatcc ggtaagcggc agggtcggaa caggagagcg cacgagggag cttccagggg    5040 gaacgcctg gtatctttat agtcctgtcg ggtttcgcca cctctgactt gagcgtcgat    5100
ttttgtgatg ctcgtcaggg gggcgagcc tatggaaaaa cgccagcaac gcggcctttt    5160
tacggttcct ggccttttgc tggccttttg ctcacatgtt ctttcctgcg ttatcccctg    5220
attctgtgga taaccgtatt accgcctttg agtgagctga taccgctcgc cgcagccgaa    5280
cgaccgagcg cagcgagtca gtgagcgagg aagcggaaga gcgcccaata cgcaaaccgc    5340
ctctccccgc gcgttggccg attcattaat gcagctggca cgacaggttt cccgactgga    5400
aagcgggcag tgagcgcaac gcaattaatg tgagttacct cactcattag gcaccccagg    5460
```

```
ctttacactt tatgcttccg gctcctatgt tgtgtggaat tgtgagcgga taacaatttc     5520
acacaggaaa cagctatgac catgattacg ccaagctcgg aattaaccct cactaaaggg     5580
aacaaaagct ggctagt                                                   5597

<210> SEQ ID NO 57
<211> LENGTH: 13
<212> TYPE: PRT
<213> ORGANISM: Artificial Sequence
<220> FEATURE:
<223> OTHER INFORMATION: Synthetic U6-HC7 hinge

<400> SEQUENCE: 57

Glu Pro Lys Ser Cys Asp Cys His Cys Pro Pro Cys Pro
1               5                   10

<210> SEQ ID NO 58
<211> LENGTH: 435
<212> TYPE: DNA
<213> ORGANISM: Artificial Sequence
<220> FEATURE:
<223> OTHER INFORMATION: Synthetic polynucleotide encoding CDR-L3
      derived from L3-1 clone

<400> SEQUENCE: 58
gaattcacta gtgattaatt cgccgccacc atggattcac aggcccaggt cctcatgttg      60
ctgctgctat cggtatctgg tacctgtgga gatatccaga tgacccagtc cccgagctcc     120
ctgtccgcct ctgtgggcga tagggtcacc atcacctgca agtccagtca gagtctttta     180
gctagtggca accaaaataa ctacttggcc tggcaccaac agaaaccagg aaaagctccg     240
aaaatgctga ttatttgggc atccactagg gtatctggag tcccttctcg cttctctgga     300
tccgggtctg ggacggattt cactctgacc atcagcagtc tgcagccgga agacttcgca     360
acttattact gtcagcagtc ctacagccgc ccgtacacgt tcggacaggg taccaaggtg     420
gagatcaaac gtacg                                                     435

<210> SEQ ID NO 59
<211> LENGTH: 435
<212> TYPE: DNA
<213> ORGANISM: Artificial Sequence
<220> FEATURE:
<223> OTHER INFORMATION: Synthetic polynucleotide encoding CDR-L3
      derived from L3-2 clone

<400> SEQUENCE: 59
gaattcacta gtgattaatt cgccgccacc atggattcac aggcccaggt cctcatgttg      60
ctgctgctat cggtatctgg tacctgtgga gatatccaga tgacccagtc cccgagctcc     120
ctgtccgcct ctgtgggcga tagggtcacc atcacctgca agtccagtca gagtctttta     180
gctagtggca accaaaataa ctacttggcc tggcaccaac agaaaccagg aaaagctccg     240
aaaatgctga ttatttgggc atccactagg gtatctggag tcccttctcg cttctctgga     300
tccgggtctg ggacggattt cactctgacc atcagcagtc tgcagccgga agacttcgca     360
acttattact gtgggcagtc ctacagccgt ccgctcacgt tcggacaggg taccaaggtg     420
gagatcaaac gtacg                                                     435

<210> SEQ ID NO 60
<211> LENGTH: 435
<212> TYPE: DNA
<213> ORGANISM: Artificial Sequence
<220> FEATURE:
```

-continued

<223> OTHER INFORMATION: Synthetic polynucleotide encoding CDR-L3
      derived from L3-3 clone

<400> SEQUENCE: 60

```
gaattcacta gtgattaatt cgccgccacc atggattcac aggcccaggt cctcatgttg      60
ctgctgctat cggtatctgg tacctgtgga gatatccaga tgacccagtc cccgagctcc     120
ctgtccgcct ctgtgggcga tagggtcacc atcacctgca agtccagtca gagtctttta     180
gctagtggca accaaaataa ctacttggcc tggcaccaac agaaaccagg aaaagctccg     240
aaaatgctga ttatttgggc atccactagg gtatctggag tcccttctcg cttctctgga     300
tccgggtctg ggacggattt cactctgacc atcagcagtc tgcagccgga agacttcgca     360
acttattact gtgcacagtc ctacagccat ccgttctctt tcggacaggg taccaaggtg     420
gagatcaaac gtacg                                                     435
```

<210> SEQ ID NO 61
<211> LENGTH: 435
<212> TYPE: DNA
<213> ORGANISM: Artificial Sequence
<220> FEATURE:
<223> OTHER INFORMATION: Synthetic polynucleotide encoding CDR-L3
      derived from L3-5 clone

<400> SEQUENCE: 61

```
gaattcacta gtgattaatt cgccgccacc atggattcac aggcccaggt cctcatgttg      60
ctgctgctat cggtatctgg tacctgtgga gatatccaga tgacccagtc cccgagctcc     120
ctgtccgcct ctgtgggcga tagggtcacc atcacctgca agtccagtca gagtctttta     180
gctagtggca accaaaataa ctacttggcc tggcaccaac agaaaccagg aaaagctccg     240
aaaatgctga ttatttgggc atccactagg gtatctggag tcccttctcg cttctctgga     300
tccgggtctg ggacggattt cactctgacc atcagcagtc tgcagccgga agacttcgca     360
acttattact gtcagcagtc ctacagccgc ccgtttacgt tcggacaggg taccaaggtg     420
gagatcaaac gtacg                                                     435
```

<210> SEQ ID NO 62
<211> LENGTH: 462
<212> TYPE: PRT
<213> ORGANISM: Artificial Sequence
<220> FEATURE:
<223> OTHER INFORMATION: Synthetic polypeptide consisting of heavy chain
      of huAbF46-H4-A1, U6-HC7 hinge and constant region of
      human IgG1

<400> SEQUENCE: 62

```
Met Glu Trp Ser Trp Val Phe Leu Val Thr Leu Leu Asn Gly Ile Gln
1               5                   10                  15

Cys Glu Val Gln Leu Val Glu Ser Gly Gly Gly Leu Val Gln Pro Gly
            20                  25                  30

Gly Ser Leu Arg Leu Ser Cys Ala Ala Ser Gly Phe Thr Phe Thr Asp
        35                  40                  45

Tyr Tyr Met Ser Trp Val Arg Gln Ala Pro Gly Lys Gly Leu Glu Trp
    50                  55                  60

Leu Gly Phe Ile Arg Asn Lys Ala Asn Gly Tyr Thr Thr Glu Tyr Ser
65                  70                  75                  80

Ala Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
```

```
                100             105             110
Tyr Tyr Cys Ala Arg Asp Asn Trp Phe Ala Tyr Trp Gly Gln Gly Thr
            115             120             125
Leu Val Thr Val Ser Ser Ala Ser Thr Lys Gly Pro Ser Val Phe Pro
        130             135             140
Leu Ala Pro Ser Ser Lys Ser Thr Ser Gly Gly Thr Ala Ala Leu Gly
145             150             155             160
Cys Leu Val Lys Asp Tyr Phe Pro Glu Pro Val Thr Val Ser Trp Asn
                165             170             175
Ser Gly Ala Leu Thr Ser Gly Val His Thr Phe Pro Ala Val Leu Gln
            180             185             190
Ser Ser Gly Leu Tyr Ser Leu Ser Ser Val Val Thr Val Pro Ser Ser
        195             200             205
Ser Leu Gly Thr Gln Thr Tyr Ile Cys Asn Val Asn His Lys Pro Ser
    210             215             220
Asn Thr Lys Val Asp Lys Lys Val Glu Pro Lys Ser Cys Asp Cys His
225             230             235             240
Cys Pro Pro Cys Pro Ala Pro Glu Leu Leu Gly Gly Pro Ser Val Phe
                245             250             255
Leu Phe Pro Pro Lys Pro Lys Asp Thr Leu Met Ile Ser Arg Thr Pro
            260             265             270
Glu Val Thr Cys Val Val Val Asp Val Ser His Glu Asp Pro Glu Val
        275             280             285
Lys Phe Asn Trp Tyr Val Asp Gly Val Glu Val His Asn Ala Lys Thr
    290             295             300
Lys Pro Arg Glu Glu Gln Tyr Asn Ser Thr Tyr Arg Val Val Ser Val
305             310             315             320
Leu Thr Val Leu His Gln Asp Trp Leu Asn Gly Lys Glu Tyr Lys Cys
                325             330             335
Lys Val Ser Asn Lys Ala Leu Pro Ala Pro Ile Glu Lys Thr Ile Ser
            340             345             350
Lys Ala Lys Gly Gln Pro Arg Glu Pro Gln Val Tyr Thr Leu Pro Pro
        355             360             365
Ser Arg Glu Glu Met Thr Lys Asn Gln Val Ser Leu Thr Cys Leu Val
    370             375             380
Lys Gly Phe Tyr Pro Ser Asp Ile Ala Val Glu Trp Glu Ser Asn Gly
385             390             395             400
Gln Pro Glu Asn Asn Tyr Lys Thr Thr Pro Pro Val Leu Asp Ser Asp
                405             410             415
Gly Ser Phe Phe Leu Tyr Ser Lys Leu Thr Val Asp Lys Ser Arg Trp
            420             425             430
Gln Gln Gly Asn Val Phe Ser Cys Ser Val Met His Glu Ala Leu His
        435             440             445
Asn His Tyr Thr Gln Lys Ser Leu Ser Leu Ser Pro Gly Lys
    450             455             460

<210> SEQ ID NO 63
<211> LENGTH: 1410
<212> TYPE: DNA
<213> ORGANISM: Artificial Sequence
<220> FEATURE:
<223> OTHER INFORMATION: Synthetic polynucleotide encoding polypeptide
      consisting of heavy chain of huAbF46-H4-A1, U6-HC7 hinge and
      constant region of human IgG1

<400> SEQUENCE: 63
```

```
gaattcgccg ccaccatgga atggagctgg gttttctcg taacactttt aaatggtatc      60
cagtgtgagg ttcagctggt ggagtctggc ggtggcctgg tgcagccagg ggctcactc     120
cgtttgtcct gtgcagcttc tggcttcacc ttcactgatt actacatgag ctgggtgcgt    180
caggccccgg gtaagggcct ggaatggttg gttttatta gaaacaaagc taatggttac     240
acaacagagt acagtgcatc tgtgaagggt cgtttcacta taagcagaga taattccaaa    300
aacacactgt acctgcagat gaacagcctg cgtgctgagg acactgccgt ctattattgt    360
gctagagata actggtttgc ttactggggc caagggactc tggtcaccgt ctcctcggct    420
agcaccaagg gcccatcggt cttccccctg gcaccctcct ccaagagcac ctctgggggc    480
acagcggccc tgggctgcct ggtcaaggac tacttccccg aaccggtgac ggtgtcgtgg    540
aactcaggcg ccctgaccag cggcgtgcac accttcccgg ctgtcctaca gtcctcagga    600
ctctactccc tcagcagcgt ggtgaccgtg ccctccagca gcttgggcac ccagacctac    660
atctgcaacg tgaatcacaa gcccagcaac accaaggtgg acaagaaagt tgagcccaaa    720
agctgcgatt gccactgtcc tccatgtcca gcacctgaac tcctgggggg accgtcagtc    780
ttcctcttcc ccccaaaacc caaggacacc ctcatgatct cccggacccc tgaggtcaca    840
tgcgtggtgg tggacgtgag ccacgaagac cctgaggtca agttcaactg gtacgtggac    900
ggcgtggagg tgcataatgc caagacaaag ccgcggagg agcagtacaa cagcacgtac    960
cgtgtggtca gcgtcctcac cgtcctgcac caggactggc tgaatggcaa ggagtacaag   1020
tgcaaggtct ccaacaaagc cctcccagcc cccatcgaga aaaccatctc caaagccaaa   1080
gggcagcccc gagaaccaca ggtgtacacc ctgcccccat cccgggagga gatgaccaag   1140
aaccaggtca gcctgacctg cctggtcaaa ggcttctatc ccagcgacat cgccgtggag   1200
tgggagagca atgggcagcc ggagaacaac tacaagacca cgcctcccgt gctggactcc   1260
gacggctcct tcttcctcta cagcaagctc accgtggaca agagcaggtg gcagcagggg   1320
aacgtcttct catgctccgt gatgcatgag gctctgcaca accactacac gcagaagagc   1380
ctctccctgt ctccgggtaa atgactcgag                                    1410
```

<210> SEQ ID NO 64
<211> LENGTH: 461
<212> TYPE: PRT
<213> ORGANISM: Artificial Sequence
<220> FEATURE:
<223> OTHER INFORMATION: Synthetic polypeptide consisting of heavy chain
of huAbF46-H4-A1, human IgG2 hinge and constant region of
human IgG1

<400> SEQUENCE: 64

```
Met Glu Trp Ser Trp Val Phe Leu Val Thr Leu Leu Asn Gly Ile Gln
1               5                   10                  15

Cys Glu Val Gln Leu Val Glu Ser Gly Gly Gly Leu Val Gln Pro Gly
            20                  25                  30

Gly Ser Leu Arg Leu Ser Cys Ala Ala Ser Gly Phe Thr Phe Thr Asp
        35                  40                  45

Tyr Tyr Met Ser Trp Val Arg Gln Ala Pro Gly Lys Gly Leu Glu Trp
    50                  55                  60

Leu Gly Phe Ile Arg Asn Lys Ala Asn Gly Tyr Thr Thr Glu Tyr Ser
65                  70                  75                  80

Ala Ser Val Lys Gly Arg Phe Thr Ile Ser Arg Asp Asn Ser Lys Asn
                85                  90                  95
```

```
Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Arg Lys Cys Cys Val Glu Cys
225                 230                 235                 240

Pro Pro Cys Pro Ala Pro Glu Leu Leu Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Lys
        275                 280                 285

Phe Asn Trp Tyr Val Asp Gly Val Glu Val His Asn Ala Lys Thr Lys
    290                 295                 300

Pro Arg Glu Glu Gln Tyr Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Ala Leu Pro Ala Pro Ile Glu Lys Thr Ile Ser Lys
            340                 345                 350

Ala Lys Gly Gln Pro Arg Glu Pro Gln Val Tyr Thr Leu Pro Pro Ser
        355                 360                 365

Arg Glu Glu Met Thr Lys Asn Gln Val Ser Leu Thr Cys Leu Val Lys
    370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Tyr Ser Lys Leu Thr Val Asp Lys Ser Arg Trp Gln
            420                 425                 430

Gln Gly Asn Val Phe Ser Cys Ser Val Met His Glu Ala Leu His Asn
        435                 440                 445

His Tyr Thr Gln Lys Ser Leu Ser Leu Ser Pro Gly Lys
    450                 455                 460

<210> SEQ ID NO 65
<211> LENGTH: 1407
<212> TYPE: DNA
<213> ORGANISM: Artificial Sequence
<220> FEATURE:
<223> OTHER INFORMATION: Synthetic polynucleotide encoding polypeptide
      consisting of heavy chain of huAbF46-H4-A1, human IgG2 hinge and
      constant region of human IgG1
```

<400> SEQUENCE: 65

```
gaattcgccg ccaccatgga atggagctgg gttttctcg taacactttt aaatggtatc       60
cagtgtgagg ttcagctggt ggagtctggc ggtggcctgg tgcagccagg gggctcactc      120
cgtttgtcct gtgcagcttc tggcttcacc ttcactgatt actacatgag ctgggtgcgt      180
caggccccgg gtaagggcct ggaatggttg ggttttatta gaaacaaagc taatggttac      240
acaacagagt acagtgcatc tgtgaagggt cgtttcacta agcagaga taattccaaa        300
aacacactgt acctgcagat gaacagcctg cgtgctgagg acactgccgt ctattattgt      360
gctagagata actggtttgc ttactggggc caagggactc tggtcaccgt ctcctcggct      420
agcaccaagg gcccatcggt cttccccctg gcaccctcct ccaagagcac ctctgggggc      480
acagcggccc tgggctgcct ggtcaaggac tacttccccg aaccggtgac ggtgtcgtgg      540
aactcaggcg ccctgaccag cggcgtgcac accttcccgg ctgtcctaca gtcctcagga      600
ctctactccc tcagcagcgt ggtgaccgtg ccctccagca gcttgggcac ccagacctac      660
atctgcaacg tgaatcacaa gcccagcaac accaaggtgg acaagaaagt tgagaggaag     720
tgctgtgtgg agtgccccc ctgcccagca cctgaactcc tgggggggacc gtcagtcttc      780
ctcttccccc caaaacccaa ggacaccctc atgatctccc ggacccctga ggtcacatgc     840
gtggtggtgg acgtgagcca cgaagaccct gaggtcaagt tcaactggta cgtggacggc      900
gtggaggtgc ataatgccaa gacaaagccg cgggaggagc agtacaacag cacgtaccgt      960
gtggtcagcg tcctcaccgt cctgcaccag gactggctga atggcaagga gtacaagtgc     1020
aaggtctcca acaaagccct cccagccccc atcgagaaaa ccatctccaa agccaaaggg     1080
cagccccgag aaccacaggt gtacaccctg cccccatccc gggaggagat gaccaagaac     1140
caggtcagcc tgacctgcct ggtcaaaggc ttctatccca gcgacatcgc cgtggagtgg     1200
gagagcaatg ggcagccgga gaacaactac aagaccacgc ctcccgtgct ggactccgac     1260
ggctccttct tcctctacag caagctcacc gtggacaaga gcaggtggca gcaggggaac     1320
gtcttctcat gctccgtgat gcatgaggct ctgcacaacc actacacgca gaagagcctc     1380
tccctgtctc cgggtaaatg actcgag                                         1407
```

<210> SEQ ID NO 66
<211> LENGTH: 460
<212> TYPE: PRT
<213> ORGANISM: Artificial Sequence
<220> FEATURE:
<223> OTHER INFORMATION: Synthetic polypeptide consisting of heavy chain of huAbF46-H4-A1, human IgG2 hinge and constant region of human IgG2

<400> SEQUENCE: 66

```
Met Glu Trp Ser Trp Val Phe Leu Val Thr Leu Leu Asn Gly Ile Gln
1               5                   10                  15

Cys Glu Val Gln Leu Val Glu Ser Gly Gly Gly Leu Val Gln Pro Gly
            20                  25                  30

Gly Ser Leu Arg Leu Ser Cys Ala Ala Ser Gly Phe Thr Phe Thr Asp
        35                  40                  45

Tyr Tyr Met Ser Trp Val Arg Gln Ala Pro Gly Lys Gly Leu Glu Trp
    50                  55                  60

Leu Gly Phe Ile Arg Asn Lys Ala Asn Gly Tyr Thr Thr Glu Tyr Ser
65                  70                  75                  80

Ala Ser Val Lys Gly Arg Phe Thr Ile Ser Arg Asp Asn Ser Lys Asn
                85                  90                  95
```

```
Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
            115                 120                 125

Leu Val Thr Val Ser Ser Ala Ser Thr Lys Gly Pro Ser Val Phe Pro
130                 135                 140

Leu Ala Pro Cys Ser Arg Ser Thr Ser Glu Ser Thr Ala Ala Leu Gly
145                 150                 155                 160

Cys Leu Val Lys Asp Tyr Phe Pro Glu Pro Val Thr Val Ser Trp Asn
            165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
            195                 200                 205

Asn Phe Gly Thr Gln Thr Tyr Thr Cys Asn Val Asp His Lys Pro Ser
            210                 215                 220

Asn Thr Lys Val Asp Lys Thr Val Glu Arg Lys Cys Cys Val Glu Cys
225                 230                 235                 240

Pro Pro Cys Pro Ala Pro Pro Val Ala Gly Pro Ser Val Phe Leu Phe
            245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Gln Phe
            275                 280                 285

Asn Trp Tyr Val Asp Gly Val Glu Val His Asn Ala Lys Thr Lys Pro
            290                 295                 300

Arg Glu Glu Gln Phe Asn Ser Thr Phe Arg Val Val Ser Val Leu Thr
305                 310                 315                 320

Val Val His Gln Asp Trp Leu Asn Gly Lys Glu Tyr Lys Cys Lys Val
            325                 330                 335

Ser Asn Lys Gly Leu Pro Ala Pro Ile Glu Lys Thr Ile Ser Lys Thr
            340                 345                 350

Lys Gly Gln Pro Arg Glu Pro Gln Val Tyr Thr Leu Pro Pro Ser Arg
            355                 360                 365

Glu Glu Met Thr Lys Asn Gln Val Ser Leu Thr Cys Leu Val Lys Gly
            370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Met Leu Asp Ser Asp Gly Ser
            405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
            435                 440                 445

Tyr Thr Gln Lys Ser Leu Ser Leu Ser Pro Gly Lys
            450                 455                 460

<210> SEQ ID NO 67
<211> LENGTH: 1404
<212> TYPE: DNA
<213> ORGANISM: Artificial Sequence
<220> FEATURE:
<223> OTHER INFORMATION: Synthetic polynucleotide encoding polypeptide
      consisting of heavy chain of huAbF46-H4-A1, human IgG2 hinge and
      constant region of human IgG2
```

<400> SEQUENCE: 67

```
gaattcgccg ccaccatgga atggagctgg gttttctctg taacactttt aaatggtatc      60
cagtgtgagg ttcagctggt ggagtctggc ggtggcctgg tgcagccagg gggctcactc     120
cgtttgtcct gtgcagcttc tggcttcacc ttcactgatt actacatgag ctgggtgcgt     180
caggccccgg gtaagggcct ggaatggttg ggttttatta aaacaaagc taatggttac      240
acaacagagt acagtgcatc tgtgaagggt cgtttcacta aagcagaga taattccaaa      300
aacacactgt acctgcagat gaacagcctg cgtgctgagg acactgccgt ctattattgt     360
gctagagata actggtttgc ttactgggc aagggactc tggtcaccgt ctcctcggct      420
agcaccaagg gcccatcggt cttccccctg gcgccctgct ccaggagcac ctccgagagc     480
acagcggccc tgggctgcct ggtcaaggac tacttcccg aaccggtgac ggtgtcgtgg      540
aactcaggcg ctctgaccag cggcgtgcac accttccag ctgtcctaca gtcctcagga     600
ctctactccc tcagcagcgt ggtgaccgtg ccctccagca acttcggcac ccagacctac     660
acctgcaacg tagatcacaa gcccagcaac accaaggtgg acaagacagt tgagcgcaaa     720
tgttgtgtcg agtgcccacc gtgcccagca ccacctgtgg caggaccgtc agtcttcctc     780
ttccccccaa aacccaagga caccctcatg atctcccgga cccctgaggt cacgtgcgtg     840
gtggtggacg tgagccacga agaccccgag gtccagttca actggtacgt ggacggcgtg     900
gaggtgcata atgccaagac aaagccacgg gaggagcagt tcaacagcac gttccgtgtg     960
gtcagcgtcc tcaccgttgt gcaccaggac tggctgaacg gcaaggagta caagtgcaag    1020
gtctccaaca aaggcctccc agcccccatc gagaaaacca tctccaaaac caaagggcag    1080
ccccgagaac cacaggtgta caccctgccc ccatcccggg aggagatgac caagaaccag    1140
gtcagcctga cctgcctggt caaaggcttc taccccagcg acatcgccgt ggagtgggag    1200
agcaatgggc agccggagaa caactacaag accacgcctc ccatgctgga ctccgacggc    1260
tccttcttcc tctacagcaa gctcaccgtg gacaagagca ggtggcagca ggggaacgtc    1320
ttctcatgct ccgtgatgca tgaggctctg cacaaccact acacgcagaa gagcctctcc    1380
ctgtctccgg gtaaatgact cgag                                          1404
```

<210> SEQ ID NO 68
<211> LENGTH: 240
<212> TYPE: PRT
<213> ORGANISM: Artificial Sequence
<220> FEATURE:
<223> OTHER INFORMATION: Synthetic polypeptide consisting of light chain of huAbF46-H4-A1(H36Y) and human kappa constant region

<400> SEQUENCE: 68

```
Met Asp Ser Gln Ala Gln Val Leu Met Leu Leu Leu Leu Ser Val Ser
1               5                   10                  15

Gly Thr Cys Gly Asp Ile Gln Met Thr Gln Ser Pro Ser Ser Leu Ser
            20                  25                  30

Ala Ser Val Gly Asp Arg Val Thr Ile Thr Cys Lys Ser Ser Gln Ser
        35                  40                  45

Leu Leu Ala Ser Gly Asn Gln Asn Asn Tyr Leu Ala Trp Tyr Gln Gln
    50                  55                  60

Lys Pro Gly Lys Ala Pro Lys Met Leu Ile Ile Trp Ala Ser Thr Arg
65                  70                  75                  80

Val Ser Gly Val Pro Ser Arg Phe Ser Gly Ser Gly Ser Gly Thr Asp
                85                  90                  95
```

```
Phe Thr Leu Thr Ile Ser Ser Leu Gln Pro Glu Asp Phe Ala Thr Tyr
            100                 105                 110

Tyr Cys Gln Gln Ser Tyr Ser Arg Pro Tyr Thr Phe Gly Gln Gly Thr
        115                 120                 125

Lys Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240
```

<210> SEQ ID NO 69
<211> LENGTH: 758
<212> TYPE: DNA
<213> ORGANISM: Artificial Sequence
<220> FEATURE:
<223> OTHER INFORMATION: Synthetic polynucleotide encoding polypeptide consisting of light chain of huAbF46-H4-A1(H36Y) and human kappa constant region

<400> SEQUENCE: 69

```
aattcactag tgattaattc gccgccacca tggattcaca ggcccaggtc ctcatgttgc      60
tgctgctatc ggtatctggt acctgtggag atatccagat gacccagtcc ccgagctccc     120
tgtccgcctc tgtgggcgat agggtcacca tcacctgcaa gtccagtcag agtcttttag     180
ctagtggcaa ccaaaataac tacttggcct ggtaccaaca gaaaccagga aaagctccga     240
aaatgctgat tatttgggca tccactaggg tatctggagt cccttctcgc ttctctggat     300
ccgggtctgg gacggatttc actctgacca tcagcagtct gcagccggaa gacttcgcaa     360
cttattactg tcagcagtcc tacagccgcc cgtacacgtt cggacagggt accaaggtgg     420
agatcaaacg tacggtggct gcaccatctg tcttcatctt cccgccatct gatgagcagt     480
tgaaatctgg aactgcctct gttgtgtgcc tgctgaataa cttctatccc agagaggcca     540
aagtacagtg gaaggtggat aacgccctcc aatcgggtaa ctcccaggag agtgtcacag     600
agcaggacag caaggacagc acctacagcc tcagcagcac cctgacgctg agcaaagcag     660
actacgagaa acacaaagtc tacgcctgcg aagtcaccca tcagggcctg agctcgcccg     720
tcacaaagag cttcaacagg ggagagtgtt gactcgag                            758
```

<210> SEQ ID NO 70
<211> LENGTH: 240
<212> TYPE: PRT
<213> ORGANISM: Artificial Sequence
<220> FEATURE:
<223> OTHER INFORMATION: Synthetic polypeptide consisting of light chain of huAbF46-H4-A1 and human kappa constant region

<400> SEQUENCE: 70

```
Met Asp Ser Gln Ala Gln Val Leu Met Leu Leu Leu Leu Ser Val Ser
1               5                   10                  15
```

```
Gly Thr Cys Gly Asp Ile Gln Met Thr Gln Ser Pro Ser Ser Leu Ser
                20                  25                  30

Ala Ser Val Gly Asp Arg Val Thr Ile Thr Cys Lys Ser Ser Gln Ser
        35                  40                  45

Leu Leu Ala Ser Gly Asn Gln Asn Asn Tyr Leu Ala Trp His Gln Gln
50                  55                  60

Lys Pro Gly Lys Ala Pro Lys Met Leu Ile Ile Trp Ala Ser Thr Arg
65                  70                  75                  80

Val Ser Gly Val Pro Ser Arg Phe Ser Gly Ser Gly Ser Gly Thr Asp
                85                  90                  95

Phe Thr Leu Thr Ile Ser Ser Leu Gln Pro Glu Asp Phe Ala Thr Tyr
            100                 105                 110

Tyr Cys Gln Gln Ser Tyr Ser Arg Pro Tyr Thr Phe Gly Gln Gly Thr
        115                 120                 125

Lys Val Glu Ile Lys Arg Thr Val Ala Ala Pro Ser Val Phe Ile Phe
130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
210                 215                 220

Gln Gly Leu Ser Ser Pro Val Thr Lys Ser Phe Asn Arg Gly Glu Cys
225                 230                 235                 240

<210> SEQ ID NO 71
<211> LENGTH: 19
<212> TYPE: PRT
<213> ORGANISM: Artificial Sequence
<220> FEATURE:
<223> OTHER INFORMATION: Synthetic epitope in SEMA domain of c-Met

<400> SEQUENCE: 71

Phe Ser Pro Gln Ile Glu Glu Pro Ser Gln Cys Pro Asp Cys Val Val
1               5                   10                  15

Ser Ala Leu

<210> SEQ ID NO 72
<211> LENGTH: 10
<212> TYPE: PRT
<213> ORGANISM: Artificial Sequence
<220> FEATURE:
<223> OTHER INFORMATION: Synthetic epitope in SEMA domain of c-Met

<400> SEQUENCE: 72

Pro Gln Ile Glu Glu Pro Ser Gln Cys Pro
1               5                   10

<210> SEQ ID NO 73
<211> LENGTH: 5
<212> TYPE: PRT
<213> ORGANISM: Artificial Sequence
<220> FEATURE:
<223> OTHER INFORMATION: Synthetic epitope in SEMA domain of c-Met
```

<400> SEQUENCE: 73

Glu Glu Pro Ser Gln
1               5

<210> SEQ ID NO 74
<211> LENGTH: 117
<212> TYPE: PRT
<213> ORGANISM: Artificial Sequence
<220> FEATURE:
<223> OTHER INFORMATION: Synthetic heavy chain variable region of anti-
      c-Met antibody (AbF46 or huAbF46-H1)

<400> SEQUENCE: 74

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 75
<211> LENGTH: 114
<212> TYPE: PRT
<213> ORGANISM: Artificial Sequence
<220> FEATURE:
<223> OTHER INFORMATION: Synthetic light chain variable region of anti-
      c-Met antibody (AbF46 or huAbF46-H1)

<400> SEQUENCE: 75

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp His Gln Gln Lys Pro Gly Gln
        35                  40                  45

Pro Pro Lys Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gly Gly Thr Lys Val Glu Ile
            100                 105                 110

Lys Arg

<210> SEQ ID NO 76
<211> LENGTH: 1416
<212> TYPE: DNA
<213> ORGANISM: Artificial Sequence

```
<220> FEATURE:
<223> OTHER INFORMATION: Synthetic nucleotide sequence of heavy chain of
      anti-c-Met antibody (AbF46 or huAbF46-H1)
<220> FEATURE:
<221> NAME/KEY: misc_feature
<222> LOCATION: (1)..(6)
<223> OTHER INFORMATION: EcoRI restriction site
<220> FEATURE:
<221> NAME/KEY: misc_feature
<222> LOCATION: (7)..(66)
<223> OTHER INFORMATION: signal sequence
<220> FEATURE:
<221> NAME/KEY: misc_feature
<222> LOCATION: (67)..(417)
<223> OTHER INFORMATION: VH - heavy chain variable region
<220> FEATURE:
<221> NAME/KEY: misc_feature
<222> LOCATION: (418)..(423)
<223> OTHER INFORMATION: NdeI restriction site
<220> FEATURE:
<221> NAME/KEY: misc_feature
<222> LOCATION: (418)..(1407)
<223> OTHER INFORMATION: CH - heavy chain constant region
<220> FEATURE:
<221> NAME/KEY: misc_feature
<222> LOCATION: (1408)..(1410)
<223> OTHER INFORMATION: TGA - stop codon
<220> FEATURE:
<221> NAME/KEY: misc_feature
<222> LOCATION: (1411)..(1416)
<223> OTHER INFORMATION: XhoI restriction site

<400> SEQUENCE: 76
gaattcgccg ccaccatgga atggagctgg gttttctcg taacactttt aaatggtatc      60
cagtgtgagg tgaagctggt ggagtctgga ggaggcttgg tacagcctgg gggttctctg     120
agactctcct gtgcaacttc tgggttcacc ttcactgatt actacatgag ctgggtccgc     180
cagcctccag gaaaggcact tgagtggttg ggttttatta gaaacaaagc taatggttac     240
acaacagagt acagtgcatc tgtgaagggt cggttcacca tctccagaga taattcccaa     300
agcatcctct atcttcaaat ggacaccctg agagctgagg acagtgccac ttattactgt     360
gcaagagata actggtttgc ttactggggc caagggactc tggtcactgt ctctgcagct     420
agcaccaagg gcccatcggt cttcccctg gcaccctcct ccaagagcac ctctgggggc     480
acagcggccc tgggctgcct ggtcaaggac tacttccccg aaccggtgac ggtgtcgtgg     540
aactcaggcg ccctgaccag cggcgtgcac accttcccgg ctgtcctaca gtcctcagga     600
ctctactccc tcagcagcgt ggtgaccgtg ccctccagca gcttgggcac ccagacctac     660
atctgcaacg tgaatcacaa gcccagcaac accaaggtgg acaagaaagt tgagcccaaa     720
tcttgtgaca aaactcacac atgcccaccg tgcccagcac ctgaactcct ggggggaccg     780
tcagtcttcc tcttcccccc aaaacccaag gacaccctca tgatctcccg gacccctgag     840
gtcacatgcg tggtggtgga cgtgagccac gaagaccctg aggtcaagtt caactggtac     900
gtggacggcg tggaggtgca taatgccaag acaaagccgc gggaggagca gtacaacagc     960
acgtaccgtg tggtcagcgt cctcaccgtc ctgcaccagg actggctgaa tggcaaggag    1020
tacaagtgca aggtctccaa caaagccctc ccagccccca tcgagaaaac catctccaaa    1080
gccaaagggc agccccgaga accacaggtg tacaccctgc ccccatcccg ggaggagatg    1140
accaagaacc aggtcagcct gacctgcctg gtcaaaggct tctatcccag cgacatcgcc    1200
gtggagtggg agagcaatgg gcagccggag aacaactaca agaccacgcc tcccgtgctg    1260
gactccgacg gctccttctt cctctacagc aagctcaccg tggacaagag caggtggcag    1320
caggggaacg tcttctcatg ctccgtgatg catgaggctc tgcacaacca ctacacgcag    1380
```
aagagcctct ccctgtctcc gggtaaatga ctcgag                                    1416

<210> SEQ ID NO 77
<211> LENGTH: 759
<212> TYPE: DNA
<213> ORGANISM: Artificial Sequence
<220> FEATURE:
<223> OTHER INFORMATION: Synthetic nucleotide sequence of light chain of
      anti-c-Met antibody (AbF46 or huAbF46-H1)
<220> FEATURE:
<221> NAME/KEY: misc_difference
<222> LOCATION: (1)..(6)
<223> OTHER INFORMATION: EcoRI restriction site
<220> FEATURE:
<221> NAME/KEY: misc_difference
<222> LOCATION: (7)..(90)
<223> OTHER INFORMATION: signal sequence
<220> FEATURE:
<221> NAME/KEY: misc_difference
<222> LOCATION: (91)..(432)
<223> OTHER INFORMATION: VL - light chain variable region
<220> FEATURE:
<221> NAME/KEY: misc_difference
<222> LOCATION: (430)..(435)
<223> OTHER INFORMATION: BsiWI restriction site
<220> FEATURE:
<221> NAME/KEY: misc_difference
<222> LOCATION: (433)..(750)
<223> OTHER INFORMATION: CL - light chain constant region
<220> FEATURE:
<221> NAME/KEY: misc_difference
<222> LOCATION: (751)..(753)
<223> OTHER INFORMATION: stop codon
<220> FEATURE:
<221> NAME/KEY: misc_difference
<222> LOCATION: (754)..(759)
<223> OTHER INFORMATION: XhoI restriction site

<400> SEQUENCE: 77
gaattcacta gtgattaatt cgccgccacc atggattcac aggcccaggt cctcatgttg     60
ctgctgctat cggtatctgg tacctgtgga gacattttga tgacccagtc tccatcctcc    120
ctgactgtgt cagcaggaga aaggtcact atgagctgca agtccagtca gagtcttttta    180 gctagtggca accaaaataa ctacttggcc tggcaccagc agaaaccagg acgatctcct    240
aaaatgctga taatttgggc atccactagg gtatctggag tccctgatcg cttcataggc    300
agtggatctg ggacggattt cactctgacc atcaacagtg tgcaggctga agatctggct    360
gtttattact gtcagcagtc ctacagcgct ccgctcacgt tcggtgctgg gaccaagctg    420
gagctgaaac gtacggtggc tgcaccatct gtcttcatct tcccgccatc tgatgagcag    480
ttgaaatctg gaactgcctc tgttgtgtgc ctgctgaata acttctatcc cagagaggcc    540
aaagtacagt ggaaggtgga taacgccctc caatcgggta actcccagga gagtgtcaca    600
gagcaggaca gcaaggacag cacctacagc ctcagcagca ccctgacgct gagcaaagca    660
gactacgaga aacacaaagt ctacgcctgc gaagtcaccc atcagggcct gagctcgccc    720
gtcacaaaga gcttcaacag gggagagtgt tgactcgag                           759

<210> SEQ ID NO 78
<211> LENGTH: 4170
<212> TYPE: DNA
<213> ORGANISM: Artificial Sequence
<220> FEATURE:
<223> OTHER INFORMATION: Synthetic polynucleotide encoding c-Met protein

<400> SEQUENCE: 78
atgaaggccc ccgctgtgct tgcacctggc atcctcgtgc tcctgtttac cttggtgcag    60

```
aggagcaatg gggagtgtaa agaggcacta gcaaagtccg agatgaatgt gaatatgaag     120
tatcagcttc ccaacttcac cgcggaaaca cccatccaga atgtcattct acatgagcat     180
cacattttcc ttggtgccac taactacatt tatgttttaa atgaggaaga ccttcagaag     240
gttgctgagt acaagactgg gcctgtgctg aacacccag attgtttccc atgtcaggac      300
tgcagcagca aagccaattt atcaggaggt gtttggaaag ataacatcaa catggctcta     360
gttgtcgaca cctactatga tgatcaactc attagctgtg gcagcgtcaa cagagggacc     420
tgccagcgac atgtctttcc ccacaatcat actgctgaca tacagtcgga ggttcactgc     480
atattctccc cacagataga agagcccagc cagtgtcctg actgtgtggt gagcgccctg     540
ggagccaaag tcctttcatc tgtaaaggac cggttcatca acttctttgt aggcaatacc     600
ataaattctt cttatttccc agatcatcca ttgcattcga tatcagtgag aaggctaaag     660
gaaacgaaag atggttttat gttttgacg gaccagtcct acattgatgt tttacctgag      720
ttcagagatt cttaccccat taagtatgtc catgcctttg aaagcaacaa ttttatttac     780
ttcttgacgg tccaaaggga aactctagat gctcagactt tcacacaag aataatcagg      840 ttctgttcca taaactctgg attgcattcc tacatggaaa tgcctctgga gtgtattctc     900
acagaaaaga gaaaaagag atccacaaag aaggaagtgt ttaatatact tcaggctgcg      960
tatgtcagca gcctggggc ccagcttgct agacaaatag gagccagcct gaatgatgac     1020
attcttttcg gggtgttcgc acaaagcaag ccagattctg ccgaaccaat ggatcgatct    1080
gccatgtgtg cattccctat caaatatgtc aacgacttct tcaacaagat cgtcaacaaa    1140
aacaatgtga gatgtctcca gcattttac ggacccaatc atgagcactg ctttaatagg     1200
acacttctga gaaattcatc aggctgtgaa gcgcgccgtg atgaatatcg aacagagttt    1260
accacagctt tgcagcgcgt tgacttattc atgggtcaat tcagcgaagt cctcttaaca    1320
tctatatcca ccttcattaa aggagacctc accatagcta atcttgggac atcagagggt    1380
cgcttcatgc aggttgtggt ttctcgatca ggaccatcaa cccctcatgt gaattttctc    1440
ctggactccc atccagtgtc tccagaagtg attgtggagc atacattaaa ccaaaatggc    1500
tacacactgg ttatcactgg gaagaagatc acgaagatcc cattgaatgg cttgggctgc    1560
agacatttcc agtcctgcag tcaatgcctc tctgccccac cctttgttca gtgtggctgg    1620
tgccacgaca aatgtgtgcg atcggaggaa tgcctgagcg gacatggac tcaacagatc      1680 tgtctgcctg caatctacaa ggttttccca aatagtgcac cccttgaagg agggacaagg    1740
ctgaccatat gtggctggga ctttggattt cggaggaata taaatttga tttaaagaaa      1800 actagagttc tccttggaaa tgagagctgc accttgactt taagtgagag cacgatgaat    1860
acattgaaat gcagttggg tcctgccatg aataagcatt tcaatatgtc cataattatt     1920
tcaaatggcc acgggacaac acaatacagt acattctcct atgtggatcc tgtaataaca    1980
agtatttcgc cgaaatacgg tcctatggct ggtggcacta cttactttt aactggaaat    2040 tacctaaaca gtgggaattc tagacacatt tcaattggtg gaaaaacatg tactttaaaa    2100
agtgtgtcaa acagtattct tgaatgttat accccagccc aaaccatttc aactgagttt    2160
gctgttaaat tgaaaattga cttagccaac cgagagacaa gcatcttcag ttaccgtgaa    2220
gatcccattg tctatgaaat tcatccaacc aaatctttta ttagtggtgg gagcacaata    2280
acaggtgttg ggaaaaacct gaattcagtt agtgtcccga aatggtcat aaatgtgcat     2340 gaagcaggaa ggaactttac agtggcatgt caacatcgct ctaattcaga gataatctgt    2400
```

| | |
|---|---|
| tgtaccactc cttccctgca acagctgaat ctgcaactcc ccctgaaaac caaagccttt | 2460 |
| ttcatgttag atgggatcct ttccaaatac tttgatctca tttatgtaca taatcctgtg | 2520 |
| tttaagcctt ttgaaaagcc agtgatgatc tcaatgggca atgaaaatgt actggaaatt | 2580 |
| aagggaaatg atattgaccc tgaagcagtt aaaggtgaag tgttaaaagt tggaaataag | 2640 |
| agctgtgaga atatacactt acattctgaa gccgttttat gcacggtccc caatgacctg | 2700 |
| ctgaaattga acagcgagct aaatatagag tggaagcaag caatttcttc aaccgtcctt | 2760 |
| ggaaaagtaa tagttcaacc agatcagaat ttcacaggat tgattgctgg tgttgtctca | 2820 |
| atatcaacag cactgttatt actacttggg ttttcctgt ggctgaaaaa gagaaagcaa | 2880 |
| attaaagatc tgggcagtga attagttcgc tacgatgcaa gagtacacac tcctcatttg | 2940 |
| gataggcttg taagtgcccg aagtgtaagc ccaactacag aaatggtttc aaatgaatct | 3000 |
| gtagactacc gagctacttt tccagaagat cagtttccta attcatctca gaacggttca | 3060 |
| tgccgacaag tgcagtatcc tctgacagac atgtccccca tcctaactag tgggactct | 3120 |
| gatatatcca gtccattact gcaaaatact gtccacattg acctcagtgc tctaaatcca | 3180 |
| gagctggtcc aggcagtgca gcatgtagtg attgggccca gtagcctgat tgtgcatttc | 3240 |
| aatgaagtca taggaagagg gcatttggt tgtgtatatc atgggacttt gttggacaat | 3300 |
| gatggcaaga aaattcactg tgctgtgaaa tccttgaaca gaatcactga cataggagaa | 3360 |
| gtttcccaat ttctgaccga gggaatcatc atgaaagatt ttagtcatcc caatgtcctc | 3420 |
| tcgctcctgg aatctgcct gcgaagtgaa gggtctccgc tggtggtcct accatacatg | 3480 |
| aaacatggag atcttcgaaa tttcattcga atgagagactc ataatccaac tgtaaaagat | 3540 |
| cttattggct ttggtcttca agtagccaaa ggcatgaaat atcttgcaag caaaaagttt | 3600 |
| gtccacagag acttggctgc aagaaactgt atgctggatg aaaaattcac agtcaaggtt | 3660 |
| gctgattttg gtcttgccag agacatgtat gataaagaat actatagtgt acacaacaaa | 3720 |
| acaggtgcaa agctgccagt gaagtggatg gctttggaaa gtctgcaaac tcaaaagttt | 3780 |
| accaccaagt cagatgtgtg gtcctttggc gtgctcctct gggagctgat gacaagagga | 3840 |
| gccccacctt atcctgacgt aaacaccttt gatataactg tttacttgtt gcaagggaga | 3900 |
| agactcctac aacccgaata ctgcccagac cccttatatg aagtaatgct aaaatgctgg | 3960 |
| caccctaaag ccgaaatgcg cccatccttt tctgaactgg tgtcccggat atcagcgatc | 4020 |
| ttctctactt tcattgggga gcactatgtc catgtgaacg ctacttatgt gaacgtaaaa | 4080 |
| tgtgtcgctc cgtatccttc tctgttgtca tcagaagata acgctgatga tgaggtggac | 4140 |
| acacgaccag cctccttctg ggagacatca | 4170 |

<210> SEQ ID NO 79
<211> LENGTH: 444
<212> TYPE: PRT
<213> ORGANISM: Artificial Sequence
<220> FEATURE:
<223> OTHER INFORMATION: Synthetic SEMA domain of c-Met

<400> SEQUENCE: 79

Leu His Glu His His Ile Phe Leu Gly Ala Thr Asn Tyr Ile Tyr Val
1               5                   10                  15

Leu Asn Glu Glu Asp Leu Gln Lys Val Ala Glu Tyr Lys Thr Gly Pro
            20                  25                  30

Val Leu Glu His Pro Asp Cys Phe Pro Cys Gln Asp Cys Ser Ser Lys
        35                  40                  45

Ala Asn Leu Ser Gly Gly Val Trp Lys Asp Asn Ile Asn Met Ala Leu
 50                  55                  60

Val Val Asp Thr Tyr Tyr Asp Asp Gln Leu Ile Ser Cys Gly Ser Val
 65                  70                  75                  80

Asn Arg Gly Thr Cys Gln Arg His Val Phe Pro His Asn His Thr Ala
                 85                  90                  95

Asp Ile Gln Ser Glu Val His Cys Ile Phe Ser Pro Gln Ile Glu Glu
            100                 105                 110

Pro Ser Gln Cys Pro Asp Cys Val Ser Ala Leu Gly Ala Lys Val
        115                 120                 125

Leu Ser Ser Val Lys Asp Arg Phe Ile Asn Phe Val Gly Asn Thr
130                 135                 140

Ile Asn Ser Ser Tyr Phe Pro Asp His Pro Leu His Ser Ile Ser Val
145                 150                 155                 160

Arg Arg Leu Lys Glu Thr Lys Asp Gly Phe Met Phe Leu Thr Asp Gln
                165                 170                 175

Ser Tyr Ile Asp Val Leu Pro Glu Phe Arg Asp Ser Tyr Pro Ile Lys
            180                 185                 190

Tyr Val His Ala Phe Glu Ser Asn Asn Phe Ile Tyr Phe Leu Thr Val
        195                 200                 205

Gln Arg Glu Thr Leu Asp Ala Gln Thr Phe His Thr Arg Ile Ile Arg
210                 215                 220

Phe Cys Ser Ile Asn Ser Gly Leu His Ser Tyr Met Glu Met Pro Leu
225                 230                 235                 240

Glu Cys Ile Leu Thr Glu Lys Arg Lys Arg Ser Thr Lys Lys Glu
                245                 250                 255

Val Phe Asn Ile Leu Gln Ala Ala Tyr Val Ser Lys Pro Gly Ala Gln
            260                 265                 270

Leu Ala Arg Gln Ile Gly Ala Ser Leu Asn Asp Asp Ile Leu Phe Gly
        275                 280                 285

Val Phe Ala Gln Ser Lys Pro Asp Ser Ala Glu Pro Met Asp Arg Ser
290                 295                 300

Ala Met Cys Ala Phe Pro Ile Lys Tyr Val Asn Asp Phe Phe Asn Lys
305                 310                 315                 320

Ile Val Asn Lys Asn Asn Val Arg Cys Leu Gln His Phe Tyr Gly Pro
                325                 330                 335

Asn His Glu His Cys Phe Asn Arg Thr Leu Leu Arg Asn Ser Ser Gly
            340                 345                 350

Cys Glu Ala Arg Arg Asp Glu Tyr Arg Thr Glu Phe Thr Thr Ala Leu
        355                 360                 365

Gln Arg Val Asp Leu Phe Met Gly Gln Phe Ser Glu Val Leu Leu Thr
370                 375                 380

Ser Ile Ser Thr Phe Ile Lys Gly Asp Leu Thr Ile Ala Asn Leu Gly
385                 390                 395                 400

Thr Ser Glu Gly Arg Phe Met Gln Val Val Ser Arg Ser Gly Pro
                405                 410                 415

Ser Thr Pro His Val Asn Phe Leu Leu Asp Ser His Pro Val Ser Pro
            420                 425                 430

Glu Val Ile Val Glu His Thr Leu Asn Gln Asn Gly
        435                 440

<210> SEQ ID NO 80
<211> LENGTH: 451
<212> TYPE: PRT

<213> ORGANISM: Artificial Sequence
<220> FEATURE:
<223> OTHER INFORMATION: Synthetic PSI-IPT domain of c-Met

<400> SEQUENCE: 80

```
Tyr Thr Leu Val Ile Thr Gly Lys Lys Ile Thr Lys Ile Pro Leu Asn
1               5                   10                  15

Gly Leu Gly Cys Arg His Phe Gln Ser Cys Ser Gln Cys Leu Ser Ala
            20                  25                  30

Pro Pro Phe Val Gln Cys Gly Trp Cys His Asp Lys Cys Val Arg Ser
        35                  40                  45

Glu Glu Cys Leu Ser Gly Thr Trp Thr Gln Gln Ile Cys Leu Pro Ala
    50                  55                  60

Ile Tyr Lys Val Phe Pro Asn Ser Ala Pro Leu Glu Gly Gly Thr Arg
65                  70                  75                  80

Leu Thr Ile Cys Gly Trp Asp Phe Gly Phe Arg Arg Asn Asn Lys Phe
                85                  90                  95

Asp Leu Lys Lys Thr Arg Val Leu Leu Gly Asn Glu Ser Cys Thr Leu
            100                 105                 110

Thr Leu Ser Glu Ser Thr Met Asn Thr Leu Lys Cys Thr Val Gly Pro
        115                 120                 125

Ala Met Asn Lys His Phe Asn Met Ser Ile Ile Ile Ser Asn Gly His
    130                 135                 140

Gly Thr Thr Gln Tyr Ser Thr Phe Ser Tyr Val Asp Pro Val Ile Thr
145                 150                 155                 160

Ser Ile Ser Pro Lys Tyr Gly Pro Met Ala Gly Gly Thr Leu Leu Thr
                165                 170                 175

Leu Thr Gly Asn Tyr Leu Asn Ser Gly Asn Ser Arg His Ile Ser Ile
            180                 185                 190

Gly Gly Lys Thr Cys Thr Leu Lys Ser Val Ser Asn Ser Ile Leu Glu
        195                 200                 205

Cys Tyr Thr Pro Ala Gln Thr Ile Ser Thr Glu Phe Ala Val Lys Leu
    210                 215                 220

Lys Ile Asp Leu Ala Asn Arg Glu Thr Ser Ile Phe Ser Tyr Arg Glu
225                 230                 235                 240

Asp Pro Ile Val Tyr Glu Ile His Pro Thr Lys Ser Phe Ile Ser Thr
                245                 250                 255

Trp Trp Lys Glu Pro Leu Asn Ile Val Ser Phe Leu Phe Cys Phe Ala
            260                 265                 270

Ser Gly Gly Ser Thr Ile Thr Gly Val Gly Lys Asn Leu Asn Ser Val
        275                 280                 285

Ser Val Pro Arg Met Val Ile Asn Val His Glu Ala Gly Arg Asn Phe
    290                 295                 300

Thr Val Ala Cys Gln His Arg Ser Asn Ser Glu Ile Ile Cys Cys Thr
305                 310                 315                 320

Thr Pro Ser Leu Gln Gln Leu Asn Leu Gln Leu Pro Leu Lys Thr Lys
                325                 330                 335

Ala Phe Phe Met Leu Asp Gly Ile Leu Ser Lys Tyr Phe Asp Leu Ile
            340                 345                 350

Tyr Val His Asn Pro Val Phe Lys Pro Phe Glu Lys Pro Val Met Ile
        355                 360                 365

Ser Met Gly Asn Glu Asn Val Leu Glu Ile Lys Gly Asn Asp Ile Asp
    370                 375                 380

Pro Glu Ala Val Lys Gly Glu Val Leu Lys Val Gly Asn Lys Ser Cys
```

```
               385                 390                 395                 400
Glu Asn Ile His Leu His Ser Glu Ala Val Leu Cys Thr Val Pro Asn
                    405                 410                 415

Asp Leu Leu Lys Leu Asn Ser Glu Leu Asn Ile Glu Trp Lys Gln Ala
                420                 425                 430

Ile Ser Ser Thr Val Leu Gly Lys Val Ile Val Gln Pro Asp Gln Asn
            435                 440                 445

Phe Thr Gly
        450

<210> SEQ ID NO 81
<211> LENGTH: 313
<212> TYPE: PRT
<213> ORGANISM: Artificial Sequence
<220> FEATURE:
<223> OTHER INFORMATION: Synthetic TyrKc domain of c-Met

<400> SEQUENCE: 81

Val His Phe Asn Glu Val Ile Gly Arg Gly His Phe Gly Cys Val Tyr
1               5                   10                  15

His Gly Thr Leu Leu Asp Asn Asp Gly Lys Lys Ile His Cys Ala Val
            20                  25                  30

Lys Ser Leu Asn Arg Ile Thr Asp Ile Gly Glu Val Ser Gln Phe Leu
        35                  40                  45

Thr Glu Gly Ile Ile Met Lys Asp Phe Ser His Pro Asn Val Leu Ser
    50                  55                  60

Leu Leu Gly Ile Cys Leu Arg Ser Glu Gly Ser Pro Leu Val Val Leu
65                  70                  75                  80

Pro Tyr Met Lys His Gly Asp Leu Arg Asn Phe Ile Arg Asn Glu Thr
                85                  90                  95

His Asn Pro Thr Val Lys Asp Leu Ile Gly Phe Gly Leu Gln Val Ala
            100                 105                 110

Lys Gly Met Lys Tyr Leu Ala Ser Lys Lys Phe Val His Arg Asp Leu
        115                 120                 125

Ala Ala Arg Asn Cys Met Leu Asp Glu Lys Phe Thr Val Lys Val Ala
    130                 135                 140

Asp Phe Gly Leu Ala Arg Asp Met Tyr Asp Lys Glu Tyr Tyr Ser Val
145                 150                 155                 160

His Asn Lys Thr Gly Ala Lys Leu Pro Val Lys Trp Met Ala Leu Glu
                165                 170                 175

Ser Leu Gln Thr Gln Lys Phe Thr Thr Lys Ser Asp Val Trp Ser Phe
            180                 185                 190

Gly Val Leu Leu Trp Glu Leu Met Thr Arg Gly Ala Pro Pro Tyr Pro
        195                 200                 205

Asp Val Asn Thr Phe Asp Ile Thr Val Tyr Leu Leu Gln Gly Arg Arg
    210                 215                 220

Leu Leu Gln Pro Glu Tyr Cys Pro Asp Pro Leu Tyr Glu Val Met Leu
225                 230                 235                 240

Lys Cys Trp His Pro Lys Ala Glu Met Arg Pro Ser Phe Ser Glu Leu
                245                 250                 255

Val Ser Arg Ile Ser Ala Ile Phe Ser Thr Phe Ile Gly Glu His Tyr
            260                 265                 270

Val His Val Asn Ala Thr Tyr Val Asn Val Lys Cys Val Ala Pro Tyr
        275                 280                 285

Pro Ser Leu Leu Ser Ser Glu Asp Asn Ala Asp Asp Glu Val Asp Thr
```

```
              290                 295                 300
Arg Pro Ala Ser Phe Trp Glu Thr Ser
305                 310
```

<210> SEQ ID NO 82
<211> LENGTH: 1332
<212> TYPE: DNA
<213> ORGANISM: Artificial Sequence
<220> FEATURE:
<223> OTHER INFORMATION: Synthetic polynucleotide encoding SEMA domain
      of c-Met

<400> SEQUENCE: 82

| | | |
|---|---|---|
| ctacatgagc atcacatttt ccttggtgcc actaactaca tttatgtttt aaatgaggaa | 60 |
| gaccttcaga aggttgctga gtacaagact gggcctgtgc tggaacaccc agattgtttc | 120 |
| ccatgtcagg actgcagcag caaagccaat ttatcaggag gtgtttggaa agataacatc | 180 |
| aacatggctc tagttgtcga cacctactat gatgatcaac tcattagctg tggcagcgtc | 240 |
| aacagaggga cctgccagcg acatgtcttt ccccacaatc atactgctga catacagtcg | 300 |
| gaggttcact gcatattctc cccacagata gaagagccca gccagtgtcc tgactgtgtg | 360 |
| gtgagcgccc tgggagccaa agtccttttca tctgtaaagg accggttcat caacttcttt | 420 |
| gtaggcaata ccataaaattc ttcttatttc ccagatcatc cattgcattc gatatcagtg | 480 |
| agaaggctaa aggaaacgaa agatggtttt atgttttga cggaccagtc ctacattgat | 540 |
| gttttacctg agttcagaga ttcttacccc attaagtatg tccatgcctt tgaaagcaac | 600 |
| aatttttattt acttcttgac ggtccaaagg gaaactctag atgctcagac ttttcacaca | 660 |
| agaataatca ggttctgttc cataaactct ggattgcatt cctacatgga aatgcctctg | 720 |
| gagtgtattc tcacagaaaa gagaaaaaag agatccacaa gaaggaagt gtttaatata | 780 |
| cttcaggctg cgtatgtcag caagcctggg gcccagcttg ctagacaaat aggagccagc | 840 |
| ctgaatgatg acattctttt cggggtgttc gcacaaagca agccagattc tgccgaacca | 900 |
| atggatcgat ctgccatgtg tgcattccct atcaaatatg tcaacgactt cttcaacaag | 960 |
| atcgtcaaca aaaacaatgt gagatgtctc cagcatttt acggacccaa tcatgagcac | 1020 |
| tgctttaata ggacacttct gagaaattca tcaggctgtg aagcgcgccg tgatgaatat | 1080 |
| cgaacagagt ttaccacagc tttgcagcgc gttgacttat tcatgggtca attcagcgaa | 1140 |
| gtcctcttaa catctatatc caccttcatt aaaggagacc tcaccatagc taatcttggg | 1200 |
| acatcagagg tcgcttcat gcaggttgtg gtttctcgat caggaccatc aacccctcat | 1260 |
| gtgaattttc tcctggactc ccatccagtg tctccagaag tgattgtgga gcatacatta | 1320 |
| aaccaaaatg gc | 1332 |

<210> SEQ ID NO 83
<211> LENGTH: 1299
<212> TYPE: DNA
<213> ORGANISM: Artificial Sequence
<220> FEATURE:
<223> OTHER INFORMATION: Synthetic polynucleotide encoding PSI-IPT
      domain of c-Met

<400> SEQUENCE: 83

| | | |
|---|---|---|
| tacacactgg ttatcactgg gaagaagatc acgaagatcc cattgaatgg cttgggctgc | 60 |
| agacatttcc agtcctgcag tcaatgcctc tctgccccac cctttgttca gtgtggctgg | 120 |
| tgccacgaca aatgtgtgcg atcggaggaa tgcctgagcg ggacatggac tcaacagatc | 180 |

```
tgtctgcctg caatctacaa ggttttccca aatagtgcac cccttgaagg agggacaagg      240
ctgaccatat gtggctggga ctttggattt cggaggaata ataaatttga tttaaagaaa      300
actagagttc tccttggaaa tgagagctgc accttgactt taagtgagag cacgatgaat      360
acattgaaat gcacagttgg tcctgccatg aataagcatt tcaatatgtc cataattatt      420
tcaaatggcc acgggacaac acaatacagt acattctcct atgtggatcc tgtaataaca      480
agtatttcgc cgaaatacgg tcctatggct ggtggcactt tacttacttt aactggaaat      540
tacctaaaca gtgggaattc tagacacatt tcaattggtg gaaaaacatg tactttaaaa      600
agtgtgtcaa acagtattct tgaatgttat accccagccc aaaccatttc aactgagttt      660
gctgttaaat tgaaaattga cttagccaac cgagagacaa gcatcttcag ttaccgtgaa      720
gatcccattg tctatgaaat tcatccaacc aaatctttta ttagtggtgg gagcacaata      780
acaggtgttg ggaaaaacct gaattcagtt agtgtcccga gaatggtcat aaatgtgcat      840
gaagcaggaa ggaactttac agtggcatgt caacatcgct ctaattcaga gataatctgt      900
tgtaccactc cttccctgca acagctgaat ctgcaactcc ccctgaaaac caaagccttt      960
ttcatgttag atgggatcct ttccaaatac tttgatctca tttatgtaca taatcctgtg     1020
tttaagcctt tgaaaagcc agtgatgatc tcaatgggca atgaaaatgt actggaaatt     1080
aagggaaatg atattgaccc tgaagcagtt aaaggtgaag tgttaaaagt tggaaataag     1140
agctgtgaga atatacactt acattctgaa gccgttttat gcacggtccc caatgacctg     1200
ctgaaattga acagcgagct aaatatagag tggaagcaag caatttcttc aaccgtcctt     1260
ggaaaagtaa tagttcaacc agatcagaat ttcacagga                           1299
```

<210> SEQ ID NO 84
<211> LENGTH: 939
<212> TYPE: DNA
<213> ORGANISM: Artificial Sequence
<220> FEATURE:
<223> OTHER INFORMATION: Synthetic polynucleotide encoding TyrKc domain of c-Met

<400> SEQUENCE: 84

```
gtgcatttca atgaagtcat aggaagaggg cattttggtt gtgtatatca tgggactttg       60
ttggacaatg atggcaagaa aattcactgt gctgtgaaat ccttgaacag aatcactgac      120
ataggagaag tttcccaatt tctgaccgag ggaatcatca tgaaagattt tagtcatccc      180
aatgtcctct cgctcctggg aatctgcctg cgaagtgaag ggtctccgct ggtggtccta      240
ccatacatga acatggagag tcttcgaaat ttcattcgaa atgagactca taatccaact      300
gtaaaagatc ttattggctt tggtcttcaa gtagccaaag gcatgaaata tcttgcaagc      360
aaaaagtttg tccacagaga cttggctgca agaaactgta tgctggatga aaaattcaca      420
gtcaaggttg ctgattttgg tcttgccaga gacatgtatg ataaagaata ctatagtgta      480
cacaacaaaa caggtgcaaa gctgccagtg aagtggatgg ctttggaaag tctgcaaact      540
caaaagttta ccaccaagtc agatgtgtgg tcctttggcg tgctcctctg ggagctgatg      600
acaagaggag ccccacctta tcctgacgta aacacctttg atataactgt ttacttgttg      660
caagggagaa gactcctaca acccgaatac tgcccagacc ccttatatga agtaatgcta      720
aaatgctggc accctaaagc cgaaatgcgc ccatcctttt ctgaactggt gtcccggata      780
tcagcgatct tctctacttt cattggggag cactatgtcc atgtgaacgc tacttatgtg      840
aacgtaaaat gtgtcgctcc gtatccttct ctgttgtcat cagaagataa cgctgatgat      900
```
gaggtggaca cacgaccagc ctccttctgg gagacatca                    939

<210> SEQ ID NO 85
<211> LENGTH: 13
<212> TYPE: PRT
<213> ORGANISM: Artificial Sequence
<220> FEATURE:
<223> OTHER INFORMATION: Synthetic heavy chain CDR3 of anti-c-Met
      antibody

<400> SEQUENCE: 85

Asp Asn Trp Phe Ala Tyr Trp Gly Gln Gly Thr Leu Val
1               5                   10

<210> SEQ ID NO 86
<211> LENGTH: 10
<212> TYPE: PRT
<213> ORGANISM: Artificial Sequence
<220> FEATURE:
<223> OTHER INFORMATION: Synthetic light chain CDR3 of anti-c-Met
      antibody

<400> SEQUENCE: 86

Leu Thr Phe Gly Ala Gly Thr Lys Leu Glu
1               5                   10

<210> SEQ ID NO 87
<211> LENGTH: 117
<212> TYPE: PRT
<213> ORGANISM: Artificial Sequence
<220> FEATURE:
<223> OTHER INFORMATION: Synthetic heavy chain variable region of
      monoclonal antibody AbF46

<400> SEQUENCE: 87

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Ala Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Gln Ser Ile
65                  70                  75                  80

Leu Tyr Leu Gln Met Asp Thr Leu Arg Ala Glu Asp Ser Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ala
        115

<210> SEQ ID NO 88
<211> LENGTH: 114
<212> TYPE: PRT
<213> ORGANISM: Artificial Sequence
<220> FEATURE:
<223> OTHER INFORMATION: Synthetic light chain variable region of anti-
      c-Met antibody

<400> SEQUENCE: 88

Asp Ile Leu Met Thr Gln Ser Pro Ser Ser Leu Thr Val Ser Ala Gly
1               5                   10                  15

```
Glu Lys Val Thr Met Ser Cys Lys Ser Ser Gln Ser Leu Leu Ala Ser
             20                  25                  30

Gly Asn Gln Asn Asn Tyr Leu Ala Trp His Gln Lys Pro Gly Arg
         35                  40                  45

Ser Pro Lys Met Leu Ile Ile Trp Ala Ser Thr Arg Val Ser Gly Val
 50                  55                  60

Pro Asp Arg Phe Ile Gly Ser Gly Ser Gly Thr Asp Phe Thr Leu Thr
 65                  70                  75                  80

Ile Asn Ser Val Gln Ala Glu Asp Leu Ala Val Tyr Tyr Cys Gln Gln
                 85                  90                  95

Ser Tyr Ser Ala Pro Leu Thr Phe Gly Ala Gly Thr Lys Leu Glu Leu
            100                 105                 110

Lys Arg
```

```
<210> SEQ ID NO 89
<211> LENGTH: 17
<212> TYPE: PRT
<213> ORGANISM: Artificial Sequence
<220> FEATURE:
<223> OTHER INFORMATION: Synthetic light chain CDR3 of anti-c-Met
      antibody

<400> SEQUENCE: 89

Gln Gln Ser Tyr Ser Ala Pro Leu Thr Phe Gly Ala Gly Thr Lys Leu
1               5                  10                  15

Glu
```

```
<210> SEQ ID NO 90
<211> LENGTH: 117
<212> TYPE: PRT
<213> ORGANISM: Artificial Sequence
<220> FEATURE:
<223> OTHER INFORMATION: Synthetic heavy chain variable region of AT-VH1

<400> SEQUENCE: 90

Glu Val Lys Leu Val Glu Ser Gly Gly Gly Leu Val Gln Pro Gly Gly
1               5                  10                  15

Ser Leu Arg Leu Ser Cys Ala Thr Ser Gly Phe Thr Phe Thr Asp Tyr
             20                  25                  30

Tyr Met Ser Trp Val Arg Gln Pro Pro Gly Lys Gly Leu Glu Trp Leu
         35                  40                  45

Gly Phe Ile Arg Asn Lys Ala Asn Gly Tyr Thr Thr Glu Tyr Ser Ala
 50                  55                  60

Ser Val Lys Gly Arg Phe Thr Ile Ser Arg Asp Asn Ser Lys Ser Thr
 65                  70                  75                  80

Leu Tyr Leu Gln Met Asn Ser Leu Arg Ala Glu Asp Ser Ala Thr Tyr
                 85                  90                  95

Tyr Cys Ala Arg Asp Asn Trp Phe Ala Tyr Trp Gly Gln Gly Thr Leu
            100                 105                 110

Val Thr Val Ser Ser
        115
```

```
<210> SEQ ID NO 91
<211> LENGTH: 117
<212> TYPE: PRT
<213> ORGANISM: Artificial Sequence
<220> FEATURE:
<223> OTHER INFORMATION: Synthetic heavy chain variable region of AT-VH2

<400> SEQUENCE: 91
```

```
Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
        50                  55                  60

Ser Val Lys Gly Arg Phe Thr Ile Ser Arg Asp Asn Ser Lys Ser Thr
65                  70                  75                  80

Leu Tyr Leu Gln Met Asn Ser Leu Arg Ala Glu Asp Thr Ala Thr Tyr
                85                  90                  95

Tyr Cys Ala Arg Asp Asn Trp Phe Ala Tyr Trp Gly Gln Gly Thr Leu
                100                 105                 110

Val Thr Val Ser Ser
            115

<210> SEQ ID NO 92
<211> LENGTH: 117
<212> TYPE: PRT
<213> ORGANISM: Artificial Sequence
<220> FEATURE:
<223> OTHER INFORMATION: Synthetic heavy chain variable region of AT-VH3

<400> SEQUENCE: 92

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
        50                  55                  60

Ser Val Lys Gly Arg Phe Thr Ile Ser Arg Asp Asn Ser Lys Ser Thr
65                  70                  75                  80

Leu Tyr Leu Gln Met Asn Ser Leu Arg Ala Glu Asp Thr Ala Thr Tyr
                85                  90                  95

Tyr Cys Ala Arg Asp Asn Trp Phe Ala Tyr Trp Gly Gln Gly Thr Leu
                100                 105                 110

Val Thr Val Ser Ser
            115

<210> SEQ ID NO 93
<211> LENGTH: 117
<212> TYPE: PRT
<213> ORGANISM: Artificial Sequence
<220> FEATURE:
<223> OTHER INFORMATION: Synthetic heavy chain variable region of AT-VH4

<400> SEQUENCE: 93

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
```

```
                    50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Thr Tyr
                     85                  90                  95

Tyr Cys Ala Arg Asp Asn Trp Phe Ala Tyr Trp Gly Gln Gly Thr Leu
                100                 105                 110

Val Thr Val Ser Ser
            115

<210> SEQ ID NO 94
<211> LENGTH: 117
<212> TYPE: PRT
<213> ORGANISM: Artificial Sequence
<220> FEATURE:
<223> OTHER INFORMATION: Synthetic heavy chain variable region of AT-VH5

<400> SEQUENCE: 94

Glu Val Gln Leu Val Glu Ser Gly Gly Gly Leu Val Gln Pro Gly Gly
 1               5                  10                  15

Ser Leu Arg Leu Ser Cys Ala Thr Ser Gly Phe Thr Phe Thr Asp Tyr
                20                  25                  30

Tyr Met Ser Trp Val Arg Gln Pro Pro Gly Lys Gly Leu Glu Trp Leu
            35                  40                  45

Gly Phe Ile Arg Asn Lys Ala Asn Gly Tyr Thr Thr Glu Tyr Ser Ala
 50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                     85                  90                  95

Tyr Cys Ala Arg Asp Asn Trp Phe Ala Tyr Trp Gly Gln Gly Thr Leu
                100                 105                 110

Val Thr Val Ser Ser
            115

<210> SEQ ID NO 95
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 95

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
                20                  25                  30

Gly Asn Gln Asn Asn Tyr Leu Ala Trp His Gln Gln Lys Pro Gly Lys
            35                  40                  45

Ala Pro Lys Met Leu Ile Ile Trp Ala Ser Thr Arg Val Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                     85                  90                  95

Ser Tyr Ser Ala Pro Leu Thr Phe Gly Gln Gly Thr Lys Val Glu Ile
                100                 105                 110
```

Lys Arg

<210> SEQ ID NO 96
<211> LENGTH: 113
<212> TYPE: PRT
<213> ORGANISM: Artificial Sequence
<220> FEATURE:
<223> OTHER INFORMATION: Synthetic light chain variable region of AT-Vk1

<400> SEQUENCE: 96

```
Asp Ile Leu Met Thr Gln Ser Pro Ser Ser Leu Thr Ala Ser Val Gly
1               5                   10                  15
Asp Arg Val Thr Met Thr Cys Lys Ser Ser Gln Ser Leu Leu Ala Ser
            20                  25                  30
Gly Asn Gln Asn Asn Tyr Leu Ala Trp His Gln Gln Lys Pro Gly Lys
        35                  40                  45
Ala Pro Lys Met Leu Ile Ile Trp Ala Ser Thr Arg Val Ser Gly Val
    50                  55                  60
Pro Asp Arg Phe Ile Gly Ser Gly Ser Gly Thr Asp Phe Thr Leu Thr
65                  70                  75                  80
Ile Ser Ser Leu Gln Ala Glu Asp Val Ala Val Tyr Tyr Cys Gln Gln
                85                  90                  95
Ser Tyr Ser Ala Pro Leu Thr Phe Gly Gln Gly Thr Lys Leu Glu Ile
            100                 105                 110
Lys
```

<210> SEQ ID NO 97
<211> LENGTH: 113
<212> TYPE: PRT
<213> ORGANISM: Artificial Sequence
<220> FEATURE:
<223> OTHER INFORMATION: Synthetic light chain variable region of AT-Vk2

<400> SEQUENCE: 97

```
Asp Ile Leu Met Thr Gln Ser Pro Ser Ser Leu Ser Ala Ser Val Gly
1               5                   10                  15
Asp Arg Val Thr Ile Thr Cys Lys Ser Ser Gln Ser Leu Leu Ala Ser
            20                  25                  30
Gly Asn Gln Asn Asn Tyr Leu Ala Trp His Gln Gln Lys Pro Gly Lys
        35                  40                  45
Ala Pro Lys Met Leu Ile Ile Trp Ala Ser Thr Arg Val Ser Gly Val
    50                  55                  60
Pro Asp Arg Phe Ile Gly Ser Gly Ser Gly Thr Asp Phe Thr Leu Thr
65                  70                  75                  80
Ile Ser Ser Leu Gln Ala Glu Asp Val Ala Val Tyr Tyr Cys Gln Gln
                85                  90                  95
Ser Tyr Ser Ala Pro Leu Thr Phe Gly Gln Gly Thr Lys Leu Glu Ile
            100                 105                 110
Lys
```

<210> SEQ ID NO 98
<211> LENGTH: 113
<212> TYPE: PRT
<213> ORGANISM: Artificial Sequence
<220> FEATURE:
<223> OTHER INFORMATION: Synthetic light chain variable region of AT-Vk3

<400> SEQUENCE: 98

```
Asp Ile Gln Met Thr Gln Ser Pro Ser Ser Leu Ser Ala Ser Val Gly
1               5                   10                  15

Asp Arg Val Thr Ile Thr Cys Lys Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Asp Arg Phe Ile Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110

Lys

<210> SEQ ID NO 99
<211> LENGTH: 113
<212> TYPE: PRT
<213> ORGANISM: Artificial Sequence
<220> FEATURE:
<223> OTHER INFORMATION: Synthetic light chain variable region of AT-Vk4

<400> SEQUENCE: 99

Asp Ile Gln Met Thr Gln Ser Pro Ser Ser Leu Ser Ala Ser Val Gly
1               5                   10                  15

Asp Arg Val Thr Ile Thr Cys Lys Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110

Lys

<210> SEQ ID NO 100
<211> LENGTH: 13
<212> TYPE: PRT
<213> ORGANISM: Artificial Sequence
<220> FEATURE:
<223> OTHER INFORMATION: Synthetic modified hinge region(U7-HC6)

<400> SEQUENCE: 100

Glu Pro Ser Cys Asp Lys His Cys Cys Pro Pro Cys Pro
1               5                   10

<210> SEQ ID NO 101
<211> LENGTH: 13
<212> TYPE: PRT
<213> ORGANISM: Artificial Sequence
<220> FEATURE:
<223> OTHER INFORMATION: Synthetic modified hinge region(U6-HC7)

<400> SEQUENCE: 101
```

Glu Pro Lys Ser Cys Asp Cys His Cys Pro Pro Cys Pro
1               5                   10

<210> SEQ ID NO 102
<211> LENGTH: 12
<212> TYPE: PRT
<213> ORGANISM: Artificial Sequence
<220> FEATURE:
<223> OTHER INFORMATION: Synthetic modified hinge region(U3-HC9)

<400> SEQUENCE: 102

Glu Arg Lys Cys Cys Val Glu Cys Pro Pro Cys Pro
1               5                   10

<210> SEQ ID NO 103
<211> LENGTH: 14
<212> TYPE: PRT
<213> ORGANISM: Artificial Sequence
<220> FEATURE:
<223> OTHER INFORMATION: Synthetic modified hinge region(U6-HC8)

<400> SEQUENCE: 103

Glu Pro Arg Asp Cys Gly Cys Lys Pro Cys Pro Pro Cys Pro
1               5                   10

<210> SEQ ID NO 104
<211> LENGTH: 13
<212> TYPE: PRT
<213> ORGANISM: Artificial Sequence
<220> FEATURE:
<223> OTHER INFORMATION: Synthetic modified hinge region(U8-HC5)

<400> SEQUENCE: 104

Glu Lys Cys Asp Lys Thr His Thr Cys Pro Pro Cys Pro
1               5                   10

<210> SEQ ID NO 105
<211> LENGTH: 15
<212> TYPE: PRT
<213> ORGANISM: Artificial Sequence
<220> FEATURE:
<223> OTHER INFORMATION: Synthetic human hinge region

<400> SEQUENCE: 105

Glu Pro Lys Ser Cys Asp Lys Thr His Thr Cys Pro Pro Cys Pro
1               5                   10                  15

<210> SEQ ID NO 106
<211> LENGTH: 17
<212> TYPE: PRT
<213> ORGANISM: Artificial Sequence
<220> FEATURE:
<223> OTHER INFORMATION: Synthetic CDR-L1 of antibody L3-11Y

<400> SEQUENCE: 106

Lys Ser Ser Gln Ser Leu Leu Ala Trp Gly Asn Gln Asn Asn Tyr Leu
1               5                   10                  15

Ala

<210> SEQ ID NO 107
<211> LENGTH: 114
<212> TYPE: PRT
<213> ORGANISM: Artificial Sequence
<220> FEATURE:
<223> OTHER INFORMATION: Synthetic amino acid sequence of light chain
      variable region of antibody L3-11Y

<400> SEQUENCE: 107

Asp Ile Gln Met Thr Gln Ser Pro Ser Ser Leu Ser Ala Ser Val Gly
1               5                   10                  15

Asp Arg Val Thr Ile Thr Cys Lys Ser Gln Ser Leu Leu Ala Trp
            20                  25                  30

Gly Asn Gln Asn Asn Tyr Leu Ala Trp Tyr Gln Gln Lys Pro Gly Lys
            35                  40                  45

Ala Pro Lys Met Leu Ile Ile Trp Ala Ser Thr Arg Val Ser Gly Val
50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Tyr Thr Phe Gly Gln Gly Thr Lys Val Glu Ile
                100                 105                 110

Lys Arg

<210> SEQ ID NO 108
<211> LENGTH: 220
<212> TYPE: PRT
<213> ORGANISM: Artificial Sequence
<220> FEATURE:
<223> OTHER INFORMATION: Synthetic amino acid sequence of light chain of
      antibody L3-11Y

<400> SEQUENCE: 108

Asp Ile Gln Met Thr Gln Ser Pro Ser Ser Leu Ser Ala Ser Val Gly
1               5                   10                  15

Asp Arg Val Thr Ile Thr Cys Lys Ser Gln Ser Leu Leu Ala Trp
            20                  25                  30

Gly Asn Gln Asn Asn Tyr Leu Ala Trp Tyr Gln Gln Lys Pro Gly Lys
            35                  40                  45

Ala Pro Lys Met Leu Ile Ile Trp Ala Ser Thr Arg Val Ser Gly Val
50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Tyr Thr Phe Gly Gln Gly Thr Lys Val Glu Ile
                100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
210                 215                 220

```
<210> SEQ ID NO 109
<211> LENGTH: 188
<212> TYPE: PRT
<213> ORGANISM: Artificial Sequence
<220> FEATURE:
<223> OTHER INFORMATION: Synthetic wild type KRAS (accession number
      NP_004976)

<400> SEQUENCE: 109

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185

<210> SEQ ID NO 110
<211> LENGTH: 766
<212> TYPE: PRT
<213> ORGANISM: Artificial Sequence
<220> FEATURE:
<223> OTHER INFORMATION: Synthetic wild type BRAF (accession number
      NP_004324)

<400> SEQUENCE: 110

Met Ala Ala Leu Ser Gly Gly Gly Gly Gly Ala Glu Pro Gly Gln
1               5                   10                  15

Ala Leu Phe Asn Gly Asp Met Glu Pro Glu Ala Gly Ala Gly Ala Gly
            20                  25                  30

Ala Ala Ala Ser Ser Ala Ala Asp Pro Ala Ile Pro Glu Glu Val Trp
        35                  40                  45

Asn Ile Lys Gln Met Ile Lys Leu Thr Gln Glu His Ile Glu Ala Leu
    50                  55                  60

Leu Asp Lys Phe Gly Gly Glu His Asn Pro Pro Ser Ile Tyr Leu Glu
65                  70                  75                  80

Ala Tyr Glu Glu Tyr Thr Ser Lys Leu Asp Ala Leu Gln Gln Arg Glu
                85                  90                  95

Gln Gln Leu Leu Glu Ser Leu Gly Asn Gly Thr Asp Phe Ser Val Ser
            100                 105                 110

Ser Ser Ala Ser Met Asp Thr Val Thr Ser Ser Ser Ser Ser Ser Leu
```

```
            115                 120                 125
Ser Val Leu Pro Ser Ser Leu Ser Val Phe Gln Asn Pro Thr Asp Val
            130                 135                 140
Ala Arg Ser Asn Pro Lys Ser Pro Gln Lys Pro Ile Val Arg Val Phe
145                 150                 155                 160
Leu Pro Asn Lys Gln Arg Thr Val Val Pro Ala Arg Cys Gly Val Thr
                165                 170                 175
Val Arg Asp Ser Leu Lys Lys Ala Leu Met Met Arg Gly Leu Ile Pro
                180                 185                 190
Glu Cys Cys Ala Val Tyr Arg Ile Gln Asp Gly Glu Lys Lys Pro Ile
                195                 200                 205
Gly Trp Asp Thr Asp Ile Ser Trp Leu Thr Gly Glu Glu Leu His Val
            210                 215                 220
Glu Val Leu Glu Asn Val Pro Leu Thr Thr His Asn Phe Val Arg Lys
225                 230                 235                 240
Thr Phe Phe Thr Leu Ala Phe Cys Asp Phe Cys Arg Lys Leu Leu Phe
                245                 250                 255
Gln Gly Phe Arg Cys Gln Thr Cys Gly Tyr Lys Phe His Gln Arg Cys
            260                 265                 270
Ser Thr Glu Val Pro Leu Met Cys Val Asn Tyr Asp Gln Leu Asp Leu
            275                 280                 285
Leu Phe Val Ser Lys Phe Phe Glu His His Pro Ile Pro Gln Glu Glu
            290                 295                 300
Ala Ser Leu Ala Glu Thr Ala Leu Thr Ser Gly Ser Ser Pro Ser Ala
305                 310                 315                 320
Pro Ala Ser Asp Ser Ile Gly Pro Gln Ile Leu Thr Ser Pro Ser Pro
                325                 330                 335
Ser Lys Ser Ile Pro Ile Pro Gln Pro Phe Arg Pro Ala Asp Glu Asp
                340                 345                 350
His Arg Asn Gln Phe Gly Gln Arg Asp Arg Ser Ser Ser Ala Pro Asn
                355                 360                 365
Val His Ile Asn Thr Ile Glu Pro Val Asn Ile Asp Asp Leu Ile Arg
            370                 375                 380
Asp Gln Gly Phe Arg Gly Asp Gly Gly Ser Thr Thr Gly Leu Ser Ala
385                 390                 395                 400
Thr Pro Pro Ala Ser Leu Pro Gly Ser Leu Thr Asn Val Lys Ala Leu
                405                 410                 415
Gln Lys Ser Pro Gly Pro Gln Arg Glu Arg Lys Ser Ser Ser Ser Ser
                420                 425                 430
Glu Asp Arg Asn Arg Met Lys Thr Leu Gly Arg Arg Asp Ser Ser Asp
            435                 440                 445
Asp Trp Glu Ile Pro Asp Gly Gln Ile Thr Val Gly Gln Arg Ile Gly
            450                 455                 460
Ser Gly Ser Phe Gly Thr Val Tyr Lys Gly Lys Trp His Gly Asp Val
465                 470                 475                 480
Ala Val Lys Met Leu Asn Val Thr Ala Pro Thr Pro Gln Gln Leu Gln
                485                 490                 495
Ala Phe Lys Asn Glu Val Gly Val Leu Arg Lys Thr Arg His Val Asn
                500                 505                 510
Ile Leu Leu Phe Met Gly Tyr Ser Thr Lys Pro Gln Leu Ala Ile Val
            515                 520                 525
Thr Gln Trp Cys Glu Gly Ser Ser Leu Tyr His His Leu His Ile Ile
            530                 535                 540
```

Glu Thr Lys Phe Glu Met Ile Lys Leu Ile Asp Ile Ala Arg Gln Thr
545                 550                 555                 560

Ala Gln Gly Met Asp Tyr Leu His Ala Lys Ser Ile Ile His Arg Asp
            565                 570                 575

Leu Lys Ser Asn Asn Ile Phe Leu His Glu Asp Leu Thr Val Lys Ile
        580                 585                 590

Gly Asp Phe Gly Leu Ala Thr Val Lys Ser Arg Trp Ser Gly Ser His
    595                 600                 605

Gln Phe Glu Gln Leu Ser Gly Ser Ile Leu Trp Met Ala Pro Glu Val
610                 615                 620

Ile Arg Met Gln Asp Lys Asn Pro Tyr Ser Phe Gln Ser Asp Val Tyr
625                 630                 635                 640

Ala Phe Gly Ile Val Leu Tyr Glu Leu Met Thr Gly Gln Leu Pro Tyr
            645                 650                 655

Ser Asn Ile Asn Asn Arg Asp Gln Ile Ile Phe Met Val Gly Arg Gly
        660                 665                 670

Tyr Leu Ser Pro Asp Leu Ser Lys Val Arg Ser Asn Cys Pro Lys Ala
    675                 680                 685

Met Lys Arg Leu Met Ala Glu Cys Leu Lys Lys Lys Arg Asp Glu Arg
690                 695                 700

Pro Leu Phe Pro Gln Ile Leu Ala Ser Ile Glu Leu Leu Ala Arg Ser
705                 710                 715                 720

Leu Pro Lys Ile His Arg Ser Ala Ser Glu Pro Ser Leu Asn Arg Ala
            725                 730                 735

Gly Phe Gln Thr Glu Asp Phe Ser Leu Tyr Ala Cys Ala Ser Pro Lys
        740                 745                 750

Thr Pro Ile Gln Ala Gly Gly Tyr Gly Ala Phe Pro Val His
    755                 760                 765

<210> SEQ ID NO 111
<211> LENGTH: 442
<212> TYPE: PRT
<213> ORGANISM: Artificial Sequence
<220> FEATURE:
<223> OTHER INFORMATION: Synthetic Heavy chain of anti-c-Met antibody
      LY2875358

<400> SEQUENCE: 111

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Met
        35                  40                  45

Gly Arg Val Asn Pro Asn Arg Gly Thr Thr Tyr Asn Gln Lys Phe
50                  55                  60

Glu Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
            85                  90                  95

Ala Arg Ala Asn Trp Leu Asp Tyr Trp Gly Gln Gly Thr Thr Val Thr
        100                 105                 110

Val Ser Ser Ala Ser Thr Lys Gly Pro Ser Val Phe Pro Leu Ala Pro
    115                 120                 125

Cys Ser Arg Ser Thr Ser Glu Ser Thr Ala Ala Leu Gly Cys Leu Val

```
                130             135             140
Lys Asp Tyr Phe Pro Glu Pro Val Thr Val Ser Trp Asn Ser Gly Ala
145                 150             155                 160

Leu Thr Ser Gly Val His Thr Phe Pro Ala Val Leu Gln Ser Ser Gly
            165             170             175

Leu Tyr Ser Leu Ser Ser Val Val Thr Val Pro Ser Ser Ser Leu Gly
            180             185             190

Thr Lys Thr Tyr Thr Cys Asn Val Asp His Lys Pro Ser Asn Thr Lys
            195             200             205

Val Asp Lys Arg Val Glu Ser Lys Tyr Gly Pro Pro Cys Pro Pro Cys
            210             215             220

Pro Ala Pro Glu Ala Ala Gly Gly Pro Ser Val Phe Leu Phe Pro Pro
225             230             235             240

Lys Pro Lys Asp Thr Leu Met Ile Ser Arg Thr Pro Glu Val Thr Cys
            245             250             255

Val Val Val Asp Val Ser Gln Glu Asp Pro Glu Val Gln Phe Asn Trp
            260             265             270

Tyr Val Asp Gly Val Glu Val His Asn Ala Lys Thr Lys Pro Arg Glu
            275             280             285

Glu Gln Phe Asn Ser Thr Tyr Arg Val Val Ser Val Leu Thr Val Leu
            290             295             300

His Gln Asp Trp Leu Asn Gly Lys Glu Tyr Lys Cys Lys Val Ser Asn
305             310             315             320

Lys Gly Leu Pro Ser Ser Ile Glu Lys Thr Ile Ser Lys Ala Lys Gly
            325             330             335

Gln Pro Arg Glu Pro Gln Val Tyr Thr Leu Pro Pro Ser Gln Glu Glu
            340             345             350

Met Thr Lys Asn Gln Val Ser Leu Thr Cys Leu Val Lys Gly Phe Tyr
            355             360             365

Pro Ser Asp Ile Ala Val Glu Trp Glu Ser Asn Gly Gln Pro Glu Asn
            370             375             380

Asn Tyr Lys Thr Thr Pro Pro Val Leu Asp Ser Asp Gly Ser Phe Phe
385             390             395             400

Leu Tyr Ser Arg Leu Thr Val Asp Lys Ser Arg Trp Gln Glu Gly Asn
            405             410             415

Val Phe Ser Cys Ser Val Met His Glu Ala Leu His Asn His Tyr Thr
            420             425             430

Gln Lys Ser Leu Ser Leu Ser Leu Gly Lys
            435             440

<210> SEQ ID NO 112
<211> LENGTH: 215
<212> TYPE: PRT
<213> ORGANISM: Artificial Sequence
<220> FEATURE:
<223> OTHER INFORMATION: Synthetic Light chain of anti-c-Met antibody
      LY2875358

<400> SEQUENCE: 112

Asp Ile Gln Met Thr Gln Ser Pro Ser Ser Leu Ser Ala Ser Val Gly
1               5                   10                  15

Asp Arg Val Thr Ile Thr Cys Ser Val Ser Ser Val Ser Ser Ile
            20                  25                  30

Tyr Leu His Trp Tyr Gln Gln Lys Pro Gly Lys Ala Pro Lys Leu Leu
            35                  40                  45
```

```
Ile Tyr Ser Thr Ser Asn Leu Ala Ser Gly Val Pro Ser Arg Phe Ser
        50                  55                  60
Gly Ser Gly Ser Gly Thr Asp Phe Thr Leu Thr Ile Ser Ser Leu Gln
 65                  70                  75                  80
Pro Glu Asp Phe Ala Thr Tyr Tyr Cys Gln Val Tyr Ser Gly Tyr Pro
                85                  90                  95
Leu Thr Phe Gly Gly Gly Thr Lys Val Glu Ile Lys Arg Thr Val Ala
            100                 105                 110
Ala Pro Ser Val Phe Ile Phe Pro Pro Ser Asp Glu Gln Leu Lys Ser
        115                 120                 125
Gly Thr Ala Ser Val Val Cys Leu Leu Asn Asn Phe Tyr Pro Arg Glu
130                 135                 140
Ala Lys Val Gln Trp Lys Val Asp Asn Ala Leu Gln Ser Gly Asn Ser
145                 150                 155                 160
Gln Glu Ser Val Thr Glu Gln Asp Ser Lys Asp Ser Thr Tyr Ser Leu
                165                 170                 175
Ser Ser Thr Leu Thr Leu Ser Lys Ala Asp Tyr Glu Lys His Lys Val
            180                 185                 190
Tyr Ala Cys Glu Val Thr His Gln Gly Leu Ser Ser Pro Val Thr Lys
        195                 200                 205
Ser Phe Asn Arg Gly Asp Cys
        210                 215

<210> SEQ ID NO 113
<211> LENGTH: 114
<212> TYPE: PRT
<213> ORGANISM: Artificial Sequence
<220> FEATURE:
<223> OTHER INFORMATION: Synthetic light chain variable region of anti
      c-Met antibody

<400> SEQUENCE: 113

Asp Ile Gln Met Thr Gln Ser Pro Ser Ser Leu Ser Ala Ser Val Gly
 1                5                  10                  15
Asp Arg Val Thr Ile Thr Cys Lys Ser Ser Gln Ser Leu Leu Ala Ser
                20                  25                  30
Gly Asn Gln Asn Asn Tyr Leu Ala Trp Tyr Gln Gln Lys Pro Gly Lys
            35                  40                  45
Ala Pro Lys Met Leu Ile Ile Trp Ala Ser Thr Arg Val Ser Gly Val
        50                  55                  60
Pro Ser Arg Phe Ser Gly Ser Gly Ser Gly Thr Asp Phe Thr Leu Thr
 65                  70                  75                  80
Ile Ser Ser Leu Gln Pro Glu Asp Phe Ala Thr Tyr Tyr Cys Gln Gln
                85                  90                  95
Ser Tyr Ser Arg Pro Tyr Thr Phe Gly Gln Gly Thr Lys Val Glu Ile
            100                 105                 110
Lys Arg

<210> SEQ ID NO 114
<211> LENGTH: 5765
<212> TYPE: DNA
<213> ORGANISM: Artificial Sequence
<220> FEATURE:
<223> OTHER INFORMATION: Synthetic human KRAS gene

<400> SEQUENCE: 114
tcctaggcgg cggccgcggc ggcggaggca gcagcggcgg cggcagtggc ggcggcgaag    60
```

-continued

```
gtggcggcgg ctcggccagt actcccggcc cccgccattt cggactggga gcgagcgcgg    120
cgcaggcact gaaggcggcg gcggggccag aggctcagcg gctcccaggt gcgggagaga    180
ggcctgctga aaatgactga atataaactt gtggtagttg gagctggtgg cgtaggcaag    240
agtgccttga cgatacagct aattcagaat cattttgtgg acgaatatga tccaacaata    300
gaggattcct acaggaagca agtagtaatt gatggagaaa cctgtctctt ggatattctc    360
gacacagcag gtcaagagga gtacagtgca atgagggacc agtacatgag gactggggag    420
ggctttcttt gtgtatttgc cataaataat actaaatcat ttgaagatat tcaccattat    480
agagaacaaa ttaaaagagt taaggactct gaagatgtac ctatggtcct agtaggaaat    540
aaatgtgatt tgccttctag aacagtagac acaaaacagg ctcaggactt agcaagaagt    600
tatggaattc cttttattga acatcagca aagacaagac agggtgttga tgatgccttc    660
tatacattag ttcgagaaat tcgaaaacat aaagaaaaga tgagcaaaga tggtaaaaag    720
aagaaaaaga agtcaaagac aaagtgtgta attatgtaaa tacaatttgt acttttttct    780
taaggcatac tagtacaagt ggtaattttt gtacattaca ctaaattatt agcatttgtt    840
ttagcattac ctaattttt tcctgctcca tgcagactgt tagcttttac cttaaatgct    900
tattttaaaa tgacagtgga agtttttttt tcctctaagt gccagtattc ccagagtttt    960 ggttttgaa ctagcaatgc ctgtgaaaaa gaaactgaat acctaagatt tctgtcttgg   1020 ggttttggt gcatgcagtt gattacttct tattttctt accaattgtg aatgttggtg   1080
tgaaacaaat taatgaagct tttgaatcat ccctattctg tgttttatct agtcacataa   1140
atggattaat tactaatttc agttgagacc ttctaattgg ttttactga aacattgagg   1200 gaacacaaat ttatgggctt cctgatgatg attcttctag gcatcatgtc ctatagtttg   1260
tcatccctga tgaatgtaaa gttacactgt tcacaaggt tttgtctcct ttccactgct   1320
attagtcatg gtcactctcc ccaaaatatt atattttttc tataaaaga aaaaaatgga   1380 aaaaaattac aaggcaatgg aaactattat aaggccattt ccttttcaca ttagataaat   1440
tactataaag actcctaata gcttttcctg ttaaggcaga cccagtatga atggggatt   1500 attatagcaa ccattttggg gctatattta catgctacta aatttttata ataattgaaa   1560
agattttaac aagtataaaa aattctcata ggaattaaat gtagtctccc tgtgtcagac   1620
tgctcttcca tagtataact ttaaatcttt tcttcaactt gagtctttga agatagtttt   1680
aattctgctt gtgacattaa aagattattt gggccagtta tagcttatta ggtgttgaag   1740
agaccaaggt tgcaaggcca ggccctgtgt gaacctttga gctttcatag agagtttcac   1800
agcatggact gtgtccccac ggtcatccag tgttgtcatg cattggttag tcaaaatggg   1860
gagggactag ggcagtttgg atagctcaac aagatacaat ctcactctgt ggtggtcctg   1920
ctgacaaatc aagagcattg cttttgtttc ttaagaaaac aaactctttt ttaaaaatta   1980
cttttaaata ttaactcaaa agttgagatt tggggtggt ggtgtgccaa gacattaatt   2040
ttttttttaa acaatgaagt gaaaagtttt acaatctct aggtttggct agttctctta   2100
acactggtta aattaacatt gcataaacac ttttcaagtc tgatccatat ttaataatgc   2160
tttaaaataa aataaaaac aatccttttg ataaatttaa aatgttactt atttaaaat   2220 aaatgaagtg agatggcatg gtgaggtgaa agtatcactg gactaggaag aaggtgactt   2280
aggttctaga taggtgtctt ttaggactct gattttgagg acatcactta ctatccattt   2340
cttcatgtta aaagaagtca tctcaaactc ttagtttttt tttttacaa ctatgtaatt   2400 tatattccat ttacataagg atacacttat ttgtcaagct cagcacaatc tgtaaatttt   2460
```

```
taacctatgt tacaccatct tcagtgccag tcttgggcaa aattgtgcaa gaggtgaagt    2520
ttatatttga atatccattc tcgttttagg actcttcttc catattagtg tcatcttgcc    2580
tccctacctt ccacatgccc catgacttga tgcagtttta atacttgtaa ttcccctaac    2640
cataagattt actgctgctg tggatatctc catgaagttt tcccactgag tcacatcaga    2700
aatgccctac atcttatttc ctcagggctc aagagaatct gacagatacc ataaagggat    2760
ttgacctaat cactaattt tcaggtggtgg ctgatgcttt gaacatctct ttgctgccca    2820
atccattagc gacagtagga ttttcaaac ctggtatgaa tagacagaac cctatccagt    2880
ggaaggagaa tttaataaag atagtgctga aagaattcct taggtaatct ataactagga    2940
ctactcctgg taacagtaat acattccatt gttttagtaa ccagaaatct tcatgcaatg    3000
aaaaatactt taattcatga agcttacttt tttttttgg tgtcagagtc tcgctcttgt    3060
cacccaggct ggaatgcagt ggcgccatct cagctcactg caacctccat ctcccaggtt    3120
caagcgattc tcgtgcctcg gcctcctgag tagctgggat tacaggcgtg tgccactaca    3180
ctcaactaat ttttgtattt ttaggagaga cggggtttca ccctgttggc caggctggtc    3240
tcgaactcct gacctcaagt gattcaccca ccttggcctc ataaacctgt tttgcagaac    3300
tcatttattc agcaaatatt tattgagtgc ctaccagatg ccagtcaccg cacaaggcac    3360
tgggtatatg gtatccccaa acaagagaca taatcccggt ccttaggtag tgctagtgtg    3420
gtctgtaata tcttactaag gcctttggta tacgacccag agataacacg atgcgtattt    3480
tagttttgca aagaaggggt ttggtctctg tgccagctct ataattgttt tgctacgatt    3540
ccactgaaac tcttcgatca agctacttta tgtaaatcac ttcattgttt taaaggaata    3600
aacttgatta tattgtttt ttatttggca taactgtgat tcttttagga caattactgt    3660
acacattaag gtgtatgtca gatattcata ttgacccaaa tgtgtaatat tccagttttc    3720
tctgcataag taattaaaat atacttaaaa attaatagtt ttatctgggt acaaataaac    3780
aggtgcctga actagttcac agacaaggaa acttctatgt aaaaatcact atgatttctg    3840
aattgctatg tgaaactaca gatctttgga acactgttta ggtagggtgt taagacttac    3900
acagtacctc gtttctacac agagaaagaa atggccatac ttcaggaact gcagtgctta    3960
tgaggggata tttaggcctc ttgaattttt gatgtagatg ggcatttttt taaggtagtg    4020
gttaattacc tttatgtgaa ctttgaatgg tttaacaaaa gatttgtttt tgtagagatt    4080
ttaaaggggg agaattctag aaataaatgt tacctaatta ttacagcctt aaagacaaaa    4140
atccttgttg aagttttttt aaaaaaagct aaattacata gacttaggca ttaacatgtt    4200
tgtggaagaa tatagcagac gtatattgta tcatttgagt gaatgttccc aagtaggcat    4260
tctaggctct atttaactga gtcacactgc ataggaattt agaacctaac ttttataggt    4320
tatcaaaact gttgtcacca ttgcacaatt ttgtcctaat atatacatag aaactttgtg    4380
gggcatgtta agttacagtt tgcacaagtt catctcattt gtattccatt gattttttt    4440
ttcttctaaa catttttct tcaaacagta tataactttt tttagggat ttttttttag    4500
acagcaaaaa ctatctgaag atttccattt gtcaaaagt aatgattct tgataattgt    4560
gtagtaatgt tttttagaac ccagcagtta ccttaaagct gaatttatat ttagtaactt    4620
ctgtgttaat actggatagc atgaattctg cattgagaaa ctgaatagct gtcataaaat    4680
gaaactttct ttctaaagaa agatactcac atgagttctt gaagaatagt cataactaga    4740
ttaagatctg tgttttagtt taatagtttg aagtgcctgt ttgggataat gataggtaat    4800
```

| | |
|---|---|
| ttagatgaat ttaggggaaa aaaaagttat ctgcagatat gttgagggcc catctctccc | 4860 |
| cccacacccc cacagagcta actgggttac agtgttttat ccgaaagttt ccaattccac | 4920 |
| tgtcttgtgt tttcatgttg aaaatacttt tgcattttc ctttgagtgc caatttctta | 4980 |
| ctagtactat ttcttaatgt aacatgttta cctggaatgt attttaacta tttttgtata | 5040 |
| gtgtaaactg aaacatgcac attttgtaca ttgtgctttc ttttgtggga catatgcagt | 5100 |
| gtgatccagt tgttttccat catttggttg cgctgaccta ggaatgttgg tcatatcaaa | 5160 |
| cattaaaaat gaccactctt ttaattgaaa ttaacttta aatgtttata ggagtatgtg | 5220 |
| ctgtgaagtg atctaaaatt tgtaatattt ttgtcatgaa ctgtactact cctaattatt | 5280 |
| gtaatgtaat aaaaatagtt acagtgacta tgagtgtgta tttattcatg aaatttgaac | 5340 |
| tgtttgcccc gaaatggata tggaatactt tataagccat agacactata gtataccagt | 5400 |
| gaatctttta tgcagcttgt tagaagtatc ctttatttct aaaaggtgct gtggatatta | 5460 |
| tgtaaaggcg tgtttgctta aacttaaaac catatttaga agtagatgca aaacaaatct | 5520 |
| gcctttatga caaaaaaata ggataacatt atttatttat ttccttttat caagaaggt | 5580 |
| aattgataca caacaggtga cttggtttta ggcccaaagg tagcagcagc aacattaata | 5640 |
| atggaaataa ttgaatagtt agttatgtat gttaatgcca gtcaccagca ggctatttca | 5700 |
| aggtcagaag taatgactcc atacatatta tttatttcta taactacatt taaatcatta | 5760 |
| ccagg | 5765 |

<210> SEQ ID NO 115
<211> LENGTH: 2949
<212> TYPE: DNA
<213> ORGANISM: Artificial Sequence
<220> FEATURE:
<223> OTHER INFORMATION: Synthetic human BRAF gene

<400> SEQUENCE: 115

| | |
|---|---|
| cgcctcccctt cccctcccc gcccgacagc ggccgctcgg gccccggctc tcggttataa | 60 |
| gatggcggcg ctgagcggtg gcggtggtgg cggcgcggag ccgggccagg ctctgttcaa | 120 |
| cggggacatg gagcccgagg ccggcgccgg cgccggcgcc gcggcctctt cggctgcgga | 180 |
| ccctgccatt ccggaggagg tgtggaatat caaacaaatg attaagttga cacaggaaca | 240 |
| tatagaggcc ctattggaca aatttggtgg ggagcataat ccaccatcaa tatatctgga | 300 |
| ggcctatgaa gaatacacca gcaagctaga tgcactccaa caaagagaac aacagttatt | 360 |
| ggaatctctg gggaacggaa ctgatttttc tgtttctagc tctgcatcaa tggataccgt | 420 |
| tacatcttct tcctcttcta gcctttcagt gctaccttca tctctttcag tttttcaaaa | 480 |
| tcccacagat gtggcacgga gcaaccccaa gtcaccacaa aaacctatcg ttagagtctt | 540 |
| cctgcccaac aaacagagga cagtggtacc tgcaaggtgt ggagttacag tccgagacag | 600 |
| tctaaagaaa gcactgatga tgagaggtct aatcccagag tgctgtgctg tttacagaat | 660 |
| tcaggatgga gagaagaaac caattggttg ggacactgat atttcctggc ttactggaga | 720 |
| agaattgcat gtggaagtgt tggagaatgt tccacttaca acacacaact tgtacgaaaa | 780 |
| aacgttttc accttagcat tttgtgactt ttgtcgaaag ctgcttttcc agggtttccg | 840 |
| ctgtcaaaca tgtggttata aatttcacca gcgttgtagt acagaagttc cactgatgtg | 900 |
| tgttaattat gaccaacttg atttgctgtt tgtctccaag ttctttgaac caccccaat | 960 |
| accacaggaa gaggcgtcct tagcagagac tgccctaaca tctggatcat ccccttccgc | 1020 |
| acccgcctcg gactctattg ggccccaaat tctcaccagt ccgtctcctt caaaatccat | 1080 |

-continued

```
tccaattcca cagcccttcc gaccagcaga tgaagatcat cgaaatcaat ttgggcaacg    1140
agaccgatcc tcatcagctc ccaatgtgca tataaacaca atagaacctg tcaatattga    1200
tgacttgatt agagaccaag gatttcgtgg tgatggagga tcaaccacag gtttgtctgc    1260
taccccccct gcctcattac ctggctcact aactaacgtg aaagccttac agaaatctcc    1320
aggacctcag cgagaaagga agtcatcttc atcctcagaa gacaggaatc gaatgaaaac    1380
acttggtaga cgggactcga gtgatgattg ggagattcct gatgggcaga ttacagtggg    1440
acaaagaatt ggatctggat catttggaac agtctacaag ggaaagtggc atggtgatgt    1500
ggcagtgaaa atgttgaatg tgacagcacc tacacctcag cagttacaag ccttcaaaaa    1560
tgaagtagga gtactcagga aaacacgaca tgtgaatatc ctactcttca tgggctattc    1620
cacaaagcca caactggcta ttgttaccca gtggtgtgag ggctccagct tgtatcacca    1680
tctccatatc atttgagacca aatttgagat gatcaaactt atagatattg cacgacagac    1740
tgcacagggc atggattact tacacgccaa gtcaatcatc cacagagacc tcaagagtaa    1800
taatatattt cttcatgaag acctcacagt aaaaataggt gattttggtc tagctacagt    1860
gaaatctcga tggagtgggt cccatcagtt tgaacagttg tctggatcca ttttgtggat    1920
ggcaccagaa gtcatcagaa tgcaagataa aaatccatac agctttcagt cagatgtata    1980
tgcatttgga attgttctgt atgaattgat gactggacag ttaccttatt caaacatcaa    2040
caacagggac cagataattt ttatggtggg acgaggatac ctgtctccag atctcagtaa    2100
ggtacggagt aactgtccaa aagccatgaa gagattaatg gcagagtgcc tcaaaaagaa    2160
aagagatgag agaccactct ttccccaaat tctcgcctct attgagctgc tggcccgctc    2220
attgccaaaa attcaccgca gtgcatcaga accctccttg aatcgggctg gtttccaaac    2280
agaggatttt agtctatatg cttgtgcttc tccaaaaaca cccatccagg caggggata    2340 tggtgcgttt cctgtccact gaaacaaatg agtgagagag ttcaggagag tagcaacaaa    2400
aggaaaataa atgaacatat gtttgcttat atgttaaatt gaataaaata ctctcttttt    2460
ttttaaggtg aaccaaagaa cacttgtgtg gttaaagact agatataatt tttccccaaa    2520
ctaaaattta tacttaacat tggattttta acatccaagg gttaaaatac atagacattg    2580
ctaaaaattg gcagagcctc ttctagaggc tttactttct gttccgggtt tgtatcattc    2640
acttggttat tttaagtagt aaacttcagt ttctcatgca acttttgttg ccagctatca    2700
catgtccact agggactcca gaagaagacc ctacctatgc ctgtgtttgc aggtgagaag    2760
ttggcagtcg gttagcctgg gttagataag gcaaactgaa cagatctaat ttaggaagtc    2820
agtagaattt aataattcta ttattattct taataatttt tctataacta tttcttttta    2880
taacaatttg gaaaatgtgg atgtcttta tttccttgaa gcaataaact aagtttcttt    2940
ttataaaaa                                                           2949
```

PREDICTION OF EFFECT OF A C-MET INHIBITOR USING MUTATION OF KRAS OR BRAF

CROSS-REFERENCE TO RELATED APPLICATIONS

This application claims the benefit of Korean Patent Application No. 10-2014-0130560 filed on Sep. 29, 2014 in the Korean Intellectual Property Office, the entire disclosure of which is hereby incorporated by reference.

INCORPORATION BY REFERENCE OF ELECTRONICALLY SUBMITTED MATERIALS

Incorporated by reference in its entirety herein is a computer-readable nucleotide/amino acid sequence listing submitted herewith and identified as follows: One 157,756 byte ASCII (Text) file named "721498_ST25.TXT," created Sep. 28, 2015.

BACKGROUND OF THE INVENTION

1. Field

The present disclosure relates to methods for predicting and/or monitoring the effect of administration of a c-Met inhibitor to a subject by analyzing one or more biomarkers, a method for selecting a subject suitable for the application of a c-Met inhibitor using one or more biomarkers, and a method for preventing and/or treating cancer comprising administering a c-Met inhibitor to the selected subject.

2. Description of the Related Art

A biomarker generally refers to a measured characteristic (e.g., a naturally occurring protein) which may be used as an indicator of some change caused in an organism by an external factor (e.g., injury). Active studies have recently been made to apply biomarkers to the diagnosis of various diseases, such as cancer, stroke, dementia, etc., and the prediction or monitoring of therapeutic effects of some agents. Among biomarkers relevant to drug development are pharmacodynamic markers (PD markers) for indicating whether drugs are functionally effective in vivo, and predictive markers for indicating the most likely response to particular drugs before administration. The use of such markers is helpful in establishing the clinical strategy of drugs. For example, a predictive marker, designed to indicate sensitivity or resistance to drug action, may be applied to the selection of patients to allow for more effective drug therapy while the activity of a drug in individual patients can be monitored with a pharmacodynamic marker, which together can lead to the establishment of effective therapeutic strategies. Further, even in the absence of a predictive marker, a pharmacodynamic marker permits the early monitoring of responses to a drug, thus allowing one to identify drug-effective groups from drug-ineffective groups at an early stage. Consequentially, more effective and successful drug therapies can be developed. In addition, when applied to the monitoring of responses to a drug as a function of concentrations, a pharmacodynamic marker can be an index for calculating suitable doses of the drug.

To date, cancer is one of the leading causes of death. Although the development of medical techniques has brought about a remarkable progress in cancer therapy, the 5-year survival rate of all cancers has only improved by 10% over the past two decades. This is because cancer characteristics, such as rapid growth, metastasis, etc., make it difficult to diagnose and treat within a suitable time. The identification of suitable biomarkers that provide information regarding the efficacy of a cancer therapy can greatly impact the ability to provide the most suitable cancer therapies at the most optimal times. For example, patients with lung cancer may differ from each other in cancer classification, genotype, and protein secretion, and thus must be treated with different, proper therapeutics. For chemotherapy using a specific drug, a corresponding biomarker, if present, would reduce the number of erroneous trials and increase possibility of success. In this regard, it is very important to explore biomarkers for predicting or monitoring the effect of anti-cancer therapeutics. A proper biomarker, if successfully exploited, can make a great contribution to the utility and value of anti-cancer drugs and the success rate of treatment with them.

c-Met is a hepatocyte growth factor (HGF) receptor. Hepatocyte growth factor (HGF) acts as a multi-functional cytokine which binds to the extracellular domain of the c-Met receptor to regulate cell division, cell motility, and morphogenesis in various normal and tumor cells. The c-Met receptor is a membrane receptor that possesses tyrosine kinase activity. c-Met is a proto-oncogene, that encodes the representative receptor tyrosine kinase. Occasionally, it takes part in a variety of mechanisms responsible for the development of cancer such as oncogenesis, metastasis, migration, angiogenesis, and invasion of cancer cells, etc., irrespective of the ligand HGF, and thus has attracted intensive attention as a target for anti-cancer therapy. Thus targeted therapies, such as antibodies against c-Met, have been developed.

A therapy with a developed c-Met targeting drug might be more effective treating cancer, with an elevated probability of success if there is a biomarker that is capable of predicting and monitoring the therapeutic effect of the drug to select patients suitable for the drug therapy and to monitor patient responses to the drug. Thus, the use of biomarkers could be applied to the establishment of effective therapeutic strategies.

BRIEF SUMMARY OF THE INVENTION

Also provided is a method for predicting and/or monitoring the effect of a c-Met inhibitor, or selecting a subject suitable for the application of a c-Met inhibitor, including measuring the existence (presence/absence), the level, and/or detecting/testing for a mutation of at least one selected from the group consisting of IL-8, b-IG-H3, MIF, KRAS/BRAF, and nucleic acids encoding the proteins, in a biological sample.

Another embodiment provides a method for inhibiting c-Met or preventing and/or treating a cancer, which methods including administering a c-Met inhibitor to the selected subject selected by the disclosed methods as being suitable for application of the c-Met inhibitor.

BRIEF DESCRIPTION OF THE DRAWINGS

FIG. 3 contains graphs showing the serum level changes of IL-8 in response to the different doses of the anti-c-Met antibody in responder and non-responder groups of the human cancer cell-implanted mouse models.

DETAILED DESCRIPTION OF THE INVENTION

Figure 1A:
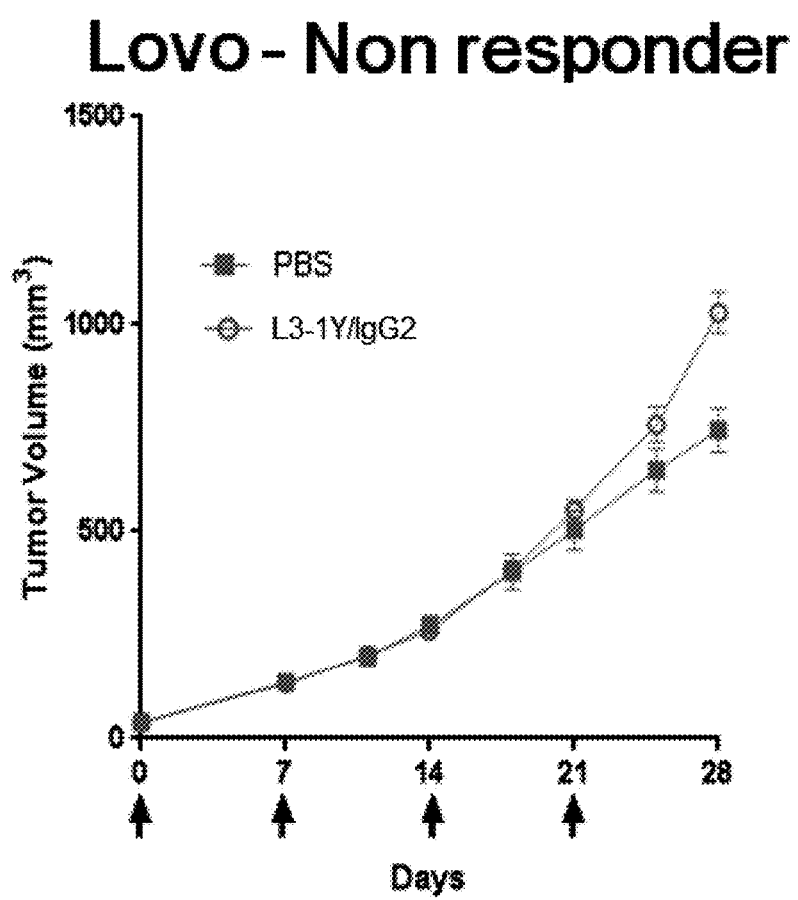
FIGS. 1A, 1B, 1C, 1D, and 1E are graphs showing the anticancer activity of an anti-c-Met antibody in terms of changes in tumor size with treatment with the anti-c-Met antibody in mouse models implanted with Lovo cells (FIG. 1A), HT29 cells (FIG. 1B), EBC-1 cells (FIG. 1C), Hs746T cells (FIG. 1D), and MKN45 cells (FIG. 1E).
Figure 1B:
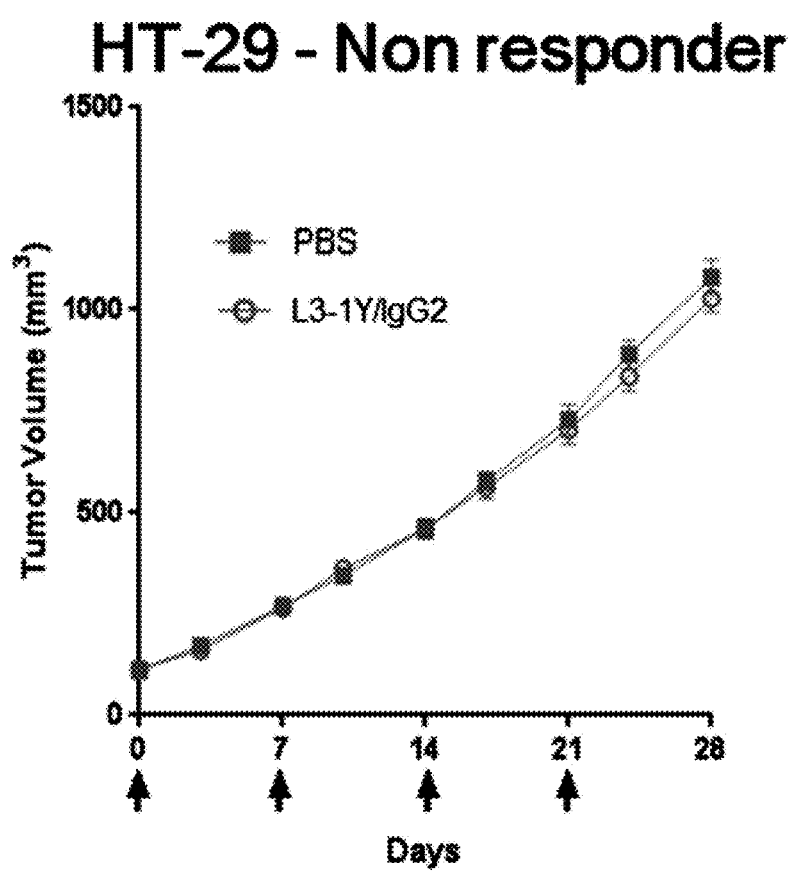
Figure 1C:
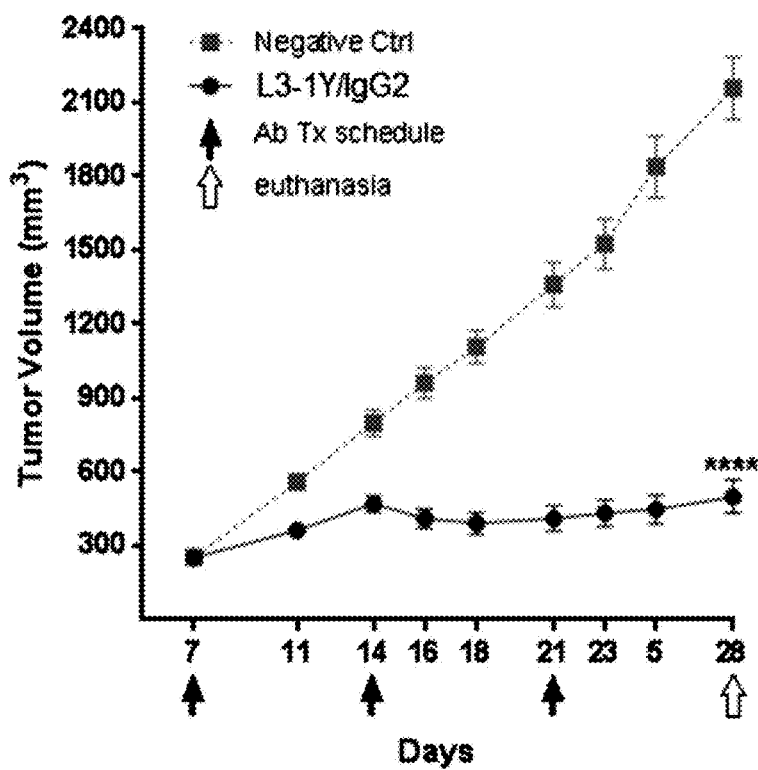
Figure 1D:
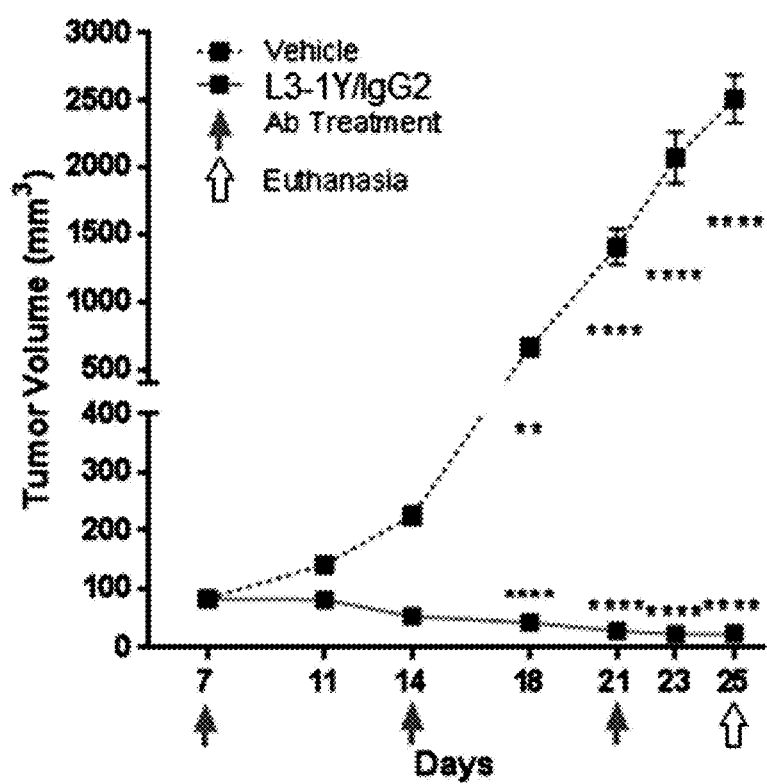

One embodiment provides a biomarker for use in predicting and/or monitoring the therapeutic effect of a c-Met inhibitor or selecting a subject suitable for the application of a c-Met inhibitor, wherein the biomarker includes at least one selected from the group consisting of IL-8, b-IG-H3, MIF, KRAS/BRAF, and nucleic acids encoding the proteins.

Another embodiment provides a use of a biomarker for predicting and/or monitoring the therapeutic effect of a c-Met inhibitor or selecting a subject suitable for the application of a c-Met inhibitor, wherein the biomarker includes at least one selected from the group consisting of IL-8, b-IG-H3, MIF, KRAS/BRAF, and nucleic acids encoding the proteins.

Another embodiment provides a composition and a kit for use in predicting and/or monitoring the effect of a c-Met inhibitor or selecting a subject to which a c-Met inhibitor is applicable (i.e., will exhibit efficacy), comprising a material interacting with at least one selected from the group consisting of IL-8, b-IG-H3, MIF, KRAS/BRAF, and nucleic acids encoding the proteins.

Another embodiment provides a use of a composition and a kit comprising a material interacting with at least one selected from the group consisting of IL-8, b-IG-H3, MIF, KRAS/BRAF, and nucleic acids encoding the proteins, for predicting and/or monitoring the effect of a c-Met inhibitor or selecting a subject suitable for the application of a c-Met inhibitor or for preparing an agent (pharmaceutical composition) for predicting and/or monitoring the effect of a c-Met inhibitor or selecting a subject suitable for the application of a c-Met inhibitor.

Another embodiment provides a material interacting with at least one selected from the group consisting of IL-8, b-IG-H3, MIF, KRAS/BRAF, and nucleic acids encoding the proteins, for use in predicting and/or monitoring the effect of a c-Met inhibitor or selecting a subject suitable for the application of a c-Met inhibitor.

Another embodiment provides a use of a material interacting with at least one selected from the group consisting of IL-8, b-IG-H3, MIF, KRAS/BRAF, and nucleic acids encoding the proteins, for predicting and/or monitoring the effect of a c-Met inhibitor or selecting a subject suitable for the application of a c-Met inhibitor.

Another embodiment provides a method for predicting and/or monitoring the effect of a c-Met inhibitor or selecting a subject to which a c-Met inhibitor is applicable (i.e., will exhibit efficacy), comprising the analysis of at least one biomarker selected from the group consisting of IL-8, b-IG-H3, MIF, KRAS/BRAF, and nucleic acids encoding the proteins.

Another embodiment provides a method for predicting and/or monitoring the efficacy of c-Met inhibitor or for providing information on the prediction and/or monitoring of the efficacy of a c-Met inhibitor, comprising measuring existence, level, and/or mutation of at least one selected from the group consisting of IL-8, b-IG-H3, MIF, KRAS/BRAF, and nucleic acids encoding the proteins, in a biological sample.

Another embodiment provides a method for selecting a subject suitable for the application of a c-Met inhibitor, comprising measuring for existence, level and/or mutation of at least one selected from the group consisting of IL-8, b-IG-H3, MIF, KRAS/BRAF, and nucleic acids encoding the proteins, in a biological sample obtained from a subject.

Another embodiment provides a c-Met inhibitor or a pharmaceutical composition including a c-Met inhibitor, for use in inhibiting c-Met and/or treating a cancer in a subject, wherein the subject has a high level of IL-8 or a nucleic acid encoding IL-8 compared to a reference sample in which a c-Met inhibitor is not effective; shows a decreased level of IL-8, bIG-H3, MIF, and/or nucleic acids encoding them after administering a c-Met inhibitor (compared to that of before the administration); and/or has a mutation of KRAS, BRAF, and/or nucleic acids encoding them.

Another embodiment provides a use of a c-Met inhibitor or a pharmaceutical composition including a c-Met inhibitor, for inhibiting c-Met and/or treating a cancer in a subject or for preparing a pharmaceutical composition for inhibiting c-Met and/or treating a cancer in a subject, wherein the subject has a high level of IL-8 or a nucleic acid encoding IL-8 compared to a reference sample in which a c-Met inhibitor is not effective; shows a decreased level of IL-8, bIG-H3, MIF, and/or nucleic acids encoding them after administering a c-Met inhibitor (compared to that of before the administration); and/or has a mutation of KRAS, BRAF, and/or nucleic acids encoding them.

Another embodiment provides a method for preventing and/or treating cancer, comprising administering a c-Met inhibitor to a subject, wherein the subject has a high level of IL-8 or a nucleic acid encoding IL-8 compared to a reference sample in which a c-Met inhibitor is not effective, as defined below; shows a decreased level of IL-8, bIG-H3, MIF, and/or nucleic acids encoding them after administering a c-Met inhibitor (compared to that of before the administration); and/or has a mutation of KRAS, BRAF, and/or nucleic acids encoding them. For example, the subject may be selected by the above method for selecting a subject suitable for the application of a c-Met inhibitor. This preventing or treating method may further comprise selecting a subject suitable for the application of the c-Met inhibitor, prior to the administration.

Another embodiment provides a method for inhibiting c-Met, comprising administering a c-Met inhibitor to a subject, wherein the subject has a high level of IL-8 or a nucleic acid encoding IL-8 compared to a reference sample in which a c-Met inhibitor is not effective, as defined below; shows a decreased level of IL-8, bIG-H3, MIF, and/or nucleic acids encoding them after administering a c-Met inhibitor (compared to that of before the administration); and/or has a mutation of KRAS, BRAF, and/or nucleic acids encoding them. For example, the subject may be selected by the above method for selecting a subject suitable for the application of a c-Met inhibitor. This inhibiting method may further comprise selecting a subject suitable for the application of the c-Met inhibitor, prior to the administration.

As used herein, the term "efficacy" of a c-Met inhibitor refers to a c-Met inhibitory effect and/or the pharmaceutical activity of a c-Met inhibitor resulting in the prevention, amelioration, reduction, or treatment of a c-Met-related disease, for instance, a cancer. As regards cancer, the efficacy refers to an anticancer or antitumor effect, for example, an ability to induce the reduction or death of cancer cells or tissues, and the suppression of cancer cell migration and/or invasion responsible for cancer metastasis. In other words, the efficacy may refer to responsiveness of a subject, who is administered with a c-Met inhibitor, to the c-Met inhibitor.

As used herein, the term "predicting an efficacy of a c-Met inhibitor" may refer to determining whether or not a c-Met inhibitor is likely to be effective, or estimating how much of an effect (e.g., an antitumor or anticancer efficacy) the c-Met inhibitor is likely to exhibit on a subject who is to be treated therewith.

As used herein, the wording "a subject suitable for the application of a c-Met inhibitor" may refer to "a subject suitable for administration or treatment with a c-Met inhibitor" or "a subject with a disease (e.g., cancer) that is likely to respond to the c-Met inhibitor".

The expression level of a certain protein may be determined by quantitatively analyzing the protein or the gene (nucleic acid) encoding it, such as DNA, cDNA or mRNA. As used herein, the term "gene" refers to any nucleic acid encoding the protein, whether genomic DNA, cDNA, or RNA (mRNA). The determination of KRAS/BRAF mutations may be achieved at a gene level or a protein level.

IL-8 (Interleukin 8) is a chemokine functioning as an important mediator of immune responses. IL-8, also known as neutrophil chemotactic factor, has two primary functions: it induces chemotaxis in target cells, primarily neutrophils but also other granulocytes, causing them to migrate toward the site of infection; and also phagocytosis once they have arrived. IL-8 is also known to be a potent promoter of angiogenesis contributing to the proliferation and metastasis of tumor cells. In one exemplary embodiment of the present invention, a response to a c-Met inhibitor varies depending on the expression level of IL-8, and a difference in the expression level of IL-8 between biological samples before and after treatment with an c-Met inhibitor is dependent on the response to the c-Met inhibitor (see Example 1). Briefly, a higher level of IL-8 or its gene in a biological sample indicates that a c-Met inhibitor, e.g., an anti-c-Met antibody, more efficiently exerts its function on the biological sample or a patient from which the biological sample is sourced. In addition, a biological sample in which a c-Met inhibitor, for example, an anti-c-Met antibody, functions well (drug response group), a decrease in the level of IL-8 or its gene after the application of the c-Met inhibitor, compared to before the application, is typically observed.

That is, an expression level of IL-8 can be used to predict the efficacy of an c-Met inhibitor and thus to select a subject suitable for treatment with the c-Met inhibitor, or a change in the expression level of IL-8 according to, or before and after treatment with a c-Met inhibitor allows for the evaluation (identification) or monitoring of the efficacy of the c-Met inhibitor, thereby being useful in determining whether the c-Met inhibitor should continue to be applied, or in establishing the therapeutic strategy of the c-Met inhibitor with regard to dose, dosing interval, and dosing number. Based on this finding, the use of IL-8 as a marker for indicating and/or monitoring the efficacy of a c-Met inhibitor is suggested.

The IL-8 may originate from vertebrates including mammals, such as rodents, e.g., mice, rat, etc., and primates, e.g., humans, monkeys, etc., birds, reptiles, amphibians, and fishes. For example, the IL-8 may be selected from the group consisting of NP_000575, NC_000004, NG_029889, NC_018915.2, and AC_000136. An IL-8-encoding gene (mRNA) may be selected from among NM_000584, BC013615, M28130.1, NM_001032965.1, S78555.1, and U19849.1.

One embodiment is directed to the analysis of a biomarker for the prediction and/or monitoring of the efficacy of a c-Met inhibitor comprising the analysis of (e.g., measuring the level of) at least one selected from the group consisting of IL-8 and a nucleic acid (e.g., gene) encoding IL-8.

Another embodiment is directed to the analysis of a biomarker for the selection of a subject suitable to the application of a c-Met inhibitor, comprising the analysis of (e.g., measuring the level of) at least one selected from the group consisting of IL-8 and a nucleic acid (e.g., gene) encoding IL-8.

A further is directed to a composition and a kit for the prediction and/or monitoring of the efficacy of a c-Met inhibitor, comprising a material capable of interacting with at least one selected from the group consisting of IL-8 and a nucleic acid (e.g., gene) encoding IL-8.

A further embodiment addresses a composition and a kit for the selection of a subject suitable to the application of a c-Met inhibitor, comprising a material interacting with at least one selected from the group consisting of IL-8 and a nucleic acid (e.g., gene) encoding IL-8.

Another embodiment is a method for predicting and/or monitoring the efficacy of a c-Met inhibitor or for offering information on the prediction and/or monitoring of the efficacy of a c-Met inhibitor, comprising measuring a biological sample for a level of at least one selected from the group consisting of IL-8 and a nucleic acid (e.g., gene) encoding IL-8.

Another embodiment provides a method for selecting a subject suitable to the application of a c-Met inhibitor or for offering information on the selection of a subject suitable to the application of a c-Met inhibitor, comprising measuring a biological sample for a level of at least one selected from the group consisting of IL-8 and a nucleic acid (e.g., gene) encoding IL-8.

Provided according to one embodiment is a method for predicting the efficacy of a c-Met inhibitor, for offering information on the prediction of the efficacy of a c-Met inhibitor, for selecting a subject suitable to the application of a c-Met inhibitor, or for offering information of the selection of a subject suitable to the application of a c-Met inhibitor, comprising measuring a level of at least one selected from the group consisting of IL-8 and a nucleic acid (e.g., gene) encoding IL-8 in a biological sample. In the method for predicting the efficacy of a c-Met inhibitor or for offering information on the efficacy of a c-Met inhibitor, when a biological sample is measured to have a high level of at least one selected from the group consisting of IL-8 and a nucleic acid (e.g., gene) encoding IL-8, the biological sample or a patient from which the biological sample is originated can be predicted to allow the c-Met inhibitor to effectively exert its activity or may be considered to be suitable for the application of the c-Met inhibitor. Hence, the method for predicting the efficacy of a c-Met inhibitor or for offering information on the efficacy of a c-Met inhibitor may further comprise determining that the c-Met inhibitor exhibits its efficacy in the biological sample or the patient when the biological sample is observed to have a high level of at least one selected from the group IL-8 or a nucleic acid (e.g., gene) encoding IL-8 after the measurement. In addition, the method for selecting a subject suitable to the application of a c-Met inhibitor or for offering information on the selection may further comprise determining the biological sample or the patient as a subject suitable for the application of the c-Met inhibitor when the biological sample is observed to have a high level of at least one selected from the group IL-8 or a nucleic acid (e.g., gene) encoding IL-8 after the measurement.

"A high level of at least one selected from the group consisting of IL-8 and a nucleic acid (e.g., gene) encoding IL-8" may refer to a large amount of IL-8 protein and/or a nucleic acid (e.g., gene) encoding IL-8 (DNA, cDNA or mRNA), compared to a biological sample (reference sample) from a patient in which a c-Met inhibitor to be applied does not exert therapeutic activity. For example, when the level of at least one selected from IL-8 and a nucleic acid (e.g., gene) encoding IL-8 in a test biological sample from a test patient is at least about 1.5-, about 2-, about 3-, about 4-, or about 5-fold, for example, about 1.5- to about 100-fold, about 2- to about 100-fold, about 3- to about 100-fold, about 4- to about 100-fold, or about 5- to about 100-fold greater in weight than that in a reference biological sample on which the c-Met inhibitor to be applied does not exert its efficacy (e.g., a c-Met inhibitory efficacy or an anticancer efficacy), the c-Met inhibitor is predicted to effectively exert its efficacy (e.g., a c-Met inhibitory efficacy or an anticancer efficacy) in the test biological sample or the test patient, or the test biological sample or the test patient can be considered as a subject suitable to the application of the c-Met inhibitor. The c-Met inhibitor may be, for example, an anti-c-Met antibody. The reference biological sample can be any sample useful for comparing the expression of the c-Met biomarker and/or c-Met inhibitor efficacy, such as a biological sample comprising cells, such as a mammalian cancer cell, in which the c-Met inhibitor does not have its efficacy (e.g., a c-Met inhibitory or anticancer efficacy). Examples of the reference biological sample on which the c-Met inhibitor does not exert its efficacy include, but are not limited to, the Lovo cell line (CCL-229, ATCC), and the HT-29 cell line (HTB-38, ATCC). Therefore, the method for predicting the efficacy of a c-Met inhibitor (or for offering information on the prediction of the efficacy of a c-Met inhibitor) or for selecting a subject suitable to the application of a c-Met inhibitor (or for offering information of the selection of a subject suitable to the application of a c-Met inhibitor) may further comprise a step of measuring a level of at least one selected from the group consisting of IL-8 and a nucleic acid (e.g., gene) encoding IL-8 in a reference biological sample. The measurement of the level of IL-8 and/or a nucleic acid (e.g., gene) encoding IL-8 (e.g., quantitative analysis) may be performed by the same method in both the test biological sample and the reference biological sample.

Measuring the biological sample for a level of at least one selected from among IL-8 and a nucleic acid (e.g., gene) encoding IL-8 may comprise i) treating (reacting or contacting) the biological sample with a material interacting with at least one selected from the group consisting of IL-8 and a nucleic acid (e.g., gene) encoding IL-8; and ii) quantitatively analyzing the reaction mixture to determine the level of at least one selected from IL-8 and a nucleic acid (e.g., gene) encoding IL-8. In an embodiment, prior to step i), a step of preparing a biological sample may be further performed, wherein the preparation step may comprise obtaining (isolating) a biological sample from a patient or obtaining a biological sample which has been isolated from a patient. In step i), the interacting material may be at least one selected from the group consisting of compounds (a small molecular chemical; e.g., general label such as a fluorescent, a dye, etc.), proteins (antibodies, aptamers, etc.) nucleic acid (DNA, RNA, etc.), and the like, binding to IL-8 or IL-8 gene, and for example, the interacting material may be a compound (a small molecular chemical; e.g., general label such as a fluorescent, a dye, etc.), an antibody, or an aptamer, all binding (e.g., specifically binding) to IL-8, a polynucleotide (e.g., a primer, a probe, an aptamer) binding to a part or entirety of a nucleic acid (e.g., gene) encoding IL-8, or any combination thereof; and optionally, may be conjugated with a general label, such as a fluorescent, a secondary antibody, a bead (e.g., a magnetic bead or polystyrene bead), a dye, or any combination thereof. The step i) may be configured to form a complex by adding the interacting material to the biological sample. In step ii), the reaction mixture may be the complex resulting from interaction (binding) between at least one selected from the group consisting of IL-8 and a nucleic acid (e.g., gene) encoding IL-band the interacting material, which can be obtained in step i). Quantitatively analyzing may comprise quantifying the complex, the label conjugated to the complex, or the IL-8 or nucleic acid (e.g., gene) encoding IL-8 segregated from the complex after the isolation of the complex from the biological sample.

Provided in accordance with another embodiment is a method for monitoring (evaluating or identifying) the efficacy of a c-Met inhibitor or for offering information on the monitoring (evaluation or identification) of the efficacy of a c-Met inhibitor, comprising measuring a level of at least one selected from the group consisting of IL-8 and a nucleic acid (e.g., gene) encoding IL-8 in a biological sample. In the method for monitoring the efficacy of a c-Met inhibitor or for offering information on the monitoring of the efficacy of a c-Met inhibitor, levels of at least one selected from the group consisting of IL-8 and a nucleic acid (e.g., gene) encoding IL-8 in biological samples from a patient before and after treatment with the c-Met inhibitor (or in a c-Met inhibitor-untreated biological sample and a c-Met inhibitor-treated biological sample) may be measured and compared to each other. When the post-treatment level of at least one selected from the group consisting of IL-8 and a nucleic acid (e.g., gene) encoding IL-8 is lower (decreased) compared to the pre-treatment level, the c-Met inhibitor is determined to exert its efficacy in the patient from which the biological sample is sourced (obtained), whereas when the post-treatment level of at least one selected from the group consisting of IL-8 and a nucleic acid (e.g., gene) encoding IL-8 is the same with or higher (increase) compared to the pre-treatment level, it is determined that the c-Met inhibitor does not exert its efficacy or a resistance to the c-Met inhibitor occurs in the patient from which the biological sample is sourced (obtained). Therefore, the method for monitoring the efficacy of a c-Met inhibitor or for offering information on the monitoring of the efficacy of a c-Met inhibitor may further comprise 1) comparing the levels of at least one selected from the group consisting of IL-8 and a nucleic acid (e.g., gene) encoding IL-8 in a biological sample from the c-Met inhibitor-treated group with that in a biological sample from the untreated group, and/or 2) determining that the c-Met inhibitor exerts its efficacy in the biological sample-derived patient when the level of at least one selected from the group consisting of IL-8 and a nucleic acid (e.g., gene) encoding IL-8 in the biological sample of the c-Met inhibitor-treated group is reduced, compared to that of the untreated group (in this case, it may be determined to maintain (continue) the administration of a c-Met inhibitor to the subject), and/or 3) determining that the c-Met inhibitor does not exert its efficacy or a resistance to the c-Met inhibitor occurs in the biological sample-derived patient when the level of at least one selected from the group consisting of IL-8 and a nucleic acid (e.g., gene) encoding IL-8 in the biological sample of the c-Met inhibitor-treated group is maintained or increased (in this case, it may be determined to stop the administration of a c-Met inhibitor to the subject). The c-Met inhibitor may be an anti-c-Met antibody.

As used herein, the c-Met inhibitor-treated group and the untreated group mean the same biological sample after and before treatment with a c-Met inhibitor, respectively, or aliquots of the same biological sample which are treated with and are not treated with a c-Met inhibitor (for example, treated only with a vehicle), respectively. Unless stated otherwise, the terms "c-Met inhibitor-untreated group (or biological sample)" and "biological sample before treatment with a c-Met inhibitor" or "pre-treatment biological sample" are identical to each other while the terms "c-Met inhibitor-treated group (or biological sample)" and "biological sample after treatment with a c-Met inhibitor" or "post-treatment biological sample" share the same meaning. In an embodiment, the term "c-Met inhibitor-untreated group (or biological sample)" and "biological sample before treatment with a c-Met inhibitor" or "pre-treatment biological sample" may refer to a biological sample obtained from a subject prior to the administration with a c-Met inhibitor to the subject, and the terms "c-Met inhibitor-treated group (or biological sample)" and "biological sample after treatment with a c-Met inhibitor" or "post-treatment biological sample" may refer to a biological sample obtained from a subject after the administration with a c-Met inhibitor to the subject.

The level of at least one selected from the group consisting of IL-8 and a nucleic acid (e.g., gene) encoding IL-8 may be measured by quantifying an IL-8 protein and/or a nucleic acid (e.g., gene) encoding IL-8 (DNA, cDNA or mRNA). For example, when the level of at least one selected from the group consisting of IL-8 and a nucleic acid (e.g., gene) encoding IL-8 in the c-Met inhibitor-treated group or in the biological sample after treatment with a c-Met inhibitor is about 0 to about 80 wt %, about 0 to about 70 wt %, about 0 to about 60 wt %, about 0 to about 50 wt %, about 0 to about 40 wt %, about 0 to about 30 wt %, about 0 to about 20 wt %, or about 0 to about 10 wt % compared to that (considering 100 wt %) of the c-Met inhibitor-untreated group or the pre-treatment biological sample, the c-Met inhibitor-treated group, or the post-treatment sample biological, is determined to decrease in the level of at least one selected from the group consisting of IL-8 and a nucleic acid (e.g., gene) encoding IL-8, compared to the c-Met inhibitor-untreated or the pre-treatment biological sample. When the level of IL-8 and a nucleic acid (e.g., gene) encoding IL-8 in the c-Met inhibitor-treated group or the post-treatment biological sample is about 0 wt % of that in the c-Met inhibitor-untreated group or the pre-treatment biological sample there is no detection (absence) of at least one selected from the IL-8 and a nucleic acid (e.g., gene) encoding IL-8 in the c-Met inhibitor-treated group or the post-treatment biological sample. Levels of IL-8 and/or a nucleic acid (e.g., gene) encoding IL-8 in the c-Met inhibitor-untreated group (or pre-treatment) and the c-Met inhibitor-treated group (or post-treatment) may be measured by conducting the same procedure on sample samples from the same patient.

Monitoring the efficacy of an c-Met inhibitor, IL-8 and/or a nucleic acid (e.g., gene) encoding IL-8 may be quantitatively analyzed within a relatively short period of time, for example, a week, 5 days, 3 days, 2 days or 1 day after administration of the c-Met inhibitor, and comparison between levels of the marker before and after administration thereof can evaluate the efficacy of c-Met inhibitor. Henceforth, the advantage of establishing a more effective therapeutic strategy can be achieved, since it is possible to evaluate the efficacy of the c-Met inhibitor in an early stage of therapy.

In one embodiment, the measuring of a level of at least one selected from the group consisting of IL-8 and a nucleic acid (e.g., gene) encoding IL-8 in a biological sample may comprise 1) determining a level of at least one selected from the group consisting of IL-8 and a nucleic acid (e.g., gene) encoding IL-8 in a biological sample from a patient prior to treatment with a c-Met inhibitor (or a c-Met inhibitor untreated biological sample which is a part of biological sample from a patient) and 2) determining a level of at least one selected from the group consisting of IL-8 and a nucleic acid (e.g., gene) encoding IL-8 in a biological sample from the patient after treatment with a c-Met inhibitor (or a c-Met inhibitor treated biological sample which is the other part of biological sample from a patient). Each of the steps 1) and 2) may comprise i) applying (adding) a material interacting with at least one selected from the group consisting of IL-8 and a nucleic acid (e.g., gene) encoding IL-8 to the biological sample, and ii) quantitatively analyzing the resulting reaction mixture to determine a level of at least one selected from the group consisting of IL-8 and a nucleic acid (e.g., gene) encoding IL-8. In an embodiment, prior to the step i), a step of preparing a biological sample may be further performed, wherein the preparation step may comprise obtaining (isolating) a biological sample from the patient or obtaining a biological sample which has been isolated from a patient. In step i), as will be further elucidated below, the interacting material may be at least one selected from the group consisting of compounds (a small molecular chemical; e.g., general label such as a fluorescent, a dye, etc.), proteins (antibodies, aptamers, etc.) nucleic acid (DNA, RNA, etc.), and the like, binding to IL-8 or IL-8 gene, and for example, the interacting material may be at least one selected from the group consisting of a compound, an antibody, an aptamer, all specifically binding to IL-8, and a polynucleotide (e.g., a primer, a probe, an aptamer) binding to a part or entirety of a gene encoding IL-8, and optionally, may be conjugated with a label, such as a fluorescent or a dye. The step i) may be configured to form a complex by applying (adding) the interacting material to the biological sample. In step ii), the reaction mixture may be a complex resulting from interaction (binding) between at least one selected from the group consisting of IL-8 and a nucleic acid (e.g., gene) encoding IL-8 and the interacting material, which can be obtained in step i). The quantitatively analyzing step may comprise quantifying the complex, the marker conjugated to the complex, or the IL-8 or the gene segregated from the complex after the isolation of the complex from the biological sample. The quantitative analysis of IL-8 may be performed by any general quantifying means of proteins, such as ELISA, immunohistochemistry, and the like, and the quantitative analysis of IL-8 gene may be performed by any general quantifying means of genes (DNA or RNA), such as qPCR, mRNA microarray, and the like, but not limited thereto.

The monitoring method may be useful in determining whether the c-Met inhibitor continues to be used, and/or suitable dosing conditions of the c-Met inhibitor (dose, dosing interval, number of doses, etc.). For example, when the level of at least one selected from the group consisting of IL-8 and a nucleic acid (e.g., gene) encoding IL-8 in the c-Met inhibitor-treated group or in the post-treatment biological sample is reduced, compared to the c-Met inhibitor-untreated group or the pre-treatment biological sample, for example, when the level of at least one selected from the group consisting of IL-8 and a nucleic acid (e.g., gene) encoding IL-8 in the c-Met inhibitor-treated group or in the post-treatment biological sample is about 0 to about 80 wt %, about 0 to about 70 wt %, about 0 to about 60 wt %, about 0 to about 50 wt %, about 0 to about 40 wt %, about 0 to about 30 wt %, about 0 to about 20 wt %, or about 0 to about 10 wt % of that of the c-Met inhibitor-untreated group or the pre-treatment biological sample, the use of c-Met inhibitor may be determined to be continued. In addition, when the level of at least one selected from the group consisting of IL-8 and a nucleic acid (e.g., gene) encoding IL-8 in the c-Met inhibitor-treated group or in the post-treatment biological sample is reduced, compared to the c-Met inhibitor-untreated group or the pre-treatment biological sample, for example, when the level of at least one selected from the group consisting of IL-8 and a nucleic acid (e.g., gene) encoding IL-8 in the c-Met inhibitor-treated group or in the post-treatment biological sample is about 0 to about 80 wt %, about 0 to about 70 wt %, about 0 to about 60 wt %, about 0 to about 50 wt %, about 0 to about 40 wt %, about 0 to about 30 wt %, about 0 to about 20 wt %, or about 0 to about 10 wt %, of that of the c-Met inhibitor-untreated group or the pre-treatment biological sample, the dosing condition of the c-Met inhibitor may be determined to be suitable. The dosing condition may be at least one selected from the group consisting of a dose, a dosing interval, and a number of doses.

Another embodiment provides a method for inhibiting c-Met, comprising administering a c-Met inhibitor to a subject who has a high level of IL-8 and/or a nucleic acid encoding IL-8 (wherein the high level is defined above) and/or shows a decreased level of IL-8 and/or a nucleic acid encoding IL-8 after administration of a c-Met inhibitor (compared to before administration of the c-Met inhibitor). The subject may be 1) selected by the above method for selecting a subject suitable for the application of a c-Met inhibitor or 2) determined by the above method of monitoring efficacy of a c-Met inhibitor as a subject wherein a c-Met inhibitor exert its efficacy thereon.

Another embodiment provides a method for preventing and/or treating cancer, comprising administering a c-Met inhibitor to a subject who has a high level of IL-8 or a nucleic acid encoding IL-8 (wherein the high level is defined above) and/or shows a decreased level of IL-8 and/or a nucleic acid encoding IL-8 after administration of a c-Met inhibitor (compared to before administration of the c-Met inhibitor). The subject may be 1) selected by the above method for selecting a subject suitable for the application of a c-Met inhibitor or 2) determined by the above method of monitoring efficacy of a c-Met inhibitor as a subject wherein a c-Met inhibitor exert its efficacy thereon.

The method for inhibiting c-Met or the method for preventing and/treating cancer may further comprise selecting a subject to which the c-Met inhibitor is applicable, prior to the administering step. Details of the selection are as described above. The c-Met inhibitor may be an anti-c-Met antibody.

In an embodiment, the method for inhibiting c-Met or for preventing and/or treating cancer may comprise:

identifying a subject to which a c-Met inhibitor is applicable; and administering a pharmaceutically effective amount of the c-Met inhibitor to the subject.

In another embodiment, the method for inhibiting c-Met or for preventing and/or treating cancer may comprise:

measuring a level of IL-8 and/or a nucleic acid (e.g., gene) encoding IL-8 in a biological sample to select a c-Met inhibitor-applicable subject; and administering a pharmaceutically effective amount of the c-Met inhibitor to the subject.

With regard to dosing conditions of the c-Met inhibitor, such as doses, dosing intervals and/or number of doses, they may be determined in the method for monitoring a c-Met inhibitor for efficacy.

Some anti-cancer agents such as sunitinib, cis-platin, paclitaxel, etc. often cannot exert their anticancer effects in individuals with a high level of IL-8 because they provoke resistance. In contrast, c-Met inhibitors, for example, anti-c-Met antibodies, particularly, those described below, can exhibit high anticancer activity in individuals with a high level of IL-8, thereby allowing for the suggestion of more effective therapeutic strategies.

bIG-H3, also known as TGFBI (transforming growth factor beta-induced), is RGD-containing protein that binds to type I, II and IV collagens. The RGD motif is found in ECM (extracellular matrix). Serves as a ligand binding to a3b1 integrin, bIG-H3 is involved in cell adhesion, and migration. bIG-H3 is a soluble protein and plays a role in cancer metastasis and angiogenesis in the tumor microenvironment. No reports have been made on a relationship between c-Met and bIG-H3, so far.

MIF (Macrophage migration inhibitory factor) is an important regulator of innate immunity and is classified as an inflammatory cytokine.

In the Example section of the specification, a difference in the expression level of bIG-H3 and/or MIF between c-Met inhibitor-treated groups and untreated groups or between a post-treatment group and a pre-treatment group was observed to vary depending in response to the c-Met inhibitor (refer to Examples 2 and 3). In detail, when a c-Met inhibitor, e.g., an anti-c-Met antibody functions well (drug responsive group), the level of at least one selected from the group consisting of bIG-H3, ME and nucleic acids encoding the proteins is lower after application of the c-Met inhibitor than before the application.

In other words, expression levels of at least one selected from the group consisting of bIG-H3, ME, and nucleic acids encoding the proteins before or after the application of a c-Met inhibitor are measured to assay (identify) or monitor the effect of the c-Met inhibitor, so that the measurements can be effectively used to determine whether the c-Met inhibitor should continue to be applied or not, or to establish a therapeutic strategy with regard to, for example, doses, dosing intervals, dose numbers of the c-Met inhibitor. Based on this finding, bIG-H3 and/or MIF as appear to be viable pharmacodynamic markers for c-Met inhibitors.

The bIG-H3 may originate from vertebrates including mammals, such as rodents, e.g., mice, rat, etc., and primates, e.g., humans, monkeys, etc., birds, reptiles, amphibians, and fishes. For example, the bIG-H3 may be selected from the group consisting of, but not limited to, human bIG-H3 (NP_000349, AAC24944, AAC08449, AAH00097), mouse bIG-H3 (NP_033395, AAI29901, AAI29902), rat bIG-H3 (NP_446254), and zebrafish bIG-H3 (NP_878282). A bIG-H3 encoding gene (mRNA) may be selected from the group consisting of, but not limited to, NM_000358, NM_009369, NM_182862, and NM_053802.

MIF may originate from vertebrates including mammals, birds, reptiles, amphibians, and fishes. For example, the MIF may be selected from the group consisting of, but not limited to, human ME (NP_002406), mouse MIF (NP_034928), rat ME (NP_112313), cow ME (NP_001028780) zebrafish MIF (NP_001036786), pig ME (NP_001070681), and frog ME (NP_001083650). An MIF-encoding gene (mRNA) may be selected from among, but not limited to, NM_002415, NM_010798, NM_001033608, NM_001043321, NM_001077213, NM_001124581, NM_001113675, NM_001279827, NM_001141547, NM_001078655, NM_001032915, and NM_001032717.

An embodiment provides a biomarker for evaluating the effect of a c-Met inhibitor, comprising at least one selected from the group consisting of bIG-H3, MIF, and nucleic acids encoding the proteins.

Another embodiment provides a composition and a kit for evaluating the effect of a c-Met inhibitor, comprising at least one selected from the group consisting of bIG-H3, MIF, and nucleic acids encoding the proteins.

Another embodiment provides a method for evaluating (or identifying or monitoring) the efficacy of a c-Met inhibitor or for offering information on the evaluation (or identifying or monitoring) of the efficacy of a c-Met inhibitor, comprising measuring a level of at least one selected from the group consisting of bIG-H3, MIF, and nucleic acids encoding the proteins in a biological sample.

In the method for monitoring the efficacy of a c-Met inhibitor or for offering information on the monitoring of the efficacy of a c-Met inhibitor, levels of at least one selected from the group consisting of bIG-H3, MIF and nucleic acids encoding the proteins in biological samples from a patient before and after treatment with the c-Met inhibitor (or in a c-Met inhibitor treated group biological sample and a c-Met inhibitor untreated biological sample) are measured and compared. When the post-treatment level of at least one selected from the group consisting of bIG-H3, MIF, and nucleic acids encoding the proteins is lower (decreased) compared to the pre-treatment level, the c-Met inhibitor is determined to exert its activity in the patient from which the biological sample is sourced (obtained), whereas when the post-treatment level of at least one selected from the group consisting of bIG-H3, MIF, and nucleic acids encoding the proteins is the same with or higher (increase) compared to the pre-treatment level, it is determined that the c-Met inhibitor does not exert its efficacy or a resistance to the c-Met inhibitor occurs in the patient from which the biological sample is sourced (obtained). Therefore, the method for monitoring the efficacy of a c-Met inhibitor or for offering information on the monitoring of the efficacy of a c-Met inhibitor may further comprise 1) comparing the level of at least one selected from the group consisting of bIG-H3, MIF, and nucleic acids encoding the proteins in a biological sample from the c-Met inhibitor-treated group with that in a biological sample from the untreated group, and/or 2) determining that the c-Met inhibitor exerts its efficacy in the biological sample-derived patient when the level of at least one selected from the group consisting of IL-8 and a nucleic acid (e.g., gene) encoding IL-8 in the biological sample of the c-Met inhibitor-treated group is reduced, compared to that of the untreated group (in this case, it may be determined to maintain (continue) the administration of a c-Met inhibitor to the subject), and/or 3) determining that the c-Met inhibitor does not exert its efficacy or a resistance to the c-Met inhibitor occurs in the biological sample-derived patient when the level of at least one selected from the group consisting of bIG-H3, MIF, and nucleic acids encoding the proteins in the biological sample of the c-Met inhibitor-treated group is maintained or increased (in this case, it may be determined to stop the administration of a c-Met inhibitor to the subject). The c-Met inhibitor may be an anti-c-Met antibody.

The level of at least one selected from the group consisting of bIG-H3, MIF and nucleic acids encoding the proteins may be measured by quantifying an bIG-H3 protein, an MIF protein and nucleic acids (DNA, cDNA or mRNA) encoding the proteins using the quantification techniques described, above. For example, when the level of at least one selected from the group consisting of bIG-H3, MIF and nucleic acids encoding the proteins in the c-Met inhibitor-treated group or in the biological sample after treatment with a c-Met inhibitor is about 0 to about 80 wt %, about 0 to about 70 wt %, about 0 to about 60 wt %, about 0 to about 50 wt %, about 0 to about 40 wt %, about 0 to about 30 wt %, about 0 to about 20 wt %, or about 0 to about 10 wt % of that of the c-Met inhibitor-untreated group or the pre-treatment biological sample," the c-Met inhibitor-treated group, or the post-treatment sample biological is determined to decrease in the level of at least one selected from the group consisting of bIG-H3, MIF and nucleic acids encoding the proteins, compared to the c-Met inhibitor-untreated or the pre-treatment biological sample. When the level of at least one selected from the group consisting of bIG-H3, MIF and nucleic acids encoding the proteins in the c-Met inhibitor-treated group or the post-treatment biological sample is about 0 wt % of that in the c-Met inhibitor-untreated group or the pre-treatment biological sample, there is no detection (absence) of at least one selected from the bIG-H3, MIF and nucleic acids encoding the proteins in the c-Met inhibitor-treated group or the post-treatment biological sample. Levels of bIG-H3, MIF and nucleic acids encoding the proteins in the c-Met inhibitor-untreated group (or pre-treatment) and the c-Met inhibitor-treated group (or post-treatment) may be measured by conducting the same procedure on sample samples from the same patient.

bIG-H3, MIF and nucleic acids encoding the proteins may be quantitatively analyzed within a relatively short period of time, for example, one month, two weeks, a week, 5 days, 3 days, 2 days or 1 day after administration of the c-Met inhibitor, and comparison between levels of the marker after and before administration thereof can evaluate the efficacy of c-Met inhibitor. Henceforth, the advantage of establishing a more effective therapeutic strategy can be achieved, since it makes it possible to evaluate the efficacy of the c-Met inhibitor in an early stage of therapy.

In one embodiment, the measuring of a level of at least one selected from the group consisting of bIG-H3, MIF and nucleic acids encoding the proteins in a biological sample may comprise 1) determining a level of at least one selected from the group consisting of bIG-H3, MIF and nucleic acids encoding the proteins in a biological sample from a patient prior to treatment with a c-Met inhibitor (or in a c-Met inhibitor untreated biological sample which is a part of biological sample from a patient) and 2) determining a level of at least one selected from the group consisting of bIG-H3, MIF and nucleic acids encoding the proteins in a biological sample from the patient after treatment with a c-Met inhibitor (or in a c-Met inhibitor treated biological sample which is a part of biological sample from a patient). Each of the steps 1) and 2) may comprise i) applying (adding) a material interacting with at least one selected from the group consisting of bIG-H3, MIF and nucleic acids encoding the proteins to the biological sample, and ii) quantitatively analyzing the resulting reaction mixture to determine a level of at least one selected from the group consisting of bIG-H3, MIF and nucleic acids encoding the proteins. In an embodiment, prior to the step i), a step of preparing a biological sample may be further performed, wherein the preparation step may comprise obtaining (isolating) a biological sample from the patient or obtained a biological sample which has been isolated from a patient. In step i), as will be further elucidated below, the interacting material may be at least one selected from the group consisting of compounds (a small molecular chemical; e.g., general label such as a fluorescent, a dye, etc.), proteins (antibodies, aptamers, etc.) nucleic acid (DNA, RNA, etc.), and the like, binding to bIG-H3, MIF, bIG-H3 gene or MIF gene, and for example, the interacting material may be at least one selected from the group consisting of a compound, an antibody, an aptamer, all specifically binding to bIG-H3 or MIF, and a polynucleotide (e.g., a primer, a probe, an aptamer) binding to a part or entirety of a gene encoding bIG-H3 or MIF, and optionally, may be conjugated with a label, such as a fluorescent, a secondary antibody, a bead (e.g., a magnetic or polystyrene bead), or a dye. The step i) may be configured to form a complex by applying (adding) the interacting material to the biological sample. In step ii), the reaction mixture may be a complex resulting from interaction (binding) between at least one selected from the group consisting of bIG-H3, MIF and nucleic acids encoding the proteins and the interacting material, which can be obtained in step i). The quantitative analysis step may comprise quantifying the complex, the label conjugated to the complex, or the bIG-H3 or the MIF, or the nucleic acid encoding same segregated from the complex after the isolation of the complex from the biological sample.

The evaluating method may be useful in determining whether the c-Met inhibitor continues to be used, and/or suitable dosing conditions of the c-Met inhibitor (dose, dosing interval, and number of dosing). For example, when the level of at least one selected from the group consisting of bIG-H3, MIF and genes in the c-Met inhibitor-treated group or in the post-treatment biological sample is reduced, compared to the c-Met inhibitor-untreated group or the pre-treatment biological sample, e.g., when the level of at least one selected from the group consisting of bIG-H3, MIF and genes in the c-Met inhibitor-treated group or in the post-treatment biological sample is about 0 to about 80 wt %, about 0 to about 70 wt %, about 0 to about 60 wt %, about 0 to about 50 wt %, about 0 to about 40 wt %, about 0 to about 30 wt %, about 0 to about 20 wt %, or about 0 to about 10 wt % of that of the c-Met inhibitor-untreated group or the pre-treatment biological sample, the use of c-Met inhibitor may be determined to be continued. In addition, when the level of at least one selected from the group consisting of bIG-H3, MIF and genes in the c-Met inhibitor-treated group or in the post-treatment biological sample is reduced, compared to the c-Met inhibitor-untreated group or the pre-treatment biological sample, e.g., when the level of at least one selected from the group consisting of bIG-H3, MIF and genes in the c-Met inhibitor-treated group or in the post-treatment biological sample is about 0 to about 80 wt %, about 0 to about 70 wt %, about 0 to about 60 wt %, about 0 to about 50 wt %, about 0 to about 40 wt %, about 0 to about 30 wt %, about 0 to about 20 wt %, or about 0 to about 10 wt % of that of the c-Met inhibitor-untreated group or the pre-treatment biological sample, the dosing condition of the c-Met inhibitor may be determined to be suitable. The dosing condition may be at least one selected from the group consisting of a dose, a dosing interval, and a number of doses. The dosing condition may be determined using the techniques described, above.

Another embodiment provides a method for inhibiting c-Met, comprising administering a c-Met inhibitor to a subject in need thereof. Another embodiment provides a method for preventing and/or treating cancer, comprising administering a c-Met inhibitor to a subject in need thereof. In the method for inhibiting c-Met or for preventing and/or treating cancer, the subject may be one showing a decreased level of bIG-H3, MIF, and/or nucleic acids encoding them after administering the c-Met inhibitor (compared to before the administration). For example, the subject may be 1) selected by the above method for selecting a subject suitable for the application of a c-Met inhibitor or 2) determined by the above method of monitoring efficacy of a c-Met inhibitor as a subject wherein a c-Met inhibitor exert its efficacy thereon.

In the method for inhibiting c-Met or for preventing and/or treating cancer, the administration of the c-Met inhibitor may be conducted according to the suitable dosing conditions determined by the evaluating method, such as a dose, a dosing interval, and/or a number of doses.

Levels of IL-8, bIG-H3, MIF, and nucleic acids (e.g., genes) encoding them can be measured by any general protein or gene assay method using a material interacting with the proteins or the genes. The material interacting with any of the proteins or the genes may be a compound, an antibody, or an aptamer, all specifically binding to IL-8, bIG-H3, or MIF 8 proteins, or a polynucleotide (e.g., a primer, a probe, an aptamer) binding to a part or entirety of a gene encoding IL-8, bIG-H3, or MIF proteins. For example, the levels of IL-8, bIG-H3, or MIF protein may be measured by detecting enzymatic reactions, fluorescence, luminescence and/or radioactivity using a compound (a small molecular chemical; e.g., general label such as a fluorescent, a dye, etc.), an antibody and/or an aptamer, which binds (e.g., specifically binds) to IL-8, bIG-H3, or MIF proteins. In detail, the level of the proteins may be determined using an analysis technique selected from among, but not limited to, immunochromatography, immunohistochemical staining, enzyme linked immunosorbent assay (ELISA), radioimmunoassay (RIA), enzyme immunoassay (ETA), fluorescence immunoassay (FIA), luminescence immunoassay (LIA), Western blotting, microchip, flow cytometry assay (e.g., Cytometric Bead Array (CBA) assay(BD biosciences), Intracellular staining, etc.), Luminex assay, and the like. In addition, the level of a gene encoding IL-8, bIG-H3 or MIF may be measured by a typical gene assay method using a primer, probe or aptamer hybridizable with the gene, for example, by polymerase chain reaction (PCR; e.g., qPCR), FISH (fluorescent in situ hybridization), or microarray assay. In one embodiment, the primer is designed to detect a fragment of successive base pairs out of the gene encoding IL-8, bIG-H3 or MIF5 (full-length DNA, cDNA or mRNA), for example, a fragment of 5 to 100 bp, e.g., about 10 to about 500 bp, about 20 to about 200 bp, or about 50 to about 200 bp, and may be a pair of primers having nucleotide sequences which are respectively hybridizable with (e.g., complementary to) 3'- and 5'-terminal regions ranging in size from about 5 to about 100 bp, e.g., about 5 to about 50 bp, about 5 to about 30 bp, or about 10 to about 25 bp. The probe or the aptamer hybridizable with the gene may have a nucleotide sequence with a size of from about 3 to about 100 bp, from about 3 to about 50 bp, from about 3 to about 30 bp, or from about 3 to about 25 bp, which is hybridizable with (or complementary to) a fragment of the IL-8, bIG-H3 or MIF-encoding gene (full-length DNA, cDNA or mRNA). As used herein, the term "hybridizable" means pertaining to complementarily binding to a specific region of the gene, with a sequence complementarity of 80% or higher, e.g., 90% or higher, 95% or higher, 98% or higher, 99% or higher, or 100% between the primer, probe or aptamer and the gene region.

The RAS-RAF pathway is a representative cell proliferation signaling pathway of which cancer cells take advantage in their growth. For this reason, the RAS-RAF pathway is a main target of anticancer drugs. Hence, a mutation of the RAS-RAF pathway may be an important factor that can affect the efficacy of a drug targeting the pathway.

In one exemplary embodiment of the present invention, a response to a c-Met inhibitor varies depending on the mutation of RAS and/or RAF (see Example 4). In greater detail, when a biological sample is observed to have a RAS and/or RAF mutation, a c-Met inhibitor, e.g., an anti-c-Met antibody does not work well in the biological sample or the patient from which the biological sample originates.

In other words, detection of the mutation of RAS and/or RAF may be effectively used to predict the efficacy of a c-Met inhibitor or to select a subject to which a c-Met inhibitor is applicable. Based on this finding, RAS-RAF is first suggested as a predictive maker for c-Met inhibitors. The mutation of RAS and/or RAF may be any mutation (substitution, deletion, and/or addition) of amino acids and/or nucleotides of RAS and/or RAF that has no effect on the function of RAS and/or RAF in oncogenic signaling pathways and that induces generation of more aggressive tumor or cancer.

RAS, a member of the GTPase superfamily, may be selected from the group consisting of KRAS, NRAS, and HRAS, all of which originate from vertebrates including mammals, such as rodents, e.g., mice, rat, etc., and primates, e.g., humans, monkeys, etc., birds, reptiles, amphibians, and fishes. For example, KRAS may be selected from the group consisting of, but not limited to, human KRAS (NP_004976.2, NP_203524.1, etc.), mouse KRAS (NP_067259.4, etc.), zebrafish KRAS (NP_001003744.1, etc.), frog KRAS (NP_001095209.1, etc.), cow KRAS (NP_001103471.1, etc.), chicken KRAS (NP_001243091.1, etc.), and monkey KRAS (NP_001248441.1, etc.). A KRAS-encoding gene (mRNA) may be selected from among, but not limited to, NM_004985.4, NM_021284.6, NM_033360.3, NM_001003744.1, NM_001101739.1, NM_001110001.1, NM_001032981.2, NM_031515.3, NM_001256162.2, NM_001261512.2, and NM_001008033.1.

The mutation of KRAS connected with the prediction of the effect of c-Met inhibitors may be a substitution on the codon 12 GGT (corresponding to Gly at position 12 of the amino acid sequence NP_004976) of wild-type KRAS (accession number: NM_004985) and/or on the codon 13 GGC (corresponding to Gly at position 12 of the amino acid sequence NP_004976), as shown in Table 1, below.

The mutation may also be a substitution for at least one amino acid residue selected from the group consisting of Gly at position 13, Ile at position 24, Ala at position 59, Gln at position 61, and Ala at position 146 on the amino acid sequence of NP_004976, with an amino acid residue other than the original amino residue, and/or a mutation of a gene encoding KRAS causing the at least one amino acid mutation (e.g., substitution). For example, the mutation of KRAS may comprise at least one selected from the group consisting of G12A, G12D, G12R, G12C, G12S, G12V, A146T, A59T, L23R, G13N, G13D, I24F, Q61L, Q61H, G13C, and Q61K on the amino acid sequence of NP_004976, or at least one mutation corresponding thereto on the KRAS amino acid sequences other than NP_004976 (SEQ ID NO: 109), or a mutation of a gene encoding KRAS causing the at least one amino acid mutation (e.g., substitution), or a combination thereof. The mutation in KRAS amino acid sequences other than NP_004976 (SEQ ID NO: 109) corresponding to the above described amino acid mutation on NP_004976 (SEQ ID NO: 109) may be determined by any conventional means, such as a sequence alignment using protein (or nucleotide) blast provided by National Center for Biotechnology Information (NCBI; www.ncbi.nlm.nih.gov).

```
Amino acid sequence of NP_004976.2 (188 a.a.: SEQ
ID NO: 109; coding gene: NM_004985.4)
                                         (SEQ ID NO: 114)
MTEYKLVVVG AGGVGKSALT IQLIQNHFVD EYDPTIEDSY

RKQVVIDGET CLLDILDTAG QEEYSAMRDQ YMRTGEGFLC

VFAINNTKSF EDIHHYREQI KRVKDSEDVP MVLVGNKCDLPS

RTVDTKQA QDLARSYGIP FIETSAKTRQ GVDDAFYTLV

REIRKHKEKM SKDGKKKKKKSKTKCVIM
```

TABLE 1-1

Examples of amino acid modification of NP_004976.2

| Codon# | Base substitution | Amino acid substitution (in NP_004976) |
|---|---|---|
| 12 | GGT→GCT | Gly→Ala (G12A) |
| 12 | GGT→GAT | Gly→Asp (G12D) |
| 12 | GGT→CGT | Gly→Arg (G12R) |
| 12 | GGT→TGT | Gly→Cys (G12C) |
| 12 | GGT→AGT | Gly→Ser (G12S) |
| 12 | GGT→GTT | Gly→Val (G12V) |
| 13 | GGC→GAC | Gly→Asp (G13D) |
| 13 | GGC→AAC | Gly→Asn (G13N) |
| 13 | GGC→TGC | Gly→Cys (G13C) |
| 23 | CTA→CGA | Leu→Arg (L23R) |
| 24 | ATT→TTT or TTC | Ile→Phe (I24F) |
| 59 | GCA→ACA | Ala→Thr (A59T) |
| 61 | CAA→GAT | Gln→Leu (Q61L) |
| 61 | CAA→CAT | Gln→His (Q61H) |
| 61 | CAA→AAA | Gln→Lys (Q61K) |
| 146 | GCA→GTC | Ala→Thr (A146T) |

RAF may be selected from the group consisting of BRAF, c-RAF A-RAF, V-RAF, KSR1, and KSR2, all of which originate from vertebrates including mammals, such as rodents, e.g., mice, rats, etc., and primates, e.g., humans, monkeys, etc., birds, reptiles, amphibians, and fishes. For example, BRAF may be selected from the group consisting of, but not limited to, human BRAF (NP_004324.2, etc.), mouse BRAF (NP_647455.3, etc.), frog BRAF (NP_001083526.1, etc.), zebrafish BRAF (NP_991307.2, etc.), rat BRAF (NP_579817.1, etc.), and chicken KRAS (NP_990633.1, etc.). The BRAF-encoding gene (mRNA) may be selected from the group consisting of, but not limited to, NM_004333.4, NM_139294.5, NM_205744.3, NM_001090057.1, NM_133283.1, and NM_205302.1.

The mutation of BRAF connected with the prediction of the effect of c-Met inhibitors may be a substitution of at least one amino acid selected from the group consisting of the amino acids at positions 596 (G), 600 (V), 601 (K), 469 (G), 466 (G), 581 (N), 594(D), 597 (L), 464 (G), and the like, on NP_004324 (SEQ ID NO: 110), with an amino acid residue other than the original amino residue, and/or a mutation of a gene encoding KRAS BRAF causing the at least one amino acid mutation (e.g., substitution). For example, the mutation of BRAF connected with the prediction of the effect of c-Met inhibitors may comprise at least one following mutation, on the basis of wild-type BRAF (accession number NP_004324.2.): G596R (base G at position 596 substituted by R), V600E, V600K, V600R, K601E, K601E, G469A, V600M, G469A, V600L, G466V, V600D, G469V, D594G, D594N, N581S, L597V, L597S, L597Q, K601N, G466V, G466E, G464V, G469E, etc., or at least one mutation corresponding thereto on the other BRAF amino acid sequences than NP_004324 (SEQ ID NO: 110), or a mutation of a gene encoding BRAF causing the at least one amino acid mutation (e.g., substitution), or a combination thereof. The mutation in BRAF amino acid sequences other than NP_004324 (SEQ ID NO: 110) corresponding to the above described amino acid mutation on NP_004324 (SEQ ID NO: 110) may be determined by any conventional means, such as a sequence alignment using protein (or nucleotide) blast provided by National Center for Biotechnology Information (NCBI; www.ncbi.nlm.nih.gov).

```
Amino Acid Sequence of NP_004324.2 (766 a.a.: SEQ
ID NO: 110; coding gene: NM_004333.4)
                                         (SEQ ID NO: 115)
MAALSGGGGG GAEPGQALFN GDMEPEAGAG AGAAASSAAD

PAIPEEVWNI KQMIKLTQEHIEALLDKFGG EHNPPSIYLE

AYEEYTSKLD ALQQREQQLL ESLGNGTDFS

VSSSASMDTVTSSSSSSLSV LPSSLSVFQN PTDVARSNPK

SPQKPIVRVF LPNKQRTVVP ARCGVTVRDSLKKALMMRGL

IPECCAVYRI QDGEKKPIGW DTDISWLTGE ELHVEVLENV

PLTTHNFVRKTFFTLAFCDF CRKLLFQGFR CQTCGYKFHQ

RCSTEVPLMC VNYDQLDLLF VSKFFEHHPIPQEEASLAET

ALTSGSSPSA PASDSIGPQI LTSPSPSKSI PIPQPFRPAD

EDHRNQFGQRDRSSSAPNVH INTIEPVNID DLIRDQGFRG

DGGSTTGLSA TPPASLPGSL TNVKALQKSPGPQRERKSSS

SSEDRNRMKT LGRRDSSDDW EIPDGQITVG QRIGSGSFGT

VYKGKWHGDVAVKMLNVTAP TPQQLQAFKN EVGVLRKTRH

VNILLFMGYS TKPQLAIVTQ WCEGSSLYHHLHIIETKFEM

IKLIDIARQT AQGMDYLHAK SIIHRDLKSN NIFLHEDLTV

KIGDFGLATVKSRWSGSHQF EQLSGSILWM APEVIRMQDK

NPYSFQSDVY AFGIVLYELM TGQLPYSNINNRDQIIFMVG

RGYLSPDLSK VRSNCPKAMK RLMAECLKKK RDERPLFPQI

LASIELLARSLPKIHRSASE PSLNRAGFQT EDFSLYACAS

PKTPIQAGGY GAFPVH
```

TABLE 1-2

Examples of amino acid modification of NP_004324.2

| Codon# | Base substitution | Amino acid substitution (in NP_004324.2) |
|---|---|---|
| 464 | GGA→GTA | G464V |
| 466 | GGA→GTA | G466V |

TABLE 1-2-continued

Examples of amino acid modification of NP_004324.2

| Codon# | Base substitution | Amino acid substitution (in NP_004324.2) |
|---|---|---|
| 466 | GGA→GAA | G466E |
| 469 | GGA→GCA | G469A |
| 469 | GGA→GTA | G469V |
| 469 | GGA→GAA | G469E |
| 581 | AAT→TCT, TCC, TCA, or TCG | N581S |
| 594 | GAT→GGT | D594G |
| 594 | GAT→AAT | D594N |
| 596 | GGT→CGT | G596R |
| 597 | CTA→GTA | L597V |
| 597 | CTA→TCA | L597S |
| 597 | CTA→CAA | L597Q |
| 600 | GTG→GAG | V600E |
| 600 | GTG→AAG | V600K |
| 600 | GTG→AGG | V600R |
| 600 | GTG→ATG | V600M |
| 600 | GTG→TTG | V600L |
| 600 | GTG→GAT | V600D |
| 601 | AAA→GAA | K601E |
| 601 | AAA→AAT | K601N |

The phrase "at least mutation corresponding thereto on the other KRAS amino acid sequences than NP_004976 (SEQ ID NO: 109)" or "at least mutation corresponding thereto on the other BRAF amino acid sequences than NP_004324 (SEQ ID NO: 110)" is intended to cover any amino acid mutation (e.g. substitution) on at least one of positions on variants of SEQ ID NO: 109 or SEQ ID NO: 110 or on other KRAS or BRAF than SEQ ID NO: 109 or SEQ ID NO: 110, wherein the positions correspond to at least one of the above listed substitutable amino acid positions of SEQ ID NO: 109 or SEQ ID NO: 110 as determined by any general sequence alignment. In addition, the phrase "other amino acid residue than the original amino residue" may refer to any amino acid selected from amino acids other than the original amino acid of the position to be mutated (e.g., substituted) of un-mutated KRAS or BRAF.

An embodiment provides a composition and a kit for the prediction of the efficacy of a c-Met inhibitor, comprising a material detecting a mutation of at least one selected from the group consisting of KRAS protein, BRAF protein and nucleic acids encoding the proteins.

Another embodiment provides a composition and a kit for the selection of a subject suitable to the application of a c-Met inhibitor, comprising a material detecting a mutation of at least one selected from the group consisting of KRAS protein, BRAF protein, and nucleic acids encoding the proteins.

The material detecting a mutation may be at least one selected from the group consisting of 1) a polynucleotide (e.g., a probe or aptamer) comprising a nucleotide sequence hybridizable with (e.g., complementary to) a mutation-containing fragment of a KRAS gene and/or BRAF gene (full-length DNA, cDNA or mRNA) ranging in size from about 3 to about 100 bp, from about 3 to about 50 bp, from about 3 to about 30 bp, or from about 3 to about 25 bp; 2) a pair of primers comprising nucleotide sequences which are respectively hybridizable with (e.g., complementary to) regions flanking a mutation-containing fragment of a KRAS gene and/or BRAF gene (e.g., 3'- and 5'-terminal regions) ranging in size from about 5 to about 100 bp, from about 5 to about 50 bp, from about 5 to about 30 bp, or from about 5 to about 25 bp out of the gene fragment with a size of about 5 to about 1000 bp, e.g., from about 10 to about 500 bp, from about 20 to about 200 bp, or from about 50 to about 200 bp; and 3) a compound (a small molecular chemical; e.g., general label such as a fluorescent, a dye, etc.), an antibody, or an aptamer, all binding (e.g., specifically binding) to the KRAS or BRAF protein having the amino acid mutation. Optionally, the detecting material may be conjugated with a label, such as a fluorescent, a secondary antibody, a bead (e.g., a magnetic bead or a polystyrene bead), a dye or a combination thereof. As used herein, the term "hybridizable" means pertaining to complementarily binding to a specific region of the gene, with a sequence homology of 80% or higher, e.g., 90% or higher, 95% or higher, 98% or higher, 99% or higher, or 100% between the primer, probe or aptamer and the gene region.

Also, provided according to another embodiment is a method for predicting the efficacy of a c-Met inhibitor, for offering information on the prediction of the efficacy of a c-Met inhibitor, for selecting a subject suitable to the application of a c-Met inhibitor, or for offering information of the selection of a subject suitable to the application of a c-Met inhibitor, comprising detecting a mutation of at least one selected from the group consisting of KRAS protein, BRAF protein and nucleic acids encoding the proteins in a biological sample. When a mutation of at least one selected from the group consisting of KRAS protein, BRAF protein and nucleic acids encoding the proteins is not detected in a biological sample, the biological sample or a patient from which the biological sample is originated can be predicted to allow the c-Met inhibitor to effectively exert its activity, and a subject without such a mutation may be considered to be suitable for the application of the c-Met inhibitor. Thus, the method may further comprise determining the biological sample or the patient is suitable for the application of the c-Met inhibitor when a mutation of at least one selected from the group consisting of KRAS protein, BRAF protein and nucleic acids encoding the proteins is not detected biological sample. More particularly, the biological sample or patient may be deemed suitable for treatment with the c-Met inhibitor, i.e., selected for such treatment, when none of the particular mutations of KRAS or BRAF, and/or nucleic acids encoding same, described herein are detected.

Detecting (e.g., testing for or determining the presence or absence of) a mutation of at least one selected from the group consisting of KRAS protein, BRAF protein and nucleic acids encoding the proteins in the biological sample may be performed by any conventional gene analyzing method; for example, it may comprise i) treating (or contacting) the biological sample with a material that detects a mutation of at least one selected from the group consisting of KRAS protein, BRAF protein and nucleic acids encoding the proteins; and ii) analyzing the product (e.g., reaction mixture) to determine the presence or absence of the mutation. In an embodiment, prior to the preparing step i), a step of preparing a biological sample may be further comprised, wherein the preparation step may comprise obtaining (isolating) a biological sample from a patient or obtaining a biological sample which has been isolated from a patient. In step i), the detecting material may be at least one selected from the group consisting of 1) a polynucleotide (e.g., a probe) comprising a nucleotide sequence hybridizable with (e.g., complementary to) a mutation-containing fragment of a KRAS gene and/or BRAF gene (full-length DNA, cDNA or mRNA) ranging in size from about 3 to about 100 bp, from about 3 to about 50 bp, from about 3 to about 30 bp, or from about 3 to about 25 bp, 2) a pair of primers comprising nucleotide sequences which are respectively hybridizable with (e.g., complementary to) 3'- and 5'-terminal regions ranging in size from about 5 to about 100 bp, from about 5 to about 50 bp, from about 5 to about 30 bp, or from about 5 to about 25 bp out of the a mutation-containing gene fragment with a size of about 5 to about 1000 bp, e.g., from about 10 to about 500 bp, from about 20 to about 200 bp, or from about 50 to about 200 bp; and 3) a compound (a small molecular chemical; e.g., general label such as a fluorescent, a dye, etc.), an antibody, or an aptamer, all binding (e.g., specifically binding) to the KRAS or BRAF protein having the amino acid mutation. Optionally, the detecting material may be conjugated with a label, such as a fluorescent, a secondary antibody, a bead (e.g., a magnetic bead or a polystyrene bead), a dye or a combination thereof. As used herein, the term "hybridizable" means pertaining to complementarily binding to a specific region of the gene, with a sequence homology of 80% or higher, e.g., 90% or higher, 95% or higher, 98% or higher, 99% or higher, or 100% between the primer, probe or aptamer and the gene region. The step i) may be configured to form a complex by adding (applying) the detective material to the biological sample.

The reaction mixture may be the complex resulting from hybridization between a KRAS or BRAF gene or protein (which is mutated) and the detective material or resulting from an interaction between a compound (a small molecular chemical; e.g., general label such as a fluorescent, a dye, etc.), an antibody, or an aptamer, and a KRAS or BRAF protein having the amino acid mutation (e.g., substitution), which can be obtained in step i). The analyzing may comprise detecting the presence of the complex or the label conjugated to the complex, or base or amino acid sequencing the KRAS, BRAF, KRAS gene and/or BRAF gene fragment segregated from the complex after the isolation of the complex from the biological sample.

In an embodiment, the method for predicting the efficacy of a c-Met inhibitor, for offering information on the prediction of the efficacy of a c-Met inhibitor, for selecting a subject suitable to the application of a c-Met inhibitor, or for offering information of the selection of a subject suitable to the application of a c-Met inhibitor, may further comprise administering a c-Met inhibitor to the subject for whom it is determined that a c-Met inhibitor would have efficacy or who has been selected for the application of the c-Met inhibitor, after the determining (predicting) or selecting step.

Another embodiment provides a method for inhibiting c-Met, comprising administering a c-Met inhibitor to a subject who does not have a mutation of at least one of KRAS, BRAF, and/or nucleic acids encoding them, particularly a subject who does not have one of the mutations described in detail above. For example, the subject may be selected by the above method for selecting a subject suitable for the application of a c-Met inhibitor.

Another embodiment provides a method for preventing and/or treating a cancer characterized by cancer cells that do not have a mutation of at least one of KRAS, BRAF, and nucleic acids encoding them, particularly cancer cells that do not have one of the mutations described in detail above. For example, the cancer to be prevented and/or treated by the above method may be at least one selected from the group consisting of lung cancer, gastric (stomach) cancer, kidney cancer, ovarian cancer, pancreatic cancer, colon cancer, liver cancer, brain cancer, chronic or acute leukemia, endometrial carcinoma or uterine carcinoma, and the like, but not be limited thereto. The method for inhibiting c-Met or the method for preventing and/treating cancer may further comprise selecting a subject to which the c-Met inhibitor is applicable, prior to the administering step. Details of the selection are as described above. The c-Met inhibitor may be an anti-c-Met antibody.

In an embodiment, the method for inhibiting c-Met or for preventing and/or treating cancer may comprise:
identifying a subject to which a c-Met inhibitor is applicable; and
administering a pharmaceutically effective amount of the c-Met inhibitor to the subject.

In another embodiment, the method for inhibiting c-Met or for preventing and/or treating cancer may comprise:
detecting a mutation on KRAS, BRAF, or nucleic acid encoding them in a biological sample to select a c-Met inhibitor-applicable subject; and
administering a pharmaceutically effective amount of the c-Met inhibitor to the selected c-Met inhibitor-applicable subject.

As used herein, the mutation of KRAS or BRAF protein may refer to the above described amino acid mutation (e.g., substitution), and the mutation of a nucleic acid encoding KRAS or BRAF protein may refer to a mutation (e.g., substitution) in the nucleic acid which induce the mutation of KRAS or BRAF protein as described above.

From the point of view of using a c-Met inhibitor such as an anti-c-Met antibody, a certain expression level of c-Met in cancer cells is prerequisite for the c-Met inhibitor therapy.

Accordingly, the composition and/or kit for predicting an efficacy of a c-Met inhibitor, selecting a subject for applying a c-Met inhibitor, or monitoring efficacy of a c-Met inhibitor may further comprise a substance interacting with at least one selected from the group consisting of c-Met and c-Met coding gene, in addition to a substance interacting with at least one selected from the group consisting of IL-8, bIG-H3, MIF, KRAS/BRAF, and coding genes thereof. The interacting substance with c-Met and/or c-Met coding gene may be at least one selected from the group consisting of chemicals (small molecules; e.g., general label such as a fluorescent, a dye, etc.), proteins, peptides, nucleic acids (polynucleotides, oligonucleotides, etc.), and the like, which are specifically interact with (or bind to) c-Met and/or c-Met coding gene. For example, the substance interacting with c-Met and/or c-Met coding gene may be at least one selected from the group consisting of chemicals, antibodies, and aptamers, which specifically bind to c-Met, and nucleic acids (e.g., primers, probes, aptamers, etc.) which bind to an whole or a part (e.g., about 5 to about 100 bp, about 5 to about 50 bp, about 5 to about 30 bp, or about 5 to about 25 bp) of c-Met coding gene, which may be labeled with a general labeling material, such as a florescence, a secondary antibody, beads (e.g., a magnetic bead or polystyrene bead), a coloring material, and the like.

In addition, the method for predicting the efficacy of a c-Met inhibitor (or for offering information on the prediction of the efficacy of a c-Met inhibitor) or the method for selecting a subject suitable to the application of a c-Met inhibitor (or for offering information of the selection of a subject suitable to the application of a c-Met inhibitor) may further comprise measuring a level of c-Met protein or a gene encoding c-Met (e.g., full-length DNA, cDNA, mRNA) in the biological sample from the patient. The steps of measuring the level of c-Met and/or c-Met coding gene and measuring the level of (or detecting a mutation of) at least one selected from the group consisting of IL-8, bIG-H3, MIF, KRAS/BRAF, and coding genes thereof may be performed simultaneously or sequentially in any order. Details of the measuring step are as described above. For example, a western blotting technique may be employed. In this regard, when a predetermined amount (e.g., about 10 µg) of proteins obtained from a biological sample (e.g., cancer cells or tissues) is loaded on SDS PAGE gel, transferred onto the membrane, and reacted with an anti-c-Met antibody, and then, exposed on ECL reaction for a certain time (e.g., about 30 sec), the detection of a band may indicate that a prerequisite for the c-Met inhibitor therapy is established. In another embodiment, if the c-Met level, which is determined by immunohistochemistry (IHC) using a tissue section (e.g., (Formalin-fixed paraffin-embedded tissues (FFPE), etc.) of a tumor tissue, is +2 or more, the tumor tissue can be determined that a c-Met inhibitor can exhibit its therapeutic efficacy thereon. In another embodiment, when a biological sample is found to have a c-Met mRNA level of about 12,000 or higher, about 13,000 or higher, or about 14,000 or higher, as measured by Affymetrix array (Affymetrix GeneChip Human Genome U133 Plus 2.0 array; using the primer set "203510_at"), a prerequisite for the c-Met inhibitor therapy may be established. Cancer cells characterized by a high expression level of c-Met include cells from lung cancer, breast cancer, brain cancer, stomach cancer, liver cancer, and kidney cancer. However, any cancer cell, although derived from different kinds, may be a target of the c-Met inhibitor therapy if it expresses a high level of c-Met according to personal characteristics of patients.

In another embodiment, a biological sample used in the method for predicting the efficacy of a c-Met inhibitor (or for offering information on the prediction of the efficacy of a c-Met inhibitor) or the method for selecting a subject suitable to the application of a c-Met inhibitor (or for offering information of the selection of a subject suitable to the application of a c-Met inhibitor) may be a tissue, a cell or body fluid (blood, serum, urine, saliva, etc.) which shows a high expression level of c-Met, for example, a c-Met level of about 12,000 or higher, about 13,000 or higher, or about 14,000 or higher, as measured by Affymetrix array (Affymetrix GeneChip Human Genome U133 Plus 2.0 array; using the primer set "203510 at").

The method of predicting, monitoring, or selecting may further comprising administering a c-Met inhibitor to a subject, who is selected by the selecting method, or who is predicted or monitored that a c-Met inhibitor exerts its efficacy therein.

The method of predicting, monitoring, or selecting may further comprising optimizing the application of a c-Met inhibitor or a therapy with a c-Met inhibitor by 1) determining whether or not a c-Met inhibitor is administered to a subject according to the determination of the determining step of the predicting or selecting method (e.g., determining to administer a c-Met inhibitor to the subject when the level of IL-8 and/or a nucleic acid encoding IL-8 in a biological sample obtained (separated) from the subject is higher than that of a reference sample or when a mutation of at least one of KRAS, BRAF, and nucleic acids encoding the proteins is not present in the biological sample, or determining not to administer a c-Met inhibitor to the subject when the level of IL-8 and/or a nucleic acid encoding IL-8 in a biological sample obtained (separated) from the subject is equal to or lower than that of a reference sample or when a mutation of at least one of KRAS, BRAF, and nucleic acids encoding the proteins is present in the biological sample, or 2) determining whether the administration of a c-Met inhibitor to the subject is maintained (continued) or stopped according to the determination of the determining step of the monitoring method (e.g., determining to maintain the administration of c-Met inhibitor to the subject, when the level of IL-8, bIG-H3, MIF, and/or nucleic acids encoding the proteins in the biological sample after the administration of a c-Met inhibitor is decreased compared to before the administration, or determining to stop the administration of a c-Met inhibitor, when the level of IL-8, bIG-H3, MIF, and/or nucleic acids encoding the proteins in the biological sample after the administration of a c-Met inhibitor is equal to or increased compared to before the administration.

As used herein, the term "c-Met inhibitor-applicable subject" or "subject suitable for the application of the c-Met inhibitor" means a patient likely to respond to a c-Met inhibitor, and the term "subject" may be selected from the group consisting of mammals, such as rodents, e.g., mice, rats, etc., and primates, e.g., humans, monkeys, etc., e.g., a cancer patient. The biological sample may be or a cell, a tissue or body fluid (e.g., blood, serum, urine, saliva, etc.) isolated from a subject or patient or from an artificial culture. In some embodiments, the biological sample may be blood or a serum.

The reference sample may be selected from the group consisting of mammal, mammalian cells or tissues (including tumor (e.g., cancer) cells or tissues), and the like, on which a c-Met inhibitor has no efficacy (e.g., a c-Met inhibitory efficacy or an anti-cancer efficacy).

In an particular embodiment, the c-Met inhibitor may be at least one selected from the group consisting of an anti-c-Met antibody or an antigen-binding fragment thereof, crizotinib (PF-02341066; 3-((R)-1-(2,6-dichloro-3-fluorophenyl)ethoxy)-5-(1-(piperidin-4-yl)-1H-pyrazol-4-yl)pyridin-2-amine), cabozantinib (XL-184; N-(4-(6,7-dimethoxyquinolin-4-yloxy)phenyl)-N-(4-fluorophenyl)cyclopropane-1,1-dicarboxamide), foretinib (N-(3-fluoro-4-(6-methoxy-7-(3-morpholinopropoxy)quinolin-4-yloxy)phenyl)-N-(4-fluorophenyl)cyclopropane-1,1-dicarboxamide), PHA-665752((R,Z)-5-(2,6-dichlorobenzylsulfonyl)-3-((3,5-dimethyl-4-(2-(pyrrolidin-1-ylmethyl)pyrrolidine-1-carbonyl)-1H-pyrrol-2-yl)methylene)indolin-2-one), SU11274((Z)—N-(3-chlorophenyl)-3-((3,5-dimethyl-4-(1-methylpiperazine-4-carbonyl)-1H-pyrrol-2-yl)methylene)-N-methyl-2-oxoindoline-5-sulfonamide), SGX-523(6-(6-(1-methyl-1H-pyrazol-4-yl)-[1,2,4]triazolo[4,3-b]pyridazin-3-ylthio)quinoline), PF-04217903(2-(4-(3-(quinolin-6-ylmethyl)-3H-[1,2,3]triazolo[4,5-b]pyrazin-5-yl)-1H-pyrazol-1-yl)ethanol), EMD 1214063(Benzonitrile, 3-[1,6-Dihydro-1-[[3-[5-[(1-Methyl-4-Piperidinyl)Methoxy]-2-PyriMidinyl]Phenyl]Methyl]-6-Oxo-3-Pyridazinyl]), golvatinib (N-(2-fluoro-4-((2-(4-(4-methylpiperazin-1-yl)piperidine-1-carboxamido)pyridin-4-yl)oxy)phenyl)-N-(4-fluorophenyl)cyclopropane-1,1-dicarboxamide), INCB28060(2-fluoro-N-methyl-4-(7-(quinolin-6-ylmethyl)imidazo[1,2-b][1,2,4]triazin-2-yl)benzamide), MK-2461(N-((2R)-1,4-Dioxan-2-ylmethyl)-N-methyl-N'-[3-(1-methyl-1H-pyrazol-4-yl)-5-oxo-5H-benzo[4,5]cyclohepta[1,2-b]pyridin-7-yl]sulfamide), tivantinib (ARQ 197; (3R,4R)-3-(5,6-Dihydro-4H-pyrrolo[3,2,1-ij]quinolin-1-yl)-4-(1H-indol-3-yl)pyrrolidine-2,5-dione), NVP-BVU972(6-[[6-(1-Methyl-1H-pyrazol-4-yl)imidazo[1,2-b]pyridazin-3-yl]methyl]quinoline), AMG458({1-(2-hydroxy-2-methylpropyl)-N-[5-(7-methoxyquinolin-4-yloxy)pyridin-2-yl]-5-methyl-3-oxo-2-phenyl-2,3-dihydro-1H-pyrazole-4-carboxamide}), BMS 794833(N-(4-((2-amino-3-chloropyridin-4-yl)oxy)-3-fluorophenyl)-5-(4-fluorophenyl)-4-oxo-1,4-dihydropyridine-3-carboxamide), BMS 777607(N-[4-[(2-Amino-3-chloropyridin-4-yl)oxy]-3-fluorophenyl]-4-ethoxy-1-(4-fluorophenyl)-2-oxo-1,2-dihydropyridine-3-carboxamide), MGCD-265(N-(3-Fluoro-4-(2-(1-methyl-1H-imidazol-4-yl)thieno[3,2-b]pyridin-7- yloxy)phenylcarbamothioyl)-2-phenylacetamide), AMG-208(7-Methoxy-4-[(6-phenyl-1,2,4-triazolo[4,3-b]pyridazin-3-yl)methoxy]quinoline), BMS-754807((2S)-1-[4-[(5-Cyclopropyl-1H-pyrazol-3-yl)amino]pyrrolo[2,1-f][1,2,4]triazin-2-yl]-N-(6-fluoro-3-pyridinyl)-2-methyl-2-pyrrolidinecarboxamide), JNJ-38877605(6-[Difluoro[6-(1-methyl-1H-pyrazol-4-yl)-1,2,4-triazolo[4,3-b]pyridazin-3-yl]methyl]quinoline), and pharmaceutically acceptable salts thereof; or any combination thereof.

The anti-c-Met antibody or an antigen-binding fragment thereof may be any antibody which specifically recognizes c-Met as an antigen and/or specifically binds to c-Met, or an antigen-binding fragment thereof. For example, the anti-c-Met antibody may be any antibody that acts on c-Met to induce intracellular internalization and degradation of c-Met, or antigen-binding fragment thereof. The anti-c-Met antibody may recognize any specific region of c-Met, e.g., a specific region in the SEMA domain, as an epitope.

Herein, unless stated otherwise, the term "anti-c-Met antibody" may be intended to cover not only an anti-c-Met antibody in a complete form (e.g., an IgG form) but also its antigen-binding fragment. The antigen-binding fragment thereof may be at least one selected from the group consisting of scFv, (scFv)2, scFv-Fc, Fab, Fab', and F(ab')2 of an anti-c-Met antibody.

"c-Met" or "c-Met protein" refers to a receptor tyrosine kinase (RTK) which binds hepatocyte growth factor (HGF). c-Met may be derived (obtained) from any species, particularly a mammal, for instance, primates such as human c-Met (e.g., GenBank Accession No. NP_000236), monkey c-Met (e.g., *Macaca mulatta*, GenBank Accession No. NP_001162100), or rodents such as mouse c-Met (e.g., GenBank Accession No. NP_032617.2), rat c-Met (e.g., GenBank Accession No. NP_113705.1), and the like. The c-Met protein may include a polypeptide encoded by the nucleotide sequence identified as GenBank Accession No. NM_000245, a polypeptide having the amino acid sequence identified as GenBank Accession No. NP_000236 or extracellular domains thereof. The receptor tyrosine kinase c-Met participates in various mechanisms, such as cancer incidence, metastasis, migration of cancer cells, invasion of cancer cells, angiogenesis, and the like.

c-Met, a receptor for hepatocyte growth factor (HGF), may be divided into three portions: extracellular, transmembrane, and intracellular. The extracellular portion is composed of an α-subunit and a β-subunit which are linked to each other through a disulfide bond, and includes a SEMA domain responsible for binding HGF, a PSI domain (plexin-semaphorins-integrin identity/homology domain) and an IPT domain (immunoglobulin-like fold shared by plexins and transcriptional factors domain) The SEMA domain of c-Met protein may have the amino acid sequence of SEQ ID NO: 79, and is an extracellular domain that functions to bind HGF. A specific region of the SEMA domain, that is, a region having the amino acid sequence of SEQ ID NO: 71, which corresponds to a range from amino acid residues 106 to 124 of the amino acid sequence of the SEMA domain (SEQ ID NO: 79), is a loop region between the second and the third beta propellers within the epitopes of the SEMA domain. This region acts as an epitope for the anti-c-Met antibody.

The term "epitope," as used herein, refers to an antigenic determinant, a part of an antigen recognized by an antibody. In one embodiment, the epitope may be a region including about 5 or more contiguous (consecutive on primary, secondary (two-dimensional), or tertiary (three-dimensional) structure) amino acid residues within the SEMA domain (SEQ ID NO: 79) of c-Met protein, for instance, about 5 to about 19 contiguous amino acid residues within the amino acid sequence of SEQ ID NO: 71. For example, the epitope may be a polypeptide having about 5 to about 19 contiguous amino acids selected from among partial combinations of the amino acid sequence of SEQ ID NO: 71, wherein the polypeptide includes at least the amino sequence of SEQ ID NO: 73 (EEPSQ) which serves as an essential element for the epitope. For example, the epitope may be a polypeptide including, consisting essentially of, or consisting of the amino acid sequence of SEQ ID NO: 71, SEQ ID NO: 72, or SEQ ID NO: 73.

The epitope having the amino acid sequence of SEQ ID NO: 72 corresponds to the outermost part of the loop between the second and third beta propellers within the SEMA domain of a c-Met protein. The epitope having the amino acid sequence of SEQ ID NO: 73 is a site to which the antibody or antigen-binding fragment according to one embodiment most specifically binds.

Thus, the anti-c-Met antibody may specifically bind to an epitope which includes about 5 to about 19 contiguous amino acids selected from among partial combinations of the amino acid sequence of SEQ ID NO: 71, including SEQ ID NO: 73 as an essential element. For example, the anti-c-Met antibody may specifically bind to an epitope comprising the amino acid sequence of SEQ ID NO: 71, SEQ ID NO: 72, or SEQ ID NO: 73.

In one embodiment, the anti-c-Met antibody or an antigen-binding fragment thereof may comprise or consist essentially of:

(i) at least one heavy chain complementarity determining region (CDR) selected from the group consisting of (a) a CDR-H1 comprising the amino acid sequence of SEQ ID NO: 4; (b) a CDR-H2 comprising the amino acid sequence of SEQ ID NO: 5, the amino acid sequence of SEQ ID NO: 2, or an amino acid sequence comprising 8-19 consecutive amino acids within the amino acid sequence of SEQ ID NO: 2 comprising amino acid residues from the $3^{rd}$ to $10^{th}$ positions of the amino acid sequence of SEQ ID NO: 2; and (c) a CDR-H3 comprising the amino acid sequence of SEQ ID NO: 6, the amino acid sequence of SEQ ID NO: 85, or an amino acid sequence comprising 6-13 consecutive amino acids within the amino acid sequence of SEQ ID NO: 85 comprising amino acid residues from the $1^{st}$ to $6^{th}$ positions of the amino acid sequence of SEQ ID NO: 85, or a heavy chain variable region comprising the at least one heavy chain complementarity determining region;

(ii) at least one light chain complementarity determining region (CDR) selected from the group consisting of (a) a CDR-L1 comprising the amino acid sequence of SEQ ID NO: 7, (b) a CDR-L2 comprising the amino acid sequence of SEQ ID NO: 8, and (c) a CDR-L3 comprising the amino acid sequence of SEQ ID NO: 9, the amino acid sequence of SEQ ID NO: 15, the amino acid sequence of SEQ ID NO: 86, or an amino acid sequence comprising 9-17 consecutive amino acids within the amino acid sequence of SEQ ID NO: 89 comprising amino acid residues from the $1^{st}$ to $9^{th}$ positions of the amino acid sequence of SEQ ID NO: 89, or a light chain variable region including the at least one light chain complementarity determining region;

(iii) a combination of the at least one heavy chain complementarity determining region and at least one light chain complementarity determining region; or (iv) a combination of the heavy chain variable region and the light chain variable region.

Herein, the amino acid sequences of SEQ ID NOS: 4 to 9 are respectively represented by following Formulas I to VI, below:

Formula I: $Xaa_1$-$Xaa_2$-Tyr-Tyr-Met-Ser (SEQ ID NO: 4), wherein $Xaa_1$ is absent or Pro or Ser, and $Xaa_2$ is Glu or Asp, Formula II: Arg-Asn-$Xaa_3$-$Xaa_4$-Asn-Gly-$Xaa_5$-Thr (SEQ ID NO: 5), wherein $Xaa_3$ is Asn or Lys, $Xaa_4$ is Ala or Val, and $Xaa_5$ is Asn or Thr, Formula III: Asp-Asn-Trp-Leu-$Xaa_6$-Tyr (SEQ ID NO: 6), wherein $Xaa_6$ is Ser or Thr, Formula IV: Lys-Ser-Ser-$Xaa_7$-Ser-Leu-Leu-Ala-$Xaa_8$-Gly-Asn-$Xaa_9$-$Xaa_{10}$-Asn-Tyr-Leu-Ala (SEQ ID NO: 7), wherein $Xaa_7$ is His, Arg, Gln, or Lys, $Xaa_8$ is Ser or Trp, $Xaa_9$ is His or Gln, and $Xaa_{10}$ is Lys or Asn, Formula V: Trp-$Xaa_{ii}$-Ser-$Xaa_{12}$-Arg-Val-$Xaa_{13}$(SEQ ID NO: 8), wherein $Xaa_{11}$ is Ala or Gly, $Xaa_{12}$ is Thr or Lys, and $Xaa_{13}$ is Ser or Pro, and Formula VI: $Xaa_{14}$-Gln-Ser-Tyr-Ser-$Xaa_{15}$-Pro-$Xaa_{16}$-Thr (SEQ ID NO: 9), wherein $Xaa_{14}$ is Gly, Ala, or Gln, $Xaa_{15}$ is Arg, His, Ser, Ala, Gly, or Lys, and $Xaa_{16}$ is Leu, Tyr, Phe, or Met.

In one embodiment, the CDR-H1 may comprise an amino acid sequence selected from the group consisting of SEQ ID NO: 1, SEQ ID NO: 22, SEQ ID NO: 23, and SEQ ID NO: 24. The CDR-H2 may comprise an amino acid sequence selected from the group consisting of SEQ ID NO: 2, SEQ ID NO: 25, and SEQ ID NO: 26. The CDR-H3 may comprise an amino acid sequence selected from the group consisting of SEQ ID NO: 3, SEQ ID NO: 27, SEQ ID NO: 28, and SEQ ID NO: 85.

The CDR-L1 may comprise an amino acid sequence selected from the group consisting of SEQ ID NO: 10, SEQ ID NO: 29, SEQ ID NO: 30, SEQ ID NO: 31, SEQ ID NO: 32, SEQ ID NO: 33, and SEQ ID NO: 106. The CDR-L2 may comprise an amino acid sequence selected from the group consisting of SEQ ID NO: 11, SEQ ID NO: 34, SEQ ID NO: 35, and SEQ ID NO: 36. The CDR-L3 may comprise an amino acid sequence selected from the group consisting of SEQ ID NO: 12, SEQ ID NO: 13, SEQ ID NO: 14, SEQ ID NO: 15, SEQ ID NO: 16, SEQ ID NO: 37, SEQ ID NO: 86, and SEQ ID NO: 89.

In another embodiment, the anti-c-Met antibody or an antigen-binding fragment thereof may comprise or consisting essentially of:

a heavy variable region comprising or consisting essentially of a polypeptide (CDR-H1) comprising an amino acid sequence selected from the group consisting of SEQ ID NO: 1, SEQ ID NO: 22, SEQ ID NO: 23, and SEQ ID NO: 24, a polypeptide (CDR-H2) comprising an amino acid sequence selected from the group consisting of SEQ ID NO: 2, SEQ ID NO: 25, and SEQ ID NO: 26, and a polypeptide (CDR-H3) comprising an amino acid sequence selected from the group consisting of SEQ ID NO: 3, SEQ ID NO: 27, SEQ ID NO: 28, and SEQ ID NO: 85; and a light variable region comprising or consisting essentially of a polypeptide (CDR-L1) comprising an amino acid sequence selected from the group consisting of SEQ ID NO: 10, SEQ ID NO: 29, SEQ ID NO: 30, SEQ ID NO: 31, SEQ ID NO: 32, SEQ ID NO: 33, and SEQ ID NO: 106, a polypeptide (CDR-L2) comprising an amino acid sequence selected from the group consisting of SEQ ID NO: 11, SEQ ID NO: 34, SEQ ID NO: 35, and SEQ ID NO: 36, and a polypeptide (CDR-L3) comprising an amino acid sequence selected from the group consisting of SEQ ID NO: 12, SEQ ID NO: 13, SEQ ID NO: 14, SEQ ID NO: 15, SEQ ID NO: 16, SEQ ID NO: 37, SEQ ID NO: 86, and SEQ ID NO: 89.

In an embodiment, the anti-c-Met antibody or an antigen-binding fragment thereof may comprise or consist essentially of a heavy variable region comprising the amino acid sequence of SEQ ID NO: 17, SEQ ID NO: 74, SEQ ID NO: 87, SEQ ID NO: 90, SEQ ID NO: 91, SEQ ID NO: 92, SEQ ID NO: 93, or SEQ ID NO: 94, and a light variable region comprising the amino acid sequence of SEQ ID NO: 113, SEQ ID NO: 18, SEQ ID NO: 19, SEQ ID NO: 20, SEQ ID NO: 21, SEQ ID NO: 75, SEQ ID NO: 88, SEQ ID NO: 95, SEQ ID NO: 96, SEQ ID NO: 97, SEQ ID NO: 98, SEQ ID NO: 99, or SEQ ID NO: 107.

Animal-derived antibodies produced by immunizing non-immune animals with a desired antigen generally invoke immunogenicity when injected into humans for the purpose of medical treatment, and thus chimeric antibodies have been developed to inhibit such immunogenicity. Chimeric antibodies are prepared by replacing constant regions of animal-derived antibodies that cause an anti-isotype response with constant regions of human antibodies by genetic engineering. Chimeric antibodies are considerably improved in an anti-isotype response compared to animal-derived antibodies, but animal-derived amino acids still have variable regions, so that chimeric antibodies have side effects with respect to a potential anti-idiotype response. Humanized antibodies have been developed to reduce such side effects. Humanized antibodies are produced by grafting complementarity determining regions (CDR) which serve an important role in antigen binding in variable regions of chimeric antibodies into a human antibody framework.

The most important thing in CDR grafting to produce humanized antibodies is choosing the optimized human antibodies for accepting CDRs of animal-derived antibodies. Antibody databases, analysis of a crystal structure, and technology for molecule modeling are used. However, even when the CDRs of animal-derived antibodies are grafted to the most optimized human antibody framework, amino acids positioned in a framework of the animal-derived CDRs affecting antigen binding are present. Therefore, in many cases, antigen binding affinity is not maintained, and thus application of additional antibody engineering technology for recovering the antigen binding affinity is necessary.

The anti c-Met antibodies may be mouse-derived antibodies, mouse-human chimeric antibodies, humanized antibodies, or human antibodies. The antibodies or antigen-binding fragments thereof may be isolated from a living body or non-naturally occurring. The antibodies or antigen-binding fragments thereof may be recombinant or synthetic. The antibody may be monoclonal.

An intact antibody includes two full-length light chains and two full-length heavy chains, in which each light chain is linked to a heavy chain by disulfide bonds. The antibody includes a heavy chain constant region and a light chain constant region. The heavy chain constant region is of a gamma (γ), mu (μ), alpha (α), delta (δ), or epsilon (ε) type, which may be further categorized as gamma 1 (γ1), gamma 2(γ2), gamma 3(γ3), gamma 4(γ4), alpha 1(α1), or alpha 2(α2). The light chain constant region is of either a kappa (κ) or lambda (λ) type.

As used herein, the term "heavy chain" refers to full-length heavy chain, and fragments thereof, including a variable region $V_H$ that includes amino acid sequences sufficient to provide specificity to antigens, and three constant regions, $C_{H1}$, $C_{H2}$, and $C_{H3}$, and a hinge. The term "light chain" refers to a full-length light chain and fragments thereof, including a variable region $V_L$ that includes amino acid sequences sufficient to provide specificity to antigens, and a constant region $C_L$.

The term "complementarity determining region (CDR)" refers to an amino acid sequence found in a hyper variable region of a heavy chain or a light chain of immunoglobulin. The heavy and light chains may respectively include three CDRs (CDRH1, CDRH2, and CDRH3; and CDRL1, CDRL2, and CDRL3). The CDRs may provide contact residues that play an important role in the binding of antibodies to antigens or epitopes. The terms "specifically binding" and "specifically recognized" are well known to one of ordinary skill in the art, and indicate that an antibody and an antigen specifically interact with each other to lead to an immunological activity.

The term "antigen-binding fragment" used herein refers to fragments of an intact immunoglobulin including portions of a polypeptide including antigen-binding regions having the ability to specifically bind to the antigen. In one embodiment, the antigen-binding fragment may be selected from the group consisting of scFv, (scFv)$_2$, Fab, Fab', and F(ab')$_2$, but not be limited thereto.

Among the antigen-binding fragments, Fab that includes light chain and heavy chain variable regions, a light chain constant region, and a first heavy chain constant region $C_{H1}$, includes one antigen-binding site.

The Fab' fragment is different from the Fab fragment, in that Fab' includes a hinge region with at least one cysteine residue at the C-terminal of $C_{H1}$.

The F(ab')$_2$ antibody is formed through disulfide bridging of the cysteine residues in the hinge region of the Fab' fragment. Fv is the smallest antibody fragment with only a heavy chain variable region and a light chain variable region. Recombination techniques of generating the Fv fragment are widely known in the art.

Two-chain Fv includes a heavy chain variable region and a light chain region which are linked by a non-covalent bond. Single-chain Fv generally includes a heavy chain variable region and a light chain variable region which are linked by a covalent bond via a peptide linker or linked at the C-terminals to have a dimer structure like the two-chain Fv. The peptide linker may be a polypeptide comprising about 1 to about 100 or about 2 to about 50 amino acids, wherein the amino acids may be selected from any amino acids without limitation.

The antigen-binding fragments may be attainable using protease (for example, the Fab fragment may be obtained by restricted cleavage of a whole antibody with papain, and the F(ab)$_2$ fragment may be obtained by cleavage with pepsin), or may be prepared by using a genetic recombination technique.

The term "hinge region," as used herein, refers to a region between CH1 and CH2 domains within the heavy chain of an antibody which functions to provide flexibility for the antigen-binding site.

When an animal antibody undergoes a chimerization process, the IgG1 hinge of animal origin may be replaced with a human IgG1 hinge or IgG2 hinge while the disulfide bridges between two heavy chains are reduced from three to two in number. In addition, an animal-derived IgG1 hinge is shorter than a human IgG1 hinge. Accordingly, the rigidity of the hinge is changed. Thus, a modification of the hinge region may bring about an improvement in the antigen binding efficiency of the humanized antibody. The modification of the hinge region through amino acid deletion, addition, or substitution is well-known to those skilled in the art.

In one embodiment, the anti-c-Met antibody or an antigen-binding fragment thereof may be modified by the deletion, insertion, addition, or substitution of at least one (e.g., two, three, four, five, six, seven, eight, nine, or ten) amino acid residue of the amino acid sequence of the hinge region so that it exhibits enhanced antigen-binding efficiency. For example, the antibody may include a hinge region including the amino acid sequence of SEQ ID NO: 100 (U7-HC6), 101 (U6-HC7), 102 (U3-HC9), 103 (U6-HC8), or 104 (U8-HC5), or a hinge region including the amino acid sequence of SEQ ID NO: 105 (non-modified human hinge). Preferably, the hinge region includes the amino acid sequence of SEQ ID NO: 100 or 101.

In one embodiment, the anti-c-Met antibody may be a monoclonal antibody. The monoclonal antibody may be produced by the hybridoma cell line deposited with the Korean Cell Line Research Foundation, an international depository authority located at Yungun-Dong, Jongno-Gu, Seoul, Korea, on Oct. 6, 2009, under Accession No. KCLRF-BP-00220, which binds specifically to the extracellular region of c-Met protein (refer to Korean Patent Publication No. 2011-0047698, the entire disclosure of which is incorporated herein by reference). The anti-c-Met antibody may include all the antibodies defined in Korean Patent Publication No. 2011-0047698.

In the anti-c-Met antibody, the rest portion of the light chain and the heavy chain portion other than the CDRs, the light chain variable region, and the heavy chain variable region, e.g., a light chain constant region and/or a heavy chain constant region, may be from any subtype of immunoglobulin (e.g., IgA, IgD, IgE, IgG (IgG1, IgG2, IgG3, IgG4), IgM, etc.).

By way of further example, the anti-c-Met antibody may comprise or consist essentially of:

(a) a heavy chain comprising an amino acid sequence selected from the group consisting of the amino acid sequence of SEQ ID NO: 62 (wherein the amino acid sequence from amino acid residues from the $1^{st}$ to $17^{th}$ positions is a signal peptide), the amino acid sequence from the $18^{th}$ to $462^{nd}$ positions of SEQ ID NO: 62, the amino acid sequence of SEQ ID NO: 64 (wherein the amino acid sequence from the $1^{st}$ to $17^{th}$ positions is a signal peptide), the amino acid sequence from the $18^{th}$ to $461^{st}$ positions of SEQ ID NO: 64, the amino acid sequence of SEQ ID NO: 66 (wherein the amino acid sequence from the $1^{st}$ to $17^{th}$ positions is a signal peptide), and the amino acid sequence from the $18^{th}$ to $460^{th}$ positions of SEQ ID NO: 66; and (b) a light chain comprising an amino acid sequence selected from the group consisting of the amino acid sequence of SEQ ID NO: 68 (wherein the amino acid sequence from the $1^{st}$ to $20^{th}$ positions is a signal peptide), the amino acid sequence from the $21^{st}$ to $240^{th}$ positions of SEQ ID NO: 68, the amino acid sequence of SEQ ID NO: 70 (wherein the amino acid sequence from the $1^{st}$ to $20^{th}$ positions is a signal peptide), the amino acid sequence from the $21^{st}$ to $240^{th}$ positions of SEQ ID NO: 70, and the amino acid sequence of SEQ ID NO: 108.

For example, the anti-c-Met antibody may be selected from the group consisting of:

(i) an antibody comprising (a) a heavy chain comprising the amino acid sequence of SEQ ID NO: 62 or the amino acid sequence from the $18^{th}$ to $462^{nd}$ positions of SEQ ID NO: 62 and (b) a light chain comprising the amino acid sequence of SEQ ID NO: 68 or the amino acid sequence from the $21^{st}$ to $240^{th}$ positions of SEQ ID NO: 68;

(ii) an antibody comprising (a) a heavy chain comprising the amino acid sequence of SEQ ID NO: 64 or the amino acid sequence from the $18^{th}$ to $461^{st}$ positions of SEQ ID NO: 64 and (b) a light chain including the amino acid sequence of SEQ ID NO: 68 or the amino acid sequence from the 21$^{st}$ to 240$^{th}$ positions of SEQ ID NO: 68;

(iii) an antibody comprising (a) a heavy chain comprising the amino acid sequence of SEQ ID NO: 66 or the amino acid sequence from the 18$^{th}$ to 460$^{th}$ positions of SEQ ID NO: 66 and (b) a light chain comprising the amino acid sequence of SEQ ID NO: 68 or the amino acid sequence from the 21$^{st}$ to 240$^{th}$ positions of SEQ ID NO: 68;

(iv) an antibody comprising (a) a heavy chain comprising the amino acid sequence of SEQ ID NO: 62 or the amino acid sequence from the 18$^{th}$ to 462$^{nd}$ positions of SEQ ID NO: 62 and (b) a light chain including the amino acid sequence of SEQ ID NO: 70 or the amino acid sequence from the 21$^{st}$ to 240$^{th}$ positions of SEQ ID NO: 70;

(v) an antibody comprising a heavy chain comprising (a) the amino acid sequence of SEQ ID NO: 64 or the amino acid sequence from the 18$^{th}$ to 461$^{st}$ positions of SEQ ID NO: 64 and (b) a light chain comprising the amino acid sequence of SEQ ID NO: 70 or the amino acid sequence from the 21$^{st}$ to 240$^{th}$ positions of SEQ ID NO: 70;

(v) an antibody comprising (a) a heavy chain comprising the amino acid sequence of SEQ ID NO: 66 or the amino acid sequence from the 18$^{th}$ to 460$^{th}$ positions of SEQ ID NO: 66 and (b) a light chain comprising the amino acid sequence of SEQ ID NO: 70 or the amino acid sequence from the 21$^{st}$ to 240$^{th}$ positions of SEQ ID NO: 70;

(vi) an antibody comprising (a) a heavy chain comprising the amino acid sequence of SEQ ID NO: 62 or the amino acid sequence from the 18$^{th}$ to 462$^{nd}$ positions of SEQ ID NO: 62 and (b) a light chain comprising the amino acid sequence of SEQ ID NO: 108;

(vii) an antibody comprising (a) a heavy chain comprising the amino acid sequence of SEQ ID NO: 64 or the amino acid sequence from the 18$^{th}$ to 461$^{st}$ positions of SEQ ID NO: 64 and (b) a light chain comprising the amino acid sequence of SEQ ID NO: 108; and (viii) an antibody comprising (a) a heavy chain comprising the amino acid sequence of SEQ ID NO: 66 or the amino acid sequence from the 18$^{th}$ to 460$^{th}$ positions of SEQ ID NO: 66 and (b) a light chain comprising the amino acid sequence of SEQ ID NO: 108.

The polypeptide comprising the amino acid sequence of SEQ ID NO: 70 is a light chain including human kappa (κ) constant region, and the polypeptide comprising the amino acid sequence of SEQ ID NO: 68 is a polypeptide obtained by replacing histidine at position 62 (corresponding to position 36 of SEQ ID NO: 68 according to kabat numbering) of the polypeptide comprising the amino acid sequence of SEQ ID NO: 70 with tyrosine. The production yield of the antibodies may be increased by the replacement. The polypeptide comprising the amino acid sequence of SEQ ID NO: 108 is a polypeptide obtained by replacing serine at position 32 of the polypeptide of SEQ ID NO: 108 (corresponding to position 52 of SEQ ID NO: 68, which corresponds to position 27e according to kabat numbering in the amino acid sequence from amino acid residues 21 to 240 of SEQ ID NO: 68; positioned within CDR-L1) with tryptophan. By such replacement, antibodies and antibody fragments including such sequences exhibit increased activities, such as c-Met biding affinity, c-Met degradation activity, Akt phosphorylation inhibition, and the like.

In another embodiment, the anti c-Met antibody may comprising a light chain complementarity determining region comprising the amino acid sequence of SEQ ID NO: 106, a light chain variable region comprising the amino acid sequence of SEQ ID NO: 107, or a light chain comprising the amino acid sequence of SEQ ID NO: 108.

In another embodiment, the anti-c-Met antibody or an antigen-binding fragment may be Onartuzumab (MetMab), LY2875358, Rilotumumab (AMG102), or an antigen-binding fragment thereof; and the like.

The c-Met inhibitor may be applied (administered) together with a pharmaceutically acceptable carrier. The pharmaceutically acceptable carrier may be those commonly used for the formulation of the inhibitor (e.g., antibodies), which may be one or more selected from the group consisting of lactose, dextrose, sucrose, sorbitol, mannitol, starch, gum acacia, calcium phosphate, alginates, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate, and mineral oil, but are not limited thereto. The c-Met inhibitor may further comprise one or more selected from the group consisting of a lubricant, a wetting agent, a sweetener, a flavor enhancer, an emulsifying agent, a suspension agent, and preservative.

The c-Met inhibitor may be administered orally or parenterally. The parenteral administration may selected from the group consisting of intravenous injection, subcutaneous injection, muscular injection, intraperitoneal injection, endothelial administration, local administration, intranasal administration, intrapulmonary administration, and rectal administration. Since oral administration leads to digestion of proteins or peptides, the c-Met inhibitor for oral administration must be coated or formulated to prevent digestion in stomach. In addition, the c-Met inhibitor may be administered using an optional device that enables an active substance to be delivered to target cells.

The term "the pharmaceutically effective amount" as used herein may refer to an amount of which the active ingredient can exert pharmaceutically significant effects. The pharmaceutically effective amount of the c-Met inhibitor for a single dose may be prescribed in a variety of ways, depending on factors such as formulation methods, administration manners, age of patients, body weight of patients, gender of patients, pathologic conditions of patients, diets, administration time, administration interval, administration mute, excretion speed, and reaction sensitivity. For example, the pharmaceutically effective amount of the c-Met inhibitor for a single dose may be in ranges of 0.001 to 100 mg/kg, or 0.02 to 10 mg/kg, but not limited thereto. The pharmaceutically effective amount for the single dose may be formulated into a single formulation in a unit dosage form or formulated in suitably divided dosage forms, or it may be manufactured to be contained in a multiple dosage container.

The c-Met inhibitor may be used in the prevention and/or treatment of a cancer. The cancer may be associated with over-expression and/or abnormal activation of c-Met. The cancer may be a solid cancer or a blood cancer. The cancer may be, but not limited to, one or more selected from the group consisting of squamous cell carcinoma, small-cell lung cancer, non-small-cell lung cancer, adenocarcinoma of the lung, squamous cell carcinoma of the lung, peritoneal carcinoma, skin cancer, melanoma in the skin or eyeball, rectal cancer, cancer near the anus, esophagus cancer, small intestinal tumor, endocrine gland cancer, parathyroid cancer, adrenal cancer, soft-tissue sarcoma, urethral cancer, chronic or acute leukemia, lymphocytic lymphoma, hepatoma, gastric cancer, gastrointestinal cancer, pancreatic cancer, glioblastoma, cervical cancer, ovarian cancer, liver cancer, bladder cancer, hepatocellular adenoma, breast cancer, colon cancer, large intestine cancer, endometrial carcinoma or uterine carcinoma, salivary gland tumor, kidney cancer, prostate cancer, vulvar cancer, thyroid cancer, head or neck cancer, brain cancer, osteosarcoma, and the like. The cancer may be a primary cancer or a metastatic cancer. The cancer may be a c-Met inhibitor (e.g., an anti-c-Met antibody) resistant cancer.

The prevention and/or treatment of cancer may be achieved by at least one effect of the c-Met inhibitor selected from cancer cell death, inhibition of cancer cell proliferation, inhibition of migration, invasion, or metastasis of cancer, improvement of symptoms associated with cancer, etc.

Biomarkers capable of predicting and/or monitoring an efficacy of a c-Met inhibitor may lead to improvement of the therapeutic effect of the c-Met inhibitor, and making it possible to provide a patient-tailored treatment which is optimized for individual patient, thereby increasing the therapeutic efficacy.

EXAMPLES

Hereafter, the present invention will be described in detail by examples.

The following examples are intended merely to illustrate the invention and are not construed to restrict the invention.

Reference Example

Construction of Anti-c-Met Antibody 1.1. Production of "AbF46", a Mouse Antibody to c-Met
1.1.1. Immunization of Mice To obtain immunized mice necessary for the development of a hybridoma cell line, each of five BALB/c mice (Japan SLC, Inc.), 4 to 6 weeks old, was intraperitoneally injected with a mixture of 100 μg of human c-Met/Fc fusion protein (R&D Systems) and one volume of complete Freund's adjuvant. Two weeks after the injection, a second intraperitoneal injection was conducted on the same mice with a mixture of 50 μg of human c-Met/Fc protein and one volume of incomplete Freund's adjuvant. One week after the second immunization, the immune response was finally boosted. Three days later, blood was taken from the tails of the mice and the sera were 1/1000 diluted in PBS and used to examine a titer of antibody to c-Met by ELISA. Mice found to have a sufficient antibody titer were selected for use in the cell fusion process.

1.1.2. Cell Fusion and Production of a Hybridoma

Three days before cell fusion, BALB/c mice (Japan SLC, Inc.) were immunized with an intraperitoneal injection of a mixture of 50 μg of human c-Met/Fc fusion protein and one volume of PBS. The immunized mice were anesthetized before excising the spleen from the left half of the body. The spleen was meshed to separate splenocytes which were then suspended in a culture medium (DMEM, GIBCO, Invitrogen). The cell suspension was centrifuged to recover the cell layer. The splenocytes thus obtained ($1 \times 10^8$ cells) were mixed with myeloma cells (Sp2/0) ($1 \times 10^8$ cells), followed by spinning to yield a cell pellet. The cell pellet was slowly suspended, treated with 45% polyethylene glycol (PEG) (1 mL) in DMEM for 1 min at 37° C., and supplemented with 1 mL of DMEM. To the cells was added 10 mL of DMEM over 10 min, after which incubation was conducted in a water bath at 37° C. for 5 min. Then the cell volume was adjusted to 50 mL before centrifugation. The cell pellet thus formed was resuspended at a density of $1-2 \times 10^5$ cells/mL in a selection medium (HAT medium). 0.1 mL of the cell suspension was allocated to each well of 96-well plates which were then incubated at 37° C. in a $CO_2$ incubator to establish a hybridoma cell population.

1.1.3. Selection of Hybridoma Cells Producing Monoclonal Antibodies to c-Met Protein From the hybridoma cell population established in Reference Example 1.1.2, hybridoma cells which showed a specific response to c-Met protein were screened by ELISA using human c-Met/Fc fusion protein and human Fc protein as antigens.

Human c-Met/Fc fusion protein was seeded in an amount of 50 μL (2 μg/mL)/well to microtiter plates and allowed to adhere to the surface of each well. The antibody that remained unbound was removed by washing. For use in selecting the antibodies that do not bind c-Met but recognize Fc, human Fc protein was attached to the plate surface in the same manner.

The hybridoma cell culture obtained in Reference Example 1.1.2 was added in an amount of 50 μL to each well of the plates and incubated for 1 hour. The cells remaining unreacted were washed out with a sufficient amount of Tris-buffered saline and Tween 20 (TBST). Goat anti-mouse IgG-horseradish peroxidase (HRP) was added to the plates and incubated for 1 hour at room temperature. The plates were washed with a sufficient amount of TBST, followed by reacting the peroxidase with a substrate (OPD). Absorbance at 450 nm was measured on an ELISA reader.

Hybridoma cell lines which secrete antibodies that specifically and strongly bind to human c-Met but not human Fc were selected repeatedly. From the hybridoma cell lines obtained by repeated selection, a single clone producing a monoclonal antibody was finally separated by limiting dilution. The single clone of the hybridoma cell line producing the monoclonal antibody was deposited with the Korean Cell Line Research Foundation, an international depository authority located at Yungun-Dong, Jongno-Gu, Seoul, Korea, on Oct. 6, 2009, with Accession No. KCLRF-BP-00220 according to the Budapest Treaty (refer to Korean Patent Laid-Open Publication No. 2011-0047698).

1.1.4. Production and Purification of a Monoclonal Antibody

The hybridoma cell line obtained in Reference Example 1.1.3 was cultured in a serum-free medium, and the monoclonal antibody (AbF46) was produced and purified from the cell culture.

First, the hybridoma cells cultured in 50 mL of a medium (DMEM) supplemented with 10% (v/v) FBS (fetal bovine serum) were centrifuged and the cell pellet was washed twice or more with 20 mL of PBS to remove the FBS therefrom. Then, the cells were resuspended in 50 mL of DMEM and incubated for 3 days at 37° C. in a $CO_2$ incubator.

After the cells were removed by centrifugation, the supernatant was stored at 4° C. before use or immediately used for the separation and purification of the antibody. An AKTA system (GE Healthcare) equipped with an affinity column (Protein G agarose column; Pharmacia, USA) was used to purify the antibody from 50 to 300 mL of the supernatant, followed by concentration with a filter (Amicon). The antibody was stored in PBS before use in the following examples.

1.2. Construction of chAbF46, a Chimeric Antibody to c-Met

A mouse antibody is apt to elicit immunogenicity in humans. To solve this problem, chAbF46, a chimeric antibody, was constructed from the mouse antibody AbF46 produced in Reference Example 1.1.4 by replacing the constant region, but not the variable region responsible for antibody specificity, with an amino sequence of the human IgG1 antibody.

In this regard, a gene was designed to include the nucleotide sequence of "EcoRI-signal sequence-VH-NheI-CH-TGA-XhoF" (SEQ ID NO: 38) for a heavy chain and the nucleotide sequence of "EcoRI-signal sequence-VL-BsiWI-CL-TGA-XhoF" (SEQ ID NO: 39) for a light chain and synthesized. Then, a DNA fragment having the heavy chain nucleotide sequence (SEQ ID NO: 38) and a DNA fragment having the light chain nucleotide sequence (SEQ ID NO: 39) were digested with EcoRI (NEB, R0101S) and XhoI (NEB, R0146S) before cloning into a vector from the pOptiVEC™-TOPO TA Cloning Kit enclosed in an OptiCHO™ Antibody Express Kit (Cat no. 12762-019, Invitrogen), and a vector from the pcDNA™3.3-TOPO TA Cloning Kit (Cat no. 8300-01), respectively.

Each of the constructed vectors was amplified using Qiagen Maxiprep kit (Cat no. 12662), and a transient expression was performed using Freestyle™ MAX 293 Expression System (Invitrogen). 293 F cells were used for the expression and cultured in FreeStyle™ 293 Expression Medium in a suspension culture manner. At one day before the transient expression, the cells were provided in the concentration of $5\times10^5$ cells/mL. After 24 hours, when the cell number reached to $1\times10^6$ cells/mL, the transient expression was performed. A transfection was performed by a liposomal reagent method using Freestyle™ MAX reagent (Invitrogen), wherein in a 15 mL tube, the DNA was provided in the mixture ratio of 1:1 (heavy chain DNA: light chain DNA) and mixed with 2 mL of OptiPro™ SFM (Invitrogen) (A). In another 15 mL tube, 100 μL of Freestyle™ MAX reagent and 2 mL of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

Afterwards, the cells were incubated in DMEM supplemented with 10% (v/v) FBS for 5 hours at 37° C. under a 5% $CO_2$ condition and then in FBS-free DMEM for 48 hours at 37° C. under a 5% $CO_2$ condition.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE Healthcare, 17-0405-03), followed by elution with an IgG elution buffer (Thermo Scientific, 21004). The buffer was exchanged with PBS to purify a chimeric antibody AbF46 (hereinafter referred to as "chAbF46").

1.3. Construction of Humanized Antibody huAbF46 from Chimeric Antibody chAbF46

1.3.1. Heavy Chain Humanization

To design two domains H1-heavy and H3-heavy, human germline genes which share the highest identity/homology with the VH gene of the mouse antibody AbF46 purified in Reference Example 1.2 were analyzed. An Ig BLAST search (www.ncbi.nlm.nih.gov/igblast/) result revealed that VH3-71 has an identity/identity/homology of 83% at the amino acid level. CDR-H1, CDR-H2, and CDR-H3 of the mouse antibody AbF46 were defined according to Kabat numbering. A design was made to introduce the CDR of the mouse antibody AbF46 into the framework of VH3-71. Hereupon, back mutations to the amino acid sequence of the mouse AbF46 were conducted at positions 30 (S→T), 48 (V→L), 73 (D→N), and 78 (T→L). Then, H1 was further mutated at positions 83 (R→K) and 84 (A→T) to finally establish H1-heavy (SEQ ID NO: 40) and H3-heavy (SEQ ID NO: 41).

For use in designing H4-heavy, human antibody frameworks were analyzed by a BLAST search. The result revealed that the VH3 subtype, known to be most stable, is very similar in framework and sequence to the mouse antibody AbF46. CDR-H1, CDR-H2, and CDR-H3 of the mouse antibody AbF46 were defined according to Kabat numbering and introduced into the VH3 subtype to construct H4-heavy (SEQ ID NO: 42).

1.3.2. Light Chain Humanization

To design two domains H1-light (SEQ ID NO: 43) and H2-light (SEQ ID NO: 44), human germline genes which share the highest identity/homology with the VH gene of the mouse antibody AbF46 were analyzed. An Ig BLAST search result revealed that VK4-1 has an identity/homology of 75% at the amino acid level. CDR-L1, CDR-L2, and CDR-L3 of the mouse antibody AbF46 were defined according to Kabat numbering. A design was made to introduce the CDR of the mouse antibody AbF46 into the framework of VK4-1. Hereupon, back mutations to the amino acid sequence of the mouse AbF46 were conducted at positions 36 (Y→H), 46 (L→M), and 49 (Y→I). Only one back mutation was conducted at position 49 (Y→I) on H2-light.

To design H3-light (SEQ ID NO: 45), human germline genes which share the highest identity/homology with the VL gene of the mouse antibody AbF46 were analyzed by a BLAST search. As a result, VK2-40 was selected. VL and VK2-40 of the mouse antibody AbF46 were found to have a identity/homology of 61% at an amino acid level. CDR-L1, CDR-L2, and CDR-L3 of the mouse antibody were defined according to Kabat numbering and introduced into the framework of VK4-1. Back mutations were conducted at positions 36 (Y→H), 46 (L→M), and 49 (Y→I) on H3-light.

For use in designing H4-light (SEQ ID NO: 46), human antibody frameworks were analyzed. A BLAST search revealed that the Vk1 subtype, known to be the most stable, is very similar in framework and sequence to the mouse antibody AbF46. CDR-L1, CDR-L2, and CDR-L3 of the mouse antibody AbF46 were defined according to Kabat numbering and introduced into the Vk1 subtype. Hereupon, back mutations were conducted at positions 36 (Y→H), 46 (L→M), and 49 (Y→I) on H4-light.

Thereafter, DNA fragments having the heavy chain nucleotide sequences (H1-heavy: SEQ ID NO: 47, H3-heavy: SEQ ID NO: 48, H4-heavy: SEQ ID NO: 49) and DNA fragments having the light chain nucleotide sequences (H1-light: SEQ ID NO: 50, H2-light: SEQ ID NO: 51, H3-light: SEQ ID NO: 52, H4-light: SEQ ID NO: 53) were digested with EcoRI (NEB, R0101S) and XhoI (NEB, R0146S) before cloning into a vector from the pOptiVEC™-TOPO TA Cloning Kit enclosed in an OptiCHO™ Antibody Express Kit (Cat no. 12762-019, Invitrogen) and a vector from the pcDNA™3.3-TOPO TA Cloning Kit (Cat no. 8300-01), respectively, so as to construct recombinant vectors for expressing a humanized antibody.

Each of the constructed vectors was amplified using Qiagen Maxiprep kit (Cat no. 12662), and a transient expression was performed using Freestyle™ MAX 293 Expression System (invitrogen). 293 F cells were used for the expression and cultured in FreeStyle™ 293 Expression Medium in a suspension culture manner. At one day before the transient expression, the cells were provided in the concentration of $5\times10^5$ cells/ml, and after 24 hours, when the cell number reached to $1\times10^6$ cells/mL, the transient expression was performed. A transfection was performed by a liposomal reagent method using Freestyle™ MAX reagent (Invitrogen), wherein in a 15 mL tube, the DNA was provided in the mixture ratio of 1:1 (heavy chain DNA: light chain DNA) and mixed with 2 mL of OptiPro™ SFM (invtrogen) (A). In another 15 mL tube, 100 µL of Freestyle™ MAX reagent and 2 mL of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE Healthcare, 17-0405-03), followed by elution with an IgG elution buffer (Thermo Scientific, 21004). The buffer was exchanged with PBS to purify a humanized antibody AbF46 (hereinafter referred to as "huAbF46"). The humanized antibody huAbF46 used in the following examples comprised a combination of H4-heavy (SEQ ID NO: 42) and H4-light (SEQ ID NO: 46).

1.4. Construction of scFV Library of huAbF46 Antibody

For use in constructing an scFv of the huAbF46 antibody from the heavy and light chain variable regions of the huAbF46 antibody, a gene was designed to have the structure of "VH-linker-VL" for each of the heavy and the light chain variable region, with the linker comprising the amino acid sequence "GLGGLGGGGSGGGGSGGSSGVGS" (SEQ ID NO: 54). A polynucleotide sequence (SEQ ID NO: 55) encoding the designed scFv of huAbF46 was synthesized in Bioneer and an expression vector for the polynucleotide had the nucleotide sequence of SEQ ID NO: 56.

After expression, the product was found to exhibit specificity to c-Met.

1.5. Construction of Library Genes for Affinity Maturation 1.5.1. Selection of Target CDRs and Synthesis of Primers The affinity maturation of huAbF46 was achieved. First, six complementary determining regions (CDRs) were defined according to Kabat numbering. The CDRs are given in Table 2 below.

TABLE 2

| CDR | Amino Acid Sequence |
| --- | --- |
| CDR-H1 | DYYMS (SEQ ID NO: 1) |
| CDR-H2 | FIRNKANGYTTEYSASVKG (SEQ ID NO: 2) |
| CDR-H3 | DNWFAY (SEQ ID NO: 3) |
| CDR-L1 | KSSQSLLASGNQNNYLA (SEQ ID NO: 10) |
| CDR-L2 | WASTRVS (SEQ ID NO: 11) |
| CDR-L3 | QQSYSAPLT (SEQ ID NO: 12) |

For use in the introduction of random sequences into the CDRs of the antibody, primers were designed as follows. Conventionally, N codons were utilized to introduce bases at the same ratio (25% A, 25% G, 25% C, 25% T) into desired sites of mutation. In this experiment, the introduction of random bases into the CDRs of huAbF46 was conducted in such a manner that, of the three nucleotides per codon in the wild-type polynucleotide encoding each CDR, the first and second nucleotides conserved over 85% of the entire sequence while the other three nucleotides were introduced at the same percentage (each 5%) and that the same possibility was imparted to the third nucleotide (33% G, 33% C, 33% T).

1.5.2. Construction of a Library of huAbF46 Antibodies and Affinity for c-Met

The construction of antibody gene libraries through the introduction of random sequences was carried out using the primers synthesized in the same manner as in Reference Example 1.5.1. Two PCR products were obtained using a polynucleotide covering the scFV of huAbF46 as a template, and were subjected to overlap extension PCR to give scFv library genes for huAbF46 antibodies in which only desired CDRs were mutated. Libraries targeting each of the six CDRs prepared from the scFV library genes were constructed.

The affinity for c-Met of each library was compared to that of the wildtype. Most libraries were lower in affinity for c-Met, compared to the wild-type. The affinity for c-Met was retained in some mutants.

1.6. Selection of Antibody with Improved Affinity from Libraries

After maturation of the affinity of the constructed libraries for c-Met, the nucleotide sequence of scFv from each clone was analyzed. The nucleotide sequences thus obtained are summarized in Table 3 and were converted into IgG forms. Four antibodies which were respectively produced from clones L3-1, L3-2, L3-3, and L3-5 were used in the subsequent experiments.

TABLE 3

| Clone | Library constructed | CDR Sequence |
| --- | --- | --- |
| H11-4 | CDR-H1 | PEYYMS (SEQ ID NO: 22) |
| YC151 | CDR-H1 | PDYYMS (SEQ ID NO: 23) |
| YC193 | CDR-H1 | SDYYMS (SEQ ID NO: 24) |
| YC244 | CDR-H2 | RNNANGNT (SEQ ID NO: 25) |
| YC321 | CDR-H2 | RNKVNGYT (SEQ ID NO: 26) |
| YC354 | CDR-H3 | DNWLSY (SEQ ID NO: 27) |
| YC374 | CDR-H3 | DNWLTY (SEQ ID NO: 28) |
| L1-1 | CDR-L1 | KSSHSLLASGNQNNYLA (SEQ ID NO: 29) |
| L1-3 | CDR-L1 | KSSRSLLSSGNHKNYLA (SEQ ID NO: 30) |
| L1-4 | CDR-L1 | KSSKSLLASGNQNNYLA (SEQ ID NO: 31) |
| L1-12 | CDR-L1 | KSSRSLLASGNQNNYLA (SEQ ID NO: 32) |
| L1-22 | CDR-L1 | KSSHSLLASGNQNNYLA (SEQ ID NO: 33) |
| L2-9 | CDR-L2 | WASKRVS (SEQ ID NO: 34) |
| L2-12 | CDR-L2 | WGSTRVS (SEQ ID NO: 35) |
| L2-16 | CDR-L2 | WGSTRVP (SEQ ID NO: 36) |
| L3-1 | CDR-L3 | QQSYSRPYT (SEQ ID NO: 13) |
| L3-2 | CDR-L3 | GQSYSRPLT (SEQ ID NO: 14) |

TABLE 3-continued

| Clone | Library constructed | CDR Sequence |
|---|---|---|
| L3-3 | CDR-L3 | AQSYSHPFS (SEQ ID NO: 15) |
| L3-5 | CDR-L3 | QQSYSRPFT (SEQ ID NO: 16) |
| L3-32 | CDR-L3 | QQSYSKPFT (SEQ ID NO: 37) |

1.7. Conversion of Selected Antibodies into IgG

Respective polynucleotides encoding heavy chains of the four selected antibodies were designed to have the structure of "EcoRI-signal sequence-VH-NheI-CH-XhoI" (SEQ ID NO: 38). The heavy chains of huAbF46 antibodies were used as they were because their amino acids were not changed during affinity maturation. In the case of the hinge region, however, the U6-HC7 hinge (SEQ ID NO: 57) was employed instead of the hinge of human IgG1. Genes were also designed to have the structure of "EcoRI-signal sequence-VL-BsiWI-CL-XhoI" for the light chain. Polypeptides encoding light chain variable regions of the four antibodies which were selected after the affinity maturation were synthesized in Bioneer. Then, a DNA fragment having the heavy chain nucleotide sequence (SEQ ID NO: 38) and DNA fragments having the light chain nucleotide sequences (DNA fragment comprising L3-1-derived CDR-L3: SEQ ID NO: 58, DNA fragment comprising L3-2-derived CDR-L3: SEQ ID NO: 59, DNA fragment comprising L3-3-derived CDR-L3: SEQ ID NO: 60, and DNA fragment comprising L3-5-derived CDR-L3: SEQ ID NO: 61) were digested with EcoRI (NEB, R0101S) and XhoI (NEB, R0146S) before cloning into a vector from the pOptiVEC™-TOPO TA Cloning Kit enclosed in an OptiCHO™ Antibody Express Kit (Cat no. 12762-019, Invitrogen) and a vector from the pcDNA™3.3-TOPO TA Cloning Kit (Cat no. 8300-01), respectively, so as to construct recombinant vectors for expressing affinity-matured antibodies.

Each of the constructed vectors was amplified using Qiagen Maxiprep kit (Cat no. 12662), and a transient expression was performed using Freestyle™ MAX 293 Expression System (invitrogen). 293 F cells were used for the expression and cultured in FreeStyle™ 293 Expression Medium in a suspension culture manner. At one day before the transient expression, the cells were provided in the concentration of $5 \times 10^5$ cells/mL. After 24 hours, when the cell number reached to $1 \times 10^6$ cells/mL, the transient expression was performed. A transfection was performed by a liposomal reagent method using Freestyle™ MAX reagent (Invitrogen), wherein in a 15 mL tube, the DNA was provided in the mixture ratio of 1:1 (heavy chain DNA: light chain DNA) and mixed with 2 mL of OptiPro™ SFM (Invitrogen) (A). I In another 15 mL tube, 100 μL of Freestyle™ MAX reagent and 2 mL of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE Healthcare, 17-0405-03), followed by elution with an IgG elution buffer (Thermo Scientific, 21004). The buffer was exchanged with PBS to purify four affinity-matured antibodies (hereinafter referred to as "huAbF46-H4-A1 (L3-1 origin), huAbF46-H4-A2 (L3-2 origin), huAbF46-H4-A3 (L3-3 origin), and huAbF46-H4-A5 (L3-5 origin)," respectively).

1.8. Construction of Constant Region- and/or Hinge Region-Substituted huAbF46-H4-A1

Among the four antibodies selected in Reference Example 1.7, huAbF46-H4-A1 was found to be the highest in affinity for c-Met and the lowest in Akt phosphorylation and c-Met degradation degree. In the antibody, the hinge region, or the constant region and the hinge region, were substituted.

The antibody huAbF46-H4-A1 (U6-HC7) was composed of a heavy chain comprising the heavy chain variable region of huAbF46-H4-A1, U6-HC7 hinge, and the constant region of human IgG1 constant region, and a light chain comprising the light chain variable region of huAbF46-H4-A1 and human kappa constant region. The antibody huAbF46-H4-A1 (IgG2 hinge) was composed of a heavy chain comprising a heavy chain variable region, a human IgG2 hinge region, and a human IgG1 constant region, and a light chain comprising the light chain variable region of huAbF46-H4-A1 and a human kappa constant region. The antibody huAbF46-H4-A1 (IgG2 Fc) was composed of the heavy chain variable region of huAbF46-H4-A1, a human IgG2 hinge region, and a human IgG2 constant region, and a light chain comprising the light variable region of huAbF46-H4-A1 and a human kappa constant region. Hereupon, the histidine residue at position 36 on the human kappa constant region of the light chain was changed to tyrosine in all of the three antibodies to increase antibody production.

For use in constructing the three antibodies, a polynucleotide (SEQ ID NO: 63) encoding a polypeptide (SEQ ID NO: 62) composed of the heavy chain variable region of huAbF46-H4-A1, a U6-HC7 hinge region, and a human IgG1 constant region, a polynucleotide (SEQ ID NO: 65) encoding a polypeptide (SEQ ID NO: 64) composed of the heavy chain variable region of huAbF46-H4-A1, a human IgG2 hinge region, and a human IgG1 region, a polynucleotide (SEQ ID NO: 67) encoding a polypeptide (SEQ ID NO: 66) composed of the heavy chain variable region of huAbF46-H4-A1, a human IgG2 region, and a human IgG2 constant region, and a polynucleotide (SEQ ID NO: 69) encoding a polypeptide (SEQ ID NO: 68) composed of the light chain variable region of huAbF46-H4-A1, with a tyrosine residue instead of histidine at position 36, and a human kappa constant region were synthesized in Bioneer. Then, the DNA fragments having heavy chain nucleotide sequences were inserted into a vector from the pOptiVEC™-TOPO TA Cloning Kit enclosed in an OptiCHO™ Antibody Express Kit (Cat no. 12762-019, Invitrogen) while DNA fragments having light chain nucleotide sequences were inserted into a vector from the pcDNA3.3-TOPO TA Cloning Kit (Cat no. 8300-01) so as to construct vectors for expressing the antibodies.

Each of the constructed vectors was amplified using Qiagen Maxiprep kit (Cat no. 12662), and a transient expression was performed using Freestyle™ MAX 293 Expression System (Invitrogen). 293 F cells were used for the expression and cultured in FreeStyle™ 293 Expression Medium in a suspension culture manner. At one day before the transient expression, the cells were provided in the concentration of $5 \times 10^5$ cells/mL. After 24 hours, when the cell number reached to $1 \times 10^6$ cells/mL, the transient expression was performed. A transfection was performed by a liposomal reagent method using Freestyle™ MAX reagent (Invitrogen), wherein in a 15 mL tube, the DNA was provided in the mixture ratio of 1:1 (heavy chain DNA:light chain DNA) and mixed with 2 mL of OptiPro™ SFM (Invitrogen) (A). In another 15 mL tube, 100 μL of Freestyle™ MAX reagent and 2 mL of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE Healthcare, 17-0405-03), followed by elution with IgG elution buffer (Thermo Scientific, 21004). The buffer was exchanged with PBS to finally purify three antibodies (huAbF46-H4-A1 (U6-HC7), huAbF46-H4-A1 (IgG2 hinge), and huAbF46-H4-A1 (IgG2 Fc)). Among the three antibodies, huAbF46-H4-A1 (U6-HC7) and huAbF46-H4-A1 (IgG2 Fc) were representatively selected for the following examples, and referred as anti-c-Met antibody L3-1Y and L3-1Y/IgG2, respectively.

Example 1: Prediction and Evaluation of Efficacy of Anti-c-Met Antibody Using IL-8

1.1. Assay for Predicting and Evaluating Efficacy of Anti-c-Met Antibody in Cancer Cell-Implanted Mouse Model Using IL-8

1.1.1. Construction of Cancer Cell-Implanted Mouse Model

For use in assays for predicting and evaluating the efficacy of an anti-c-Met antibody, xenograft mouse models were prepared by implanting various conventional cancer cell lines (Lovo, HT-29, EBC-1, and Hs746T) to mice.

Briefly, the human colorectal cancer cell line HT29 (Accession No. HTB-38) or Lovo (Accession No. CCL-229) were injected s.c. at a dose of $5 \times 10^6$ cells into BALB/C nude mice (4-5 week old, male; Shanghai SLAC Laboratory Animal Co. Ltd.) to construct xenograft mouse models. For modeling, 15 mice were allocated to each group. Also, the human stomach cancer cell lines Hs746T (Accession No. HTB-135) and MKN45 (Accession No. RCB1001), and the human non-small cell cancer cell line EBC-1 (Accession No. JCRB0820) were used in the same manner to construct xenograft mouse models.

That is, mouse models implanted, respectively, with Lovo, HT-29, EBC-1, Hs746T, and MKN45 were constructed, and used in the following experiments.

1.1.2. Prediction of the Efficacy of Anti-c-Met Antibody in Cancer Cell-Implanted Mouse Model Using IL-8

After the anti-c-Met antibody L3-1Y/IgG2 prepared in Reference Example 1 was administered to Lovo-, HT-29-, EBC-1-, or Hs746T-implanted mouse models constructed in Example 1.1.1, tumor sizes were measured to identify groups which were responsive to L3-1Y/IgG2 (responder; effective anticancer activity) and were not responsive (non-responder; no anticancer activity).

Figure 1E:
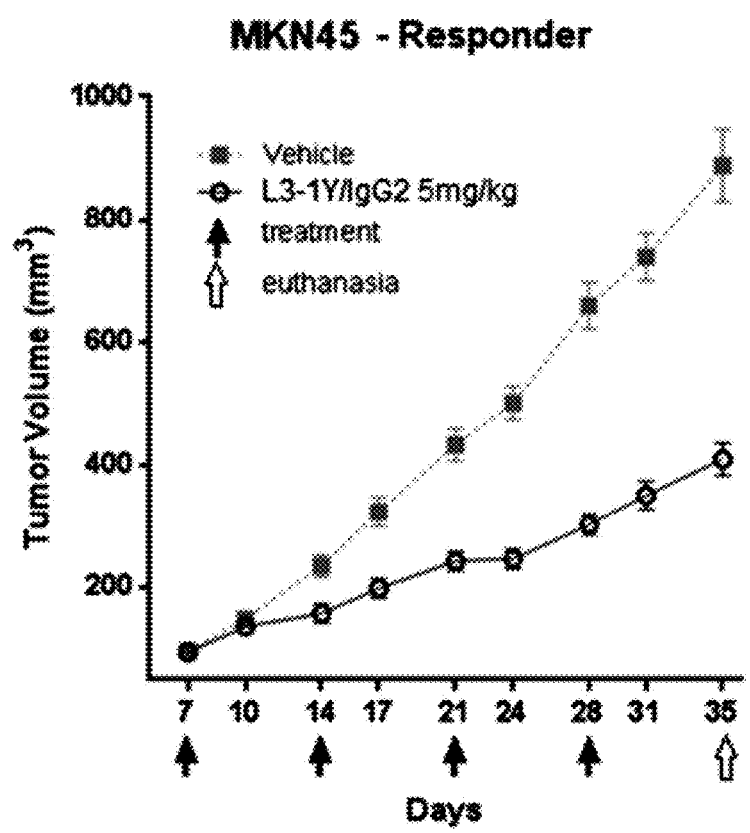

Briefly, the anti-c-Met antibody was injected to each group of the mouse models constructed in Example 1.1.1 from 7-10 days after implantation. The injection was conducted at regular intervals of 7 days for 4 weeks via an intravenous route. Tumor volumes were measured and recorded twice a week. For a control, PBS was injected. The anti-c-Met antibody was injected at a dose of 0.2, 1, 5, or 10 mg/kg to HT29- or Lovo-implanted groups, and at a dose of 0.03, 0.1, 0.3, 1.0, 3.0, or 10.0 mg/kg to EBC-1- or Hs746T-implanted groups. Results are depicted in FIGS. 1A to 1E (1a: Lovo, 1b: HT29, 1c: EBC-1, 1d: Hs746T, 1e: MKN45). FIGS. 1A to 1E show results of the control PBS group and representative anti-c-Met antibody groups (HT29, Lovo, MKN45, EBC-1 and Hs746T models, the first three were injected at a dose of 5 mg/kg while the remaining two injected at a dose of 3 mg/kg) only. Points of time of antibody injection or euthanasia are indicated by arrows. As can be seen in FIGS. 1A and 1E, the anticancer efficacy of L3-1Y/IgG2 was not detected in the Lovo- or the HT-29-implanted mouse models, but was apparent in EBC-1-, Hs746T- or MKN45-implanted mouse models. So, the Lovo- and the HT-29-implanted mouse models were determined to not be responsive to L3-1Y/IgG2 (non-responder group) while the EBC-1-, the Hs746T- and the MKN45-implanted mouse models were classified as responder groups.

An examination was made of a difference in serum IL-8 levels between the responder and the non-responder groups. Serum IL-8 levels of the Lovo-, the HT-29-, the EBC-1- and the Hs746T-implanted mouse models were compared to those of the control mice (injected with PBS only; at a dose of 100 μL every 7 days for 4 weeks), and relationship between serum IL-8 level and responsiveness to L3-1Y/IgG2 was investigated.

Briefly, sera from the control of each model were analyzed using a BD Cytometric Bead Array kit. Experiments were performed with a human inflammatory cytokine kit. According to the manufacture's guideline, mouse serum was diluted ¼ (v/v) in the assay diluent buffer and incubated for 1.5 hrs with biotinylated anti-human IL-8 antibody-coated beads (BD Cytometric Bead Array (CBA) Human inflammatory cytokines kit, BD biosciences). Thereafter, the sample was mixed with 1 mL of the wash buffer containing in the BD Cytometric Bead Array (CBA) Human inflammatory cytokines kit, and centrifuged. After removal of the supernatant, the residue was incubated for 1.5 hrs with the streptavidin-PE of the kit, mixed with 1 mL of the wash buffer. After centrifugation (200 g, 5 min), the supernatant containing unreacted materials was discarded. The precipitate was suspended in 200 uL of wash buffer before FACS analysis (BD FACS Cantoll flow cytometer, BD Bioscience). From the data thus obtained, serum IL-8 concentrations were calculated using the FCAP array program (BD Biosciences), and quantified by multiplication by the dilution factor.

Figure 2:
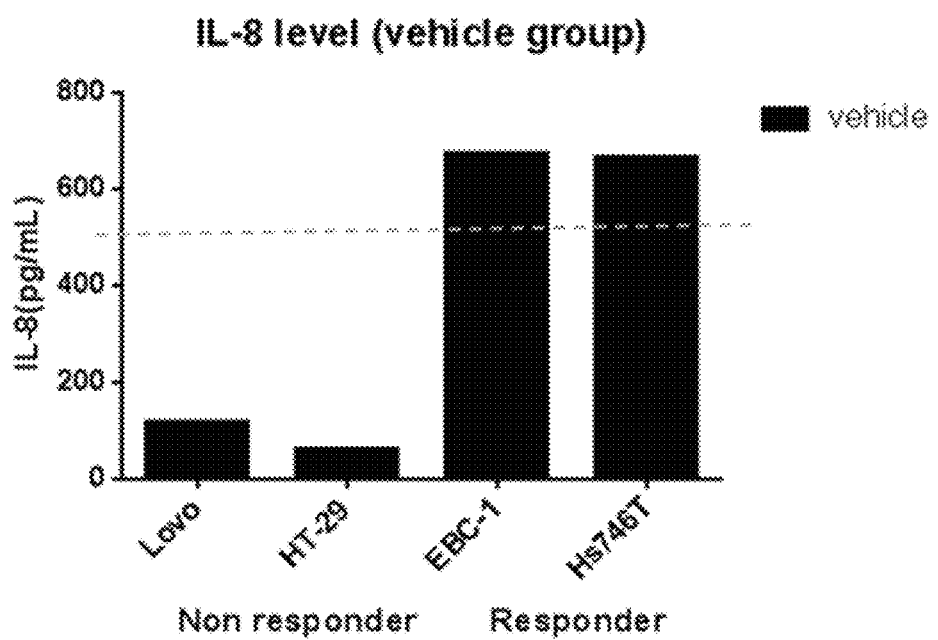
FIG. 2 is a graph of IL-8 levels in cancer cell-implanted mouse models showing relationship between IL-8 level and responsiveness to an anti-c-Met antibody.

The results are shown in FIG. 2. As can be seen in FIG. 2, the IL-8 level was measured about 500 pg/mL or higher in both the responder groups, but decreased to about 50-150 pg/ml in the non-responder groups. The serum IL-8 level of the responder groups was observed to be at least 3-fold higher than that of the non-responder. Accordingly, the cancer cells with high IL-8 levels are expected to allow L3-1Y/IgG2 to exert its anticancer activity more effectively.

1.1.3. Evaluation of the Efficacy of Anti-c-Met Antibody in Cancer Cell-Implanted Mouse Model Using IL-8

To examine the relationship between the change of IL-8 level and the responsiveness to an anti-c-Met antibody, the changes of serum IL-8 levels after treatment of the anti-c-Met antibody in cancer cell-implanted mouse models were monitored.

Briefly, among the serum samples obtained from the mouse xenograft models of Example 1.1.2, the vehicle-treated sample (PBS-treated, control) and the anti-c-Met antibody treated samples with high and low doses were prepared. To this end, serum samples were taken from HT29 and Lovo models (non-responder groups) injected at doses of 0.2 mg/kg and 5 mg/kg and from EBC-1 and Hs746T models (responder groups) injected at doses of 1 mg/kg and 3 mg/kg, and examined for the relationship between the anticancer efficacy of the anti-c-Met antibody and the change of IL-8 level after anti-c-Met antibody treatment. Serum IL-8 levels were analyzed with reference to Example 1.1.2.

Results are depicted in FIG. 3. As is understood from the data of FIG. 3, the non-responder groups showed no significant differences or an increase in the IL-8 level upon treatment with L3-1Y/IgG2 compared to the non-treated group ("vehicle-treated"; injected with vehicle only, PBS) whereas the responder groups showed a significant decrease in IL-8 level compared to the untreated group. These data imply that a patient can be monitored for responsiveness to L3-1Y/IgG2, that is, the efficacy of L3-1Y/IgG2 by measuring the expression level of IL-8 in the patient treated with L3-1Y/IgG2.

1.2. Assay for Predicting and Evaluating Efficacy of Anti-c-Met Antibody in Mouse Model Implanted with Patient-Derived Tumor Tissues by Measuring the Serum Level of IL-8.

1.2.1. Construction of Mouse Model Implanted with Patient-Derived Tumor Tissues.

For use in examining whether IL-8 can be used as a reliable biomarker in predicting or evaluating the efficacy of an anti-c-Met antibody when it is applied to patients, mouse models implanted with patient-derived tumor tissue suffering from cancer (lung cancer) were constructed.

This experiment was performed in the special company Oncotest (Oncotest GmbH, Freibrug Germany). Briefly, patient-derived lung cancer cell lines (non-small cell lung cancer (NSCLC)) LXFA297, 526, 623, 983, 1041 and 1647 were cultured and injected s.c. into NMRI nude mice (4-6 week old, female; Harlan) to construct xenograft mouse models. The construction was carried out according to the Oncotest SOP "Subcutaneous implantation" guideline. 10 mice were allocated to each group. After implantation, the mouse models were randomized to reduce measurement deviations of average tumor volumes between groups, and then injected with the drug.

The mouse models implanted with patient-derived tumor tissues were tested for responsiveness to an anti-c-Met antibody while L3-1Y/IgG2 was injected thereto.

Briefly, to monitor the anticancer efficacy of the antibody, the tumor volumes were regularly measured. Anticancer efficacy was calculated by dividing tumor volumes of each antibody-treated group (5 mg/kg, iv) by those of the control group (PBS injected) after completion of the injection (% inhibition=100−(tumor volume of test group/tumor volume of control*100)). The results are summarized in Tables 4 and 5.

A reduction of tumor volume by 30% or greater upon treatment with L3-1Y/IgG2 was considered statistically significant, which led to determining the antibody as being efficacious, and the group as a responder.

In Table 4, % inhibition=100−(tumor volume of test group/tumor volume of control*100)

TABLE 5

| Model | Gastric | | Renal | | |
| --- | --- | --- | --- | --- | --- |
|  | GXF214 | GXF251 | RXF488 | RXF1114 | RXF1220 |
| % inhibition | 8.96 | −20.77 | 24.82 | 92.56 | 6.79 |
| Result | no efficacy | no efficacy | no efficacy | efficacy | no efficacy |

As is understood from data of Tables 4 and 5, the lung cancer cell-implanted mouse models LXFA526, LXFA623, and LXFA1647, and the kidney cancer cell-implanted mouse model RXF1114 were found to respond to L3-1Y/IgG2 (responder) while the other mouse models implanted with patient-derived tumor tissue were not responsive to the antibody (non-responder)

1.2.2. Prediction of the Efficacy of Anti-c-Met Antibody in Mouse Model Implanted with Patient-Derived Tumor Tissues Using Measurement of the Serum Level of IL-8

Differences in the basal level of serum IL-8 between the responders and the non-responders were examined. In this regard, serum samples were taken from the vehicle groups of mouse models constructed in Example 1.2.1 and the IL-8 levels in the serum samples were used to examine relationship with responsiveness to L3-1Y/IgG2.

Briefly, serum samples taken from the mouse models implanted with patient-derived tumor tissues were classified according to test group. IL-8 levels were measured in vehicle treated groups from the 6 samples of lung cancer models, 2 samples of stomach cancer models, 3 samples of kidney cancer models. Measurement of the IL-8 levels was carried out in the same manner as in Example 1.1.2.

Figure 4:
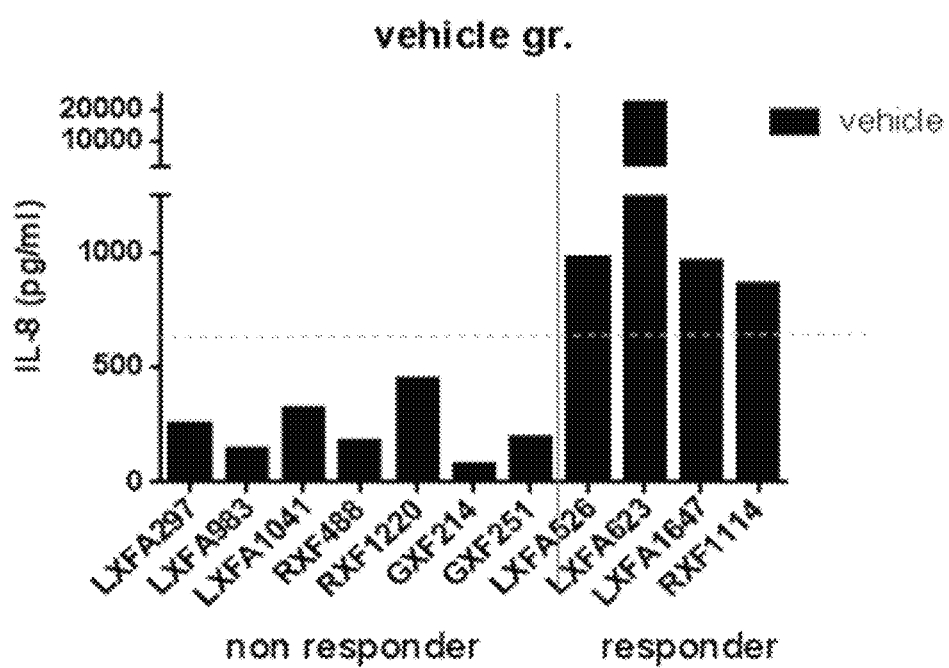
FIG. 4 is a graph showing IL-8 levels in serum samples from the control (vehicle (PBS) treated) of mouse models implanted with patient-derived tumor tissues.

The results are shown in FIG. 4. As is apparent from FIG. 4, the serum IL-8 levels were higher than 750 pg/mL in the responder groups but the levels were lower than about 500 pg/ml in the non-responder groups. The serum IL-8 level of the responder groups was observed to be at least 1.5-fold higher than that of the non-responder. Accordingly, the human cancer cells with high IL-8 levels are expected to allow L3-1Y/IgG2 to exert its anticancer activity more effectively.

1.2.3. Evaluation of the Efficacy of Anti-c-Met Antibody in Mouse Model Implanted with Patient-Derived Tumor Tissues Using Measurement of the Serum Level of IL-8

To examine the relationship between IL-8 level and responsiveness to an anti-c-Met antibody, changes of serum IL-8 levels after treatment of an anti-c-Met antibody in mouse models implanted with patient-derived tumor tissues were monitored.

Briefly, serum samples taken from the mouse models implanted with patient-derived tumor tissues were classified according to test group. IL-8 levels were measured in 6 samples of lung cancer models, 2 samples of stomach cancer models, 3 samples of kidney cancer models after injection of

TABLE 4

| | NSCLC | | | | | |
| --- | --- | --- | --- | --- | --- | --- |
| Model | LXFA297 | LXFA526 | LXFA623 | LXFA983 | LXFA1041 | LXFA1647 |
| % inhibition | −57.12 | 63.95 | 99.99 | 20.05 | −35.5 | 90.61 |
| Result | no efficacy | efficacy | efficacy | no efficacy | no efficacy | efficacy | the anti-c-Met antibody (5 mg/kg, iv) and in samples of the control (PBS injected), and examined for relationship between the anticancer efficacy of the anti-c-Met antibody and the change of IL-8 level after the anti-c-Met antibody treatment. Measurement of the IL-8 levels was carried out in the same manner as in Example 1.1.2.

Figure 5:
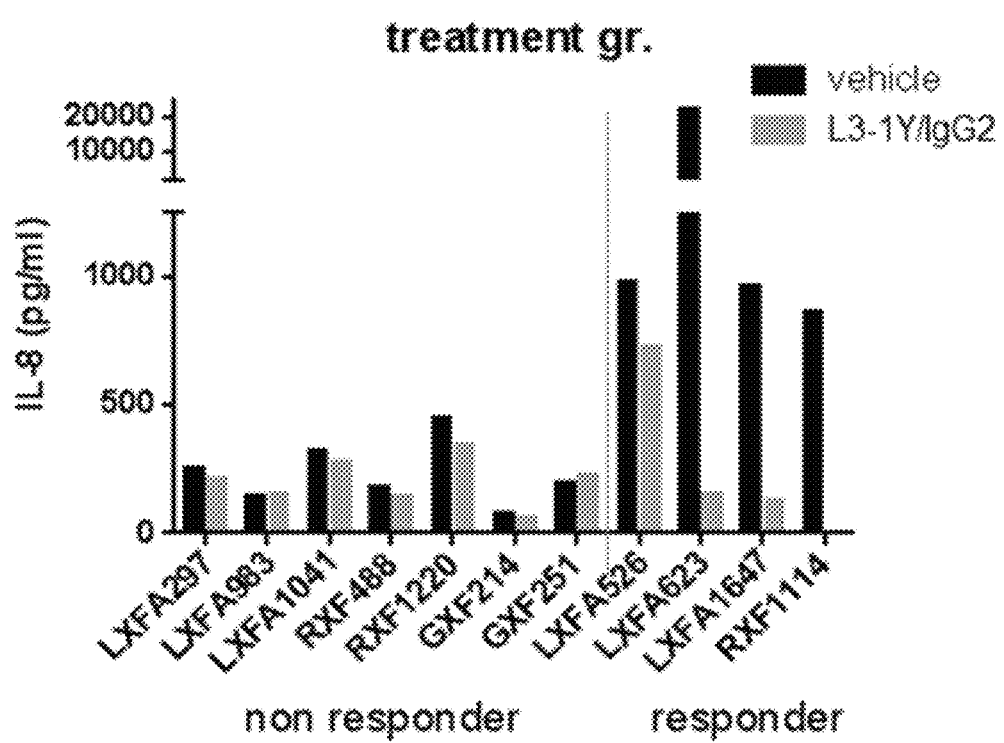
FIG. 5 is a graph of IL-8 levels in serum samples from anti-c-Met antibody-treated and untreated (control PBS treated groups of mouse models implanted with patient-derived tumor tissues, showing relationship between the anticancer efficacy of the anti-c-Met antibody and the change of IL-8 level after treatment of anti-c-Met antibody.

Results are depicted in FIG. 5. As is understood from the data of FIG. 3, there are no significant differences in serum IL-8 levels between vehicle and L3-1Y/IgG2 treatment samples of non-responder group whereas the responder group showed significant decrease in serum IL-8 levels after treatment of L3-1Y/IgG2. These data imply that a patient can be monitored for responsiveness to L3-1Y/IgG2, that is, the efficacy of L3-1Y/IgG2 by measuring the expression level of IL-8 in the patient treated with L3-1Y/IgG2.

1.3. Change in IL-8 Level with Time after Anti-c-Met Antibody Injection 1.3.1. Construction of Cancer Cell-Implanted Mouse Model and Assay for Anticancer Activity of Anti-c-Met Antibody in the Mouse Model The role of IL-8 as a pharmcodynamic marker of anti-c-Met antibodies was confirmed in xengraft mouse models which were prepared by implanting cancer cell lines known to be responsive to the antibody.

As opposed to Example 1.1, this experiment was configured to examine the responsiveness in a condition under which tumor volumes were little changed. After implantation, tumors were increased to a size of 1000 mm$^3$ and, then, the antibody was injected in various doses to the mice models. According time after injection, serum samples and tumor tissues were taken from three mice per group. In addition, tumor volumes were measured at regular intervals of time.

Briefly, xenograft mouse models implanted with the human stomach cell line Hs746T (Accession No. HTB-135) or human non-small cell lung cancer line EBC-1 (Accession No. JCRB0820) were employed. Each cancer cell line was injected s.c. at a dose of $5 \times 10^6$ cells to 150 Balb.c nude mice (Shanghai SLAC Laboratory Animal Co. Ltd.). All of the experimental animals were male and 5-6 weeks old upon the implantation, and bred in an SPF condition. In order to increase the tumor to a predetermined size, the mice implanted with the cancer cells were treated with the drug (antibody) only 16-20 days after the implantation. When the tumor grew to a size of about 1000 mm$^3$, the mice were randomly divided into groups of 30: PBS-treated group (Group 1) and anti-c-Met antibody-treated groups (Groups 2, 3, and 4). The treated groups were classified according to the dose of the antibody: 1 mg/kg (Group 2), 3 mg/kg (Group 3) and 10 mg/kg (Group 4). The antibody and the vehicle were administered twice at regular intervals of 7 days. Each sample was withdrawn 1 hr, 1 day (24 hrs), 2 days (48 hrs), 3 days (72 hrs), and 7 days (168 hrs) after the first injection. The same sampling time schedule was repeated after the second injection: 1 hr (169 hrs), 1 day (192 hrs), 2 days (216 hrs), 3 days (240 hrs), and 7 days (336 hrs). With regard to sampling, serum and tissues were taken from three mice which were sacrificed at each time point. Tumor volumes were also measured upon sampling to monitor the anticancer activity of the antibody (PharmaLegacy Laboratories Vivarium).

Figure 6:
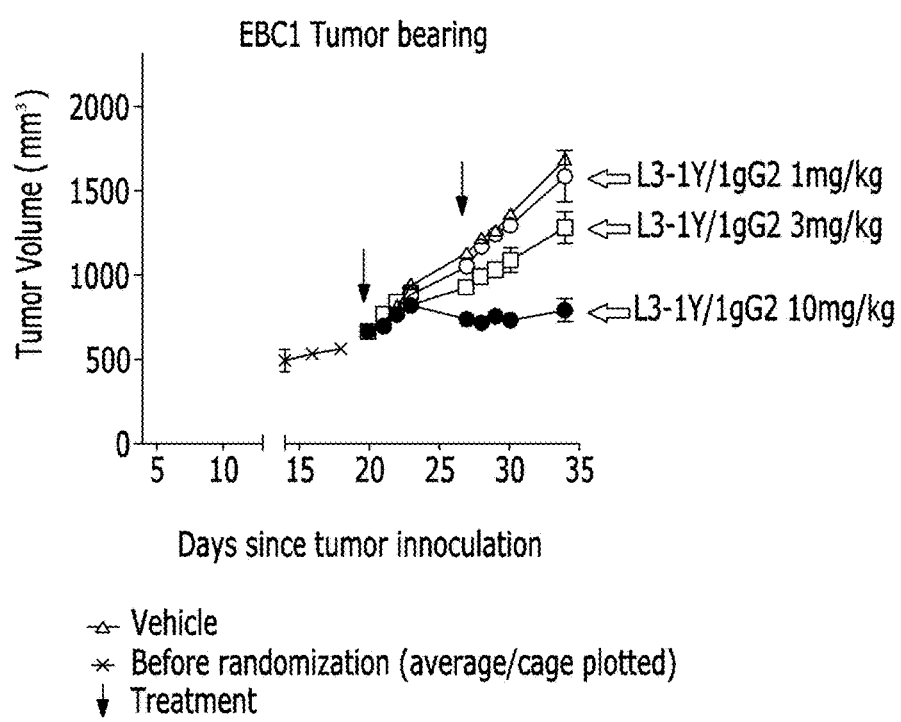
FIG. 6 is a graph showing a change in tumor size after treatment of the anti-c-Met antibody in conventional cancer cell line (EBC-1)-implanted mouse models.
Figure 7:
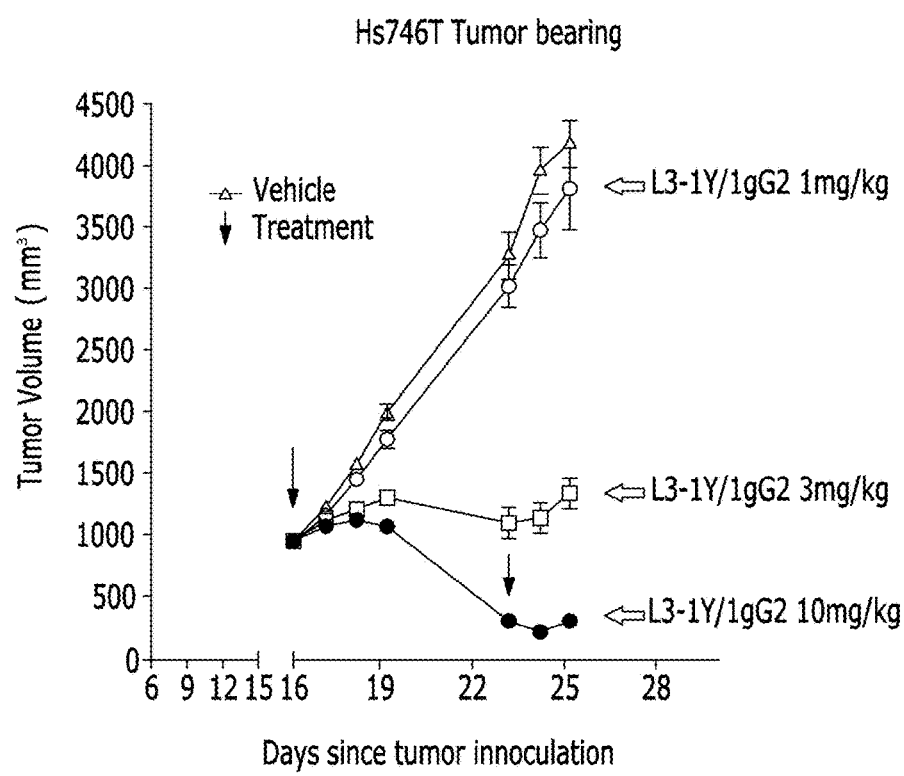
FIG. 7 is a graph a graph showing a change in tumor size after treatment of the anti-c-Met antibody in conventional cancer cell line (Hs746T)-implanted mouse models.

Anticancer activity data obtained above are depicted in FIG. 6 (EBC-1 implanted) and FIG. 7 (Hs746T implanted).

As is apparent from the data of FIGS. 6 and 7, the anti-c-Met antibody exhibited anticancer activity in mice bearing tumors of EBC-1 and Hs746T, as well, and the anticancer activity was dose-dependent.

1.3.2 Evaluation of the Efficacy of Anti-c-Met Antibody in Cancer Cell-Implanted Mouse Model Using Measurement of the Serum Level of IL-8

The following experiments were conducted with samples taken from the EBC-1- or Hs746T-implanted mouse models prepared in Example 1.3.1. To examine whether the anti-c-Met antibody-induced responsiveness of IL-8 is simply reflect the shrunken tumor size as a result from the efficacy of anti-cMet Ab, time course serum samples were analyzed from the EBC-1- or Hs746T-implanted mouse models to measure the short-term response to L3-1Y/IgG2.

Figure 8:
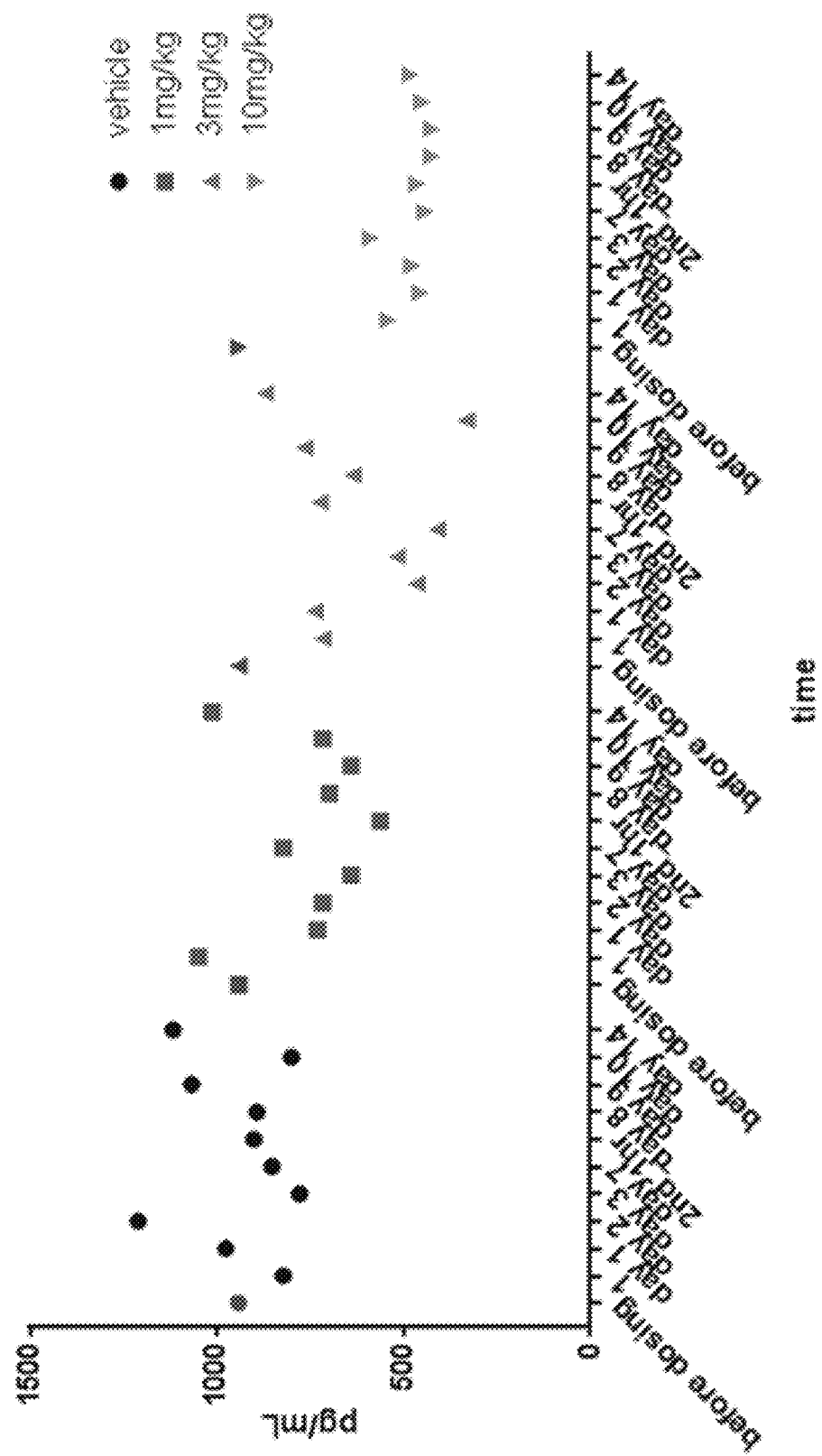
FIG. 8 is a graph showing a change in IL-8 level with time after treatment of the anti-c-Met antibody in conventional cancer cell line (EBC-1)-implanted mouse models.

Briefly, serum samples were taken in an amount of 100 μL from each of 3 mice per group according to time after antibody dosing (see FIG. 8). The serum samples from the same group were pooled, and quantitatively analyzed for IL-8 level using CBA method.

Figure 9:
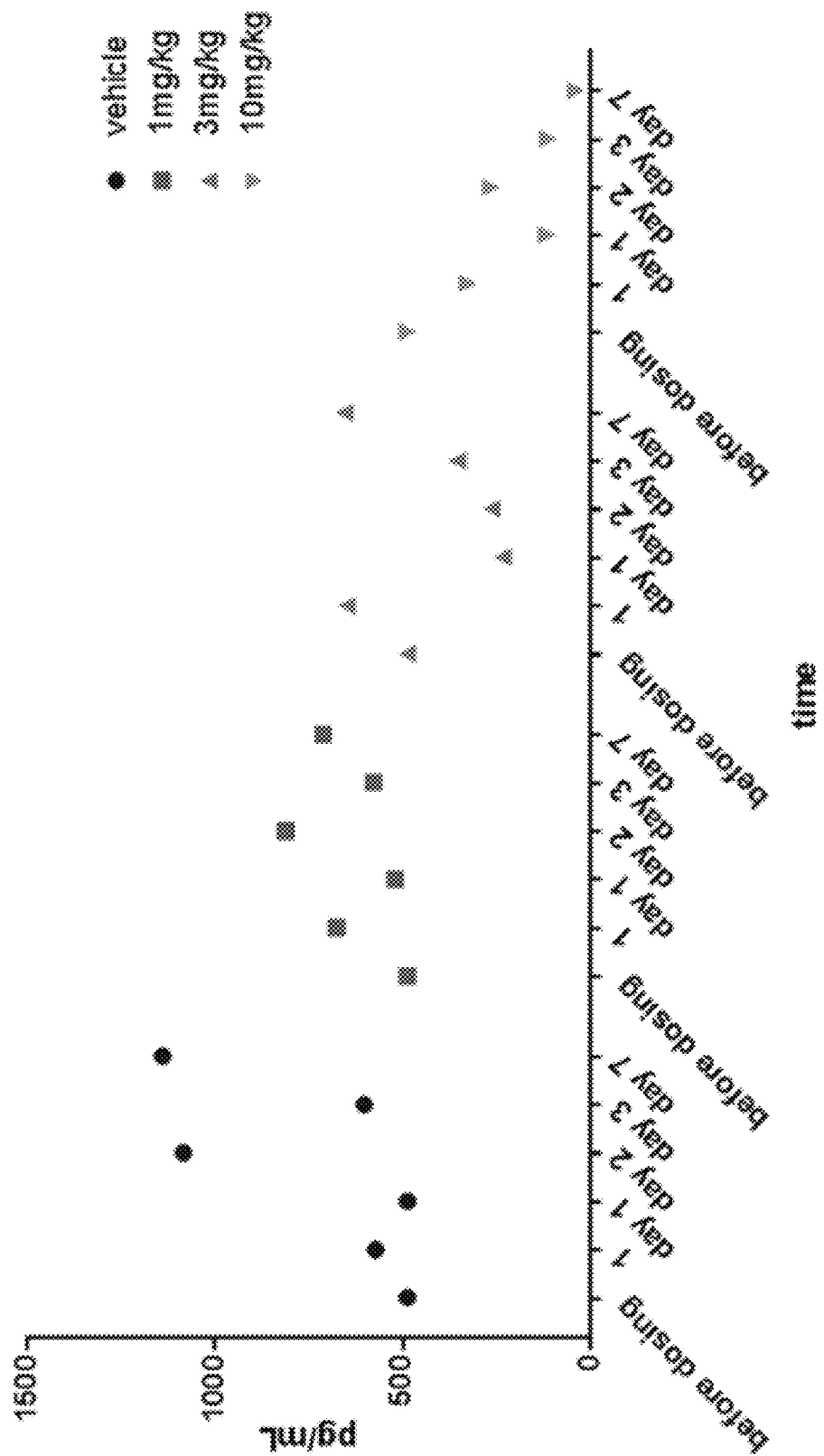
FIG. 9 is a graph showing a change in IL-8 level with time after treatment of the anti-c-Met antibody in conventional cancer cell line (Hs746T)-implanted mouse models.

The results are summarized in FIGS. 8 and 9.

As can be seen in FIGS. 8 and 9, the serum IL-8 level was observed to decrease in a dose-dependent manner upon treatment with the anti-c-Met antibody, and was already lowered at 1 hr after treatment in the high-dose treatment group (10 mg/kg). At the same time, the tumor size was not significantly change in L3-1Y/IgG2 treated mice at this time point (1 hr after treatment). These data indicate that the change of serum IL-8 level shows a drug response in vivo xenograft models and it is not solely dependent on the tumor size. So, IL-8 can be used as an early marker indicative of in vivo responsiveness to an anti-c-Met antibody. Taken together, the data demonstrates that the responsiveness of IL-8 is not attributed simply to the change in tumor size and can be useful biomarker for c-Met targeted therapy.

1.4. Test of Efficacies of c-Met Inhibitors Other than Anti-c-Met Antibodies

It was verified whether or not the change in IL-8 level can be applicable to a monitoring of responsiveness to a c-Met targeting drug other than anti-c-Met antibodies, as a marker.

In particular, EBC-1 (human lung cancer cell line; Accession No. JCRB0820) and Hs746T (human stomach cancer cell line; Accession No. HTB-135), on which anti-c-Met antibody L3-1Y/IgG2 displays anticancer efficacies (anti-c-Met antibody responder groups), and Lovo (human colon cancer cell line; Accession No. CCL-229) and HT29 (human colon cancer cell line; Accession No. HTB-38), on which anti-c-Met antibody L3-1Y/IgG2 displays no anticancer efficacies (anti-c-Met antibody non-responder groups), were selected and cultured. The 4 cell lines were seeded on a 96 well plate at the same amount ($1 \times 10^4$ cells/well) and cultured for 24 hours (media: RPMI(Gibco, Invitrogen), culture conditions: 37° C., 5% $CO_2$). The cultured cells were treated with representative c-Met inhibitor, crizotinib(Selleck chemical) and PHA665752((R,Z)-5-(2,6-dichlorobenzylsulfonyl)-3-((3,5-dimethyl-4-(2-(pyrrolidin-1-ylmethyl)pyrrolidine-1-carbonyl)-1H-pyrrol-2-yl)methylene)indolin-2-one), respectively. For comparison, human control IgG (chrompure human IgG (009-000-003, JACKSON IMMUNORESEARCH LABS INC.)) as a control and anti-c-Met antibody L3-1Y/IgG2 (Reference Example) were used respectively. Each of the inhibitors (or antibody) was treated at 10-fold serial diluted concentrations from 1000 nM to 0.01 nM. 72 hours after the treatment, the level of IL-8 in cell culture of each treatment group was assayed Cytometric Bead Array (CBA) method using BD Cytometric Bead Array kit (see Example 1.1.2). In addition, in order to verify the anticancer efficacy of the c-Met inhibitors, the cell proliferation (%) was measured at 72 hours after c-Met inhibitor treatment through Cell-Titer Glo (CTG) assay.

Figure 20:
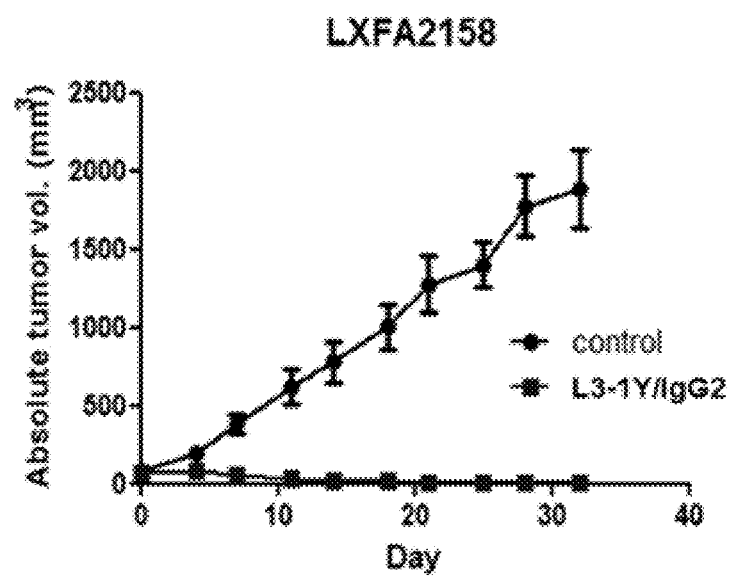
FIG. 20 contains graphs illustrating the change of tumor sizes after treatment of the anti-c-Met antibody in the presence or absence of K-RAS and B-RAF mutations in patient-derived tumor tissue-implanted mouse model LXFA 2158.
Figure 21:
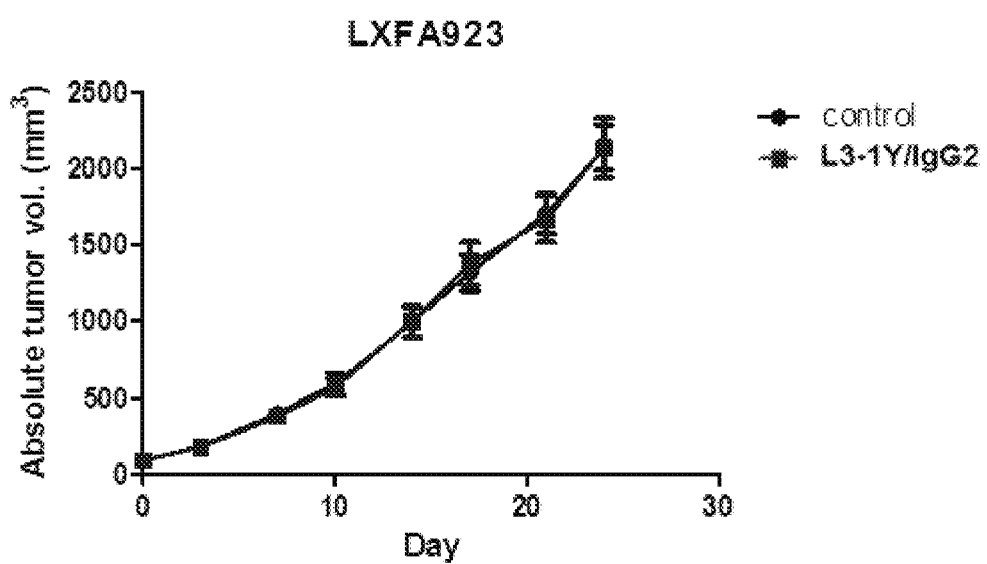
FIG. 21 contains graphs illustrating the change of tumor sizes after treatment of the anti-c-Met antibody in the presence or absence of K-RAS and B-RAF mutations in patient-derived tumor tissue-implanted mouse model LXFA 923.

The obtained results of cell proliferation (%) (i.e., results of CTG assay) at 72 hours were shown in FIG. 20 (anti-c-Met antibody responder groups) and FIG. 21 (anti-c-Met antibody non-responder groups). As shown in FIGS. 20 and 21, the profile of responsiveness to each c-Met inhibitor, crizotinib and PHA665752, is similar to that to anti-c-Met antibody L3-1Y/IgG2. That is, when crizotinib or PHA665752 was treated, the cell proliferation of L3-1Y/IgG2 responder groups, EBC-1 and Hs746T cell lines was significantly inhibited (decreased) at the inhibitor concentration of 10 nM or more (see FIG. 20), whereas the cell proliferation of L3-1Y/IgG2 non-responder groups, Lovo and HT29 cell lines displays no significant decrease (see FIG. 21).

Figure 22:
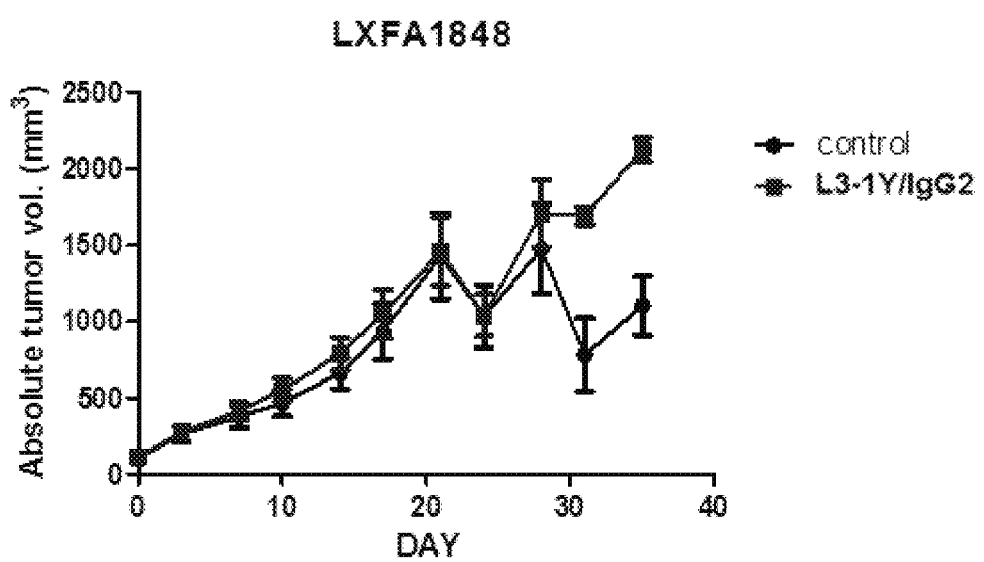
FIG. 22 contains graphs illustrating the change of tumor sizes after treatment of the anti-c-Met antibody in the presence or absence of K-RAS and B-RAF mutations in patient-derived tumor tissue-implanted mouse model LXFA 1848.
Figure 23:
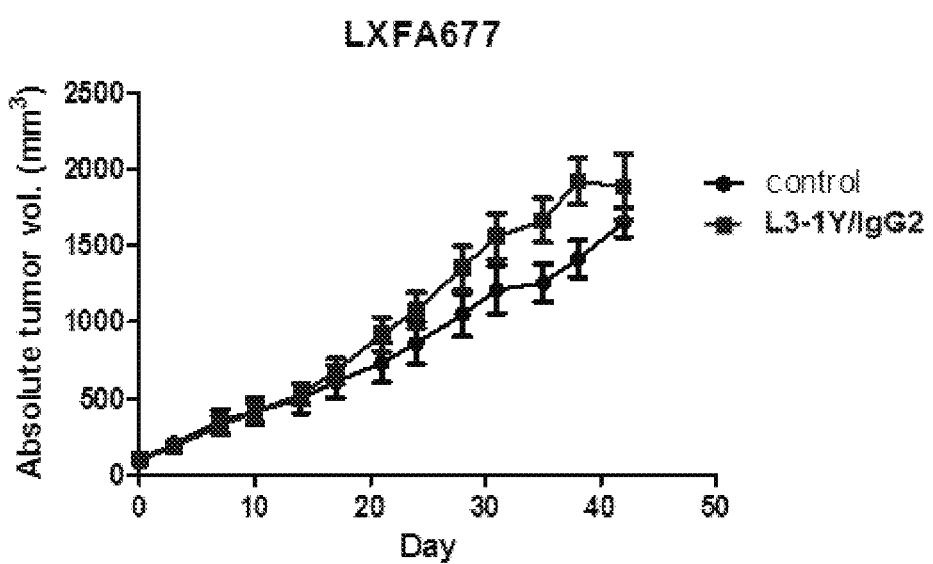
FIG. 23 contains graphs illustrating the change of tumor sizes after treatment of the anti-c-Met antibody in the presence or absence of K-RAS and B-RAF mutations in patient-derived tumor tissue-implanted mouse model LXFA 677.

In addition, at the concentration of 10 nM, from which the responsiveness to the inhibitors can be observed, the level of IL-8 in a cell culture of each treatment group was measured by Cytometric Bead Array (CBA) method using BD Cytometric Bead Array kit (see, Example 1.1.2), and the obtained results are shown in FIGS. 22 and 23 as relative ratio to the level of IL-8 in medium (100%). As shown in FIGS. 22 and 23, the level of IL-8 was significantly decreased in the responder groups, EBC-1 and Hs746T cell lines, which displayed significant decrease in cell proliferation, whereas any significant decrease in the level of IL-8 was not observed in the non-responder groups, Lovo and HT-29 cell lines.

These results indicate that the decrease in IL-8 level can also be useful as a maker for evaluation of the efficacy of not only anti-c-Met antibodies but also c-Met inhibitors other than anti-c-Met antibodies.

Example 2: Evaluation of Efficacy of Anti-c-Met Antibody Using bIG-H3

2.1. Selection of bIG-H3 as Pharmacodynamic Marker for Anti-c-Met Antibody

Proteins which showed a significant difference in the expression level between an anti-c-Met antibody-treated group and an untreated group responsive to the anti-c-Met antibody were selected as possible biomarkers for evaluating the efficacy of the anti-c-Met antibody, using an antibody array membrane capable of detecting 119 soluble receptors (R&D, cat# ARY012).

Figure 10:
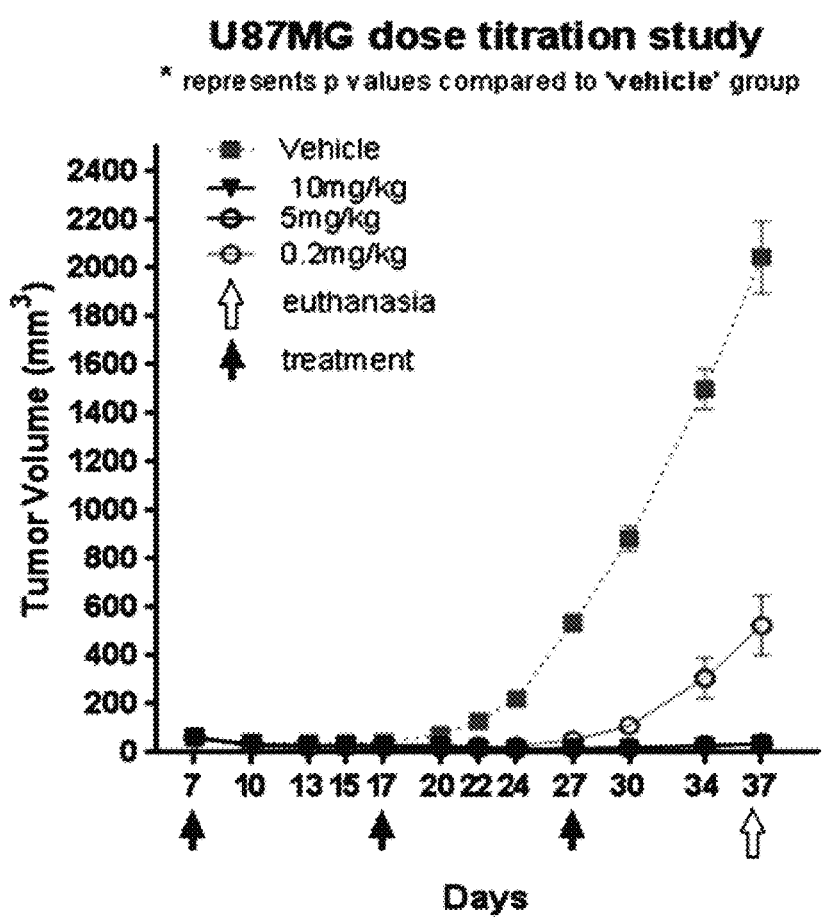
FIG. 10 is a graph showing a change in tumor size after treatment of the anti-c-Met antibody in U87MG-implanted mouse model.

In mouse models which were constructed with U87MG (Accession No. HTB-14) in the same manner as in Example 1.1.1, changes in tumor size with treatment with the anti-c-Met antibody L3-1Y/IgG2 were monitored. The results are shown in FIG. 10. As can be seen in FIG. 10, the anti-c-Met antibody L3-1Y/IgG2 exhibited anticancer activity in a dose-dependent manner in the U87MG-implanted mouse models.

Of the U87MG cells which were identified to respond to the anti-c-Met antibody, differences in protein expression level between anti-c-Met antibody-treated cells groups and untreated cells groups were investigated.

In this regard, serum samples taken from mouse models which were constructed with U87MG (Accession No. HTB-14) in the same manner as in Example 1.1.1 were incubated with the antibody array membrane (R&D, cat# ARY012) to examine responsiveness to the anti-c-Met antibody. In the membrane, 200 µl of the mouse serum was incubated for overnight at 4° C. with the buffer and the capture antibody, followed by developing the membrane in chemiluminescence immunoassay. The antibody L3-1Y/IgG2 was intravenously injected at a dose of 10 mg/ml every 7 days for 4 weeks from 7-10 days after implantation.

Figure 11:
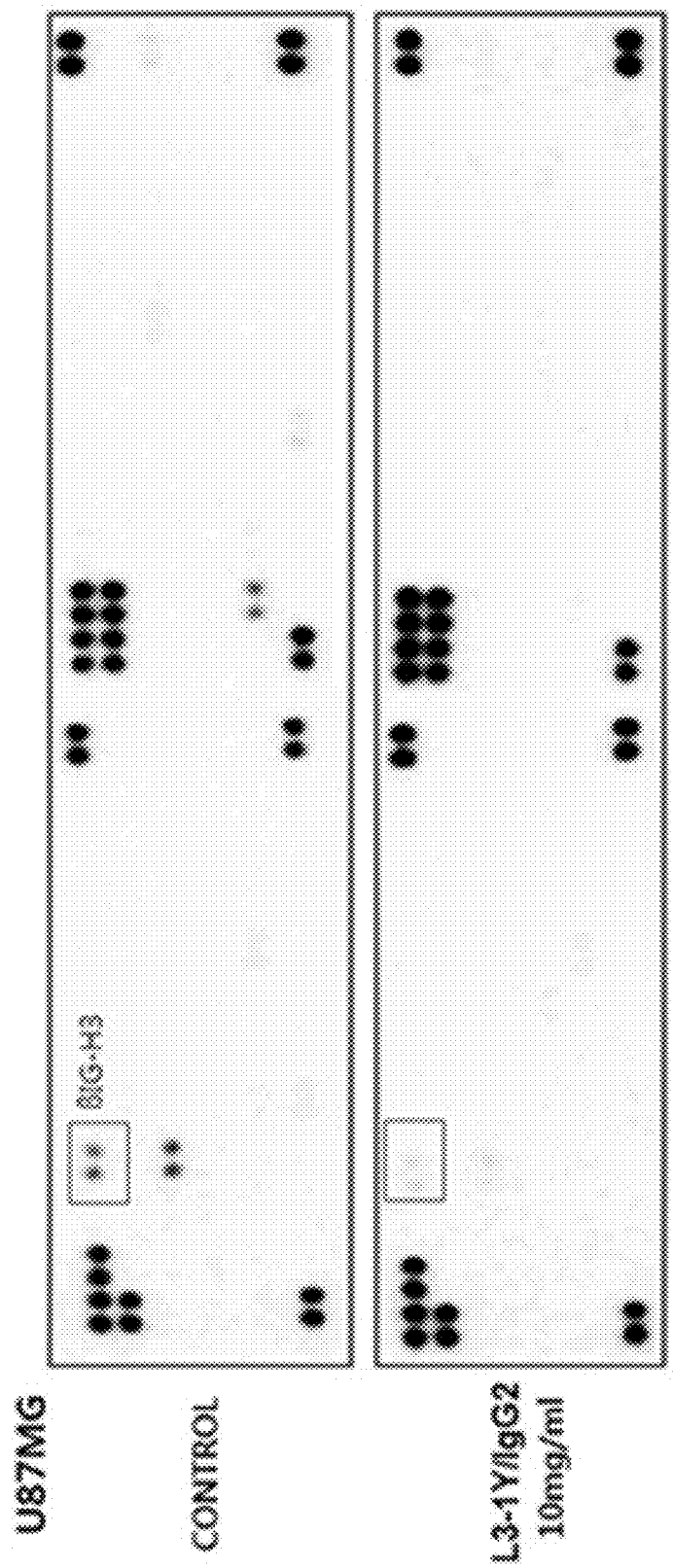
FIG. 11 is a chemiluminescence immunoassay using protein array kit, which shows a change in protein expression pattern in U87MG cells.

The results are depicted in FIG. 11. On the membrane, positive control dots appear at the corners and at middle regions while significant changes are detected as indicated by boxed dots. They were identified as bIG-H3. As compared to the control (PBS treated), L3-1Y/IgG2 significantly decreased the expression level of bIG-H3. Based on this finding, bIG-H3 is first suggested as a pharmacodynamic marker for anti-c-Met antibodies.

2.2. Evaluation of the Efficacy of Anti-c-Met Antibody in Cancer Cell-Implanted Mouse Model Using bIG-H3

2.2.1. Construction of Cancer Cell-Implanted Mouse Model

For use in assays for evaluating the efficacy of an anti-c-Met antibody, xenograft mouse models were prepared by implanting various cancer cell lines (anti-c-Met antibody-responsive cell lines: Lovo (Accession No. CCL-229), HT-29 (Accession No. HTB-38), PC3 (Accession No. CRL-1435), BxPC3 (Accession No. CRL-1687), MDAMB231 (Accession No. HTB-26); anti-c-Met antibody non-responsive cell lines: Hs746T (Accession No. HTB-135), MKN45 (Accession No. RCB1001), EBC-1 (Accession No. JCRB0820), U87MG (Accession No. HTB-14), MHCC97H (Accession No. NB 100-122)) to mice in the same manner as in Example 1.1.1.

Of the mouse models, Hs746T-, MKN45- and EBC-1-implanted mouse models were found to have responsiveness to the anti-c-Met antibody, as demonstrated in Example 1.1.2.

2.2.2. Evaluation of the Efficacy of Anti-c-Met Antibody in Cancer Cell-Implanted Mouse Model Using bIG-H3

To examine relationship between bIG-H3 level and responsiveness to anti-c-Met antibody, changes of serum bIG-H3 levels with treatment with an anti-c-Met antibody in cancer cell-implanted mouse models were monitored.

Briefly, serum samples taken from mouse models in a group were pooled, and quantitatively analyzed for bIG-H3 level using a bIG-H3 ELISA kit (R&D) in comparison with the control (injected with vehicle (PBS) only).

Figure 12:
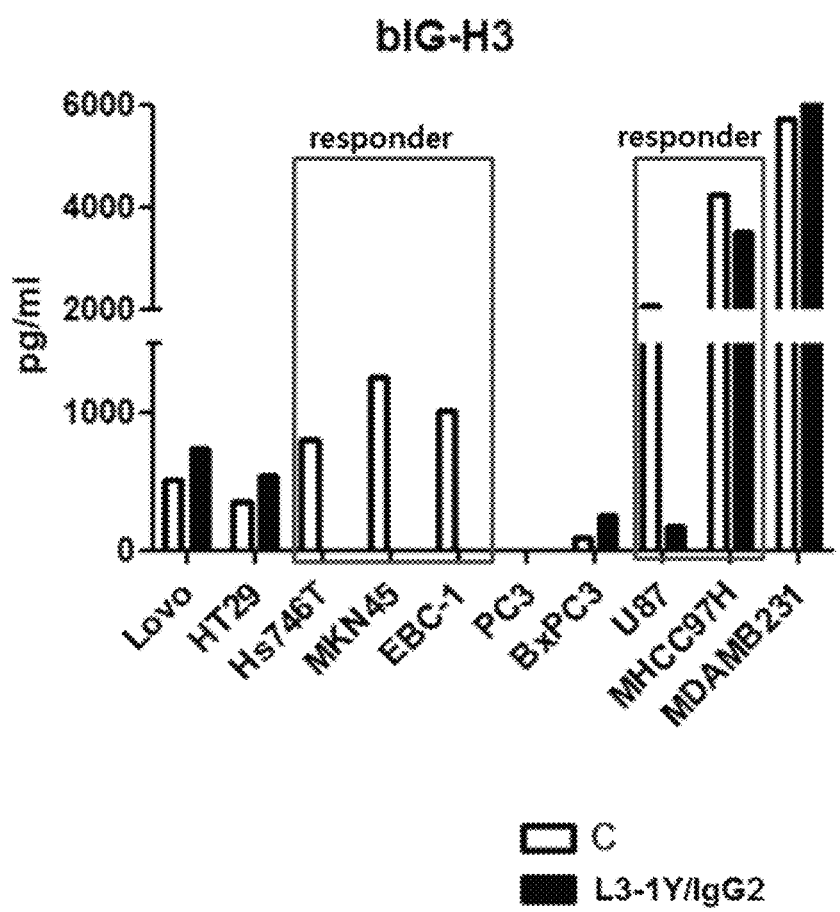
FIG. 12 is a graph showing a change in bIG-H3 level after treatment of the anti-c-Met antibody in serum from mouse models implanted with various cancer cells.

Results are depicted in FIG. 12. As is understood from the data of FIG. 12, the non-responder groups showed no significant differences or an increase in the bIG-H3 expression level upon treatment with L3-1Y/IgG2, compared to the non-treated group (injected with vehicle only, PBS) whereas the responder group significantly decreased in bIG-H3 expression level, compared to the untreated group, or expressed little bIG-H3. These data imply that a patient can be monitored for responsiveness to L3-1Y/IgG2, that is, the efficacy of L3-1Y/IgG2 by measuring the expression level of bIG-H3 in the patient treated with L3-1Y/IgG2.

2.3. Evaluation of Efficacy of Anti-c-Met Antibody in Mouse Model Implanted with Patient-Derived Tumor Tissues Using bIG-H3

2.3.1. Construction of Mouse Model Implanted with Patient-Derived Tumor Tissue

With reference to Example 1.2.1, patient-derived lung cancer cell-implanted mouse models LXFA297, LXFA526, LXFA623, LXFA983, LXFA1041, and LXFA1647 were constructed. Of them, LXFA526, LXFA623, and LXFA1647 were observed to be responsive to the anti-c-Met antibody as shown in Table 4.

2.3.2. Evaluation of Efficacy of Anti-c-Met Antibody in Mouse Model Implanted with Patient-Derived Tumor Tissues Using bIG-H3

To examine the relationship between bIG-H3 level and responsiveness to an anti-c-Met antibody, changes of serum bIG-H3 levels with treatment with an anti-c-Met antibody in patient-derived tumor tissues-implanted mouse models were monitored.

Briefly, serum samples taken from mouse models in a group were pooled, and quantitatively analyzed for bIG-H3 level using a bIG-H3 ELISA kit (R&D) in comparison with the control (injected with vehicle (PBS) only), in the same manner as in Example 2.2.2 (refer to Example 1.1.2).

Figure 13:
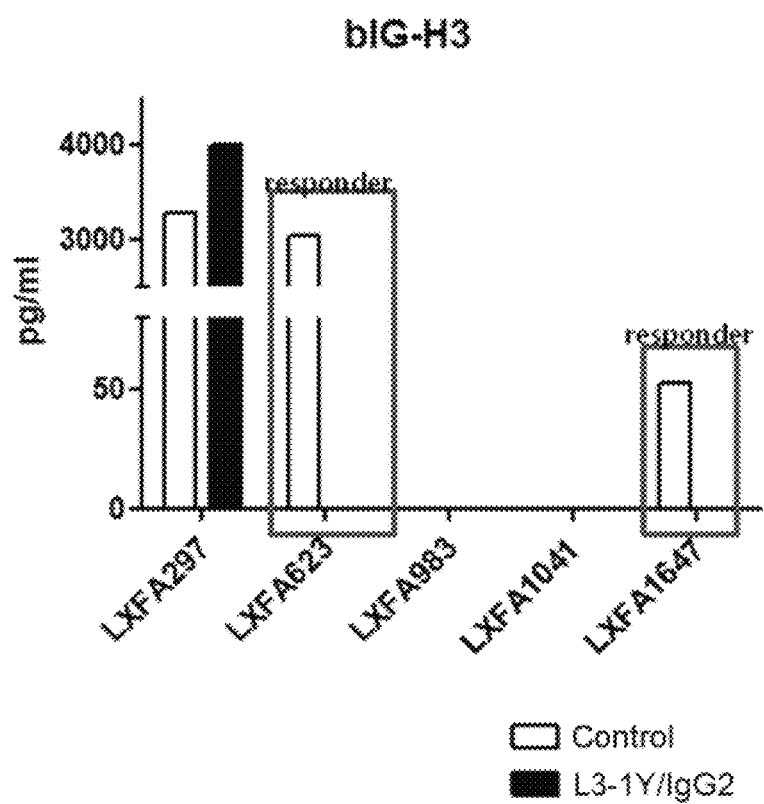
FIG. 13 is a graph showing a change in bIG-H3 level after treatment of the anti-c-Met antibody in serum from mouse models implanted with patient-derived tumor tissues.

Results are depicted in FIG. 13. As is understood from the data of FIG. 13, the non-responder groups showed no significant differences or an increase in the bIG-H3 expression level upon treatment with L3-1Y/IgG2, compared to the non-treated group (injected with vehicle only, PBS) whereas the responder group significantly decreased in bIG-H3 expression level, compared to the untreated group, or expressed little bIG-H3. These data imply that a patient can be monitored for responsiveness to L3-1Y/IgG2, that is, the efficacy of L3-1Y/IgG2 by measuring the expression level of bIG-H3 in the patient treated with L3-1Y/IgG2.

Cancer tissues isolated from L3-1Y/IgG2-treated or untreated groups of the animal models were homogenized and lysed in 500 µl of a lysis buffer (Roche). After centrifugation, the cell soup (cell lysate) was harvested and quantified. The cell soup was loaded in an amount corresponding to 1 ug of the total cell protein to plates of the bIG-H3 ELISA kit (R&D). The plates were previously coated with a capture antibody for bIG-H3. The HRP-conjugated detection antibody was applied to the plates before reading O.D 450.

Figure 14:
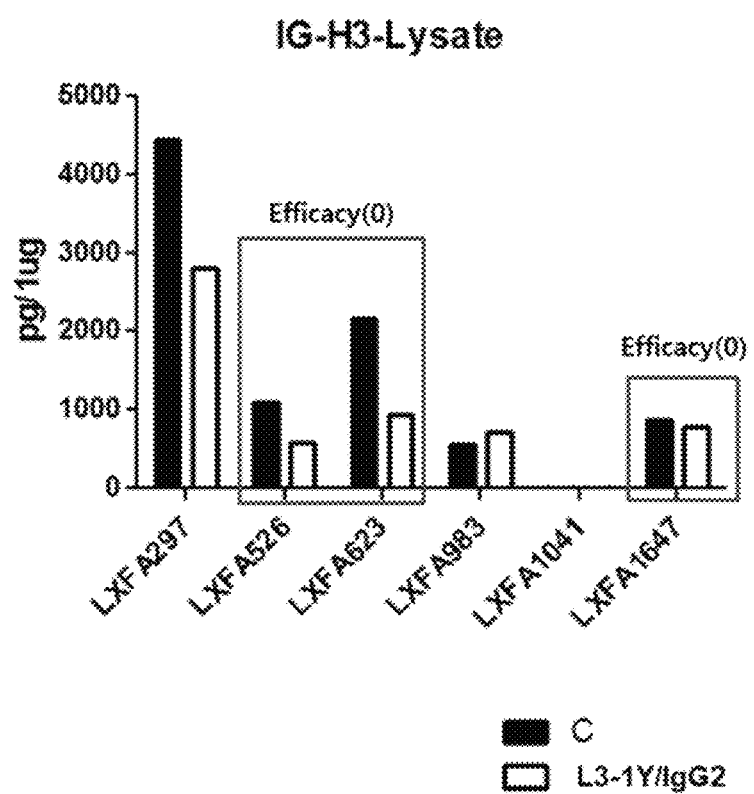
FIG. 14 is a graph showing a change in bIG-H3 level after treatment of the anti-c-Met antibody in cancer tissue lysates from mouse models implanted with patient-derived tumor tissues.

The results are depicted in FIG. 14. As can be seen in FIG. 14, it was also observed from the cell soup that the content of bIG-H3 in 1 µg of the total cell protein was remarkably reduced in the antibody-treated group of the responder, compared to the untreated group.

Example 3: Evaluation of Efficacy of Anti-c-Met Antibody Using MIF 3.1. Selection of MIF as Pharmacodynamic Marker for Anti-c-Met Antibody A protein which showed a significant difference in the expression level between an anti-c-Met antibody-treated group and an untreated group of the LXFA623 mouse model responsive to the anti-c-Met antibody (refer to Example 1.2.1 and Table 4) was selected as a marker for evaluating the efficacy of the anti-c-Met antibody, using an antibody array membrane capable of detecting 46 cytokines (R&D ARY005).

Briefly, 200 µl of each of serum samples taken from the antibody-treated group (L3-1Y/IgG2, 5 mg/kg) and the untreated group (PBS injected, control) of the LXFA623 mouse model were incubated overnight 4° C. with the buffer provided in the kit, followed by developing dots in chemiluminescence immunoassay. This experiment was performed with antibody array membrane (R&D ARY005).

Figure 15:
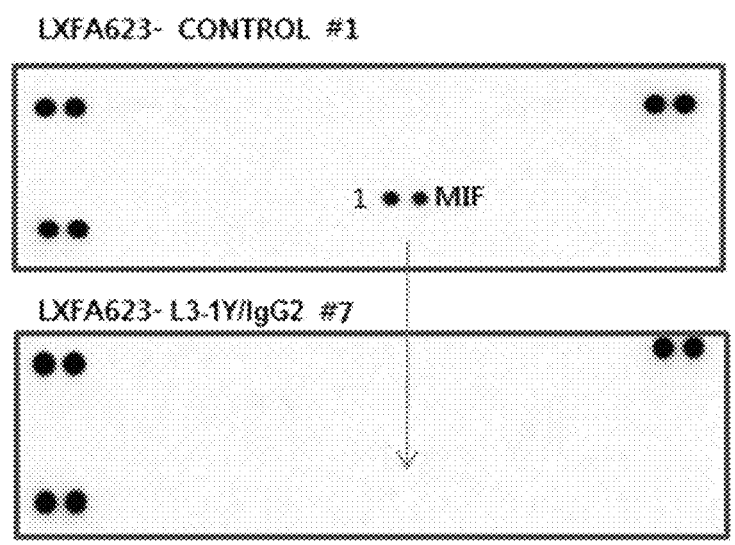
FIG. 15 shows a change in protein expression pattern in a patient-derived tumor tissue-implanted mouse model (LXFA623), as measured by a chemiluminescence immunoassay using protein array kit.

The results are depicted in FIG. 15. On the membrane of FIG. 15, L3-1Y/IgG2 remarkably reduced the level of MIF, compared to the control (PBS injected), indicating that MIF can be used as a pharmacodynamic mark for anti-c-Met antibodies.

3.2. Evaluation of the Efficacy of Anti-c-Met Antibody in Cancer Cell-Implanted Mouse Model Using MIF In the same manner as in Example 2.2.1, xenograft mouse models were constructed by implanting various cancer cell lines (non-responder: Lovo (Accession No. CCL-229), HT-29 (Accession No. HTB-38), PC3 (Accession No. CRL-1435), BxPC3 (Accession No. CRL-1687), MDAMB231 (Accession No. HTB-26); responder: Hs746T (Accession No. HTB-135), MKN45 (Accession No. RCB1001), EBC-1 (Accession No. JCRB0820), U87MG (Accession No. HTB-14), MHCC97H (Accession No. NB100-122)).

To examine relationship between MIF level and responsiveness to anti-c-Met antibody, changes of ME levels with treatment with an anti-c-Met antibody in cancer cell-implanted mouse models were monitored.

Briefly, serum samples taken from mouse models in each group, e.g., L3-1Y/IgG2-treated group or untreated group (PBS injected, control) of the xenograft animal models, were pooled, and quantitatively analyzed for MIF level using an MIF ELISA kit (R&D). The experiment was conducted according to the manufacturer's manual.

Figure 16:
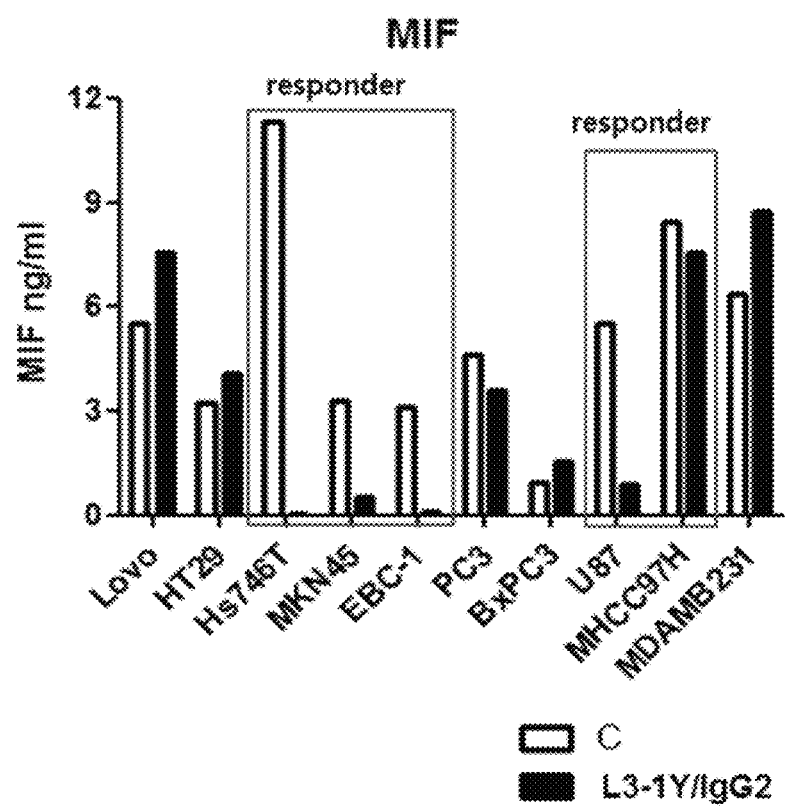
FIG. 16 is a graph showing a change in MIF level after treatment of the anti-c-Met antibody in serum samples from mouse models implanted with various cancer cell lines.

Results are depicted in FIG. 16. As is understood from the data of FIG. 16, the non-responder groups showed no significant differences or an increase in the MIF expression level upon treatment with L3-1Y/IgG2, compared to the untreated group (injected with vehicle only, PBS) whereas the responder group significantly decreased in MIF expression level, compared to the untreated group, or expressed little bIG-H3. These data imply that a patient can be monitored for responsiveness to L3-1Y/IgG2, that is, the efficacy of L3-1Y/IgG2 by measuring the expression level of ME in the patient treated with L3-1Y/IgG2.

3.3. Evaluation of Efficacy of Anti-c-Met Antibody in Mouse Model Implanted with Patient-Derived Tumor Tissues Using MIF With reference to Example 1.2.1, patient-derived lung cancer cell-implanted mouse models LXFA297, LXFA526, LXFA623, LXFA983, LXFA1041, and LXFA1647 were constructed. Of them, LXFA526, LXFA623, and LXFA1647 were observed to be responsive to the anti-c-Met antibody as shown in Table 4.

To examine the relationship between ME level and responsiveness to an anti-c-Met antibody, changes of serum MIF levels with treatment with an anti-c-Met antibody in patient-derived tumor tissues-implanted mouse models were monitored.

Briefly, MIF levels were using an ME ELISA kit in the same manner as in Example 3.2

Figure 17:
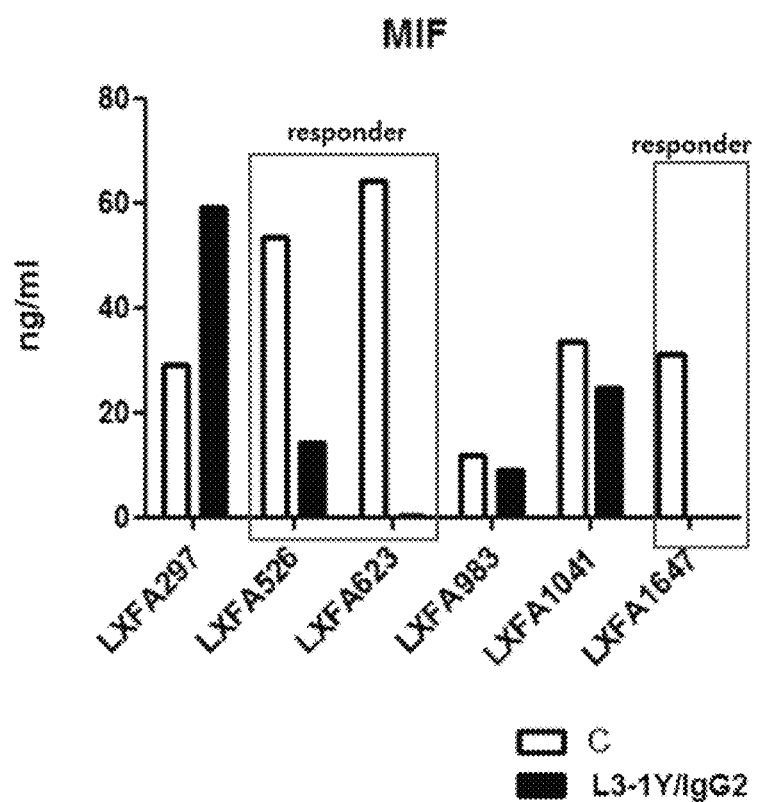
FIG. 17 is a graph showing a change in MIF level after treatment of the anti-c-Met antibody in serum samples from mouse models implanted with patient-derived tumor tissues.

Results are depicted in FIG. 17. As is understood from the data of FIG. 17, the non-responder groups showed no significant differences or an increase in the MIF expression level upon treatment with L3-1Y/IgG2, compared to the non-treated group (injected with vehicle only) whereas the responder group significantly decreased in MIF expression level, compared to the untreated group, or expressed little MIF. These data imply that a patient can be monitored for responsiveness to L3-1Y/IgG2, that is, the efficacy of L3-1Y/IgG2 by measuring the expression level of ME in the patient treated with L3-1Y/IgG2.

Example 4: Prediction of Efficacy of Anti-c-Met Antibody Using KRAS-BRAF Mutation 4.1. Assay for Predicting Efficacy of Anti-c-Met Antibody in Mouse Model Implanted with Patient-Derived Tumor Tissue Using KRAS-BRAF Mutation 4.1.1. Construction of Mouse Model Implanted with Patient-Derived Tumor Tissue For use in predicting the efficacy of anti-c-Met antibodies, xenograft mouse models implanted with patient-derived tumor tissues were constructed.

Briefly female NMRI nude mice (Charles River or Harlan, 4-6 weeks old) were implanted s.c. with cancer tissues extracted from patients (LXFA: lung cancer, GXF: stomach cancer, RXF: kidney cancer, GXA: gastric cancer, LXFL: lung large cell carcinoma, OVXF: ovarian cancer, PAXF: pancreatic cancer, CXF: colon cancer). When the tumor grew to a volume of 80 to 200 mm$^3$, the mice were randomly divided into groups of 10. The anti-c-Met antibody, L3-1Y/IgG2, was administered via i.v. injection on day 0, 7, 14, 21, 28, and 35 after randomization at a dose of 5 mg/kg. PBS was used for a control group. When the tumor volume reached 2000 mm$^3$, the mice were sacrificed and used in the following experiments.

4.1.2. Measurement of c-Met Expression Level in Patient-Derived Tumor Tissues-Implanted Mouse Model c-Met expression levels in the patient-derived cancer cell-implanted mouse models were measured using a Western blotting method.

Briefly, tumor tissues isolated from the animal models were homogenized and lyzed in 500 µl of a lysis buffer (Roche). After centrifugation, the cell soup (cell lysate) was harvested and quantified. The cell soup was loaded in an amount corresponding to 10 µg of the total cell protein (SDS-PAGE), followed by exposure to the membrane (Cell Signal; including the antibody)

Figure 18:
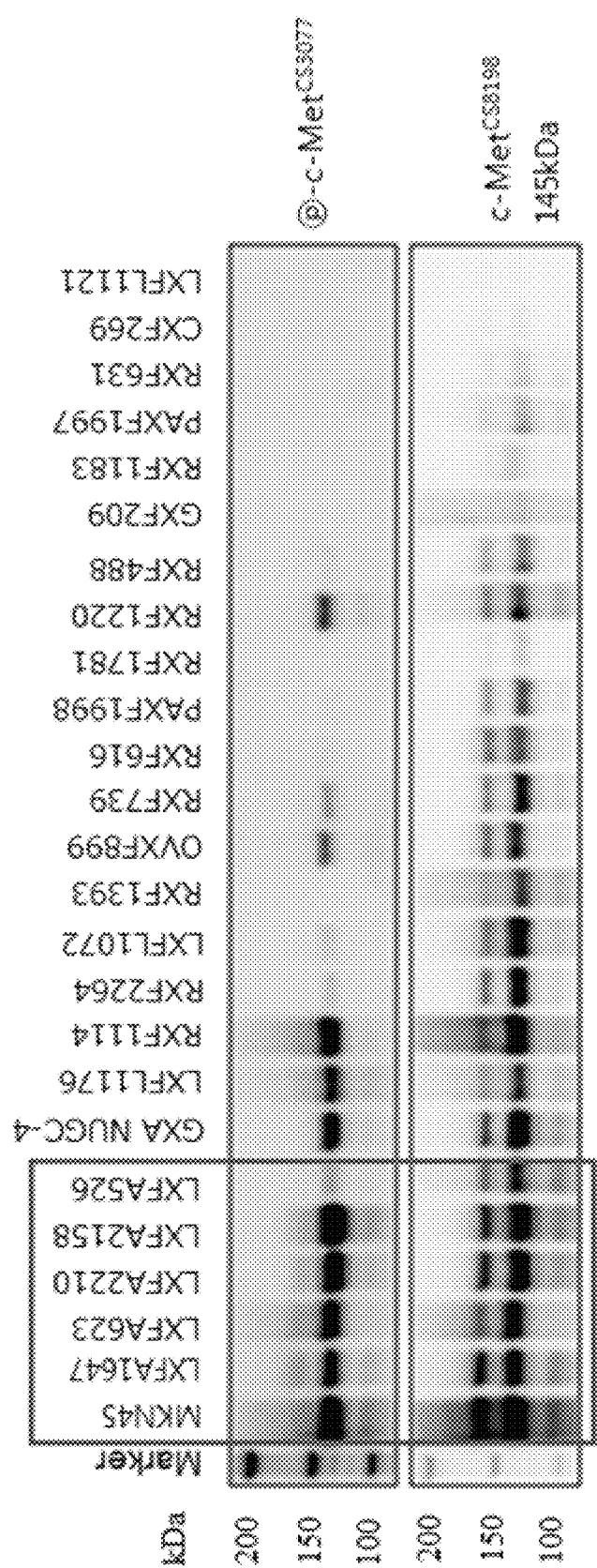
FIG. 18 shows c-Met protein expression levels in patient-derived cancer cell-implanted mouse models, as measured by Western blotting.

The results are depicted in FIG. 18. In FIG. 18, the mice which developed c-Met bands can be classified as being responsive to L3-1Y/IgG2. However, LXFA2201 did not respond to L3-1Y/IgG2 due to its RAF mutation although the band was detected.

4.1.3. Determination of KRAS-BRAF Mutation and Responsiveness to Anti-c-Met Antibody in Patient-Derived Tumor Tissues-Implanted Mouse Model Mice implanted with patient-derived tumor tissues were examined for the presence of mutation of K-RAS and B-RAF, and for responsiveness to the anti-c-Met antibody.

DNA isolated from cancer cells was amplified by PCR using a Sequenom™ system including the primers to discriminate the wild-type from mutants. Mutants were detected mostly at G12V, G12C, Q61H, and G12C for K-RAS, and at G596R and D594A for B-RAF.

This experiment was carried out with reference to Example 1.2.1.

Figure 19:
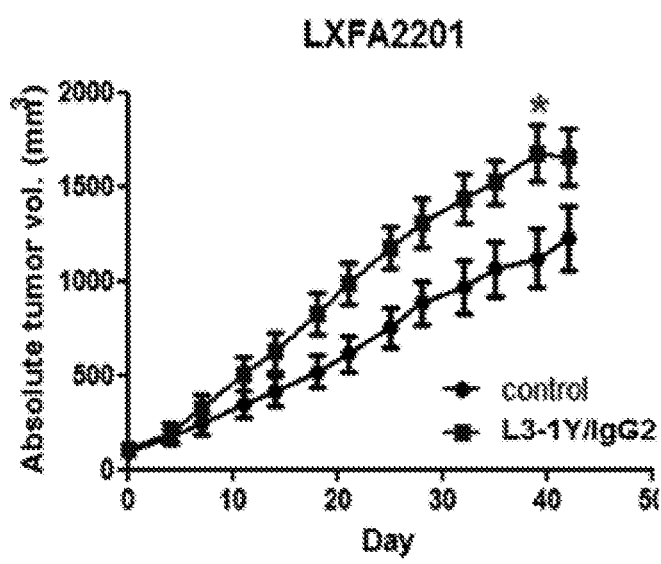
FIGS. 19A and 19B contains graphs illustrating the change of tumor sizes after treatment of the anti-c-Met antibody in the presence or absence of K-RAS and B-RAF mutations in patient-derived tumor tissue-implanted mouse model LXFA 2201.

Results are summarized in FIGS. 19A, 19B, and 20-23, wherein FIGS. 19A and 19B shows efficacy of anti-c-Met antibody in LXFA 2201 model, FIG. 20 in LXFA 2158 model, FIG. 21 in LXFA 923 model, FIG. 22 in LXFA 1848 model, and FIG. 23 in LXFA 677 model (efficacy of anti-c-Met antibody in the other mouse models is shown in Tables 4 and 5), and Table 6 (presence or absence of mutation of K-RAS and B-RAF in each mouse model).

TABLE 6

| tumor model | L3-1Y/IgG2 EFFICACY | MET level (by Affymetrix) | K-RAS mutation | B-RAF mutation |
|---|---|---|---|---|
| LXFA 2201 | NO | 14,770 | wild type | Mutation G596R |
| LXFA 2158 | Efficacy | 14,750 | wild type | wild type |
| LXFA 1647 | Efficacy | 14,000 | wild type | wild type |
| LXFA 526 | Efficacy | 14,000 | wild type | wild type |
| LXFA 623 | Efficacy | 14,000 | wild type | wild type |
| LXFA 1041 | NO | 12,390 | Mutation (G12V) | wild type |
| LXFA 923 | NO | 12,250 | Mutation (G12C) | wild type |
| LXFA 1848 | NO | 12,150 | Mutation (Q61H) | wild type |
| LXFA 677 | NO | 12,060 | wild type | Mutation (D594A) |
| LXFA 983 | NO | 12,000 | Mutation (G12C) | wild type |

As can be seen in Table 6, when one or more mutations are present in K-RAS or B-RAF, the anti-c-Met antibody is not sufficiently active in spite of a high expression level of c-Met (e.g., LXFA 2201). This indicates that the presence or absence of mutations in K-RAS or B-RAF is a critical factor to predicting the efficacy of the anti-c-Met antibody.

4.2. Assay for Predicting Efficacy of Anti-c-Met Antibody in Cancer Cell Line Using KRAS-BRAF Mutation (In Vitro)

4.2.1. Preparation of Cancer Cell Line

NCI-H441 (HTB-114), NCI-H1993 (CRL-5909), NCI-H1373 (CRL-5866), A549 (CCL-185), HCC827 (CRL-2868), and EBC-1 (Accession No. JCRB0820) cells were seeded at a density of 1×10$^4$ cells/well to plates and incubated with the antibody L3-1Y/IgG2 (1 µg/ml) for 72 hrs. Cell growth was compared between antibody-treated and untreated groups.

4.2.2. Examination of Cancer Cell-Implanted Mouse Model for Presence of RAS-RAF Mutation and Responsiveness to Anti-c-Met Antibody The cancer cell lines were examined for the presence of mutations in K-RAS and B-RAF and responsiveness to anti-c-Met antibody.

Briefly, DNA isolated from the cancer cells was amplified using a Sequenom™ system including the primers to discriminate the wild-type from mutants. Mutations were detected mostly at G12V, G12C, Q61H, and G12C for K-RAS, and at G596R and D594A for B-RAF.

Results are summarized in Table 7.

TABLE 7

| CELL LINE | L3-1Y/IgG2 EFFICACY | K-RAS mutation | B-RAF mutation |
|---|---|---|---|
| NCI-H441 | X | Mutation (G12V) | wild type |
| NCI-H1993 | Efficacy | wild type | wild type |
| NCI-H1373 | X | Mutation (G12C) | N.A |
| A549 | X | Mutation (G12S) | N.A |
| HCC827 | Efficacy | wild type | wild type |
| EBC1 | Efficacy | wild type | wild type |

(Efficacy: 30% or higher inhibition relative to the control, N.A.: not available)

As can be seen in Table 7, the anti-c-Met antibody can exert its anticancer activity in cancer models only when both K-RAS and B-RAF are wild-types.

4.3. KRAS Activity Test

To examine the activity of KRAS, it was tested whether or not KRAS binds to BRAF. The test was performed using Ras activation ELISA assay kit (17-497, Millipore) according to its protocol.

The tumor issues were separated from the mouse model (KRAS wild type: LXFA526 Model, KRAS mutant: LXFA1041 model (G12V mutation)), and each of the separated tumor tissues was grinded, lysed using 200 µl of lysis buffer (17-497, Millipore), and centrifuged to obtain cell lysate. 50 µl of total intracellular proteins was obtained from the cell lysate, loaded on 96 well plate (included in Ras activation ELISA assay kit (17-497, Millipore)) coated with RAS binding domain of RAF. A detection was conducted using HRP-conjugated RAS antibody (included in Ras activation ELISA assay kit (17-497, Millipore)), and then, the obtained results were read by luminometer.

Figure 24:
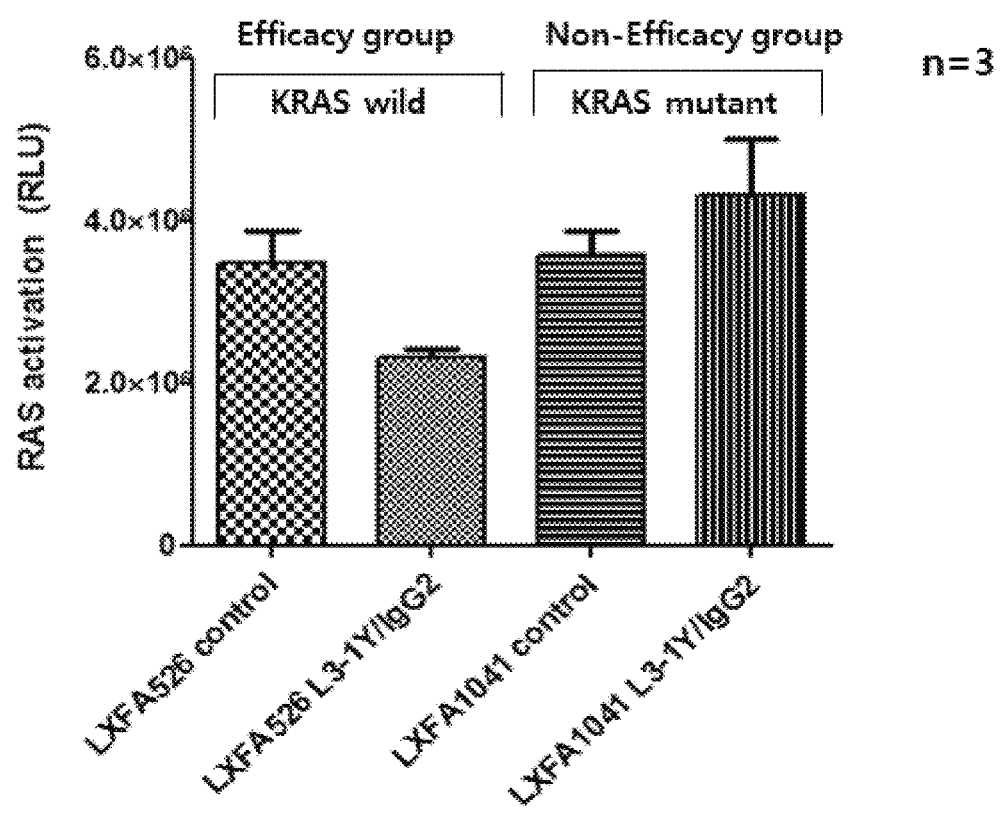
FIG. 24 is a graph showing the level of RAS activation after treatment of the anti-c-Met antibody in the presence or absence of K-RAS.

The obtained results were shown in FIG. 24, wherein "control" refers to a group treated with PBS only. As shown in FIG. 24, in wild-type RAS mice (with no KRAS mutation), treated with an anti-c-Met antibody L3-1Y/IgG2, the activity of KRAS is decreased compared to that of control; whereas in a KRAS mutant model, the treatment of anti-c-Met antibody L3-1Y/IgG2 has no effect on the activity of KRAS.

Example 5: Prediction Accuracy of Each Marker 5.1. Test of In Vivo Efficacy of Antibody Fourteen (14) mouse xenograft models, which were subjected to subcutaneously grafting of patient driven tumor tissues (Non-small cell lung cancer: NSCLC), were examined by Oncotest GmbH (Germany).

To each of the 14 mouse xenograft models, L3-1Y/IgG2 and empty vehicle (control) were administered, respectively, and the size of the tumor tissues was measured to determine the responsiveness to the antibody.

When the tumor size in the mouse xenograft models reaches 100 mm³ or more, the mouse xenograft models were administered (iv) with L3-1Y/IgG2 (PBS buffer in case of control) at the amount of 5 mg/kg once a week for 6 weeks in total, and the tumor size reaches 2000 mm³ or more, the experiment was stopped.

The tumor size (mm³) was calculated by the following formula:

Tumor size (mm³)=(major axis*minor axis*minor axis)*½

The determination of responder (efficacy) group was conducted by ANOVA analysis where the hypothesis corresponding to p-value of 0.05 or less was excluded. That is, the hypothesis that the tumor size distribution is not changed in a drug(antibody)-administered group compared to non-administered group was subjected to ANOVA testing, and the group where p-value is 0.05 or more was determined as a non-responder (non-efficacy) group, and the group where p-value is less than 0.05 was determined as a responder (efficacy) group.

The obtained results for the responsiveness of the xenograft models to L3-1Y/IgG2 were summarized in Table 8:

TABLE 8

| | Responder (Efficacy) Group | Non-Responder (Non-Efficacy) Group |
|---|---|---|
| Samples | LXFA1647, LXFA2158, LXFA526, LXFA623 | LXFA1041, LXFA677, LXFA1848, LXFA2201, LXFA289, LXFA297, LXFA400, LXFA749, LXFA923, LXFA983 |

5.2. Test of Accuracy of Prediction of Antibody Efficacy

One mouse from each of the 14 mouse xenograft models was subjected to the 7 tests described in Examples 5.2.1 to 5.2.7. For each test, each mouse was assigned one of the following results:

TP (true positive): if a mouse tested positive for a given test (one of Examples 5.2.1 to 5.2.7), that result is considered to be a true positive if the mouse also tested positive in the antibody efficacy test (Example 5.1); and TN (true negative): if a mouse tested negative for a given test (one of Examples 5.2.1 to 5.2.7), that result is considered to be a true negative if the mouse also tested negative in the antibody efficacy test (Example 5.1).

FP (false positive): if a mouse tested positive for a given test (one of Examples 5.2.1 to 5.2.7), that result is considered to be a false positive if the mouse tested negative in the antibody efficacy test (Example 5.1); and FN (false negative): if a mouse tested negative for a given test (one of Examples 5.2.1 to 5.2.7), that result is considered to be a false negative if the mouse tested positive in the antibody efficacy test (Example 5.1).

For each of the 7 tests, the prediction accuracy, prediction sensitivity, and prediction specificity were calculated as follows:

Prediction Accuracy (%)=(# of TP+# of TN)/14*100

Prediction Sensitivity (%)=(# of TP/the number of mice that tested positive in the antibody efficacy test)*100

Prediction Specificity (%)=(# of TN/the number of mice that tested negative in the antibody efficacy test)*100

The results are displayed in Tables 9 and 10.

5.2.1. c-Met IHC: Ventana (Comparison Example)

The mouse tumor tissues that have been subject to the experiment of Example 5.1 were extracted, and used in preparing a formalin fixed paraffin embedded (FFPE) block. The prepared FFPE block was used for measuring the level of surface expression c-MET by Ventana MET IHC (immunohistochemistry) (using sp44 (Ventana, Catalog Number 790-4430), which is an assay used for a clinical trial (phase III) of metmab (Genentech); see US2013089541 A1) according to a standard protocol of the manufacturer.

Samples for which the IHC score according to the Ventana MET IHC assay was 2-3, were determined to be in the responder (efficacy or positive) group.

5.2.2. Efficacy Prediction Using a Modified c-Met IHC

A modified Ventana MET IHC assay was performed, wherein the assay was identical to the Ventana MET IHC described Example 5.2.1, except that the Ventana antibody sp44 was used by ⅚ dilution. Samples for which the IHC score according to the Ventana MET IHC assay was 2-3, were determined to be in the responder (efficacy or positive) group.

5.2.3. Efficacy Prediction Using IL-8

The level of IL-8 in serum of each mouse xenograft model was quantified referring to Examples 1.1.2. The case, where the level of serum IL-8 is 500 pg/ml or more, was determined as a responder (efficacy or positive) group, and the case, where the level of serum IL-8 is less than 500 pg/ml, was determined as a non-responder (non-efficacy or negative) group.

5.2.4. Combination I (Examples 5.2.2 and 5.2.3)

The results from Example 5.2.2 (efficacy prediction by the modified Ventana MET IHC) and Example 5.2.3(efficacy prediction using IL-8) were combined to predict the efficacy of anti-c-Met antibody L3-1Y/IgG2. In particular, the case, where the IHC score according to the modified Ventana MET IHC assay of Example 5.2.2 is 2-3 and the serum IL-8 level according to Example 5.2.3 is 500 pg/ml or more, was determined as a responder (efficacy or positive) group, and the other case was determined as a non-responder (non-efficacy or negative) group.

The results from Examples 5.2.1, 5.2.2, 5.2.3, and 5.2.4 are summarized in Table 9, as below:

TABLE 9

| Model No | Model Name | in vivo antibody efficacy | c-Met IHC 5.2.1. Ventana (standard: 2+) | | c-Met IHC 5.2.2. Modified SAIT method (standard: 2+) | | Serum IL-8 5.2.3. serum level of IL-8 (vehicle group) (pg/mL) | Serum IL-8 (standard: ≥500 pg/mL) | Combined 5.2.4. Combined (modified Ventana 2+ AND IL-8 500 pg/mL or more) |
|---|---|---|---|---|---|---|---|---|---|
| 1 | LXFA297 | (—) | 3 | FP | 1 | TN* | 250.96 | TN* | TN |
| 2 | LXFA526 | moderate | 3 | TP | 3 | TP | 980.36 | TP | TP |
| 3 | LXFA623 | excellent | 3 | TP | 3 | TP | 22316.88 | TP | TP |
| 4 | LXFA983 | (—) | 3 | FP | 1 | TN* | 147.4 | TN* | TN |
| 5 | LXFA1041 | (—) | 3 | FP | 1 | TN* | 317.6 | TN* | TN |
| 6 | LXFA1647 | excellent | 3 | TP | 3 | TP | 962.88 | TP | TP |
| 1 | LXFA1848 | (—) | 3 | FP | 1 | TN* | 668.88 | FP | TN |
| 2 | LXFA2158 | excellent | 3 | TP | 3 | TP | 1921.76 | TP | TP |
| 3 | LXFA2201 | (—) | 3 | FP | 3 | FP | 1100.56 | FP | FP |
| 4 | LXFA289 | (—) | 3 | FP | 2 | FP | 444.64 | TN* | TN** |
| 5 | LXFA400 | (—) | 2 | FP | 1 | TN* | 1203.32 | FP | TN |
| 6 | LXFA677 | (—) | 3 | FP | 2 | FP | 607.08 | FP | FP |
| 7 | LXFA749 | (—) | 3 | FP | 2 | FP | 0 | TN* | TN** |
| 8 | LXFA923 | (—) | 3 | FP | 2 | FP | 138.6 | TN* | TN** |
| | Prediction accuracy | | 28.57% | | 64.29% | | 71.43% | | 85.71% |
| | Prediction sensitivity | | 100% | | 100% | | 100% | | 100% |
| | Prediction specificity | | 0% | | 50% | | 60% | | 80% |

(*improved accuracy compared to "1"; and **improved accuracy compared to "2")

5.2.5. Efficacy Prediction According to RAS-RAF Mutation

The 14 mouse xenograft models were subject to the experiment according to Example 4.1.3, to examine the presence or absence of K-RAS and/or B-RAF mutation. Mice in which both K-RAS and B-RAF were determined to be wild-type were placed in the responder group, and mice in which at least one of K-RAS and B-RAF was mutated, were placed in the non-responder group.

5.2.6. Combination II (Examples 5.2.3 and 5.2.5)

The results from Example 5.2.3 (efficacy prediction using IL-8) and Example 5.2.5 (efficacy prediction according to K-RAS and B-RAF mutation) were combined to predict the efficacy of anti-c-Met antibody L3-1Y/IgG2. In particular, the case, where the serum IL-8 level according to Example 5.2.3 is 500 pg/ml or more and both of K-RAS and B-RAF are wild-type, was determined as a responder (efficacy or positive) group, and the other case was determined as a non-responder (non-efficacy or negative) group.

5.2.7. Combination III (Examples 5.2.2, 5.2.3, and 5.2.5)

The results from Example 5.2.2 (efficacy prediction by the modified Ventana MET IHC), Example 5.2.3 (efficacy prediction using IL-8), and Example 5.2.5 (efficacy prediction according to K-RAS and B-RAF mutation) were combined to predict the efficacy of anti-c-Met antibody L3-1Y/IgG2. In particular, the case, where when the IHC score according to the modified Ventana MET IHC assay of Example 5.2.2 is 2-3, the serum IL-8 level according to Example 5.2.3 is 500 pg/ml or more, and both of K-RAS and B-RAF are wild-type, the mouse xenograft model was determined as a responder (efficacy or positive) group, was determined as a responder (efficacy or positive) group, and the other case was determined as a non-responder (non-efficacy or negative) group.

The results from Examples 5.2.5, 5.2.6, and 5.2.7 are summarized in Table 10, as below:

TABLE 10

| Model No | Model Name | in vivo antibody efficacy | 5.2.5. KRAS-BRAF mutation KRAS | 5.2.5. KRAS-BRAF mutation BRAF | 5.2.5. KRAS-BRAF mutation MUTATION | SAIT IHC + Mutation 2 + 5 Modified SAIT 2+ AND mutation status | SAIT IHC + IL8 + Mutation 2 + 3 + 5. Modified SAIT 2+ AND mutation status AND serum IL-8 |
|---|---|---|---|---|---|---|---|
| 1 | LXFA297 | (—) | W | W | FP | TN | TN |
| 2 | LXFA526 | moderate | W | W | TP | TP | TP |
| 3 | LXFA623 | excellent | W | W | TP | TP | TP |
| 4 | LXFA983 | (—) | M(G12C) | W | TN | TN | TN |
| 5 | LXFA1041 | (—) | M(G12V) | W | TN | TN | TN |
| 6 | LXFA1647 | excellent | W | W | TP | TP | TP |
| 1 | LXFA1848 | (—) | M(Q61H) | W | TN | TN | TN |
| 2 | LXFA2158 | excellent | W | W | TP | TP | TP |
| 3 | LXFA2201 | (—) | W | M(G596R) | TN | TN | TN |
| 4 | LXFA289 | (—) | W | W | FP | FP | TN |
| 5 | LXFA400 | (—) | W | W | FP | TN | TN |
| 6 | LXFA677 | (—) | W | M(D594A) | TN | TN | TN |
| 7 | LXFA749 | (—) | W | W | FP | FP | TN |
| 8 | LXFA923 | (—) | M(G12V) | W | TN | TN | TN |

TABLE 10-continued

| Model | | in vivo antibody | 5.2.5. KRAS-BRAF mutation | | | SAIT IHC + Mutation 2 + 5 Modified SAIT 2+ AND mutation status | SAIT IHC + IL8 + Mutation 2 + 3 + 5. Modified SAIT 2+ AND mutation status AND serum |
|---|---|---|---|---|---|---|---|
| No | Name | efficacy | KRAS | BRAF | MUTATION | mutation status | IL-8 |
| Prediction accuracy = | | | 71.43% | | | 85.71% | 100% |
| Prediction sensitivity | | | 100% | | | 100% | 100% |
| Prediction specificity | | | 60% | | | 80% | 100% |

W = wild-type, i.e. no mutation.

As shown in Tables 9 and 10, when the modified c-MET IHC assay, IL-8 marker, and KRAS-BRAF mutation marker are respectively used, the prediction accuracy is 64.29%, 71.43%, and 71.43%, respectively, which are all excellent compared to that of the control (Example 5.2.1; 28.57%). A combination of at least two of the modified c-MET IHC assay, IL-8 marker, and KRAS-BRAF mutation marker shows better prediction accuracy. In particular, the combination of all of the modified c-MET IHC assay, IL-8 marker, and KRAS-BRAF mutation marker shows excellent prediction accuracy (100%).

While one or more embodiments of the present invention have been described with reference to the figures, it will be understood by those of ordinary skill in the art that various changes in form and details may be made therein without departing from the spirit and scope of the present invention as defined by the following claims.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for predicting efficacy of a c-Met inhibitor in a subject or selecting a subject suitable for the application of a c-Met inhibitor, the method comprising:
   testing for a mutation of BRAF protein in an amino acid position corresponding to one or more of positions 596, 600, 601, 469, 466, 581, 594, 597, or 464 of SEQ ID NO: 110, and/or a corresponding mutation in a nucleic acid encoding BRAF, in a biological sample from a subject; and
   determining that a c-Met inhibitor would have efficacy in the subject or selecting the subject from which the biological sample is obtained for the application of the c-Met inhibitor, when
   a mutation of BRAF protein and/or a mutation of a nucleic acid encoding BRAF is not detected in the biological sample,
   further comprising a step of administering the c-Met inhibitor to the subject for whom it is determined that a c-Met inhibitor would have efficacy in the subject or who is selected for the application of the c-Met inhibitor.

2. The method of claim 1, wherein testing for a mutation comprises:
   (i) contacting the biological sample with a material that detects the mutation, thereby producing a reaction mixture, and
   (ii) analyzing the reaction mixture of step (i) to determine the presence or absence of the mutation.

3. The method of claim 2, wherein the material that detects the mutation is:
   a polynucleotide ranging in size from about 3 nucleotides to about 100 nucleotides that hybridizes with a portion of a nucleic acid encoding BRAF that contains the mutation;
   a pair of primers comprising nucleotide sequences that hybridize to 3'- and 5'-terminal regions of a 5 bp to 1000 bp portion of a nucleic acid encoding BRAF that contains the mutation; and/or
   a compound, an antibody, or an aptamer that binds to the BRAF protein containing the mutation.

4. The method of claim 1, wherein the method comprises testing for
   a mutation of BRAF protein comprising at least one amino acid mutation selected from the group consisting of G596R, V600E, V600K, V600R, K601E, D594A, K601E, G469A, V600M, G469A, V600L, G466V, V600D, G469V, D594G, D594N, N581S, L597V, L597S, L597Q, K601N, G466V, G466E, G464V, and G469E, based on the amino acid sequence of SEQ ID NO: 110; or
   a mutation in a nucleic acid encoding a BRAF protein causing the at least one amino acid mutation.

5. The method of claim 1, wherein the c-Met inhibitor is onartuzumab, LY2875358, rilotumumab, crizotinib, cabozantinib, foretinib, PHA-665752, SU11274, SGX-523, PF-04217903, EMD 1214063, golvatinib, INCB28060, MK-2461, tivantinib, NVP-BVU972, AMG458, BMS 794833, BMS 777607, MGCD-265, AMG-208, BMS-754807, JNJ-38877605, a pharmaceutically acceptable salt thereof, or combination thereof.

6. The method of claim 1, wherein the c-Met inhibitor comprises an anti-c-Met antibody or an antigen-binding fragment thereof that comprises:
   a CDR-H1 comprising SEQ ID NO: 4; a CDR-H2 comprising SEQ ID NO: 5, SEQ ID NO: 2, or an amino acid sequence comprising 8-19 consecutive amino acids within SEQ ID NO: 2 including the $3^{rd}$ to $10^{th}$ positions of SEQ ID NO: 2; and a CDR-H3 comprising SEQ ID NO: 6, SEQ ID NO: 85, or an amino acid sequence comprising 6-13 consecutive amino acids within SEQ ID NO: 85 including the $1^{st}$ to $6^{th}$ positions of the amino acid sequence of SEQ ID NO: 85; and
   a CDR-L1 comprising SEQ ID NO: 7, (b) a CDR-L2 comprising SEQ ID NO: 8, and (e) a CDR-L3 comprising SEQ ID NO: 9, SEQ ID NO: 15, SEQ ID NO: 86, or 9-17 consecutive amino acids within SEQ ID NO: 89 including the $1^{st}$ to $9^{th}$ positions of SEQ ID NO: 89.

7. A method of treating cancer in a subject, the method comprising:
   administering a c-Met inhibitor to a subject with cancer selected according to the method of claim 1.

8. The method of claim 7, wherein the c-Met inhibitor comprises an anti-c-Met antibody or an antigen-binding fragment thereof that comprises:
   a CDR-H1 comprising SEQ ID NO: 4; a CDR-H2 comprising SEQ ID NO: 5, SEQ ID NO: 2, or an amino acid sequence comprising 8-19 consecutive amino acids within SEQ ID NO: 2 including the 3rd to $10^{th}$ positions of SEQ ID NO: 2; and a CDR-H3 comprising SEQ ID NO: 6, SEQ ID NO: 85, or an amino acid sequence comprising 6-13 consecutive amino acids within SEQ ID NO: 85 including the $1^{st}$ to $6^{th}$ positions of the amino acid sequence of SEQ ID NO: 85; and
   a CDR-L1 comprising SEQ ID NO: 7, a CDR-L2 comprising SEQ ID NO: 8, and a CDR-L3 comprising SEQ ID NO: 9, SEQ ID NO: 15, SEQ ID NO: 86, or 9-17 consecutive amino acids within SEQ ID NO: 89 including the $1^{st}$ to $9^{th}$ positions of SEQ ID NO: 89.

9. A method for predicting efficacy of a c-Met inhibitor in a subject or selecting a subject suitable for the application of a c-Met inhibitor, the method comprising:
   testing for a mutation of KRAS protein in an amino acid position corresponding to one or more of positions 12, 13, 23, 24, 59, 61, or 146 of SEQ ID NO: 109, or a corresponding mutation in a nucleic acid encoding KRAS protein, in a biological sample from a subject; and
   determining that a c-Met inhibitor would have efficacy in the subject or selecting the subject from which the biological sample is obtained for the application of the c-Met inhibitor, when
   a mutation of KRAS protein or nucleic acid encoding KRAS is not detected in the biological sample,
   further comprising a step of administering the c-Met inhibitor to the subject for whom it is determined that a c-Met inhibitor would have efficacy in the subject or who is selected for the application of the c-Met inhibitor, wherein the c-Met inhibitor comprises an anti-c-Met antibody or an antigen-binding fragment thereof that comprises:
   a CDR-H1 comprising SEQ ID NO: 4; a CDR-H2 comprising SEQ ID NO: 5, SEQ ID NO: 2, or an amino acid sequence comprising 8-19 consecutive amino acids within SEQ ID NO: 2 including the $3^{rd}$ to $10^{th}$ positions of SEQ ID NO: 2; and a CDR-H3 comprising SEQ ID NO: 6, SEQ ID NO: 85, or an amino acid sequence comprising 6-13 consecutive amino acids within SEQ ID NO: 85 including the $1^{st}$ to $6^{th}$ positions of the amino acid sequence of SEQ ID NO: 85; and
   a CDR-L1 comprising SEQ ID NO: 7, a CDR-L2 comprising SEQ ID NO: 8, and a CDR-L3 comprising SEQ ID NO: 15.

10. A method for predicting efficacy of a c-Met inhibitor in a subject or selecting a subject suitable for the application of a c-Met inhibitor, the method comprising:

testing a biological sample from a subject for (a) at least one amino acid mutation of KRAS selected from the group consisting of G12A, G12D, G12R, G12C, G12S, G12V, A146T, A59T, L23R, G13N, G13D, I24F, Q61L, Q61H, G13C, and Q61K, based on the amino acid sequence of SEQ ID NO: 109; or a mutation in a nucleic acid encoding a KRAS protein causing the at least one amino acid mutation;

and (b) at least one amino acid mutation of BRAF protein selected from the group consisting of G596R, V600E, V600K, V600R, K601E, D594A, K601E, G469A, V600M, G469A, V600L, G466V, V600D, G469V, D594G, D594N, N581S, L597V, L597S, L597Q, K601N, G466V, G466E, G464V, and G469E, based on the amino acid sequence of SEQ ID NO: 110; or a mutation in a nucleic acid encoding a BRAF protein causing the at least one amino acid mutation;

determining that a c-Met inhibitor would have efficacy in the subject or selecting the subject from which the biological sample is obtained for the application of the c-Met inhibitor, when the at least one mutation of KRAS protein is not detected and the at least one mutation of BRAF protein is not detected;

and administering the c-Met inhibitor to the subject for whom it is determined that a c-Met inhibitor would have efficacy in the subject or who is selected for the application of the c-Met inhibitor.

11. The method of claim 10, wherein the c-Met inhibitor comprises an anti-c-Met antibody or an antigen-binding fragment thereof that comprises:

a CDR-H1 comprising SEQ ID NO: 4; a CDR-H2 comprising SEQ ID NO: 5, SEQ ID NO: 2, or an amino acid sequence comprising 8-19 consecutive amino acids within SEQ ID NO: 2 including the $3^{rd}$ to $10^{th}$ positions of SEQ ID NO: 2; and a CDR-H3 comprising SEQ ID NO: 6, SEQ ID NO: 85, or an amino acid sequence comprising 6-13 consecutive amino acids within SEQ ID NO: 85 including the $1^{st}$ to $6^{th}$ positions of the amino acid sequence of SEQ ID NO: 85; and a CDR-L1 comprising SEQ ID NO: 7, a CDR-L2 comprising SEQ ID NO: 8, and a CDR-L3 comprising SEQ ID NO: 15.

12. The method of claim 1, further comprising testing for a mutation of KRAS protein in an amino acid position corresponding to one or more of positions 12, 13, 23, 24, 59, 61, or 146 of SEQ ID NO: 109, or a corresponding mutation in a nucleic acid encoding a KRAS protein in a biological sample from a subject.

13. The method of claim 12, wherein the method comprises determining that a c-Met inhibitor would have efficacy in the subject, or selecting the subject from which the biological sample is obtained for the application of the c-Met inhibitor, when the mutation of BRAF protein and/or a mutation of a nucleic acid encoding BRAF is not detected in the biological sample, and the mutation of KRAS protein and/or a mutation of a nucleic acid encoding KRAS is not detected in the biological sample.

14. The method of claim 9, comprising testing for at least one amino acid mutation of KRAS selected from the group consisting of G12A, G12D, G12R, G12C, G12S, G12V, A146T, A59T, L23R, G13N, G13D, I24F, Q61L, Q61H, G13C, and Q61K, based on the amino acid sequence of SEQ ID NO: 109; or a corresponding mutation in a nucleic acid encoding a KRAS protein.

15. The method of claim 1, wherein the method comprises testing for the presence of a wild-type BRAF protein or nucleic acid encoding a wild-type BRAF protein in the biological sample, and determining that a c-Met inhibitor would have efficacy in the subject, or selecting the subject from which the biological sample is obtained for the application of the c-Met inhibitor, when a wild-type BRAF protein or nucleic acid encoding a wild-type BRAF protein is detected.

16. The method of claim 9, wherein the method comprises testing for the presence of a wild-type KRAS protein or nucleic acid encoding a wild-type KRAS protein in the biological sample, and determining that a c-Met inhibitor would have efficacy in the subject, or selecting the subject from which the biological sample is obtained for the application of the c-Met inhibitor, when a wild-type KRAS protein or nucleic acid encoding a wild-type KRAS protein is detected.

17. The method of claim 10, wherein the method comprises testing for the presence of a wild-type KRAS protein or nucleic acid encoding a wild-type KRAS protein, and a wild-type BRAF protein or nucleic acid encoding a wild-type BRAF protein, in the biological sample, and determining that a c-Met inhibitor would have efficacy in the subject, or selecting the subject from which the biological sample is obtained for the application of the c-Met inhibitor, when a wild-type KRAS protein or nucleic acid encoding a wild-type KRAS protein is detected and a wild-type BRAF protein or nucleic acid encoding a wild-type BRAF protein is detected.

* * * * *